United States Patent
Yoneyama et al.

(10) Patent No.: US 8,449,911 B2
(45) Date of Patent: May 28, 2013

(54) DRUG COMPOSITION HAVING ACTIVE INGREDIENT ADHERED AT HIGH CONCENTRATION TO SPHERICAL CORE

(75) Inventors: Shuji Yoneyama, Osaka (JP); Hiroto Bando, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 1376 days.

(21) Appl. No.: 10/548,504

(22) PCT Filed: Mar. 10, 2004

(86) PCT No.: PCT/JP2004/003075
§ 371 (c)(1),
(2), (4) Date: Sep. 9, 2005

(87) PCT Pub. No.: WO2004/080439
PCT Pub. Date: Sep. 23, 2004

(65) Prior Publication Data
US 2006/0159760 A1      Jul. 20, 2006

(30) Foreign Application Priority Data

Mar. 12, 2003 (JP) .................................. 2003-066344

(51) Int. Cl.
*A61K 31/439*   (2006.01)
*A61K 9/24*     (2006.01)
*A61K 9/209*    (2006.01)

(52) U.S. Cl.
USPC ............................ 424/472; 424/471; 514/338

(58) Field of Classification Search
USPC .................................. 424/471, 472; 514/338
See application file for complete search history.

(56) References Cited

U.S. PATENT DOCUMENTS

| | | | |
|---|---|---|---|
| 5,213,811 A * | 5/1993 | Frisbee et al. ................ 424/493 |
| 5,997,903 A | 12/1999 | Dietrich et al. | |
| 6,274,173 B1 | 8/2001 | Sachs et al. | |
| 6,328,994 B1 | 12/2001 | Shimizu et al. | |
| 6,346,269 B1 | 2/2002 | Hsiao et al. | |
| 2002/0086029 A1 | 7/2002 | Lundberg et al. | |
| 2002/0137771 A1 | 9/2002 | Makino et al. | |
| 2002/0160046 A1 | 10/2002 | Robinson et al. | |
| 2005/0003005 A1 | 1/2005 | Shimizu et al. | |

FOREIGN PATENT DOCUMENTS

| | | |
|---|---|---|
| EP | 0 174 726 A1 | 3/1986 |
| EP | 0 247 983 A2 | 12/1987 |
| EP | 0 277 741 A1 | 8/1988 |
| JP | 3-20215 | 1/1991 |
| WO | 98/19668 | 5/1998 |

(Continued)

OTHER PUBLICATIONS

Banker, G.S. et al, "Modern Pharmaceutics, Third edition", Marcel Dekker, New York, 1996, pp. 451 and 596.*

(Continued)

*Primary Examiner* — Aradhana Sasan
(74) *Attorney, Agent, or Firm* — Wenderoth, Lind & Ponack, L.L.P.

(57) ABSTRACT

Granule, fine particle or tablet of excellent leaching property, comprising a drug active ingredient in high content realized by forming a layer containing drug active ingredient on core particles through a combination of a method of dispersing and adhering an active ingredient while spraying or adding a binder with a method of spraying or adding a solution or suspension wherein an active ingredient and a binder are contained so as to effect adhesion. Further, there are provided a drug composition containing such a granule, fine particle or tablet and a process for producing the same.

18 Claims, 3 Drawing Sheets

FOREIGN PATENT DOCUMENTS

| | | |
|---|---|---|
| WO | 99/58114 | 11/1999 |
| WO | 00/06126 | 2/2000 |
| WO | 00/66171 | 11/2000 |
| WO | 2004/035020 A2 | 4/2002 |
| WO | 02/072071 A1 | 9/2002 |
| WO | 03/032953 A1 | 4/2003 |

OTHER PUBLICATIONS

Wolff, Manfred E. "Burger's Medicinal Chemistry, Fifth edition, vol. I: Principles and Practice", John Wiley & Sons, 1995, pp. 975-977.*

* cited by examiner

DRUG COMPOSITION HAVING ACTIVE INGREDIENT ADHERED AT HIGH CONCENTRATION TO SPHERICAL CORE

This application is a U.S. National Stage of International Application No. PCT/JP2004/003075 filed Mar. 10, 2004.

TECHNICAL FIELD

The present invention relates to a granule or a fine particle containing an active ingredient at a high concentration and, further, a drug composition containing such granules or the like, in particular, a release-controlled drug composition comprising granules or fine particles, and a manufacturing process for the same.

BACKGROUND ART

Among medicines, an oral dosage form is a most frequently used dosage form, and examples of a drug composition containing an active ingredient which provides these medicines include liquid preparations, powders, fine particles, granules, tablets, and capsules. In recent years, there is provided not only a drug composition simply blended with an active ingredient but also an enteric preparation which is coated with an enteric base in order that a drug composition is protected from a low pH in stomach and an objective amount of an active ingredient can be administered without degradation, for the purpose of preventing decrease in activity of an active ingredient due to degradation and the like by the environment in a digestive tract, for example, pH in stomach. In addition, many oral dosage forms whose drug efficacy lasts with once to twice a day administration have been developed from a viewpoint of QOL improvement. Although an attempt to synthesize a compound having a kinetics such that a drug efficacy lasts by once to twice a day administration from synthetic stage of compound itself has been tried, there are not a few cases that a sustained preparation is designed and kinetics is modified by a pharmaceutical technique. As a dosage form of an oral sustained preparation, various controlled release systems such as release control by compound diffusion control with a release-controlling membrane or a matrix, release control of compound by erosion of a matrix (base), pH-dependent release control of compound, timed release control for releasing a compound after a certain lag time, and the like have been developed and applied. It is considered that the sustained release property can be further prolonged by combining control of moving rate in a digestive tract with the above release controlling systems.

For example, as a dosage form affording an enteric preparation as one embodiment of a release-controlled preparation, a combination of tablets, fine particles, granules or powders prepared by mixing an active ingredient and excipients composing a drug composition, with a base having enteric property are provided, and preferred is a preparation in which an enteric base is rapidly dissolved in a lower digestive tract including duodenum after passed through the gastric environment and an active ingredient is rapidly dissolved out. From this point of view, in the case of normal size tablets, a combination of fine particles, granules, or powders with an enteric base are more preferred since the specific surface area is increased compared to tablets. Or, in the case where formulated into tablets, downsized tablets are preferable as compared with normal tablets. In addition, when an oral preparation is administered, particularly, in an enteric preparation which is not disintegrated or dissolved in stomach, transference of a preparation from stomach to a lower digestive tract including duodenum is controlled by dynamic activity of a digestive tract and, in particular, in tablets, the transference is greatly governed by a gastric emptying time and, as a result, after administration, a time of movement to a lower digestive tract including duodenum is not constant, and therefore, appearance of blood concentration of an active ingredient is not constant. For the purpose of improving this defect and appearance of a stable blood concentration with small variation, enteric preparations such as fine particles, granules, and the like are developed. Since enteric preparations such as fine particles and granules are multiple unit preparations in which the number of particles in preparations is plural, a gastric emptying time has a small variation as a whole and, after gastric evacuation, a preparation is rapidly dissolved and an active ingredient is dissolved out, therefore, quality of remedy is improved. In addition, when a release-controlled drug composition other than enteric composition is provided, and also when there are a change in solubility in each site of digestive tract based on physicochemical property of an active ingredient and a variation in dissolution and release property from a drug composition, appearance of a stable blood level with small variation and temporal transition thereof can be provided by stably providing a distribution of movement from an esophagus to a lower digestive tract.

For example, in a preparation containing a drug having acid labile property as an active ingredient such as a benzimidazole compound having a proton pump inhibitory activity (hereinafter, referred to as PPI in some cases), an enteric coat needs to be provided. That is, since a composition containing a benzimidazole compound having PPI activity is required to be rapidly disintegrated in an intestine, it is preferred to be formulated into preparations as granules or fine particles which have a greater surface area than that of tablets and are easy to be disintegrated or dissolved rapidly, and, also in the case of tablets, it is preferable to make them into downsized tablets.

Although enteric granules or fine particles can be also prepared by coating granules or fine particles prepared by the general pharmaceutical technique with an enteric base, or by mixing an enteric base with other excipients and active ingredients, for example, they are provided by coating substantially spherical granules or fine particles prepared by adhering an active ingredient or an active ingredient and a suitable excipient to a substantially spherical core prepared from a substance available as an excipient for medicines, with an enteric base.

In addition, as the relating technical documents, EPA 277741 and U.S. Pat. No. 6,274,173 are exemplified.

DISCLOSURE OF THE INVENTION

Objects of the Invention

An object of the present invention is to provide, in granules in which an active ingredient, if necessary, together with a base applicable to a medicine is adhered to a core comprising a base applicable to a medicine, a drug composition designed to a dosable size in which an active ingredient is blended with a large amount and dissolved rapidly.

SUMMARY OF THE INVENTION

According to the conventional technique, in preparation of granules in which at least an active ingredient, further if necessary, together with at least one kind base applicable to a medicine is adhered to a core comprising a base applicable to a medicine, when an active ingredient is blended with a large amount, a size of composition becomes larger due to restriction of preparation manufacturing, and dosing becomes difficult to a subject to be medicated (e.g. patient), leading to reduction in a compliance and an increased manufacturing cost resulting in increase in a medical fee.

That is, the present invention relates to:

(1) a granule, fine particle or tablet having a core particle, and on said core particle, an active ingredient-containing A layer formed by spraying a solution or suspension containing an active ingredient and a binder, and an active ingredient-containing B layer formed by dispersing a dusting powder containing an active ingredient while spraying a solution containing a binder, (2) the granule, fine particle or tablet according to the above-mentioned (1), wherein the A layer is formed on the inner side, and the B layer is formed on the outer side, (3) the granule, fine particle or tablet according to the above-mentioned (1), which comprises being further coated with a release-controlling film, (4) the granule, fine particle or tablet according to the above-mentioned (3), wherein the release-controlling film contains a pH dependently dissolved polymer, (5) the granule, fine particle or tablet according to the above-mentioned (1), wherein the active ingredient is a proton pump inhibitor (PPI), (6) the granule, fine particle or tablet according to the above-mentioned (5), wherein the PPI is a benzimidazole compound represented by the formula (I):

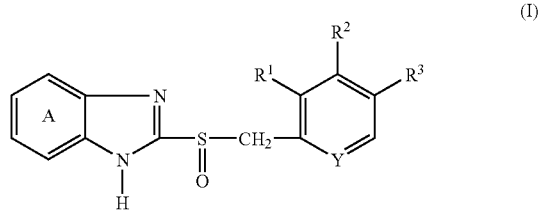

wherein ring A represents an optionally substituted benzene ring, $R^1$, $R^2$ and $R^3$ are the same or different and represent a hydrogen atom, an optionally substituted alkyl group, an optionally substituted alkoxy group or an optionally substituted amino group, and Y represents a nitrogen atom or CH, or a prodrug thereof, or an optically active compound thereof or a salt thereof, (7) the granule, fine particle or tablet according to the above-mentioned (5), wherein the PPI is lansoprazole, omeprazole, rabeprazole, pantoprazole, leminoprazole, tenatoprazole (TU-199), or a prodrug thereof, or an optically active compound thereof or a salt thereof, (8) the granule, fine particle or tablet according to the above-mentioned (5), wherein the PPI is lansoprazole, or a prodrug thereof, or an optically active compound thereof or a pharmaceutically acceptable salt thereof, (9) the granule, fine particle or tablet according to any one of the above-mentioned (5) to (8), wherein a basic inorganic salt is contained in the A layer and the B layer,

(10) the granule, fine particle or tablet according to the above-mentioned (9), wherein the basic inorganic salt is a salt of magnesium or a salt of calcium,

(11) the granule, fine particle or tablet according to any one of the above-mentioned (5) to (8), which is further coated with an enteric film,

(12) the granule, fine particle or tablet according to any one of the above-mentioned (5) to (8), which is further coated with a release-controlling film,

(13) the granule, fine particle or tablet according to the above-mentioned (11) or (12), which is coated with an intermediate layer and further coated with an enteric film or a release-controlling film,

(14) the granule, fine particle or tablet according to the above-mentioned (1), wherein an intermediate layer is provided for preventing direct contact among the core particle, the A layer and the B layer,

(15) the granule, fine particle or tablet according to the above-mentioned (3), wherein an intermediate layer is provided for preventing direct contact among the core particle, the A layer, the B layer and the release-controlling film,

(16) a solid dosage form containing the granules, fine particles or tablets according to the above-mentioned (11) and/or the granules, fine particles or tablets according to the above-mentioned (12),

(17) a manufacturing process for a granule, fine particle or tablet, comprising a combination of:

a step of spraying a solution or suspension containing an active ingredient and a binder on a core particle to form an active ingredient-containing A layer, and a step of dispersing a dusting powder containing an active ingredient while spraying a solution containing a binder, to form an active ingredient-containing B layer,

(18) the manufacturing process for a granule, fine particle or tablet according to the above-mentioned (17), wherein A layer is first formed on the core particle, and B layer is formed on said A layer,

(19) a solid dosage form containing the granules, fine particles or tablets according to the above-mentioned (1),

(20) the solid dosage form according to the above-mentioned (17), which is a table or a capsule, and

(21) a method for controlling dissolution of an active ingredient and a size of a solid dosage form containing a granule, fine particle or tablet, comprising a combination of, on a core particle, a method of spraying a solution or suspension containing an active ingredient and a binder to form an active ingredient-containing A layer, and a method of dispersing a dusting powder containing an active ingredient while spraying a solution containing a binder to form an active ingredient-containing B layer.

In addition, controlled release to be used in the present invention is obvious to a pharmacist, and means not only delayed release and extended release which fall within a category of modified release prescribed in USP, but also complex application of them, and further refers to intentional control of dissolution or release of active ingredient unlike a so-called IR (immediate release) preparation.

BEST MODE FOR CARRYING OUT THE INVENTION

Figure 1:
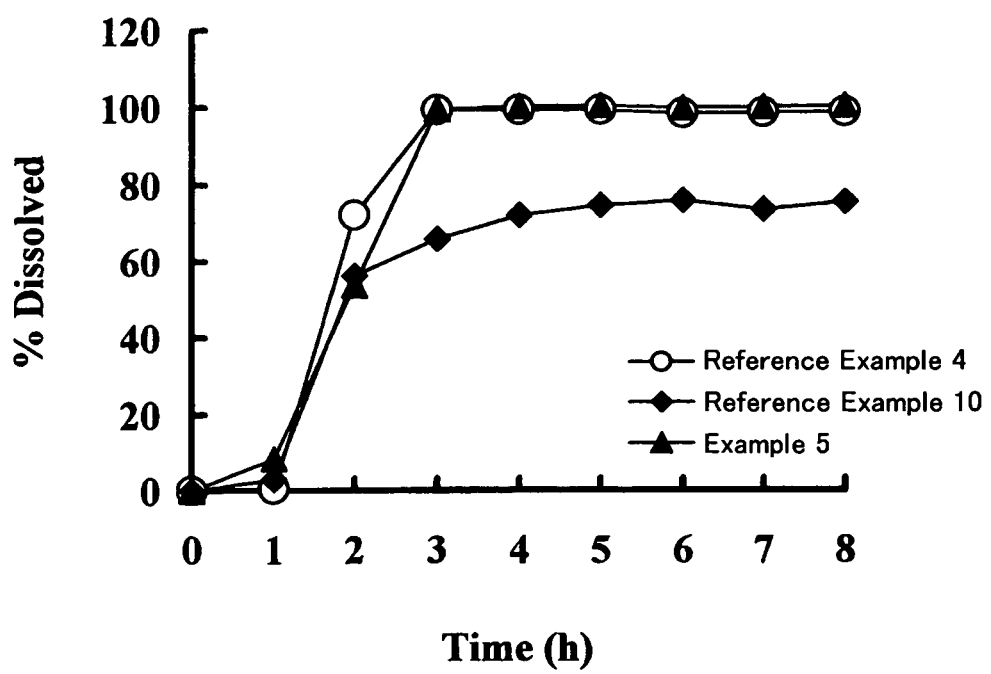
FIG. 1 shows dissolution profiles of compound A for enteric granules obtained in Reference Examples 4 and 10, and Example 5.

In preparation of a granule in which at least an active ingredient and, further if necessary, at least one kind of bases applicable to a medicine are adhered to a core comprising a base applicable to a medicine, there are defects that, when an active ingredient is blended therein at a large amount, a size of composition becomes larger due to a restriction in preparation manufacturing and, additionally, when an enteric or release-controlled drug composition is provided, since a composition is coated with a base for enteric property or release control or the base is coexisted, the size of drug composition becomes further larger or the number of granules to be taken becomes further larger, or when the granule is filled into a capsule or a tablet, a preparation to be taken itself becomes large and the number of preparations to be taken is increased.

In particular, in an enteric preparation, a method of making an easy-to-dose size includes a method of adhering an active ingredient to a core particle at a high concentration. For example, there is a method of dissolving or suspending an active ingredient in a solution containing a necessary binder for adhesion of the active ingredient, and adhering this to a core particle, but dissolution becomes slow since an active ingredient is dispersed in a binder. In an enteric preparation, since the preparation is medically preferred to be rapidly dissolved and release an active ingredient after gastric evacuation, further improvement is desired.

The present inventors intensively studied a drug composition having better dissolving out property in which an active ingredient is adhered at a high concentration to a core comprising a base applicable to a medicine, and a process for manufacturing the same and, as a result, found out that, by combining a method of dispersing and adhering an active ingredient to a core while spraying or adding a binder and a method of adhering a solution or a suspension containing an active ingredient and a binder to a core, a high content and better dissolving out property of an active ingredient can be attained, and further continued to study, which resulted in completion of the present invention.

In the present invention, as a core comprising a base applicable to a medicine, a substantially spherical core is preferable, examples thereof include cores in which a spherical particle is formed using sucrose or crystalline cellulose as a base, such as Nonpareil (Nonpareil-101 (particle diameter 850-710, 710-500, 500-355), Nonpareil-103 (particle diameter 850-710, 710-500, 500-355), Nonpareil-105 (particle, 500-355, 300-180, manufactured by Freund), and Celphere (CP-507 (particle diameter 500-710), CP-305 (particle diameter 300-500) manufactured by Asahi Kasei Chemicals Corporation), and the core can be selected in view of blending property with an active ingredient, and manufacturing property. Besides the aforementioned spherical cores, a core is not limited to the aforementioned cores as far as they comprise a base applicable to a medicine and are substantially spherical and, for example, a spherical core prepared by using, as a base raw material, corn starch, lactose, mannitol, glucose, fructose, maltose, erythritol, or sorbitol may be used, or a spherical core using a plurality of the aforementioned bases may be used. Alternatively, particles having a desired size may be obtained by the sieving a granule or a fine particle obtained by kneading and granulating an excipient such as lactose, mannitol, corn starch, and crystalline cellulose and an active ingredient with an agitation granulator using a binder such as hydroxypropylmethylcellulose, hydroxypropylcellulose, and methylcellulose and, if necessary, adding sodium carboxymethylcellulose, calcium carboxymethylcellulose, sodium croscarboxymethylcellulose, or low-substituted hydroxypropylcellulose. Alternatively, a core particle may be prepared by dry granulation with a roller compactor. It is not necessary to particularly define the size of these spherical cores, and a particle having a size of 50 µm to 5 mm, preferably 100 µm to 3 mm, further preferably 100 µm to 2 mm is used. These cores are preferably substantially spherical from the viewpoint that a sphericity of a formed granule is enhanced.

Generally, examples of a method which is generally used as a method of adhering an active ingredient to a core comprising a base applicable to a medicine include a method of preparing an active ingredient-containing particle by wet granulation using, for example, a centrifugal tumbling granulator (CF-mini, CF-360, manufactured by Freund) or a Fluid and Centrifugal granulation apparatus (Powrex MP-10), a general fluidized bed coating apparatus, or a Wurster-type coating apparatus, but not limited to.

Examples of a method of adhering an active ingredient using the above apparatus include a method of dispersing and adhering a dusting powder containing an active ingredient while a solution containing a binder is applied to a substantially spherical core referred in the present invention by spraying (hereinafter, referred to as dusting method). In this case, the dusting powder may be not only powdery but also liquid and, in a solution containing a binder, a binder may be dissolved or suspended and, further, in addition to a binder, an excipient applicable to a medicine may be dissolved or suspended. When a dusting powder containing an active ingredient is dusted, a dusting powder consisting of an active ingredient alone may be used, or a dusting powder obtained by mixing an active ingredient with a suitable excipient applicable to a medicine in advance may be used, or an active ingredient and a suitable excipient applicable to a medicine may be dusted without mixing. An order of dispersing an active ingredient and other excipients is not particularly limited, but it is enough that they can be adhered to a substantially spherical core. Naturally, it is possible to adhere a dusting powder obtained by mixing an active ingredient and a part of an excipient to be blended, and other excipient without mixing, and a dusting method is not particularly limited. As a variant of this method, a solution or a suspension of a drug may be sprayed separately from a binder solution. By such dusting method, an active ingredient-containing B layer is formed on a substantially spherical core particle.

As another mode, it is also possible to adhere to a substantially spherical core referred in the present invention by spraying a binder-containing solution in which an active ingredient is dissolved or suspended. An excipient applicable to a medicine may be added to the aforementioned solution containing an active ingredient and a binder. Further, also in a method of adhering an active ingredient by spraying a solution containing an active ingredient and a binder (hereinafter, referred to as solution adding method), an active ingredient and an excipient may be dusted simultaneously as in the aforementioned dusting method. Herein, a layer formed on a substantially spherical core particle by a solution adding method is referred to as active ingredient-containing A layer, and it is enough that the granule, fine particle or tablet of the present invention has active ingredient-containing A layer and B layer on a core particle, regardless of an order of A layer and B layer formed on a core particle.

When a drug composition is prepared by these methods, an active ingredient, or an active ingredient and an excipient can be adhered with up to around 10-fold amount relative to the weight of substantially spherical core comprising a base applicable to a medicine.

In the dusting method, adherability is influenced by physicochemical property of an active ingredient, and since substantially, a dusting powder mixed with other excipient in advance is dusted, an amount of active ingredient relative to a weight of substantially spherical core is limited. In addition, in order to render a mechanical strength of a prepared drug composition sufficient in the adhesion by the dusting method, the amount of an ingredient to be adhered is preferably 2 to 3-fold a weight of a core. Dissolution property of an active ingredient from a drug composition prepared by the dusting method is relatively rapid. On the other hand, in an active ingredient having a high dose to be administered as a medicine, the weight of drug composition to be administered becomes large, and a size as a medical preparation becomes large.

In the solution adding method, since an active ingredient is dissolved or suspended in a solution containing a binder, adhesion of an active ingredient to a substantially spherical core comprising a base applicable to a drug is tight, and since an active ingredient can be adhered to a core at a high concentration, generally, a high content can be attained as compared with the aforementioned dusting method and, as a drug composition containing the same active ingredient amount, a weight of medical preparation can be reduced, and a size and shape can be reduced. On the other hand, since an active ingredient is present in the state where it is dispersed in a binder in a drug composition, there is a tendency that a dissolution rate becomes slow as compared with the dusting method. Delay of a dissolution rate leads to delay of drug efficacy appearance, and also leads to decrease in biological availability. Further, for example, in an enteric preparation coated with an enteric base for further imparting controlled release ability to a granule in which at least active ingredient and, if necessary, at least one kind of bases applicable to a medicine are adhered to a substantially spherical core comprising a base applicable to a medicine, since it is important to rapidly dissolve out an active ingredient in a lower digestive tract after gastric evacuation, it becomes important to solve a fearing material as the solution adding method, and design a size of preparation which is a problem of the dusting method to such a size that a compliance is further improved. Alternatively, when so-called sustained release as one of release control is imparted by coating with a sustained release base, in order to control a dissolution rate with a coating membrane having sustained-release property, it is expected that an active ingredient is rapidly dissolved with penetrated water.

In a drug composition having a large amount of an active ingredient to be administered, preparation of a drug composition by the aforementioned solution adding method is preferable from a viewpoint of improvement in a compliance of dosing. For this reason, as will be explained in Examples later, in an enteric preparation in which a drug composition prepared by the solution adding method is coated with an enteric base, dissolution property of active ingredient is not preferable, and dissolution of a prescribed amount was not obtained in in vitro dissolution test.

On the other hand, according to the present invention, an active ingredient, or an active ingredient and an excipient can be adhered with up to about 10-fold amount relative to a weight of a substantially spherical core comprising a base applicable to a medicine. In a granule in which an active ingredient and, optionally, at least one kind of bases applicable to a medicine are adhered, in order to provide a drug composition in which an active ingredient is blended with a large amount and rapidly dissolved out, and, further, which is designed to a dosable size, the present invention relates to a manufacturing method which can ensure rapid dissolution property, and can design a size of medicine to be administered to such a size that a compliance at dose is improved. In particular, the present invention is suitable when applied to a controlled release preparation coated with a release-controlling base and, inter alia, effective when applied to an enteric preparation.

Although a specific method for manufacturing and providing a drug composition expected in the present invention depends on physicochemical property, particularly, solubility in water of an active ingredient, an active ingredient, or an active ingredient and an excipient can be adhered with up to around 10-fold amount relative to a weight of substantially spherical core comprising a base applicable to a medicine, and around 3-fold amount is preferred, and around 2-fold amount is more preferred. Further, an active ingredient at an amount of 80% or less of the amount of active ingredient to be finally adhered to a core, preferably an active ingredient at an amount of 50% or less, further preferably an active ingredient at an amount of 30% or less is adhered to a substantially spherical core comprising a base applicable to a medicine (hereinafter, referred to as core particle) as a first stage and, thereafter, a remaining active ingredient is adhered by the aforementioned dusting method. The binder concentration in the step of adhering an active ingredient in the first stage of the present invention is not particularly limited, and is usually 0.01 to 20 w/w %, preferably 0.5 to 10 w/w %, more preferably 1 to 5 w/w %. The amount of an active ingredient to be dissolved or suspended in the binder containing an active ingredient in this step is suitably 1 to 20-fold, preferably 2 to 10-fold of a binder weight. A binder concentration in a solution containing a binder used in a step for adhering an active ingredient by dusting method of second stage which is carried out after the adhering step of an active ingredient by solution addition of first stage is usually preferably a concentration of 0.5 to 10 w/w %, more preferably 1 to 5 w/w %.

A content of an active ingredient relative to a whole granule is not particularly limited, but is suitable for manufacturing a high content granule that an active ingredient is blended usually at about 1 to 70 w/w %, preferably 5 to 50 w/w %, further more preferably 10 to 40 w/w % relative to a whole granule.

In both of the solution adding method and dusting method, a manufacturing equipment used is not particularly limited, but in the adhering step of an active ingredient at the first stage of the solution adding method in an embodiment of the present invention, a Fluid and Centrifugal granulation apparatus (e.g. Powrex MP-10) is particularly suitable as manufacturing equipment and, in the adhering step of an active ingredient according to the dusting method of the step at the second stage, a centrifugal tumbling granulator (e.g. CF-mini, CF-360, manufactured by Freund) is particularly suitable.

A binder solution used in an embodiment in the present invention may be an aqueous solution, and usually water, and, if necessary, an alcohol (e.g. methanol, ethanol, propanol, isopropanol), acetone, acetonitrile and the like which are miscible with water may be added. Further, in the case where an active ingredient, or an excipient, or both are dissolved or suspended in a solution not containing a binder and this is adhered to a core particle, the solution may be the same form as that of the binder solution.

As a size of the tablet, granule or fine particle, a particle of 50 µm to 5 mm, preferably 100 µm to 3 mm, further more preferably 100 µm to 2 mm is used. Most preferable is a fine particle or granule of about 100 to 1500 µm. The present invention may be applied to a tablet itself, but a granule or fine particle to which the present invention is applied may be blended in a tablet, and it is also possible to blend the tablet obtained in the present invention or a tablet obtained by blending a granule or fine particle to which the present invention is applied, further into a tablet, in addition, it is also possible to combine a tablet with a granule or fine granule into one capsule, thus an embodiment thereof is not pharmaceutically limited. The aforementioned tablet, granule or fine particle may be coated with a release-controlling membrane or an enteric film, if necessary. Alternatively, the tablet, granule or fine particle of the present invention coated with a release-controlling membrane or an enteric film, if necessary, can be blended in a tablet. Thus, since it becomes possible to manufacture an extremely small granule, fine particle or tablet, it becomes possible to manufacture a capsule or a tablet which is small and has a high concentration, by using the granule or the like.

A drug composition which is small and contains an active ingredient at a high concentration may be manufactured by formulating into a capsule or tablet containing both of the tablet, granule or fine particle having only an active ingredient-containing A layer on a core particle of the present invention, and the tablet, granule or fine particle having only an active ingredient-containing B layer.

According to the present invention, further depending on attribute of an active ingredient, by adjusting a ratio of an active ingredient to be blended in A layer and B layer, dissolution property and releasability of an active ingredient can be appropriately regulated/controlled, and a size of desired granule and a size of final solid preparation such as a tablet and a capsule containing them can be regulated to a desired size. A desired size of a final preparation referred herein means a size which is easily acceptable on a market, and is No. 00 to No. 5, preferably No. 0 to No. 4, more preferably NO.1 to No. 4 in the case of a capsule. In addition, in the case of a tablet, a desired size is a tablet weight of 50 mg to 2 g, preferably 100 mg to 1 g, more preferably 100 mg to 600 mg. The function of the present invention, and characterization of an active ingredient which can be applied to this will be described functionally. More specifically, when a larger amount of an active ingredient is blended in A layer, that is, a core particle, and an active ingredient-containing layer formed by spraying a solution or a suspension containing an active ingredient and a binder on the core particle, the dissolution property is tend to reduce since a large amount of binder is used. On the other hand, when a larger amount of an active ingredient is blended in a B layer, that is, an active ingredient-containing layer formed by dispersing a dusting powder containing an active ingredient while spraying a binder-containing solution, the dissolution property can be maintained, but since a large amount of additives such as an excipient and a disintegrating agent and a solubilizer is blended, there is a tendency that a volume is increased. Therefore, by adjusting a ratio of blending an active ingredient into A layer and B layer, a tablet, granule or fine particle having desired dissolution property for an active ingredient used and size can be obtained. In the case of an active ingredient per se having a high solubility, even when a large amount is blended in an A layer, a unit preparation such as a considerably small tablet, granule or fine particle can be prepared without deteriorating dissolution property of drug in a final preparation, and, as a result, a final solid preparation of a capsule or a tablet containing them can be regulated to a desired size. As used herein, a high solubility means that any solubility in purified water, Japanese Pharmacopoeia 14$^{th}$ edition disintegration test solution No. 2 solution or a phosphate buffer (pH 6.8) (USP 27) at 37° C. is 10 mg/mL or more. On the other hand, in the case of an active ingredient per se having a low solubility, when a large amount is blended in A layer, there is a tendency that dissolution property is deteriorated depending on a solubility of an active ingredient itself. In addition, when a large amount is blended in B layer, dissolution property can be improved, but there is a tendency that a volume becomes greater due to blending of a large amount of additives such as an excipient, a disintegrating agent, and a solubilizer. As in the present invention, by combining A layer and B layer, since A layer is hydrated by the time at which B layer is completely disintegrated, the tendency of reduction in dissolution property of A layer itself is tend to be improved. As used herein, a low solubility means that a solubility in any of purified water, Japanese Pharmacopoeia 14$^{th}$ edition disintegrating test solution No. 2 solution and a phosphate buffer (pH 6.8) (USP27) at 37° C. is less than 10 mg/mL. It is considered that in an active ingredient having a low solubility, a desired size of final preparation depends on a clinical dose of an active ingredient. For example, in the case where an amount of an active ingredient per final preparation is 10 mg or less, even when a large amount of an active ingredient is blended in B layer, it becomes possible to regulate a size to a desired size. When an amount of an active ingredient per final preparation is increased, and the amount is, for example, 10 mg to 300 mg, preferably 30 mg to 200 mg, more preferably 30 mg to 100 mg, dissolution property and releasability of an active ingredient can be appropriately regulated/controlled, and a size of a desired granule and the like and a size of final solid preparation of a tablet or a capsule containing them can be regulated to a desired size.

A preferable mode and manufacturing method in the embodiment of the present invention are as described above and, when a drug composition is manufactured by these methods, an active ingredient referred herein may not be one kind of a substance, but a plurality of substances may be used simultaneously. A binder may not be one kind of a substance, but a plurality of substances may be used. A binder used herein includes not only a binder in a narrow sense, but also a pharmaceutically acceptable substance as far as the substance can adhere or fix a drug, being not limited particularly. More preferable examples of a binder include sucrose, gelatin, pullulan, hydroxypropylmethylcellulose (HPMC), hydroxypropylcellulose (HPC), methylcellulose (MC), crystalline cellulose, polyvinylpyrrolidone (PVP), macrogol, gum arabic, dextran, polyvinyl alcohol (PVA), and starch paste. An excipient used herein means not only an excipient in a narrow sense, but also a lubricant, a disintegrating agent, a coating agent, a colorant, a light shielding agent, a flavor, an antioxidant, a pH adjusting agent, a reducing agent, a chelating agent, and an antistatic agent.

Examples of the lubricant include stearic acid, magnesium stearate, calcium stearate, talc, waxes, DL-leucine, sodium laurylsulfate, magnesium laurylsulfate, macrogol, and aerosil (possible also as an antistatic agent), and examples of the disintegrating agent include carboxylmethylcellulose, calcium carboxymethylcellulose, low-substituted hydroxypropylcellulose, crosslinked polyvinylpyrrolidone, sodium carmellose, sodium croscarmellose, sodium carboxymethyl starch, cation exchange resin, partially gelatinized starch, and corn starch.

Examples of the colorant include a synthetic colorant applicable to a medicine (e.g. Sunset Yellow, and aluminum lake thereof), yellow ferric oxide (yellow rouge), red ferric oxide (red rouge), riboflavin, riboflavin organic acid ester (e.g. riboflavin butyric acid ester), riboflavin phosphate or an alkali metal or alkaline earth metal salt thereof, phenolphthalein, titanium oxide, lycopine, and β-carotin.

Examples of the light shielding agent include titanium oxide.

Examples of the antioxidant include BHT, tocopherol, tocopherol ester (e.g. tocopherol acetate), ascorbic acid or an alkali metal salt, or an alkaline earth metal salt thereof, lycopine, and β-carotin.

Examples of the reducing agent include cystine, and cysteine.

Examples of the chelating agent include EDTA, an alkali metal salt and an alkaline earth metal salt of EDTA, citric acid, and tartaric acid, and the pH adjusting agent is not limited as far as it can substantially adjust a pH, and is applicable to a medicine, and examples thereof include an inorganic salt of hydrochloric acid, sulfuric acid, and phosphoric acid (e.g. alkali metal salt, alkaline earth metal salt), a salt with an inorganic base (e.g. ammonium) or an organic base (e.g. meglumine, amino acid), and a hydrate and solvate thereof, boric acid, an organic acid (edible acid such as formic acid, acetic acid, lactic acid, malic acid, citric acid, maleic acid, tosylic acid, mesylic acid, ascorbic acid, isosorbic acid, and erysorbic acid) and an inorganic salt thereof (e.g. alkali metal salt, alkaline earth metal salt), a salt with an inorganic base (e.g. ammonium), and an organic base (e.g. meglumine, basic amino acid, thromethamol), and a hydrate and solvate thereof. Further, amino acid, basic amino acid and a salt therefore, acidic amino acid and a salt thereof, and a basic organic compound and a salt thereof (e.g. meglumine, thromethamol) may be used. In particular, examples include sodium hydroxide, potassium hydroxide, calcium hydroxide, magnesium hydroxide, calcium oxide, magnesium oxide, meglumine, calcium carbonate, magnesium carbonate, sodium dihydrogen phosphate, sodium monohydrogen phosphate, sodium phosphate, calcium acetate, sodium acetate, calcium phosphate, sodium citrate, sodium tartarate, and a hydrate thereof. In particular, in a digestion tract movement promotive drug such as mosapride and cisapride, a H2 blocker such as famotidine, ranitidine and cimetidine which are a drug for treating gastritis, stomach esophagus reflux, or stomach•duodenum ulcer, and a benzimidazole proton pump inhibitor (PPI) such lansoprazole and an optically active compound thereof (R isomer and S isomer, preferable R isomer (hereinafter referred to as compound A in some cases)), omeprazole and an optically active compound thereof (S isomer; esomeprazole), rabeprazole and an optically active compound thereof, and pantoprazole and an optically active compound thereof, sodium hydroxide, potassium hydroxide, calcium hydroxide, magnesium hydroxide, calcium acetate, sodium acetate, magnesium acetate, calcium oxide, magnesium oxide, sodium carbonate, sodium bicarbonate, calcium carbonate, magnesium carbonate, sodium dihydrogen phosphate, sodium monohydrogen phosphate, sodium phosphate, calcium phosphate, and a hydrate thereof are particularly preferred. Instead of a hydrate, a solvate such as ethanol may be used.

Examples of the excipient include further lactose, white sugar, glucose, mannitol, sorbitol, erythritol, maltose, maltitose, corn starch, wheat flour, partially gelatinized starch, dextrin, carboxymethylstarch, gelatin, light silicic anhydride, synthetic aluminum silicate, magnesium aluminate matasilicate, magnesium oxide, calcium phosphate, calcium carbonate, calcium sulfate, and tartaric acid. An embodiment of the present invention is not limited to the aforementioned excipient.

A granule containing an active ingredient prepared by the present invention can be further provided with a film coating for the purpose of light shielding, masking a taste, or preventing coloration by a conventional manufacturing process, and can be provided with a coat for release control. As a film coating base, hydroxypropylcellulose (HPC), hydroxypropylmethylcellulose (HPMC), polyvinylpyrrolidone (PVT), ethylcellulose, polyvinylacetal diethylaminoacetate, cellulose acetate phthalate, methacrylic acid copolymer (e.g. methyl methacrylate•methacrylic acid copolymer (Eudragit L100 or S100, manufactured by Rohm), methacrylic acid•ethyl acrylate copolymer (Eudragit L100-55, L30D-55), methacrylic acid•methyl acrylate•methyl methacrylate copolymer (Eudragit FS30D, manufactured by Rohm)), hydroxypropylmethylcellulose phthalate (HP-55, HP-50, manufactured by Shin-Etsu Chemical Co., Ltd.), carboxymethylethylcellulose (CMEC, manufactured by Freund Industry), hydroxypropylcellulose acetate succinate (HPMCAS manufactured by Shin-Etsu Chemical Co., Ltd.), polyvinyl acetate phthalate, and shellac are used. These may be used alone, or by combining at least two kinds. or more of the polymers, or at least two kinds or more of polymers may be successively coated.

As a coating substance for controlling release of an active ingredient pH-dependently, hydroxypropylmethylcellulose phthalate (HP-55, HP-50, manufactured by Shin-Etsu Chemical Co., Ltd.), cellulose acetate phthalate, carboxymethylethylcellulose (CMEC, manufactured by Freund Industry), methyl methacrylate•methacrylic acid copolymer (Eudragit L100 or S100, manufactured by Rohm), methacrylic acid-ethyl acrylate copolymer (Eudragit L100-55, L30D-55), methacrylic acid•methyl acrylate•methyl methacrylate (Eudragit FS30D, manufactured by Rohm), hydroxypropylecellulose acetate succinate (HPMCAS manufactured by Shin-Etsu Chemical Co., Ltd.), polyvinyl acetate phthalate, and shellac are used. When formulated into an enteric preparation, it is desirable to use a coating substance alone or, if necessary, in combination of coating substances so that the preparation is dissolved preferably at a pH>6.0, more preferably at a pH>6.5, further more preferably at a pH 6.75 or more. Herein, a pH means a pH adjusted by a McIlvain solution or a Clark-Lubs solution. Hereinafter, a pH of a pH-dependently dissolvable membrane means this pH. Further, if necessary, a plasticizer and a stabilizing agent such as polyethylene glycol, dibutyl sebacate, diethyl phthalate, triacetin, and triethyl citrate may be used for coating. The amount of coating substance is desirably 0.5% to 300%, preferably 1% to 100%, more preferably 5% to 60% relative to a particle to be coated.

The thus obtained active ingredient-containing particle may be further coated to provide an intermediate coating layer, and such particle may be used as a core particle. When the active ingredient is a drug which is unstable to an acid such as PPI, it is preferable to block direct contact between an active ingredient-containing core particle and a release-controlling membrane by providing an intermediate coating layer in order to improve stability of drug. Such intermediate coating layer may be formed of a plurality of layers.

Examples of the coating substance for an intermediate coating layer include coating substances in which a sugar such as sucrose [purified white sugar (ground (powder sugar) or not ground) etc.], starch sugar such as corn starch sugar, lactose, honey and sugar alcohol (D-mannitol, erythritol) is appropriately blended in a polymer base such as low-substituted hydroxylpropylcellulose, hydroxylpropylcellulose, hyroxylpropylmethylcellulose, (e.g. TC-5 etc.), polyvinylpyrrolidone, ployvinyl alcohol, methylcellulose, and hydroxylethylmethylcellulose.

In addition, when an active ingredient is unstable under acidic condition and an excipient are blended and a granule containing an active ingredient prepared by the present invention is coated with an enteric base, it is preferable to form a so-called intermediate layer which does not influence on stability of an active ingredient. An intermediate layer may be formed with a suitable excipient by the dusting method or the solution adding method containing no active ingredient before coating for release control, or film coating may be performed. In particular, in enteric coating, which is one aspect of release control, it is a preferable aspect to provide an intermediate layer. A coating amount of intermediate coating layer is usually about 0.02 parts by weight to about 1.5 parts by weight, preferably about 0.05 to about 1 part by weight relative to 1 part by weight of granule containing an active ingredient. Coating can be carried out with a conventional method. This intermediate layer is constructed of, for example, mannitol, sorbitol, lactose, corn starch, white sugar, titanium oxide, low-substituted hydroypropylcellulose, sodium croscarmellose, calcium carboxymethylcellulose, talc, yellow ferric oxide (yellow rouge), red ferric oxide (red rouge), magnesium carbonate, calcium phosphate, hydroxypropylcellulose, hydroxypropylmethylcellulose, gelatin, or pullulan, and substances listed as the excipient above may be added, but not limited thereto. When an intermediate layer is constructed as a film coating membrane, a film coating base preferably has no release controlling properties, a sugar coat with hydroxypropylcellulose (HPC), hydroxypropylmethylcellulose (HPMC), polyvinylpyrrolidone (PVP), pullulan, or white sugar is selected and, if desired, other excipient such as talc, titanium oxide, macrogol, yellow ferric oxide (yellow rouge), red ferric oxide (red rouge) and aerosil may be appropriately blended in the film layer.

The thus obtained drug composition in the present invention may be formulated into a tablet, granule or fine particle covered with a substance which generates viscosity by contact with water, such as polyethylene oxide (PEO, e.g., Polyox WSR-303 molecular weight 7000000, Polyox WSR Coagulant molecular weight 5000000, Polyox WSR 301 molecular weight 4000000, Polyox WSR N-60K molecular weight 2000000, Polyox WSR 205 molecular weight 600000, manufactured by Dow Chemical), hydroxylpropylmethylcellulose (HPMC, Metlose 90SH10000, Metlose 90SH50000, Metlose 90SH30000, manufactured by Shin-Etsu Chemical Co., Ltd.), carboxymethylcellulose (CMC-Na, Sanlose F-1000 mC), hydroxypropylcellulose (HPC, e.g. HPC-H, manufactured by Nippon Soda Co., Ltd.), hydroxyethylcellulose (HEC), carboxyvinyl polymer (Hiviswako (R) 103, 104, 105, manufactured by Wako Pure Chemical Industries, Ltd., Carbopol 943, manufactured by Good rich), chitosan, sodium alginate, and pectin to provide a release-controlled granule.

The drug composition in the present invention is provided as a medicine in a form which is finally administered per se, and these tablets, granule and fine particle may be further formulated into another finally administering form. Examples of such the dosage form include oral solid preparations such as capsules, caplets, oral disintegrating tablets, buccal preparations, gingival preparations, and mucosal adhering preparations (granules, tablets, sheets, gels) and, in order to obtain such the preparations, additives such as excipients (e.g. glucose, fructose, lactose, sucrose, D-mannitol, erythritol, maltitol, trehalose, sorbitol, corn starch, potato starch, wheat starch, rice starch, crystalline cellulose, silicic anhydride, anhydrous calcium phosphate, precipitated calcium carbonate, calcium silicate), binders (e.g. hydroxypropylcellulose, hydroxypropylmethylcellulose, polyvinylpyrrolidone, methylcellulose, polyvinyl alcohol, sodium carboxymethylcellulose, partially gelatinized starch, gelatinized starch, sodium alginate, pullulan, gum arabic powder, gelatin), disintegrating agents (e.g. low-substituted hydroxypropylcellulose, carmellose, calcium carmellose, sodium carboxymethylstarch, sodium croscarmellose, crospovidone, hydroxypropylstarch), corrigents (e.g. citric acid, ascorbic acid, tartaric acid, malic acid, aspartame, acesulfame potassium, thaumatin, saccharin sodium, dipotassium glycyrrhizinate, sodium glutamate, sodium 5'-inosinate, sodium 5'-guanylate), surfactants (e.g. Polysorbate (Polysorbate 80), Polyoxyethylene-polyoxypropylene copolymer, sodium laurylsulfate), flavors (e.g. lemon oil, orange oil, menthol, mentha oil), lubricants (e.g. magnesium stearate, sucrose fatty acid ester, sodium stearyl fumarate, stearic acid, talc, polyethylene glycol), colorants (e.g. titanium oxide, edible yellow No. 5, edible blue No. 2, red ferric oxide, yellow ferric oxide), antioxidants (e.g. sodium ascorbate, L-cysteine, sodium sulfite), opacifying agents (e.g. titanium oxide), and antistatic agents (e.g. talc, titanium oxide) may be added and used. In addition, the drug composition may be filled into capsules (e.g. gelatin capsules, pullulan capsules, HPMC capsules, PVA capsules) to obtain medicines.

In preparations in which an active ingredient is PPI described below, it is preferable to add a basic inorganic salt as a stabilizing agent.

Examples of a basic inorganic salt used in the present invention include basic inorganic salts of sodium, potassium, magnesium or calcium. Preferable examples include basis inorganic salts of magnesium or calcium. Further preferable examples include basic inorganic salts of magnesium. These may be a hydrate, or a solvate. In the following examples, the salt also means a hydrate and a solvate unless otherwise is indicated.

Examples of the basic inorganic salt of sodium include sodium carbonate, sodium bicarbonate, and sodium hydroxide.

Examples of the basic inorganic salt of potassium include potassium carbonate, potassium bicarbonate, and potassium hydroxide.

Examples of the basic inorganic salt of magnesium include heavy magnesium carbonate, magnesium carbonate, magnesium oxide, magnesium hydroxide, magnesium aluminate metasilicate, magnesium silicate, magnesium aluminate, synthetic hydrotalcite [$Mg_6Al_2(OH)_{16}.CO_3.4H_2O$] and alumina•magnesium hydroxide [$2.5MgO.Al_2O_3.xH_2O$], preferably heavy magnesium carbonate, magnesium carbonate, magnesium oxide, and magnesium hydroxide.

Examples of the basic inorganic salt of calcium include precipitated calcium carbonate, and calcium hydroxide.

More preferable examples of the basic inorganic salt include heavy magnesium carbonate, magnesium carbonate, magnesium oxide, and magnesium hydroxide.

As the basic inorganic salt used in the present invention, any basic inorganic salt may be used as far as a pH of its 1% aqueous solution or suspension exhibits basicity (pH 7 or higher).

One kind of, or a combination of two or more kinds of the basic inorganic salts may be blended, and a blending amount thereof is about 0.2 to about 0.6 part by weight, preferably about 0.2 to about 0.4 part by weight relative to 1 to part by weight of PPI (benzimidazole compound etc.). Inter alia, when PPI is lansoprazole or an optically active compound thereof, it is preferable to blend about 0.2 to about 0.4 part by weight of the basic inorganic salt (preferably, basic inorganic salt of magnesium or calcium, further preferably magnesium carbonate) relative to 1 to part by weight of PPI.

An active ingredient is not particularly limited, and any active ingredient may be applied regardless of a drug efficacy region. Examples include an anti-inflammatory such as indometacin and acetaminophen, an analgesic such as morphine, a cardiovascular acting drug such as diazepam and diltiazem, an anti-histamine drug such as chlorpheniramine maleate, an anti-tumor drug such as fluorouracil and aclarubicin, a hypnotic such as midazolam, anti-congestion drug such as ephedrine, a diuretic such as hydrochlorothiazide, and furosemide, a bronchodilator such as theophylline, an antitussive such codeine, an anti-arrhythmia drug such as quinidine, and dizoxin, an anti-diabetic drug such as tolbutamide, pyroglitazone, and troglitazone, vitamins such as ascorbic acid, an anticonvulsant such as phenytoin, a local anesthetic such as lidocaine, an adrenocortical hormone such as hydrocortisone, a drug which acts on a neutral nerve such as Eisai, an anti-hyperlipemia drug such as pravastatin, an antibiotic such as amoxicillin, and cefalexin, a digestive tract motion promoting drug such as mosapride and cisapride, a H2 blocker such as famotidine, ranitidine and cimetidine which are a drug for treating gastritis, stomach and esophagus reflux, or stomach•duodenum ulcer, a benzimidazole proton pump inhibitor (PPI) such as lansoprazole and an optically active compound thereof (R isomer and S isomer, preferably R isomer (hereinafter referred to as compound A in some cases)), omeprazole and an optically active compound thereof (S isomer: esomeprazole), rabeprazole and an optically active compound thereof, and pantoprazole and an optically active compound thereof, and an imidazopyridine PPI such as tenatoprazole.

Inter alia, drug efficacy lasting effect in a preparation using an acid labile active ingredient such as PPI which is a benzimidazole compound represented by the following general formula (I) or a salt thereof or an optically active compound thereof such as lansoprazole and an optically active compound thereof is remarkable, and the present invention is preferably applied to these activegredients.

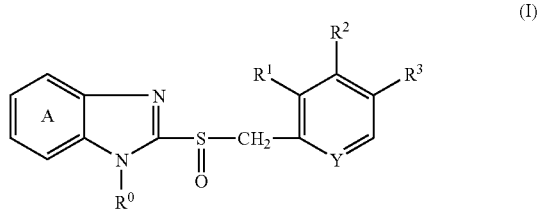

(I)

In the formula, ring A represents a benzene ring optionally having a substituent, $R^0$ represents a hydrogen atom, an optionally substituted aralkyl group, an acyl group or an acyloxy group, $R^1$, $R^2$ and $R^3$ are the same or different, and represent a hydrogen atom, an optionally substituted alkyl group, an optionally substituted alkoxy group, or an optionally substituted amino group, and Y represents a nitrogen atom or CH.

In the formula (I), a preferable compound is a compound wherein ring A is a benzene ring which may have a substituent selected from a halogen atom, an optionally halogenated $C_{1-4}$ alkyl group, an optionally halogenated $C_{1-4}$ alkoxy group and a 5- or 6-membered heterocyclic group, $R^0$ is a hydrogen atom, an optionally substituted aralkyl group, an acyl group or an acyloxy group, $R^1$ is a $C_{1-6}$ alkyl group, a $C_{1-6}$ alkoxy group, a $C_{1-6}$ alkoxy-$C_{1-6}$ alkoxy group or a di-$C_{1-6}$ alkylamino group, $R^2$ is a hydrogen atom, a $C_{1-6}$ alkoxy-$C_{1-6}$ alkoxy group or an optionally halogenated $C_{1-6}$ alkoxy group, $R^3$ is a hydrogen atom or a $C_{1-6}$ alkyl group, and Y is a nitrogen atom.

Particularly preferable is a compound represented by the formula (Ia):

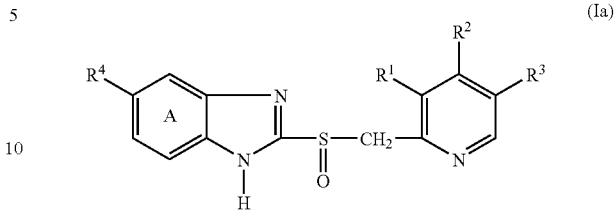

(Ia)

wherein $R^1$ represents a $C_{1-3}$ alkyl group or a $C_{1-3}$ alkoxy group, $R^2$ represents a $C_{1-3}$ alkoxy group which is optionally halogenated or substituted with a $C_{1-3}$ alkoxy group, $R^3$ represents a hydrogen atom or a $C_{1-3}$ alkyl group, and $R^4$ represents a hydrogen atom, an optionally halogenated $C_{1-3}$ alkoxy group or a pyrrolyl group (e.g. 1-, 2- or 3-pyrrolyl group).

In the formula (Ia), a compound wherein $R^1$ is a $C_{1-3}$ alkyl group, $R^2$ is an optionally halogenated $C_{1-3}$ alkoxy group, $R^3$ is a hydrogen atom, and $R^4$ is a hydrogen atom or an optionally halogenated $C_{1-3}$ alkoxy group is particularly preferred.

In the compound represented by the formula (I) [hereinafter, referred to as compound (I)], examples of the "substituent" of the "benzene ring which may have a substituent" represented by ring A include a halogen atom, a cyano group, a nitro group, an optionally substituted alkyl group, a hydroxy group, an optionally substituted alkoxy group, an aryl group, an aryloxy group, a carboxy group, an acyl group, an acyloxy group, and a 5- to 10-membered heterocyclic group. The benzene ring may be substituted with about 1 to 3 of these substituents. When the number of substituents is 2 or more, respective substituents may be the same or different. Among these substituents, a halogen atom, an optionally substituted alkyl group and an optionally substituted alkoxy group are preferred.

Examples of the halogen atom include a fluorin atom, a chlorine atom, and a bromine atom. Inter alia, fluorine atom is preferred.

Examples of the "alkyl group" of the "optionally substituted alkyl group" include a $C_{1-7}$ alkyl group (e.g. methyl, ethyl, propyl, isopropyl, butyl, isobutyl, sec-butyl, tert-butyl, pentyl, hexyl, heptyl group etc.). Examples of the "substituent" of the "optionally substituted alkyl group" include a halogen atom, a hydroxyl group, a $C_{1-6}$ alkoxy group (e.g. methoxy, ethoxy, propoxy, butoxy etc.), a $C_{1-6}$ alkoxy-carbonyl group (e.g. methoxycarbonyl, ethoxycarbonyl, propoxycarbonyl group etc.), and a carbamoyl group. The number of-these substituents may be about 1 to 3. When the number of substituents is 2 or more, respective substituents may be the same or different.

Examples of the "alkoxy gruop" of the "optionally substituted alkoxy group" include a $C_{1-6}$ alkoxy group (e.g. methoxy, ethoxy, propoxy, isopropoxy, butoxy, isobutoxy, pentoxy etc.). Examples of the "substituent" of the "optionally substituted alkoxy group" include the same substituents as those exemplified for the "substituent" of the "optionally substituted alkyl group", and the number of substituents is the same as well.

Examples of the "aryl group" include a $C_{6-14}$ aryl group (e.g. phenyl, 1-naphthyl, 2-naphthyl, biphenyl, 2-anthryl group etc.).

Examples of the "aryloxy group" include a $C_{6-14}$ aryloxy group (e.g. phenyloxy, 1-naphthyloxy, 2-naphthyloxy group etc.).

Examples of the "acyl group" include formyl, alkylcarbonyl, alkoxycarbonyl, carbamoyl, alkylcarbamoyl, alkylsulfinyl, and alkylsulfonyl group.

Examples of the "alkylcarbonyl group" include a $C_{1-6}$ alkyl-carbonyl group (e.g. acetyl, propionyl group etc.).

Examples of the "alkoxycarbonyl group" include a $C_{1-6}$ alkoxy-carbonyl group (e.g. methoxycarbonyl, ethoxycarbonyl, propoxycarbonyl, butoxycarbonyl group etc.).

Examples of the "alkylcarbamoyl group" include a N—$C_{1-6}$ alkyl-carbamoyl group (e.g. methylcarbamoyl, ethylcarbamoyl group etc.), and a N,N-di$C_{1-6}$ alkyl-carbamoyl group (e.g. N, N-dimethylcarbamoyl, N,N-diethylcarbamoyl group etc.).

Examples of the "alkylsulfinyl group" include a $C_{1-7}$ alkylsulfinyl group (e.g. methylsulfinyl, ethylsulfinyl, propylsulfinyl, isopropylsulfinyl group etc.).

Examples of the "alkylsulfonyl group" include a $C_{1-7}$ alkylsulfonyl group (e.g. methylsulfonyl, ethylsulfonyl, propylsulfonyl, isopropylsulfonyl group etc.).

Examples of the "acyloxy group" include an alkylcarbonyloxy group, an alkoxycarbonyloxy group, a carbamoyloxy group, an alkylcarbamoyl group, an alkylsulfinyloxy group, and an alkylsulfonyloxy group.

Examples of the "alkylcarbonyloxy group" include a $C_{1-6}$ alkyl-carbamoyloxy group (e.g. acetyloxy, propionyloxy group etc.).

Examples of the "alkoxycarbonyloxy group" include a $C_{1-6}$ alkoxy-carbonyloxy group (e.g. methoxycarbonyloxy, ethoxycarbonyloxy, propoxycarbonyloxy, butoxycarbonyloxy group etc.).

Examples of the "alkylcarbamoyloxy group" include a $C_{1-6}$ alkyl-carbamoyloxy group (e.g. methylcarbamoyloxy, ethylcarbamoyloxy group etc.).

Examples of the "alkylsulfinyloxy group" include a $C_{1-7}$ alkylsulfinyloxy group (e.g. methylsulfinyloxy, ethylsulfinyloxy, propylsulfinyloxy, isopropylsulfinyloxy group etc.).

Examples of the "alkylsulfonyloxy group" include a $C_{1-7}$ alkylsulfonyloxy group (e.g. methylsulfonyloxy, ethylsulfonyloxy, propylsulfonyloxy, isopropylsulfonyloxy group etc.).

Examples of the "5- to 10-membered heterocyclic group" include a 5- to 10-membered (preferably 5- or 6-membered) heterocyclic group containing one or more (e.g. 1 to 3) of heteroatoms selected from a nitrogen atom, a sulfur atom and an oxygen atom in addition to carbon atoms, and examples thereof include a 2- or 3-thienyl group, a 2-, 3- or 4-pyridyl group, a 2- or 3-furyl group, a 1-, 2- or 3-pyrrolyl group, a 2-, 3-, 4-, 5- or 8-quinolyl group, a 1-, 3-, 4- or 5-isoquinolyl group, and 1-, 2- or 3-indolyl group. Among them, preferable is a 5- or 6-membered heterocyclic group such as a 1-, 2- or 3-pyrroyl group.

Preferably, ring A is a benzene ring which may have 1 or 2 substituents selected from a halogen atom, an optionally halogenated $C_{1-4}$ alkyl group, an optionally halogenated $C_{1-4}$ alkoxy group and a 5- or 6-membered heterocyclic group.

Examples of the "aralkyl gruop" of the "optionally substituted aralkyl group" represented by $R^0$ include a $C_{7-16}$ aralkyl group (e.g. $C_{6-10}$ aryl $C_{1-6}$ alkyl group such as benzyl, phenethyl). Examples of the "substituent" of the "optionally substituted aralkyl group" include the same substituents as those exemplified for the "subsituent" of the "optionally substituted alkyl group", and the number of substituents is about 1 to 4. When the number of substituents is 2 or more, respective substituents may be the same or different.

Examples of the "acyl group" represented by $R^0$ include the "acyl group" described as the above-mentioned substituent of ring A.

Examples of the "acyloxy group" represented by $R^0$ include the "acyloxy group" described as the above-mentioned substituent of ring A.

Preferable $R^0$ is a hydrogen atom.

Examples of the "optionally substituted alkyl group" represented by $R^1$, $R^2$ or $R^3$ include the "optionally substituted alkyl group" described as the above-mentioned substituent of ring A.

Examples of the "optionally substituted alkoxy group" represented by $R^1$, $R^2$ or $R^3$ include the "optionally substituted alkoxy group" described as the above-mentioned substituent of ring A.

Examples of the "optionally substituted amino group" represented by $R^1$, $R^2$ or $R^3$ include an amino group, a mono-$C_{1-6}$ alkylamino group (e.g. methylamino, ethylamino etc.), a mono-$C_{6-14}$ arylamino group (e.g. phenylamino, 1-napthylamino, 2-naphthylamino etc.), a di-$C_{1-6}$ alkylamino group (e.g. dimethylamino, diethylamino etc.), and a di-$C_{6-14}$ arylamino group (e.g. diphenylamino etc.).

Preferable $R^1$ is a $C_{1-6}$ alkyl group, a $C_{1-6}$ alkoxy group, a $C_{1-6}$ alkoxy-$C_{1-6}$ alkoxy group, and a di-$C_{1-6}$ alkylamino group. Further more preferable $R^2$ is a $C_{1-3}$ alkyl group and a $C_{1-3}$ alkoxy group.

Preferable $R^2$ is a hydrogen atom, a $C_{1-6}$ alkoxy-$C_{1-6}$ alkoxy group or an optionally halogenated $C_{1-6}$ alkoxy group. Further more preferable $R^3$ is a $C_{1-3}$ alkoxy group which is halogenated or may be substituted with a $C_{1-3}$ alkoxy group.

Prefearble $R^3$ is a hydrogen atom or a $C_{1-6}$ alkyl group. Further more preferable $R^4$ is a hydrogen atom or a $C_{1-3}$ alkyl group (particularly hydrogen atom).

Preferable Y is a nitrogen atom.

Examples of the compound (I) include the following compounds:

2-[[[3-methyl-4-(2,2,2-trifluoroethoxy)-2-pyridinyl]methyl]sulfinyl]-1H-imidazole (lansoprazole), 2-[[(3,5-dimethyl-4-methoxy-2-pyridinyl)methyl]sulfinyl]-5-methoxy-1H-benzimidazole, 2-[[[4-(3-methoxypropoxy)-3-methyl-2-pyridinyl]methyl]sulfinyl]-1H-benzimidazole sodium salt, 5-difluoromethoxy-2-[[(3,4-dimethoxy-2-pyridinyl)methyl]sulfinyl]-1H-benzimidazole.

Among these compounds, particularly, lansoprazole, that is, 2-[[[3-methyl-4-(2,2,2-trifluoroethoxy)-2-pyridinyl]methyl]sulfinyl]-1H-benzimidazole is preferred.

In addition to the aforementioned PPI of a benzimidazole compound, PPI of an imidazopyridine compound is also suitably applied to the present invention. Examples of the PPI of the imidazopyridine compound include tenatoprazole.

In addition, the above-mentioned compound (I) or the imidazopyridine compound may be a racemic compound, or an optically active compound such as a R-isomer and a S-isomer. An optically active compound such as (R)-2-[[[3-methyl-4-(2,2,2-trifluoroethoxy)-2-pyridinyl]methyl]sulfinyl]-1H-benzimidazole and (S)-2-[[[3-methyl-4-(2,2,2-trifluoroethoxy)-2-pyridinyl]methyl]sulfinyl]-1H-benzimidazole is particularly suitable for the present invention. In addition, as for lansoprazole, lansoprazole R-isomer and lansoprazole S-isomer, a crystal is usually preferred, however, a crystal as well as a non-crystal form can be used because they are more stabilized by blending a basic inorganic salt and further providing an intermediate coating layer in addition to being stabilized by formulation into a preparation itself as described later.

As a salt of the compound (I), a pharmaceutically acceptable salt is preferred, and examples thereof include salts with an inorganic base, salts with an orgnic base, and salts with a basic amino acid.

Preferable examples of the salt with an inorganic base include an alkali metal salt such as sodium salt and potassium salt; an alkaline earth metal salt such as calcium salt and magnesium salt; and an ammonium salt.

Preferable examples of the salt with an organic base include salts with alkylamine (trimethylamine, triethylamine), heterocyclic amine (pyridine, picoline), alkanolamine (ethanolamine, diethanolamine, triethanolamine), dicyclohexylamine, N,N'-dibenzylethylenediamine, and the like.

Preferable examples of the salt with a basic amino acid include salts with arginine, lysine, and ornithine.

Among these salts, preferred are alkali metal salts and alkaline earth metal salts. Inter aria, a sodium salts is preferred.

The compound (I) can be prepared by methods known per se, and can prepared by the methods described, for example, in JP-A 61-50978, U.S. Pat. No. 4,628,098, JP-A 10-195068, WO 98/21201, JP-A 52-62275, and JP-A 54-141783, or analogous methods thereto. In addition, the optically active compound (I) can be obtained by a method such as an optical resolution method (fractional recrystallization method, chiral column method, diastereomer method, method using microorganism or enzyme) and asymmetric oxidation. Further, lansoprazole R-isomer can be prepared according to the process described, for example, in WO 00/78745, WO 01/83473.

As the benzimidazole compound and the imidazopyridine compound which are PPI having anti-tumor activity used in the present invention, lansoprazole, omeprazole, rabeprazole, pantoprazole, leminoprazole and tenatoprazole (TU-199), or an optically active compound thereof, and a pharmaceutically acceptable salt thereof are preferred, and lansoprazole or an optically activity compound thereof, particularly, R-isomer (hereinafter, referred to as compound A in some cases) is more preferred. As for lansoprazole or an optically active compound, particularly, R-isomer, a crystalline form is preferred, but an amorphous form may be used. In addition, this can be advantageously applied to a prodrug of these PPIs.

Preferable examples of these prodrugs include, in addition to prodrugs included in the compound (I), the compound represented by the following general formula (II) described in WO 03/105845 and the compound represented by the general formula (III) described later.

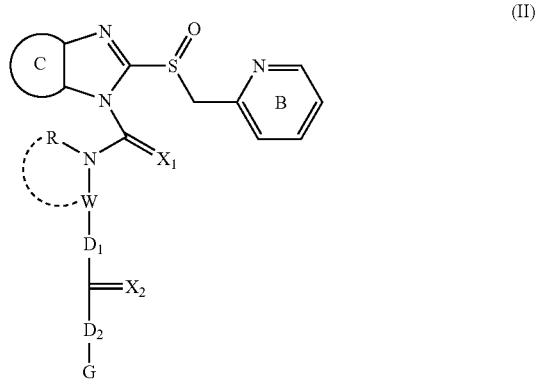

(II)

In the compound represented by the above formula (II) [hereinafter referred to as compound (II)], ring B represents an "optionally substituted pyridine ring".

The pyridine ring of the "optionally substituted pyridine ring" represented by ring B may have 1 to 4 substituents at substitutable positions thereof. Examples of the substituent include a halogen atom (e.g. fluorine, chlorine, bromine iodine etc.), an optionally substituted hydrocarbon group (e.g. alkyl group having 1 to 6 carbons such as methyl group, ethyl group, n-propyl group etc.), an optionally substituted amino group (e.g. amino; amino group mono-substituted or di-substituted with alkyl group having 1 to 6 carbons such as methylamino, dimethylamino, ethylamino, diethylamino group etc.), an amido group (e.g. $Cl_3$ acylamino group such as formamido, acetamido etc.), a lower optionally substituted alkoxy group (e.g. alkoxy group having 1 to 6 carbons such as methoxy, ethoxy, 2,2,2-trifluoroethoxy, 3-methoxypropoxy group etc.), and a lower alkylenedioxy group (e.g. $C_{1-3}$ alkylene dioxy group such as methylenedioxy, ethylenedioxy etc.).

Examples of a substituent which may be possessed by the substitent of the "optionally substituted pyridine ring" represented by ring B include a halogen atom (e.g. fluorine, chlorine, bromine, iodine etc.), a lower alkyl group (e.g. alkyl group having 1 to 6 carbons such as methyl, ethyl, propyl group etc.), a lower alkenyl group (e.g. alkenyl group having 2 to 6 carbons such as vinyl, allyl group etc.), a lower alkynyl group (e.g. alkynyl group having 2 to 6 carbons such as ethynyl, propargyl group etc.), a cycloalkyl group (e.g. cycloalkyl group having 3 to 8 carbons such as cyclopropyl, cyclobutyl, cyclopentyl, cyclohexyl group etc.), a lower alkoxy group (e.g. alkoxy group having 1 to 6 carbons such as methoxy, ethoxy group etc.), a nitro group, a cyano group, a hydroxyl group, a thiol group, a carboxyl group, a lower alkanoyl group (e.g. formyl; alkyl having 1 to 6 carbons-carbonyl group such as acetyl, propionyl, butyryl group etc.), a lower alkanoyloxy group (e.g. formyloxy; alkyl having 1 to 6 carbons-carbonyloxy group such as acetyloxy, propionyloxy group etc.), a lower alkoxy carbonyl group (e.g. alkoxy having 1 to 6 carbons-carbonyl group such as methoxycarbonyl, ethoxycarbonyl, propoxycarbonyl group), an aralkyloxycarbonyl group (e.g. aralkyloxy having 7 to 11 carbons-carbonyl group such as benzyloxycarbonyl group etc.), an aryl group (e.g. aryl group having 6 to 14 carbons such as phenyl, naphthyl group etc.), an aryloxy group (e.g. aryloxy group having 6 to 14 carbons such as phenyloxy, naphthyloxy group etc.), an arylcarbonyl group (e.g. arylcarbonyl group having 6 to 14 carbons such as benzoyl, naphthoyl group etc.), an arylcarbonyloxy group (e.g. arylcarbonyloxy group having 6 to 14 carbons such as benzoyloxy, naphthoyloxy group etc.), an optionally substituted carbamoyl group (e.g. carbamoyl; carbamoyl group mono-substituted or di-substituted with alkyl group having 1 to 6 carbons such as methylcarbamoyl, dimethylcarbamoyl group etc.), and an optionally substituted amino group (e.g. amino; amino group mono-substituted or di-substituted with alkyl group having 1 to 6 carbons such as methylamino, dimethylamio, ethylamino, diethylamino group etc.), and the number of the substituent and substitution position are not particularly limited.

The number and substitution position of the substituent of the "optionally substituted pyridine ring" represented by ring B are not particularly limited, but the pyridine ring is preferablely substituted at any of 3, 4 and 5 positions with 1 to 3 of the above substituents.

As the "optionally substituted pyridine ring" represented by ring B, 3-methyl-4-(2,2,2-trifluoroethoxy)-2-pyridyl is preferred.

In the above formula (II), ring C represents an "optionally substituted benzene ring" or an "optionally substituted aromatic monocyclic hetelocyclic ring", which is fused with an imidazole moiety and, inter alia, the former is preferred.

The benzene ring of the "optionally substituted benzene ring" represeted by ring C may have 1 to 4 substituents at substitutable positions thereof, and examples of the substituent include a halogen atom (e.g. fluorine, chlorine, bromine, iodine etc.), a optionally substituted hydrocarbon group (e.g. alkyl group having 1 to 6 carbons such as methyl group, ethyl group, n-propyl group etc.), an optionally substituted amino group (e.g. amino; amino group mono-substituted or di-substituted with alkyl group having 1 to 6 carbons such as methylamino, dimethylamino, ethylamino, diethylamino group etc.), an amido group (e.g. $C_{1-3}$ acylamino group such as formamido, acetamido etc.), a lower optionally substituted alkoxy group (e.g. alkoxy group having 1 to 6 carbons such as methoxy, ethoxy, difluoromethoxy group etc.), and a lower alkylenedioxy group (e.g. $C_{1-3}$ alkylenedioxy group such as methylenedioxy, ethylenedioxy etc.).

Examples of a substituent wich may be possessed by the substituent of the "optionally substituted benzene ring" represented by ring C include a halogen atom (e.g. fluorine, chlorine, bromine, iodine etc.), a lower alkyl group (e.g. alkyl group having 1 to 6 carbons such as methyl, ethyl, propyl group etc.), a lower alkenyl group (e.g. alkenyl group having 2 to 6 carbons such as vinyl, allyl group etc.), a lower alkynyl group (e.g. alkynyl group having 2 to 6 carbons such as ethynyl, propargyl group etc.), a cycloalkyl group (e.g. cycloalkyl group having 3 to 8 carbons such as cyclopropyl, cyclobutyl, cyclopentyl, cyclohexyl group etc.), a lower alkoxy group (e.g. alkoxy group having 1 to 6 carbons such as methoxy, ethoxy group etc.), a nitro group, a cyano group, a hydroxyl group, a thiol group, a carboxyl group, a lower alkanoyl group (e.g. formyl; alkyl having 1 to 6 carbons-carbonyl group such as acetyl, propionyl, butyryl group etc.), a lower alkanoyloxy group (e.g. formyloxy; alkyl having 1 to 6 carbons-carbonyloxy group such as acetyloxy, propionyloxy group etc.), a lower alkoxycarbonyl.group (e.g. alkoxy having 1 to 6 carbons-carbonyl group such as methoxycarbonyl, ethoxycarbonyl, propoxycarbonyl group etc.), an aralkyloxycarbonyl group (e.g. aralkyloxy having 7 to 17 carbons-carbonyl group such as benzyloxycarbonyl group etc.), an aryl group (e.g. aryl group having 6 to 14 carbons such as phenyl, naphthyl group etc.), an aryloxy group (e.g. aryloxy group having 6 to 14 carbons such as phenyloxy, naphthyloxy group etc.), an arylcarbonyl group (e.g. aryl having 6 to 14 carbons-carbonyl group such as benzoyl, naphthoyl group etc.), an arylcarbonyloxy group (e.g. aryl having 6 to 14 carbons-carbonyloxy group such as benzoyloxy, naphthoyloxy group etc.), an optionally substituted carbamoyl group (e.g. carbamoyl; carbamoyl group mono-substituted or di-substituted with alkyl group having 1 to 6 carbons such as methylcarbamoyl, dimethylcarbambyl group etc.), and an optionally substituted amino group (e.g. amino; amino group mono-substituted or di-substituted with alkyl group having 1 to 6 carbons such as methylamino, dimethylamino, ethylamino, diethylamino group etc.), and the number of substituents and substitution position are not particularly limited.

As the "optionally substituted benzene ring" represented by ring C, a benzene ring is preferred.

Examples of the "aromatic monocyclic heterocyclic ring" of the "optionally substituted aromatic monocyclic heterocyclic ring" represented by ring C include a 5- or 6-membered aromatic monocylic heterocyclic ring such as furan, thiophene, pyrrole, oxazole, isooxazole, thiazole, isothiazole, imidazole, pyrazole, 1,2,3-oxadiazole, 1,2,4-oxadiazole, 1,3, 4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, and triazine. As the "aromatic monocyclic heterocyclic ring" represented by ring C, inter alia, a pyridine ring is preferred. The heterocyclic ring may have the same 1 to 4 substituents as those exemplified for the "optionally substituted benzene ring" represented by ring C at substitutable positions thereof.

The position at which the "aromatic monocyclic heterocyclic ring" of the "optionally substituted aromatic monoyclic heterocyclic ring" is fused with the imidazole moiety is not particularly limited.

In the above formula (II), $X_1$ and $X_2$ represent an oxygen atom or a sulfur atom respectively. It is preferable that both of $X_1$ and $X_2$ represent an oxygen atom.

In the above formula (II), W represents an "optionally substituted divalent chain hydrocarbon group" or a divalent group represented by the formula:

$$-W_1-Z-W_2-$$

wherein $W_1$ and $W_2$ each represents a "divalent chain hydrocarbon group" or a bond, and Z represents an "optionally substituted divalent hydrocarbon group", an "optionally substituted divalent heterocyclic group", an oxygen atom, $SO_n$ (wherein n represents 0, 1 or 2) or >N-E (wherein E represents a hydrogen atom, an optionally substituted hydrocarbon group, an optionally substituted heterocyclic group, a lower alkanoyl group, a lower alkoxycarbonyl group, an aralkyloxycarbonyl group a thiocarbamoyl group, a lower alkylsulfinyl group, a lower alkylsulfonyl group, a sulfamoyl group, a mono-lower alkylsulfamoyl group, a di-lower alkylsulfamoyl group, an arylsulfamoyl group, an arylsulfinyl group, an arylsulfonyl group, an arylcarbonyl group, or an optionally substituted carbamoyl group) and, when Z is an oxygen atom, $SO_n$ or >N-E, $W_1$ and $W_2$ each represents a "divalent chain hydrocarbon group"). Inter alia, as W, an "optionally substituted divalent chain hydrocarbon group" is preferred.

Examples of the "divalent chain hydrocarbon group" of the "optionally substituted divalent chain hydrocarbon group" represented by W and the "divalent chain hydrocarbon group" represented by $W_1$ and $W_2$ include a $C_{1-6}$ alkylene group (e.g. methylene, ethylene, trimethylene etc.), a $C_{2-6}$ alkenylene group (e.g. ethenylene etc.), and a $C_{2-6}$ alkynylene group (e.g. ethynylene etc.). The divalent chain hydrocarbon group of W may have the same 1 to 6 substituents as those exemplified for the "optionally substituted benzene ring" represented by ring C at substitutable positions thereof.

As the "divalent chain hydrocarbon group" of the "optionally substituted divalent chain hydrocarbon group" represented by W and the "divalent chain hydrocarbon group" represented by $W_1$ or $W_2$, methylene group and ethylene group are preferred. As W, ethylene group is particularly preferred. When Z is an oxygen atom, $SO_n$ or >N-E (n and E are as defined above), as the "divalent chain hydrocarbon group" represented by $W_1$, a hydrocarbon group having 2 or more carbons is preferred.

Examples of the "hydrocarbon ring" of the "optionally substituted divalent hydrocarbon ring group" represented by Z include an alicyclic hydrocarbon ring and an aromatic hydrocarbon ring, the ring having 3 to 16 carbons is preferred, and the ring may have the same 1 to 4 substituents as those exemplified for the "optionally substituted benzene ring" represented by ring C at substitutable positions. As the hydrocarbon ring, for example, cycloalkane, cycloalkene and arene are used.

As the "cycloalkane" of the "optionally substituted divalent hydrocarbon ring group" represented by Z, for example, lower cycloalkane and the like are preferred and, for example, $C_{3-10}$ cycloalkane such as cyclopropane, cyclobutane, cyclopentane, cyclohexane, cycloheptane, cyclooctane, bicyclo [2.2.1]heptane and adamantane is generally used.

As the "cycloalkene" of the "optionally substituted divalent hydrocarbon ring group", for example, lower cycloalkene is preferred, and C$_{4-9}$ cycloalkene such as cyclopropene, cyclobutene, cyclopentene, cyclohexene, cycloheptene, and cyclooctene is generally used.

As the "arene" of the "optionally substituted divelant hydrocarbon ring group" represented by Z, C$_{6-14}$ arene such as benzene, naphthalene, and phenanthrene is preferred and, for example, phenylene is generally used.

Examples of the "heterocyclic group" of the "optionally substituted divalent heterocyclic group" represented by Z include a 5- to 12-membered "aromatic heterocyclic ring" or "saturated or unsaturated non-aromatic heterocyclic ring" containing at least one (preferable 1 to 4, further preferably 1 to 2) of 1 to 3 kinds (preferably 1 or 2 kinds) of heteroatoms selected from an oxygen atom, a sulfur atom and a nitrogen atom as a ring system constituent atom (ring atom), and the heterocyclic ring may have the same 1 to 4 substituents as those exemplified for the "optionally substituted benzene ring" represented by ring C at substitutable positions thereof.

Examples of the "aromatic heterocyclic ring" of the "optionally substituted divalent heterocyclic group" represented by Z include an aromatic monocyclic heterocyclic ring and an aromatic fused heterocyclic ring.

Examples of the "aromatic monocyclic heterocyclic ring" include a 5- to 6-membered aromatic monocyclic heterocyclic ring such as furan, thiophene, pyrrole, oxazole, isooxazole, thiazole, isothiazole, imidazole, pyrazole, 1,2,3-oxadiazole, 1,2,4-oxadiazole, 1,3,4-oxadiazole, furazane, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, and triazine.

Exapmles of the "aromatic fused heterocyclic ring" include a 8- to 12-membered aromatic fused heterocyclic ring such as benzofuran, isobenzofuran, benzothiophene, isobenzothiophene, indole, isoindole, 1H-indazole, benzimidazole, benzooxazole, 1,2-benzoisooxazole, benzothiazole, 1,2-benzoisothiazole, 1H-benzotriazole, quinoline, isoquinoline, cinnoline, quinazoline, quinoxaline, phthalazine, naphthyridine, purine, pteridine, carbazole, carboline, acridine, phenoxazine, phenothazine, phenazine, phenoxathyne, thianthrene, phenanthrene, phenanthridine, phenanthroline, indolizine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, and 1,2,4-triazolo[4,3-b]pyridazine.

Examples of the "saturated or unsaturated non-aromatic heterocyclic ring" of the "optionally substituted divalent heterocyclic group" represented by Z include a 3- to 8-membered (preferably 5- to 6-membered) saturated or unsaturated (preferably saturated) non-aromatic heterocyclic ring (aliphatic heterocyclic ring) such as oxirane, azetidine, oxetane, thietane, pyrrolidine, tetrahydrofuran, tetrahydrothiophene, piperidine, tetrahydropyran, tetrahydrothiopyran, morpholine, thiomorpholine, piperazine, azepane, oxepane, thiene, oxazepane, thiazepane, azokane, oxokane, thiokane, oxazokane, and thiazokane. These may be substituted with oxo, and 2-oxoazetidine, 2-oxopyrrolidine, 2-oxopiperidine, 2-oxoazepane, 2-oxoazokane, 2-oxotetrahydrofuran, 2-oxotetrapyran, 2-oxotetrahydrothiophene, 2-oxothiane, 2-oxopiperazine, 2-oxooxepane, 2-oxooxazepane, 2-oxothiepane, 2-oxothiazepane, 2-oxooxokane, 2-oxothiokane, 2-oxooxazokane and 2-oxothiazokane are exemplified.

Two bonds from the "hydrocarbon ring group" of the "optionally substituted divalent hydrocarbon ring group" or the "heterocyclic group" of the "optionally substituted divalent heterocyclic group" represented by Z may be at any of replaceable positions.

The "optionally substituted hydrocarbon group" and the "optionally substituted heterocyclic group" represented by E are as defined later.

As the "lower alkanoyl group" represented by E, formyl; a C$_{1-6}$ alkyl-carbonyl group such as acetyl, propionyl, butyryl and isobutyryl are used.

As the "lower alkoxycarbonyl group" represented by E, a C$_{1-6}$ alkoxy-carbonyl group such as methoxycarbonyl, ethoxycarbonyl, propoxycarbonyl and butoxycarbonyl is used.

As the "aralkyloxycarbonyl" represented by E, a C$_{7-11}$ aralkyloxy-carbonyl group such as benzyloxycarbonyl is used.

As the "lower alkylsulfinyl group" represented by E, a C$_{1-6}$ alkylsulfinyl group such as methylsulfinyl and ethylsulfinyl is used.

As the "lower alkylsulfonyl group" represented by E, a C$_{1-6}$ alkylsulfonyl group such as methylsulfonyl and ethylsulfonyl is used.

As the "mono-lower alkylsulfamoyl group" represented by E, a mono-C$_{1-6}$ alkylsulfamoyl group such as methylsulfamoyl and ethylsulfamoyl is used.

As the "di-lower alkylsulfamoyl group" represented by E, a di-C$_{1-6}$ alkylsulfamoyl group such as dimethylsulfamoyl and diethylsulfamoyl is used.

As the "arylsulfamoyl group" represented by E, a C$_{6-10}$ arylsulfamoyl group such as phenylsulfamoyl and naphthylsulfamoyl is used.

As the "arylsulfinyl group" represented by E, a C$_{6-10}$ arylsulfinyl group such as phenylsulfinyl and naphthylsulfinyl is used.

As the "arylsulfonyl group" represented by E, a C$_{6-10}$ arylsulfonyl group such as phenylsulfonyl and naphthylsulfonyl is used.

As the "arylcarbonyl group" represented by E, a C$_{6-10}$ aryl-carbonyl group such as benzoyl and naphthoyl is used.

As the "optionally substituted carbamoyl gourp" represented by E, for example, a group represented by the formula —CONR$_2$R$_3$ (wherein R$_2$ ad R$_3$ each represents a hydrogen atom, an optionally substituted hydrocarbon group, or an optionally substituted heterocyclic group and, in the formula —CONR$_2$R$_3$, R$_2$ and R$_3$ may be taken together with an adjacent nitrogen atom to form a ring) is used.

In the above formula (II), R represents an optionally substituted hydrocarbon group" or an "optionally substituted heterocyclic group", R can be linked with W and, among them, an optionally substituted C$_{1-6}$ hydrocarbon group, inter alia, a lower (C$_{1-6}$) alkyl group is preferred. The "optionally substituted hydrocarbon group" and the "optionally substituted heterocyclic group" represented by R are as defined later. In addition, the case where R is linked with W will be explained in detail later.

In the formula (II), D$_1$ and D$_2$ each represents a bond, an oxygen atom, a sulfur atom or >NR$_1$ and, in the formula, R$^1$ represents a hydrogen atom, an optionally substituted hydrocarbon group, provided that the case where both of D$_1$ and D$_2$ are a bond is excluded in the present invention. Inter alia, it is preferable that D$_1$ and D$_2$ each is a bond or an oxygen atom, and it is particularly preferable that D$_1$ is an oxygen atom and D$_2$ is an oxygen atom or a bond. The "optionally substituted hydrocarbon group" represented by R$_1$ is as defined later.

In the above formula (II), G represents an "optionally substituted hydrocarbon group" or an "optionally substituted heterocyclic group" and, inter alia, an optionally substituted C$_{1-6}$ hydrocarbon group, or an optionally substituted saturated heterocyclic group containing 1 to 4 heteroatoms selected from an oxygen atom, a nitrogen and a sulfur atom as a ring constituent atom is preferred. Inter alia, as G, an optionally substituted $C_{1-6}$ hydrocarbon group, or an optionally substituted saturated oxygen-containing heterocyclic group containing 1 to 3 heteroatoms selected from an oxygen atom, a nitrogen atom, and a sulfur atom as a ring constituent atom is preferred. The "optionally substituted hydrocarbon group" or an "optionally substituted heterocyclic group" represented by G is as defined later.

Examples of the "hydrocarbon group" of the "optionally substituted hydrocarbon group" represented by the above E, R, $R_1$ and G include a saturated or unsaturated aliphatic hydrocarbon group, a saturated or unsaturated alicyclic hydrocarbon group, a saturated or unsaturated alicyclic-aliphatic hydrocarbon group, an aromatic hydrocarbon group and an aromatic-saturated or unsaturated alicyclic hydrocarbon group, and preferably those group having 1 to 16 carbons, more preferably 1 to 6 carbons. Specifically, for example, an alkyl group, an alkenyl group, an alkynyl group, a cycloalkyl group, a cycloalkenyl, a cycloalkylalkyl group, a cycloalkenylalkyl group, an aryl group and an arylalkyl group are used.

As the "akyl group", for example, a lower alkyl group ($C_{1-6}$ alkyl group) is preferred, and a $C_{1-6}$ alkyl group such as methyl, ethyl, propyl, isopropyl, butyl, isobutyl, sec-butyl, tert-butyl, pentyl, 1-ethylpropyl and hexyl is generally used. In R, a lower alkyl group ($C_{1-6}$ alkyl group) is preferred, and a methyl group is particularly preferred.

As the "alkenyl group", for example, a lower alkenyl group is preferred, and a $C_{2-7}$ alkeneyl group such as vinyl, 1-propenyl, allyl, isopropenyl, butenyl, isobutenyl and 2,2-dimethyl-pent-4-enyl is generally used.

As the "alkynyl group", for example, a lower alknyl group is preferred, and a $C_{2-6}$ alkynyl group such as ethynyl, propargyl and 1-propynyl is generally used.

As the "cycloalkyl group", for example, a lower cycloalkyl group is preferred, and a $C_{3-10}$ cycloalkyl group such as cyclopropyl, cyclobutyl, cyclopentyl, cyclohexyl, cycloheptyl, cyclooctyl, bicyclo[2.2.1]heptenyl and adamantyl is generally used.

As the "cycloalkenyl", for example, a lower cycloalkenyl group is rpeferred, and a $C_{3-10}$ cycloalkenyl group such as cyclopropenyl, cyclobutenyl, cyclopentenyl, cyclohexenyl, cycloheptenyl, cyclooctenyl, and bicyclo[2.2.1]hept-5-en-2-yl is generally used.

As the "cycloalkylalkyl group", for example, a lower cycloalkylalkyl group is preferred, and a $C_{4-9}$ cycloalkylalkyl group such as cyclopropylmethyl, cyclopropylethyl, cyclobutylmethyl, cyclopentylmethyl, cyclohexylmethyl and cyclohexylethyl is generally used.

As the "cycloalkenylalkyl group", for example, a lower cycloalkenylalkyl group is preferred, and a $C_{4-9}$ cycloalkenylalkyl such as cyclopentenylmethyl, cyclohexenylmethyl, cyclohexenylethyl, cyclohexenylpropyl, cycloheptenylmethyl, cycloheptenylethyl and bicyclo[2.2.1]hept-5-en-2-ylmethyl is generally used.

As the "aryl group", a $C_{6-14}$ aryl group such as phenyl, 1-naphthyl, 2-naphthyl, biphenyl and 2-anthryl is preferred and, for example, phenyl group is generally used.

The "arylalkyl group" has the above-defined "aryl group" as the aryl moiety, and has the above defined "alkyl group" as the alkyl moiety. Inter alia, for example, a $C_{6-14}$ aryl-$C_{1-6}$ alkyl group is preferred and, for example, benzyl and phenethyl are generally used.

As the substituent which may be possessed by the "hydrocarbon group" of the "optionally substituted hydrocarbon group" represented by R, $R_1$ and G, for example, a halogen atom (e.g. fluorine, chlorine, bromine, iodine etc.), a nitro group, a cyano group, a hydroxy group, a thiol group, a sulfo group, a sulfino group, a phosphono group, an optionally halogenated lower alkyl group (e.g. $C_{1-6}$ alkyl such as methyl, ethyl, propyl, isopropyl, butyl, isobutyl, sec-butyl, tert-butyl, pentyl, 1-ethylpropyl and hexyl; and mono-, di- or tri-halogeno-$C_{1-6}$ alkyl group such as chloromethyl, dichloromethyl, trichloromethyl, fluoromethyl, difluoromethyl, trifluoromethyl, 2-bromoethyl, 2,2,2-trifluoroethyl, pentafluoroethyl, 3,3,3-trifluoropropyl, 4,4,4-trifluorobutyl, 5,5,5-trifluoropentyl, 6,6,6-trifluorohexyl etc.), an oxo group, an amidino group, an imino group, an alkylenedioxy group (e.g. $C_{1-3}$ alkylenedioxy group such as methylenedioxy, ethylenedioxy etc.), a lower alkoxy group (e.g. $C_{1-6}$ alkoxy group such as methoxy, ethoxy, propoxy, isopropoxy, butoxy, isobutoxy, pentyloxy, hexyloxy etc.), an optionally halogenated lower alkoxy group (e.g. mono-, di- or tri-halogeno-$C_{1-6}$ alkoxy group such as chloromethyloxy, dichloromethyloxy, trichloromethyloxy, fluoromethyloxy, difluoromethyloxy, trifluoromethyloxy, 2-bromoethyloxy, 2,2,2-trifluoroethyloxy, pentafluoroethyloxy, 3,3,3-trifluoropropyloxy, 4,4,4-trifluorobutyloxy, 5,5,5-trifluoropentyloxy, 6,6,6-trifluorohexyloxy etc.), a lower alkylthio group (e.g. $C_{1-6}$ alkylthio group such as methylthio, ethylthio, propylthio, isopropylthio, butylthio, isobutylthio, pentylthio, hexylthio etc.), a carboxyl group, a lower alkanoyl group (e.g. formyl; $C_{1-6}$ alkyl-carbonyl group such as acetyl, propionyl, butyryl, isobutyryl etc.), a lower alkanoyloxy group (e.g. formyloxy; $C_{1-6}$ alkyl-carbonyloxy such as acetyloxy, propionyloxy, butyryloxy, isobutyryloxy etc.), a lower alkoxycarbonyl group (e.g. $C_{1-6}$ alkoxy-carbonyl group such as methoxycarbonyl, ethoxycarbonyl, propoxycarbonyl, butoxycarbonyl etc.), an aralkyloxycarbonyl group (e.g. $C_{7-11}$ aralkyloxycarbonyl group such as benzyloxycarbonyl etc.), a thiocarbamoyl group, a lower alkylsulfinyl group (e.g. $C_{1-6}$ alkylsulfinyl group such as methylsulfinyl, ethylsulfinyl etc.), a lower alkylsulfonyl group (e.g. $C_{1-6}$ alkylsulfonyl group such as methylsulfonyl, ethylsulfonyl etc.), a sulfamoyl group, a mono-lower alkylsulfamoyl group (e.g. a mono-$C_{1-6}$ alkylsulfamoyl group such as methylsulfamoyl, ethylsulfamoyl etc.), a di-lower alkylsulfamoyl group (e.g. di-$C_{1-6}$ alkylsulfamoyl group such as dimethylsulfamoyl, diethylsulfamoyl etc.), an arylsulfamoyl group (e.g. $C_{6-10}$ arylsulfamoyl group such as phenylsulfamoyl, naphthylsulfamoyl etc.), an aryl group (e.g. $C_{6-10}$ aryl group such as phenyl, naphthyl etc.), an aryloxy group (e.g. $C_{6-10}$ aryloxy group such as phenyloxy, naphthyloxy etc.), an arylthio group (e.g. $C_{6-10}$ arylthio group such as phenylthio, naphthylthio etc.), an arylsulfinyl group (e.g. $C_{6-10}$ arylsulfinyl group such as phenylsulfinyl, naphthylsulfinyl etc.), an arylsulfonyl group (e.g. $C_{6-10}$ arylsulfonyl group such as phenylsulfonyl, naphthylsulfonyl etc.), an arylcarbonyl group (e,g, $C_{6-10}$ aryl-carbonyl group such as benzoyl, naphthoyl etc.), an arylcarbonyloxy group (e.g. $C_{6-10}$ arylcarbonyloxy group such as benzoyloxy, naphthoyloxy etc.), an optionally halogenated lower alkylcarbonylamino group (e.g. optionally halogenated $C_{1-6}$ alkyl-carbonylamino group such as acetylamino, trifluoroacetylamino etc.), a optionally substituted carbamoyl group (e.g. a group represented by the formula —CONR$_2$R$_3$ (wherein R$_2$ and R$_3$ each represents a hydrogen atom, an optionally substituted hydrocarbon group, or an optionally substituted heterocyclic group and, in the formula —CONR$_2$R$_3$, R$_2$ and R$_3$ may be taken together with an adjacent nitrogen atom to form a ring)), an optionally substituted amino group (e.g. a group represented by the formula —NR$_2$R$_3$ (wherein R$_2$ and R$_3$ are as defined above, and, in the formula —NR$_2$R$_3$, R$_2$ and R$_3$ may be taken together with an adjacent nitrogen atom to form a ring)), an optionally substituted ureido group (e.g. a group represented by the formula —NHCONR$_2$R$_3$ (wherein R$_2$ and R$_3$ are as defined above and, in the formula —NHCONR$_2$R$_3$, R$_2$ and R$_3$ may be taken together with an adjacent nitrogen atom to form a ring)), an optionally substituted carboxyamide group (e.g. a group represented by the formula —NR$_2$COR$_3$ (wherein R$_2$ and R$_3$ are as defined above)), an optionally substituted sulfonamide group (e.g. a group represented by the formula —NR$_2$SO$_2$R$_3$ (wherein R$_2$ and R$_3$ are as defined above)), and an optionally substituted heterocyclic group (R$_2$ and R$_3$ are as defined above) are used.

Examples of the "hydrocarbon group" of the "optionally substituted hydrocarbon group" in R$_2$ and R$_3$ include a lower alkyl group (e.g. alkyl group having 1 to 6 carbons such as methyl, ethyl, propyl group etc.), a lower alkenyl group (e.g. alkenyl group having 2 to 6 carbons such as vinyl, allyl group etc.), a lower alkynyl group (e.g. alkynyl group having 2 to 6 carbons such as ethynyl, propargyl group etc.), a cycloalkyl group (e.g. cycloalkyl group having 3 to 8 carbons such as cyclopropyl, cyclobutyl, cyclopentyl, cyclohexyl group etc.), a cycloalkenyl group (e.g. cycloalkenyl group having 3 to 8 carbons such as cyclobutenyl, cyclopentenyl, cyclohexenyl group etc.), a cycloalkylalkyl group (e.g. cycloalkyl having 3 to 8 carbons-alkyl group having 1 to 6 carbons such as cyclopropylmethyl, cyclobutylmethyl, cyclopentylmethyl, cyclohexylmethyl etc.), a cycloalkenylalkyl group (e.g. cycloalkenyl having 3 to 8 carbons-alkyl group having 1 to 6 carbons such as cyclobutenylmethyl, cyclopentenylmethyl, cyclohexenylmethyl group etc.), an aryl group (e.g. aryl group having 6 to 14 carbons such as phenyl, naphthyl group etc.), and an arylalkyl group (e.g. aryl having 6 to 14 carbons-alkyl group having 1 to 6 carbons such as benzyl, naphthylmethyl group etc.).

Examples of the "heterocyclic group" of the "optionally substituted heterocyclic group" represented by R$_2$ and R$_3$ include a 5- to 12-membered monocyclic or fused heterocyclic group containing 1 to 4 of 1 to 2 kinds of hetero atoms selected from a nitrogen atom, a sulfur atom and an oxygen atom such as pyridyl, pyrrolidinyl, piperazinyl, piperidinyl, 2-oxoazepinyl, furyl, decahydroisoquinolyl, quinolinyl, indolyl, isoquinolyl, thienyl, imidazolyl, and morpholinyl. Examples of the substituent of the "optionally substituted hydrocarbon group" and the "optionally substituted heterocyclic group" in R$_2$ and R$_3$ include a halogen atom (e.g. fluorine, chlorine, bromine, iodine etc.), a lower alkyl group (e.g. alkyl group having 1 to 6 carbons such as methyl, ethyl, propyl group etc.), a lower alkenyl group (e.g. alkenyl group having 2 to 6 carbons such as vinyl, allyl group etc.), a lower alkynyl group (e.g. alkynyl group having 2 to 6 carbons such as ethynyl, propargyl group etc.), a cycloalkyl group (e.g. cycloalkyl group having 3 to 8 carbons such as cyclopropyl, cyclobutyl, cyclopentyl, cyclohexyl group etc.), a lower alkoxy group (e.g. alkoxy group having 1 to 6 carbons such as methoxy, ethoxy group etc.), a nitro group, a cyano group, a hydroxyl group, a thiol group, a carboxyl group, a lower alkanoyl group (e.g. formyl; alkyl having 1 to 6 carbons-carbonyl group such as acetyl, propionyl, butyryl group etc.), a lower alkanoyloxy group (e.g. formyloxy; alkyl having 1 to 6 carbons-carbonyloxy group such as acetyloxy, propionyloxy group etc.), a lower alkoxycarbonyl group (e.g. alkoxy having 1 to 6 carbons-carbonyl group such as methoxycarbonyl, ethoxycarbonyl, propoxycarbonyl group etc.), an aralkyloxycarbonyl group (e.g. aralkyloxy having 7 to 17 carbons of carbon number of 7 to 17-carbonyl group such as benzyloxycarbonly group etc.), an aryl group (e.g. aryl group having 6 to 14 carbons such as phenyl, naphthyl group etc.), an aryloxy group (e.g. aryloxy group having 6 to 14 carbons such as phenyloxy, naphthyloxy group etc.), an arylcarbonyl group (e.g. aryl having 6 to 14 carbons-carbonyl group such as benzoyl, naphthoyl group etc.), an arylcarbonyloxy group (e.g. aryl having 6 to 14 carbons-carbonyloxy group such as benzoyloxy, naphthoyloxy group etc.), an optionally substituted carbamoyl group (e.g. carbamoyl; carbamoyl group mono-substituted or di-substituted with alkyl group having 1 to 6 carbons such as methylcarbamoyl, dimethylcarbamoyl group etc.), and an optionally substituted amino group (e.g. amino; amino group mono-substituted or a di-substituted with alkyl group having 1 to 6 carbons such as methylamino, dimethylamino, ethylamino, diethylamino group etc.). The number and position of substituents are not particularly limited.

Examples of the ring which is formed by combining R$_2$ and R$_3$ together with an adjacent nitrogen atom include pyrrolidine, piperidine, homopiperidine, morpholine, piperazine, tetrahydroquinoline, and tetrahydroisoquinoline.

The "hydrocarbon group" of the "optionally substituted hydrocarbon group" represented by R, R$_1$ and G may have 1 to 5, preferably 1 to 3 of the aforementioned substituents at substitutable positions of the hydrocarbon group and, when the number of substituents is 2 or more, respective substituents may be the same or different.

Examples of the "heterocyclic group" of the "optionally substituted heterocyclic group" represented by E, R or G include a 5- to 12-membered aromatic heterocyclic group or saturated or unsaturated non-aromatic heterocyclic group containing at least one (preferably 1 to 4, further preferably 1 to 3) of 1 to 3 kinds (preferably 1 to 2 kinds) of heteroatoms selected from an oxygen atom, a sulfur atom and a nitrogen atom as a ring system constituent atom (ring atom). As the "heterocyclic group" of the "optionally substituted heterocyclic group" represented by G, as described above, a saturated oxygen-containing heterocyclic group, inter alia, a 5- to 12-membered saturated oxygen-containing heterocyclic group containing 1 to 4, further preferably 1 to 3 heteroatoms selected from an oxygen atom, a sulfur atom and a nitrogen atom as ring atoms is preferred.

Examples of the "aromatic heterocyclic group" include an aromatic monocyclic heterocyclic group and an aromatic fused heterocyclic group.

Examples of the "aromatic monocyclic heterocyclic group include a 5- to 6-membered aromatic monocyclic heterocyclic group such as furyl, thienyl, pyrrolyl, oxazolyl, isooxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, and triazinyl.

Examples of the "aromatic fused heterocyclic group" include a 8- to 12-membered aromatic fused heterocyclic group (preferably a heterocyclic ring wherein the aforementioned 5- to 6-membered aromatic monocyclic heterocyclic group is fused with a benzene ring, or a heterocyclic ring wherein two same or different heterocyclic rings of the aforementioned 5- to 6-membered aromatic monocyclic heterocyclic group are fused) such as benzofuranyl, isobenzofuranyl, benzothienyl, isobenzothienyl, indolyl, isoindolyl, 1H-indazolyl, benzimidazolyl, benzooxazolyl, 1,2-benzoisooxazolyl, benzothiazolyl, 1,2-benzoisothiazolyl, 1H-benzotriazolyl, quinolyl, isoquinolyl, cinnolinyl, quinazolinyl, quinoxalinyl, phthalazinyl, naphthyridinyl, purinyl, pteridinyl, carbazolyl, α-carbolinyl, β-carbolinyl, γ-carbolinyl, acridinyl, phenoxazilyl, phenothiazinyl, phenazinyl, phenoxathiyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo

[1,2-b]pyridazinyl, imidazo[1,2-a]pyrimidinyl, 1,2,4-triazolo[4,3-a]pyridyl, and 1,2,4-triazolo[4,3-b]pyridazinyl.

Examples of the "saturated or unsaturated non-aromatic heterocyclic group" include a 3- to 8-membered (preferably 5- to 6-membered) saturated or unsaturated (preferably saturated) non-aromatic heterocyclic group (aliphatic heterocyclic group) such as oxiranyl, azetidinyl, oxetanyl, thietanyl, pyrrolidinyl, tetrahydrofuryl, thiolanyl, piperidinyl, tetrahydropyranyl, thianyl, morpholinyl, thiomorpholinyl, piperazinyl, azepanyl, oxepanyl, thiepanyl, oxazepanyl, thiazepanyl, azokanyl, oxokanyl, thiokanyl, oxazokanyl, and thiazokanyl. These may be substituted with oxo, and examples thereof include 2-oxoazetidinyl, 2-oxopyrrolidinyl, 2-oxopiperidinyl, 2-oxoazepanyl, 2-oxoazokanyl, 2-oxotetrahydrofuryl, 2-oxotetrahydropyranyl, 2-oxothiolanyl, 2-oxothianyl, 2-oxopiperazinyl, 2-oxooxepanyl, 2-oxooxazepanyl, 2-oxothiepanyl, 2-oxothiazepanyl, 2-oxooxokanyl, 2-oxothiokanyl, 2-oxooxazokanyl, and 2-oxothiazokanyl. Preferred is a 5-membered non-aromatic heterocyclic group such as 2-oxopyrrolidinyl.

As the substituent which may be possessed by the "heterocyclic group" of the "optionally substituted heterocyclic group" represented by E, R and G, for example, the same groups as those exemplified for the "substituent" of the "optionally substituted hydrocarbon group" represented by E, R, $R_1$ or G are used.

The "heterocyclic group" of the "optionally substituted heterocyclic group" represented by E, R and G may have 1 to 5, preferably 1 to 3 of the aforementioned substituents at substitutable positions of the heterocyclic group and, when the number of substituents is 2 or more, respective substituents may be the same or different.

The case where R is combined with W in the above formula (II) will be explained. When R and W are linked, the position at which R and W are bound is not particularly limited as far as it is a bindable position in R and W, respectively.

Examples of a bindable position in R include a bindable position in the "hydrocarbon group" and the "substituent" of the "optionally substituted hydrocarbon group" defined in the aforementioned R and a bindable position in the "heterocyclic group" and the "substituent" of the optionally substituted heterocyclic group" defined in the aforementioned R.

Examples of a bindable position in W include a bindable position in the "divalent chain hydrocarbon group" of the "optionally substituted divalent chain hydrocarbon group" defined in the aforementioned W, and a bindable position in the "divalent chain hydrocarbon group" defined in the aforementioned $W_1$ or $W_2$, as well as a bindable position in the "hydrocarbon ring" of the "optionally substituted hydrocarbon ring" defined in the aforementioned Z ring and a bindable position in the "heterocyclic ring" of the "optionally substituted heterocyclic ring" defined in the aforementioned Z ring.

R and W can bind at a mutual bindable position and can be taken together with an adjacent nitrogen atom to form a ring. Examples of the ring include a saturated nitrogen-containing ring (e.g. azetidine, pyrrolidine, piperidine, homopiperidine etc.), an unsaturated nitrogen-containing ring (e.g. tetrahydropyridine etc.), an aromatic nitrogen-containing ring (e.g. pyrrole etc.), a heterocyclic ring containing at least one heteroatom selected from the group consisting of the nitrogen, oxygen and sulfur in addition to a nitrogen atom adjacent to R and W (e.g. piperazine, morpholine etc.), and a fused ring (e.g. indole, indoline, isoindole, isoindoline, tetrahydroquinoline, tetrahydroisoquinoline etc.). Inter alia, a 4- to 7-membered ring is preferred.

The ring wherein R and W are bound at a mutual bindable position and are taken together with an adjacent nitrogen atom to form a ring may have 1 to 4 substituents at a substitutable position thereof. When the number of substituents is 2 or more, respective substituents may be the same or different. Examples of the substituent include the substituent of the "optionally substituted hydrocarbon group" and the "optionally substituted heterocyclic group" defined in R, and the substituent of the "optionally substituted divalent chain hydrocarbon group" defined in W. Specifically, substituents such as a halogen atom (e.g. fluorine, chlorine, bromine, iodine etc.) and a $C_{1-6}$ alkyl group such as methyl, ethyl, propyl, isopropyl, butyl, isobutyl, sec-butyl, tert-butyl, pentyl, 1-ethylpropyl and hexyl are exemplified.

By combining of R and W, for example,

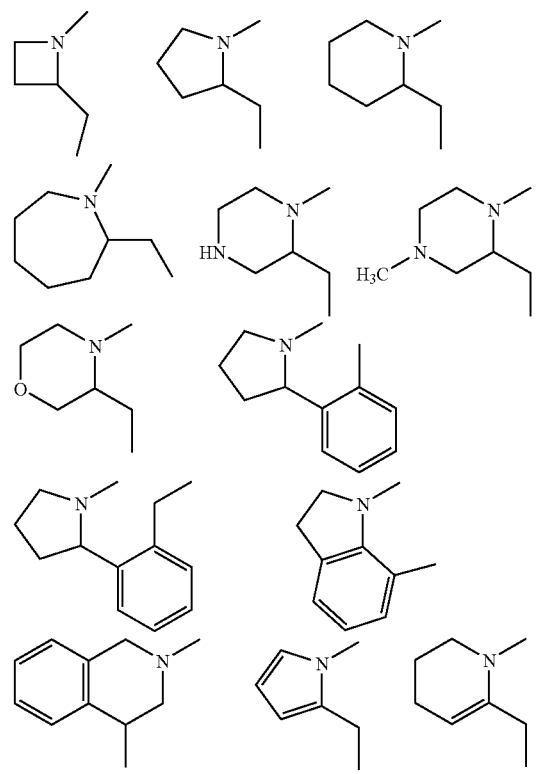

are formed, but not limited thereto. These may have a substituent as defined above, and it should be understood by a person skilled in the art that they can include an isomer.

In the present invention, X represents a leaving group such as a halogen atom, a benzotriazolyl group, and a (2,5-dioxypyrrolidin-1-yl)oxy group and, inter alia, a halogen atom such as fluorine, chlorine, bromine and iodine is preferred, and chlorine is particularly preferred.

In the present invention, M represents a hydrogen atom, a metal cation or a quaternary ammonium ion.

Examples of the "metal cation" in the present invention include an alkali metal ion (e.g. $Na^+$, $K^+$, $Li^+$, $Cs^+$ etc.) and, inter alia, $Na^+$ is preferred.

Examples of the "quaternary ammonium ion" in the present invention include a tetramethylammonium ion, a tetraethylammonium ion, a teterapropylammonium ion, and a tetrabutylammonium ion and, inter alia, a tetrabutylammonium ion is preferred.

In the compound (II), an acidic group in a molecule and an inorganic base or an organic base can form a pharmaceutically acceptable base salt, and a basic group in a molecule and an inorganic acid or an organic acid can form a pharmaceutically acceptable acid addition salt.

Examples of the inorganic base salt of the compound (II) include salts with an alkali metal (e.g. sodium, potassium etc.), an alkaline earth metal (e.g. calcium etc.) and ammonia, and examples of the organic base salt of the compound (II) include salts with dimethylamine, triethylamine, piperazine, pyrrolidine, piperidine, 2-phenylethylamine, benzylamine, ethanolamine, diethanolamine, pyridine, or collidine.

Examples of the acid addition salt of the compound (II) include inorganic salts (e.g. hydrochloride, sulfate, hydrobromide, phosphate etc.), and organic acid salts (e.g. acetate, trifluoroacetate, succinate, maleate, fumarate, propionate, citrate, tartarate, lactate, oxalate, methanesulfonate, p-toluenesulfonate etc.).

The compound (II) of the present invention includes a hydrate. Examples of the "hydrate" include a 0.5 hydrate to a 5.0 hydrate. Among them, a 0.5 hydrate, a 1.0 hydrate, a 1.5 hydrate, and a 2.0 hydrate are preferred.

The compound (II) of the present invention includes a racemic compound and an optically active compound. As the optically active compound, a compound in which one enantiomer has an enantiomer excessive rate (e.e.) of 90% or more is preferred, and a compound in which one enantiomer has an enantiomer excessive rate of 99% or more is more preferred. As the optically active compound, a (R)-isomer represented by the general formula:

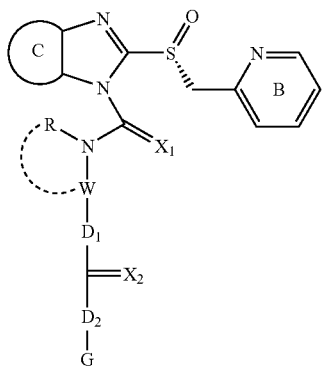

wherein symbols in the formula are as defined above, is preferred. Examples of a preferable compound included in the compound (II) are specifically the following compounds:
That is,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl trimethylacetate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl cyclohexanecarboxylate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl benzoate,
2-[methyl[[2-[[[3-methyl-4-(2,2,2-trifluoroethoxy)-2-pyridyl]methyl]sulfinyl]-1H-benzimidazol-1-yl]carbonyl]amino]ethyl benzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3-chlorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate, ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate, isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate, benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate,
2-methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate, ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate,
2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate,
2-[cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl ethyl carbonate,
2-[[[(R)-2-[[[3-methyl-4-(2,2,2-trifluoroethoxy)-2-pyridyl]methyl]sulfinyl]-1H-benzimidazol-1-yl]carbonyl](phenyl)amino]ethyl acetate,
2-[[[2-[[[3-methyl-4-(2,2,2-trifluoroethoxy)-2-pyridyl]methyl]sulfinyl]-1H-benzimidazol-1-yl]carbonyl](phenyl)amino]ethyl acetate, tert-butyl [2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate,
2-[methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate,
2-[[2-(acetyloxy)ethyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate, [(2S)-1-[[(R)-2-[[[3- methyl-4-(2,2,²-trifluoroethoxy)-2-pyridyl]methyl]
sulfinyl]-1H-benzimidazol-1-yl]carbonyl]-2-pyrrolidinyl]
methyl acetate, ethyl [methyl-[[(R)-2-[[[3-methyl-4-(2,2,
2-trifluoroethoxy)-2-pyridyl]methyl]sulfinyl]-1H-
benzimidazol-1-yl]carbonyl]amino]acetate, 2-[[[5-methoxy-2-[[(4-methoxy-3,5-dimethyl-2-pyridyl]
methyl]sulfinyl]-1H-benzimidazol-1-yl]carbonyl](me-
thyl)amino]ethyl benzoate, 3-[methyl[[(R)-²-[[[³-methyl-4-(2,2,2-trifluoroethoxy)-2-
pyridyl]methyl]sulfinyl]-1H-benzimidazol-1-yl]carbo-
nyl]amino]propyl benzoate, 2-[methyl[[2-[[[3-methyl-4-(2,2,2-trifluoroethoxy)-2-py-
ridyl]methyl]sulfinyl]-1H-benzimidazol-1-yl]carbonyl]
amino]ethyl tetrahydropyran-4-yl carbonate, ethyl 2-[me-
thyl[[2-[[[3-methyl-4-(2,2,2-trifluoroethoxy)-2-pyridyl]
methyl]sulfinyl]-1H-benzimidazol-1-yl]carbonyl]amino]
ethyl carbonate, ethyl ²-[methyl[[(S)-2-[[[3-methyl-4-(2,
2,2-trifluoroethoxy)-2-pyridyl]methyl]sulfinyl]-1H-
benzimidazol-1-yl]carbonyl]amino]ethyl carbonate, ethyl
2-[[[5-methoxy-2-[[(4-methoxy-3,5-dimethyl-2-pyridyl)
methyl]sulfinyl]-3H-imidazo[4,5-b]pyridin-3-yl]carbo-
nyl](methyl)amino]ethyl carbonate, 2-[[[5-methoxy-2-[[(4-methoxy-3,5-dimethyl-2-pyridyl)
methyl]sulfinyl]-3H-imidazo[4,5-b]pyridin-3-yl]carbo-
nyl](methyl)amino]ethyl acetate, 2-[[[5-methoxy-2-[[(4-methoxy-3,5-dimethyl-2-pyridyl)
methyl]sulfinyl]-3H-imidazo[4,5-b]pyridin-3-yl]carbo-
nyl](phenyl)amino]ethyl acetate, 4-[methyl[[(R)-2-[[[3-methyl-4-(2,2,2-trifluoroethoxy)-2-
pyridyl]methyl]sulfinyl]-1H-benzimidazol-1-yl]carbo-
nyl]amino]butyl acetate, ethyl 4-[methyl[[(R)-2-[[[3-me-
thyl-4-(2,2,2-trifluoroethoxy)-2-pyridyl]methyl]sulfinyl]-
1H-benzimidazol-1-yl]carbonyl]amino]butyl carbonate,
ethyl 3-[methyl[[(R)-2-[[[3-methyl-4-(2,2,2-trifluoroet-
hoxy)-2-pyridyl]methyl]sulfinyl]-1H-benzimidazol-1-yl]
carbonyl]amino]propyl carbonate, 3-[methyl[[(R)-2-[[[3-methyl-4-(2,2,2-trifluoroethoxy)-2-
pyridyl]methyl]sulfinyl]-1H-benzimidazol-1-yl]carbo-
nyl]amino]propyl acetate, 3-[methyl[[(R)-2-[[[3-methyl-4-(2,2,2-trifluoroethoxy)-2-
pyridyl]methyl]sulfinyl]-1H-benzimidazol-1-yl]carbo-
nyl]amino]propan-1,2-diyl diacetate, diethyl 3-[methyl
[[(R)-2-[[[3-methyl-4-(2,2,2-trifluoroethoxy)-2-pyridyl]
methyl]sulfinyl]-1H-benzimidazol-1-yl]carbonyl]amino]
propan-1,2-diyl biscarbonate, 2-[[[5-methoxy-2-[[(4-methoxy-3,5-dimethyl-2-pyridyl)
methyl]sulfinyl]-3H-imidazo[4,5-b]pyridin-3-yl]carbo-
nyl](methyl)amino]ethyl 3-chlorobenzoate, 2-[methyl[[2-[[[3-methyl-4-(2,2,2-trifluoroethoxy)-2-py-
ridyl]methyl]sulfinyl]-1H-benzimidazol-1-yl]carbonyl]
amino]ethyl acetate, 2-ethoxyethyl 2-[methyl[[(R)-2-[[[3-methyl-4-(2,2,2-trif-
luoroethoxy)-2-pyridyl]methyl]sulfinyl]-1H-benzimida-
zol-1-yl]carbonyl]amino]ethyl carbonate, 3-methoxypropyl 2-[methyl[[(R)-2-[[[3-methyl-4-(2,2,2-tri-
fluoroethoxy)-2-pyridyl]methyl]sulfinyl]-1H-benzimida-
zol-1-yl]carbonyl]amino]ethyl carbonate, 2-[methyl[[(R)-2-[[[3-methyl-4-(2,2,2-trifluoroethoxy)-2-
pyridyl]methyl]sulfinyl]-1H-benzimidazol-1-yl]carbo-
nyl]amino]ethyl N,N-dimethylglycinate, S-[2-[methyl[[(R)-2-[[[3-methyl-4-(2,2,2-trifluoroethoxy)-
2-pyridyl]methyl]sulfinyl]-1H-benzimidazol-1-yl]carbo-
nyl]amino]ethyl]thioacetate, ethyl 2-[2-[methyl[[(R)-2-
[[[3-methyl-4-(2,2,2-trifluoroethoxy)-2-pyridyl]methyl]
sulfinyl]-1H-benzimidazol-1-yl]carbonyl]amino]ethoxy]
ethyl carbonate, ethyl 2-[methyl[[2-[methyl[[(R)-2-[[[3-
methyl-4-(2,2,2-trifluoroethoxy)-2-pyridyl]methyl]
sulfinyl]-1H-benzimidazol-1-yl]carbonyl]amino]ethoxy]
carbonyl]amino]ethyl carbonate, ethyl 2-[[[5-methoxy-2-
[[(4-methoxy-3,5-dimethyl-2-pyridyl)methyl]sulfinyl]-
1H-benzimidazol-1-yl]carbonyl](methyl)amino]ethyl
carbonate, 2-[[[5-methoxy-2-[[(4-methoxy-3,5-dimethyl-2-pyridyl)
methyl]sulfinyl]-1H-benzimidazol-1-yl]carbonyl](phe-
nyl)amino]ethyl acetate, ethyl 2-[[[(S)-5-methoxy-2-[[(4-
methoxy-3,5-dimethyl-2-pyridyl)methyl]sulfinyl]-1H-
benzimidazol-1-yl]carbonyl](methyl)amino]ethyl
carbonate, ethyl 2-[[[2-[[[4-(3-methoxypropoxy)-3-me-
thyl-2-pyridyl)methyl]sulfinyl]-1H-benzimidazol-1-yl]
carbonyl](methyl)amino]ethyl carbonate, 2-[[[2-[[[4-(3-methoxypropoxy)-3-methyl-2-pyridyl)me-
thyl]sulfinyl]-1H-benzimidazol-1-yl]carbonyl](phenyl)
amino]ethyl acetate, 2-[[[5-(difluoromethoxy)-2-[[(3,4-dimethoxy-2-pyridyl)
methyl]sulfinyl]-1H-benzimidazol-1-yl]carbonyl](me-
thyl)amino]ethyl ethyl carbonate, 2-[methyl[[(R)-2-[[[3-methyl-4-(2,2,2-trifluoroethoxy)-2-
pyridyl]methyl]sulfinyl]-1H-benzimidazol-1-yl]carbo-
nyl]amino]ethyl 1-methylpiperidine-4-carboxylate, 2-[[4-(aminocarbonyl)phenyl][[(R)-2-[[[3-methyl-4-(2,2,2-
trifluoroethoxy)-2-pyridyl]methyl]sulfinyl]-1H-benzimi-
dazol-1-yl]carbonyl]amino]ethyl acetate, 2-[methyl[[(R)-2-[[[3-methyl-4-(2,2,2-trifluoroethoxy)-2-
pyridyl]methyl]sulfinyl]-1H-benzimidazol-1-yl]carbo-
nyl]amino]ethyl 1-methyl-4-piperidinyl carbonate, 2-[[4-(aminocarbonyl)phenyl][[2-[[[3-methyl-4-(2,2,2-trif-
luoroethoxy)-2-pyridyl]methyl]sulfinyl]-1H-benzimida-
zol-1-yl]carbonyl]amino]ethyl acetate, (−)-ethyl 2-[[[5-methoxy-2-[[(4-methoxy-3,5-dimethyl-2-
pyridyl)methyl]sulfinyl]-3H-imidazo[4,5-b]pyridin-3-yl]
carbonyl](methyl)amino]ethyl carbonate, and (+)-ethyl 2-[[[5-methoxy-2-[[(4-methoxy-3,5-dimethyl-2-
pyridyl)methyl]sulfinyl]-3H-imidazo[4,5-b]pyridin-3-yl]
carbonyl](methyl)amino]ethyl carbonate, and a salt thereof.

In particular, the following compounds and salts thereof
are preferred.

2-[methyl[[(R)-2-[[[3-methyl-4-(2,2,2-trifluoroethoxy)-2-
pyridyl]methyl]sulfinyl]-1H-benzimidazol-1-yl]carbo-
nyl]amino]ethyl acetate, ethyl 2-[methyl[[(R)-2-[[[3-me-
thyl-4-(2,2,2-trifluoroethoxy)-2-pyridyl]methyl]sulfinyl]-
1H-benzimidazol-1-yl]carbonyl]amino]ethyl carbonate, 2-[methyl[[(R)-2-[[[3-methyl-4-(2,2,2-trifluoroethoxy)-2-
pyridyl]methyl]sulfinyl]-1H-benzimidazol-1-yl]carbo-
nyl]amino]ethyl tetrahydropyran-4-yl carbonate, 2-[methyl[[2-[[[3-methyl-4-(2,2,2-trifluoroethoxy)-2-py-
ridyl]methyl]sulfinyl]-1H-benzimidazol-1-yl]carbonyl]
amino]ethyl tetrahydropyran-4-yl carbonate, ethyl 2-[me-
thyl[[2-[[[3-methyl-4-(2,2,2-trifluoroethoxy)-2-pyridyl]
methyl]sulfinyl]-1H-benzimidazol-1-yl]carbonyl]amino]
ethyl carbonate, ethyl 2-[[[5-methoxy-2-[[(4-methoxy-3,
5-dimethyl-2-pyridyl)methyl]sulfinyl]-3H-imidazo[4,5-
b]pyridin-3-yl]carbonyl](methyl)amino]ethyl carbonate, 2-[[[5-methoxy-2-[[(4-methoxy-3,5-dimethyl-2-pyridyl)
methyl]sulfinyl]-3H-imidazo[4,5-b]pyridin-3-yl]carbo-
nyl](methyl)amino]ethyl acetate, 2-[methyl[[2-[[[3-methyl-4-(2,2,2-trifluoroethoxy)-2-py-
ridyl]methyl]sulfinyl]-1H-benzimidazol-1-yl]carbonyl]
amino]ethyl acetate, ethyl 2-[[[5-methoxy-2-[[(4-meth-
oxy-3,5-dimethyl-2-pyridyl)methyl]sulfinyl]-1H-
benzimidazol-1-yl]carbonyl](methyl)amino]ethyl
carbonate, ethyl 2-[[[(S)-5-methoxy-2-[[(4-methoxy-3,5-
dimethyl-2-pyridyl)methyl]sulfinyl]-1H-benzimidazol-1-
yl]carbonyl](methyl)amino]ethyl carbonate, ethyl 2-[[[2-

[[[4-(3-methoxypropoxy)-3-methyl-2-pyridyl)methyl]
sulfinyl]-1H-benzimidazol-1-yl]carbonyl](methyl)amino]
ethyl carbonate, and
2-[[[5-(difluoromethoxy)-2-[[(3,4-dimethoxy-2-pyridyl)
methyl]sulfinyl]-1H-benzimidazol-1-yl]carbonyl](methyl)amino]ethyl ethyl carbonate.

The compound (II) can be produced by the following process A or B.

(Process A)

The compound (II) or a salt thereof can be obtained by fusing a compound (IV) or a salt thereof with a compound (V) or a salt thereof in the presence or the absence of a base. Examples of a salt compound (IV) and a salt of the compound (V) include the same salts as those of the compound (II). Examples include acid addition salts such as inorganic acid salts (e.g. hydrochloride, sulfate, hydrobromide, phosphate etc.), and organic acid salts (e.g. acetate, trifluoroacetate, succinate, maleate, fumarate, propionate, citrate, tartarate, lactate, oxalate, methanesulfonate, p-toluenesulfonate etc.).

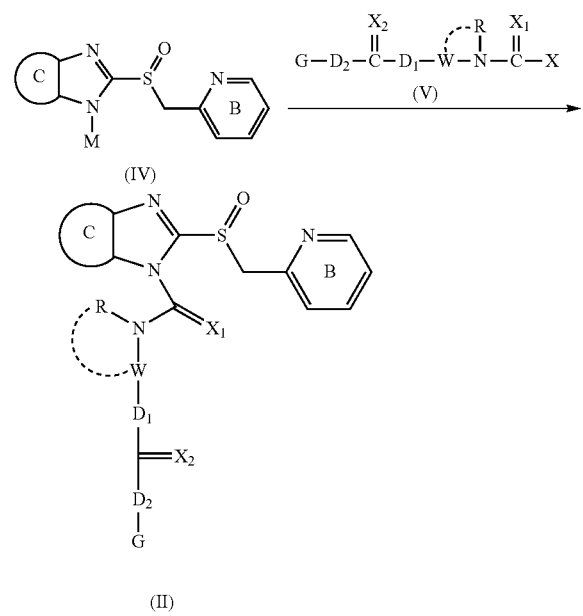

wherein, respective symbols in the formula are as defined above.

The reaction in the process A is usually carried out in a solvent, and a solvent which does not suppress the reaction of the process A is appropriately selected. Examples thereof include ethers (e.g. dioxane, tetrahydrofuran, diethyl ethetr, tert-butyl methyl ether, diisopropyl ether, ethylene glycol dimethyl ether etc.), esters (e.g. ethyl formate, ethyl acetate, butyl acetate etc.), halogenated hydrocarbons (e.g. dichloromethane, chloroform, carbon tetrachloride, trichlene, 1,2-dichloroethane etc.), hydrocarbons (e.g. n-hexane, benzene, toluene etc.), amides (e.g. formamide, N,N-dimethylformamide, N,N-dimethylacetamide etc.), ketones (e.g. acetone, methyl ethyl ketone, methyl isobutyl ketone etc.), and nitrites (e.g. acetonitrile, propionitrile etc.), as well as dimethyl sulfoxide, sulfolane, hexamethylphosphoramide, and water. These solvents to be used are not particularly limited as far as it is an amount at which the reaction mixture can be stirred, and is usually 2 to 100-fold weight, preferably 5 to 50-fold weight relative to 1 mole of the compound (IV) or a salt thereof.

An amount of the compound (V) or a salt thereof to be used is usually 1 mole to 10 mole, preferably 1 mole to 3 mole relative to 1 mole of the compound (IV) or a salt thereof.

The reaction of the process A is carried out in a temperature range of usually 0° C. to 100° C., preferably 20° C. to 80° C.

The reaction time of the process A differs depending on a kind of the compound (IV) or (V) or a salt thereof and the solvent and a reaction temperature, and is usually 1 minute to 96 hours, preferably 1 minute to 72 hours, more preferably 15 minutes to 24 hours.

Examples of the base of the process A include inorganic bases (e.g. sodium carbonate, potassium carbonate, calcium carbonate, sodium bicarbonate etc.), tertiary amines (e.g. triethylamine, tripropylamine, tributylamine, cyclohexyldimethylamine, pyridine, lutidine, α-collidine, N,N-dimethylaniline, N-methylpiperidine, N-methylpyrrolidine, N-methylmorpholine, 4-dimethylaminopyridine etc.) and alkylene oxides (e.g. propylene oxide, epichlorohydrin etc.). The amount of the base is usually 0.01 mole to 10 mole, preferably 1 mole to 3 mole relative to 1 mole of the compound (V) or a salt thereof.

The compound (IV) or a salt thereof can be prepared by the method described in JP-A 61-50978 and U.S. Pat. No. 4,628,098 or a similar method thereto.

The compound (V) or a salt thereof can be prepared by a method known per se or a similar method thereto. For example, when X is chlorine atom, the compound can be obtained by acting phosgene, trichloromethyl chloroformate, bis(trichloromethyl) carbonate, or thiophosgene on a compound represented by the formula (VII):

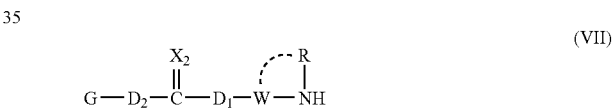

wherein, respective symbols are as defined above, or a salt thereof in a solvent (e.g. tetrahydrofuran, acetonitrile, dichloromethane etc.) in the presence of a deoxidizer. Alternatively, the compound can be also obtained by treating an ethylcarbamate compound obtained by reacting the compound (VII) or a salt thereof and ethyl chloroformate with phosphorus oxychloride according to the method described in Synthetic Communications, vol. 17, p 1887 (1987) or a similar method thereto. Examples of a salt of the compound (VII) include acid addition salts such as inorganic acid salts (e.g. hydrochloride, sulfate, hydrobromide, phosphate etc.), and organic acid salts (e.g. acetate, trifluoroacetate, succinate, maleate, fumarate, propionate, citrate, tartarate, lactate, oxalate, methanesulfonate, p-toluenesulfonate etc.).

Examples of the deoxidizer referred herein include inorganic bases (e.g. sodium carbonate, potassium carbonate, calcium carbonate, sodium bicarbonate etc.) and tertiary amines (e.g. triethylamine, tripropylamine, tributylamine, cyclohexyldimethylamine, pyridine, lutidine, γ-collidine, N,N-dimethylaniline, N-methylpiperidine, N-methylpyrrolidine, N-methylmorpholine, 4-dimethylaminopyridine etc.).

The compound (VII) or a salt thereof can be prepared by a method known per se or a similar method thereto. For example, when $D_1$ is other than a bond, the compound can be obtained by fusing a compound represented by the formula (VIII):

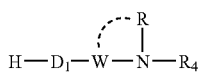

(VIII)

wherein, $R_4$ is a hydrogen atom or a protecting group for a nitrogen atom, and other symbols are as defined above, or a salt thereof, with carboxylic acid or thionic acid represented by the formula (IX):

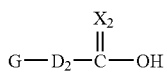

(IX)

wherein, respective symbols are as defined above, or a reactive derivative thereof (e.g. anhydride, halide etc.), or a salt thereof in a suitable solvent (e.g. ethyl acetate, tetrahydrofuran, dichloromethane, N,N-dimethylformamide etc.) and, if necessary, deprotecting the product. Examples of a salt of the compound (VIII) include acid addition salts such as inorganic acid salts (e.g. hydrochloride, sulfate, hydrobromide, phosphate etc.), and organic acid salts (e.g. acetate, trifluoroacetate, succinate, maleate, fumarate, propionate, citrate, tartarate, lactate, oxalate, methanesulfonate, p-toluenesulfonate etc.).

Alternatively, when $D_1$ is a bond, the compound can be obtained by fusing carboxylic acid or thionic acid represented by the formula (X):

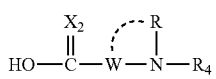

(X)

wherein, respective symbols are as defined above, or a reactive derivative thereof (e.g. anhydride, halide etc.), or a salt thereof with a compound represented by G-$D_2$-H in a suitable solvent (e.g. ethylene acetate, tetrahydrofuran, dichloromethane, N,N-dimethylformamide etc.) and, if necessary, deprotecting this. Examples of a salt of the compound (X) include acid addition salts such as inorganic acid salts (e.g. hydrochloride, sulfate, hydrobromide, phosphate etc.), organic acid salts (e.g. acetate, trifluoroacetate, succinate, maleate, fumarate, propionate, citrate, tartarate, lactate, oxalate, methanesulfonate, p-toluenesulfonate etc.), salts with alkali metals (e.g. sodium potassium etc.), alkali earth metals (e.g. calcium etc.), or ammonia, and organic base salts with dimethylamine, triethylamine, pioperazine, pyrrolidine, piperidine, 2-phenylethylamine, benzylamine, ethanolamine, diethanolamine, pyridine, or collidine.

As the protecting group represented by $R_4$ in the formula (VIII) or the formula (X), for example, a formyl group, a $C_{1-6}$ alkyl-carbonyl group (e.g. acetyl, ethylcarbonyl etc.), a benzyl group, a tert-butyloxycarbonyl group, a benzyloxycarbonyl group, an allyloxycarbonyl group, a $C_{7-10}$ aralkyl-carbonyl group (e.g. benzylcarbonyl etc.), and trityl group are used. These groups may be substituted with 1 to 3 of halogen atoms (e.g. fluorine, chlorine, bromine etc.), and nitro group.

As a method of removing these protecting groups, a method known per se or a similar method thereto is used and, for example, a method using an acid, a base, reduction, ultraviolet light, or palladium acetate is used.

(Process B)

The compound (II) or a salt thereof can be obtained by subjecting a compound (VI) or a salt thereof to oxidation reaction.

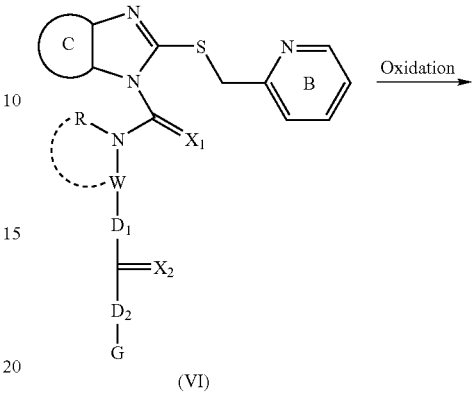

(VI)

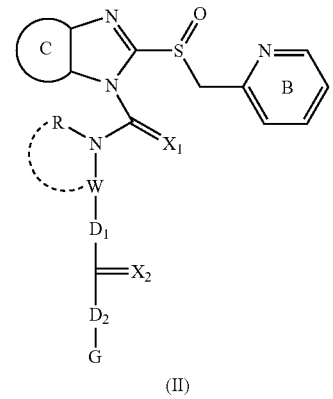

(II)

wherein, respective symbols are as defined above.

The reaction in the process B can be carried out by using an oxidizing agent such as nitric acid, hydrogen peroxide, peracids, perester, ozone, dinitrogen tetraoxide, iodosobenzene, N-halosuccinimide, 1-chlorobenzotriazole, tert-butyl hypochlorite, diazabicyclo[2.2.2]octane bromine complex, sodium metaperiodate, selenium dioxide, manganese dioxide, chromic acid, cerium nitrate ammonium, bromine, chlorine, sulfuryl chloride, and magnesium monoperoxyphthalate. The amount of the oxidizing agent to be used is usually 0.5 mole to 2 mole, preferably 0.8 mole to 1.2 mole relative to 1 mole of the compound (VI) or a salt thereof. Oxidation may be also performed using the aforementioned oxidizing agent such as hydrogen peroxide and peracids and in the presence of a catalyst such as vanadium acetate, vanadium oxide acetylacetonate, and titanium tetraisopropoxide.

The reaction of the process B is carried out usually in a solvent which is inert to the oxidation reaction. Examples of the "inert solvent" include water, alcohols (e.g. methanol, ethanol, 1-propanol, 2-propanol etc.), ketones (e.g. acetone, methyl ethyl ketone), nitrites (e.g. acetonitrile, propionitrile etc.), amides (e.g. formamide, N,N-dimethylformamide etc.), ethers (e.g. diethyl ether, tert-butyl methyl ether, diisopropyl ether, dioxane, tetrahydrofuran etc.), sulfoxides (e.g. dimethyl sulfoxide etc.), and polar solvents (e.g. solfolane, hexamethylphosphoramide etc.), and these are used alone or as a mixed solvent of two or more kinds. The "inert solvent" is used usually at 1-fold weight to 100-fold weight relative to the compound (VI) or a salt thereof.

The reaction temperature is usually −80° C. to 80° C., preferably 0° C. to 30° C.

The reaction time is usually 1 minute to 6 hours, preferably 15 minutes to 1 hour.

The compound (VI) which is a raw material of the process B can be obtained, for example, using a compound represented by the following formula (XI): (XI):

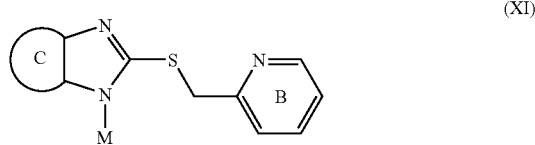

wherein, respective symbols are as defined above, in place of the compound (IV) by the analogous reaction to that of the process A.

The compound (XI) can be synthesized according to the methods described in the following references or a similar method: JP-A 61-50978, JP-A 54-141783, JP-A 61-22079, JP-A 1-6270, JP-A 63-146882.

Examples of the salt of the compound (VI) include the same salts as those for the salt of the compound (II), for example, acid addition salts such as inorganic acid salts (e.g. hydrochloride, sulfate, hydrobromide, phosphate etc.), and organic acid salts (e.g. acetate, trifluoroacetate, succinate, maleate, fumarate, propionate, citrate, tartarate, lactate, oxalate, methanesulfonate, p-toluenesulfonate etc.).

The compound (II) obtained in the process A or B or a salt thereof can be isolated and purified from the reaction mixture by separating means known per se (e.g. concentration, concentration under reduced pressure, solvent extraction, crystallization, recrystallization, dissolution transfer, chromatography etc.). In addition, since the compound (II) obtained by the process A or B or a salt thereof includes all isomers, an optically pure compound (II) or a salt thereof can be obtained by subjecting the compound (II) or a salt thereof to optical resolution or asymmetrically oxidizing the compound (VI) or a salt thereof.

Examples of a method of optical resolution include a method known per se and, for example, a fractional recrystallization method, a chiral column method, and a diastereomer method are used. As asymmetric oxidation, a method known per se such as the method described in WO 96/02535 may be used.

Examples of the "fractional recrystallization method" include a method of forming a salt between a racemic compound and an optically active compound [e.g. (+)-mandelic acid, (−) mandelic acid, (+)-tartaric acid, (−)-tartaric acid (+)-1-phenethylamine, (−)-1-phenethylamine, cinchonine, (−)-cinchonidine, brucine etc.], separating this by a fractional recrystallization method and, optionally, subjecting the separated compound to a neutralization step to obtain a free optical isomer.

Examples of the "chiral column method" include a method of subjecting a racemic compound or a salt thereof to column for separating optical isomer (chiral column). For example, in the case of liquid chromatography, a method of adding a racemic compound to a chiral column such as ENANTIO-OVM (manufactured by Tosoh Corporation) and CHIRAL series manufactured by Daicel Chemical Industries, Ltd., and developing this with water, a buffer (e.g. phosphate buffer etc.), an organic solvent (e.g. hexane, ethanol, methanol, isopropanol, acetonitrile, trifluoroacetic acid, diethylamine, triethylamine etc.), or a mixed solvent of them to separate an optical isomer is exemplified. For example, in the case of gas chromatography, a method of separating an optical isomer using a chiral column such as CP-Chirasil-DeXcb (manufactured by GL Science) is exemplified.

Examples of the "diastereomer method" include a method of reacting a racemic compound and an optically active reagent to obtain a mixture of diastereomers, then obtaining one of diastereomers by a conventional separating means (e.g. fractional recrystallization, chromatography method etc.), and subjecting this to a chemical reaction (e.g. acid hydrolysis reaction, basic hydrolysis reaction, hydrogenation degradation reaction etc.) to sever an optically active regent site, to obtain an objective optical isomer. Examples of the "optically active regent" include optically active organic acids such as MTPA [α-methoxy-α-(trifluoromethyl)phenylacetic acid], and (−)-methoxyacetic acid; optically active alkoxymethyl halides such as (1R-endo)-2-(chloromethoxy)-1,3,3-trimethylbicyclo[2.2.1]heptane.

In addition, a benzimidazole compound represented by the following general formula (III):

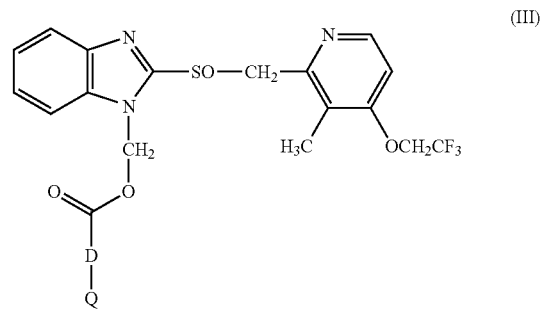

or a salt thereof is also an embodiment of the aforementioned prodrug.

In the formula (III), D represents an oxygen atom or a bond, and Q represents an optionally substituted hydrocarbon group.

The "hydrocarbon group" of the "optionally substituted hydrocarbon group" represented by Q includes aliphatic or aromatic hydrocarbon groups, and the aliphatic hydrocarbon group means a saturated or unsaturated straight, branched or cyclic hydrocarbon group. As the hydrocarbon group, a hydrocarbon group having 1 to 14 carbons is preferred, and examples thereof include a $C_{1-6}$ alkyl group, a $C_{2-6}$ alkenyl group, a $C_{2-6}$ alkynyl group, a $C_{3-8}$ cycloalkyl group, and a $C_{6-14}$ aryl group. A $C_{1-6}$ alkyl group, a $C_{3-8}$ cycloalkly group, and a $C_{6-14}$ aryl group are preferred, inter alia, a $C_{1-6}$ alkyl group and a $C_{3-8}$ cycloalkyl group are more preferred.

The above "alkyl group" is a straight or branched alkyl group, preferably an alkyl group having 1 to 6 carbons ("$C_{1-6}$ alkyl group"), and examples thereof include methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, and 2-ethylbutyl. An alkyl group having 1 to 4 carbons is more preferred. In Q, inter alia, methyl, ethyl, isopropyl, and tert-butyl are preferred, and tert-butyl is particularly preferred.

The above "$C_{2-6}$ alkenyl group" is a straight or branched alkenyl group having 2 to 6 carbons, and examples thereof include vinyl, n-propenyl, isopropenyl, n-butenyl, isobutenyl, sec-butenyl, tert-butentyl, n-pentenyl, isopentenyl, neopentenyl, 1-methylpropenyl, n-hexenyl, isohexenyl, 1,1-dimethylbutenyl, 2,2-dimethylbutenyl, 3,3-dimethylbutenyl, 3,3-dimethylpropenyl and 2-ethylbutenyl. An alkenyl group having 2 to 4 carbons is preferred, inter alia, vinyl, n-propenyl and isopropenyl are preferred.

The "$C_{2-6}$ alkynyl group" is a straight or branched alkynyl group having 2 to 6 carbons, and examples thereof include ethynyl, n-propynyl (1-propynyl), isopropynyl (2-propynyl), n-butynyl, isobutynyl, sec-butynyl, tert-butynyl, n-pentynyl, isopentynyl, neopentynyl, 1-methylpropynyl, n-hexynyl, isohexynyl, 1,1-dimethylbutynyl, 2,2-dimethylbutynyl, 3,3-dimethylbutynyl, 3,3-dimethylpropynyl, and 2-ethylbutynyl. An alkynyl group having 2 to 3 carbons is preferred, inter alia, ethynyl, 1-propynyl and 2-propynyl are preferred.

The "$C_{3-8}$ cycloalkyl group" is a straight or branched cycloalkyl group having 3 to 8 carbons, and examples thereof include cyclopropyl, cyclobutyl, cyclopentyl, cycloehexyl, cycloheptyl, and cyclooctyl. A cycloalkyl group having 5 to 7 carbons is preferred, inter alia, cyclopentyl, cyclohexyl and cycloheptyl are preferred, and cyclohexyl is particularly preferred.

The above "aryl group" is a monocyclic or fused polycyclic aromatic hydrocarbon group, preferably an aromatic hydrocarbon group having 6 to 14 carbons ("$C_{6-14}$ aryl group"), and examples thereof include phenyl, naphthyl, anthryl, phenanthryl, and acenaphthylenyl. An aromatic hydrocarbon group o having 6 to 10 carbons is preferred and, inter alia, phenyl is particularly preferred in Q.

The above "hydrocarbon group" may be substituted, and examples of the substituent include a $C_{6-14}$ aryl group, a hydroxyl group, halogen, a $C_{1-6}$ alkoxy group optionally substituted with halogen, a $C_{7-12}$ aralkyloxy group, a $C_{1-5}$ alkoxy-carbonyl group, an optionally halogenated $C_{1-6}$ alkyl group, and an amino group optionally substituted with a $C_{1-6}$ alkyl group.

Examples of the substituted in the "optionally substituted alkyl group" include an aryl group, a hydroxyl group, halogen, an alkoxy group optionally substituted with 1 to 5 halogens, a $C_{7-12}$ aralkyloxy group, and a $C_{1-5}$ alkoxy-carbonyl group. The number of substituents is 1 to 5, preferably 1 to 3.

Examples of the substituent in the "optionally substituted aryl group" include halogen, an alkyl group optionally substituted with 1 to 5 halogens, an aryl group, a hydroxy group, an alkoxy group optionally substituted with 1 to 5 halogens, a $C_{7-12}$ aralkyloxy group, and a $C_{1-5}$ alkoxy-carbonyl group. The number of substituents is 1 to 5, preferably 1 to 3.

The above "$C_{1-6}$ alkyl group", "$C_{2-6}$ alkenyl group" and "$C_{2-6}$ alkynyl group" may be substituted, and examples of the substituent include (i) a $C_{6-14}$ aryl group, (ii) hydroxyl group, (iii) halogen, (iv) an optionally halogenated $C_{1-6}$ alkoxy group, (v) a $C_{7-12}$ aralkyloxy group, (vi) a $C_{1-5}$ alkoxy-carbonyl group, (vii) an acylamino group, and (viii) an amino group optionally substituted with a $C_{1-6}$ alkyl group. Inter alia, (i) to (vii) are preferred. The number of substituents is 1 to 5, preferably 1 to 3.

The above "$C_{3-8}$ cycloalkyl group" and "$C_{6-14}$ aryl group" may be substituted, and examples of the substituent include (i) a $C_{6-14}$ aryl group, (ii) hydroxyl group, (iii) halogen, (iv) an optionally halogenated $C_{1-6}$ alkoxy group, (v) a $C_{7-12}$ aralkyloxy group, (vi) a $C_{1-5}$ alkoxy-carbonyl group, (vii) a $C_{1-6}$ alkyl group optionally substituted with halogen, and (viii) an amino group optionally substituted with a $C_{1-6}$ alkyl group. Inter alia, (i) to (vii) are preferred. The number of substituents is 1 to 5, preferably 1 to 3.

In the formula (III), Q is preferably a $C_{1-6}$ alkyl group, a $C_{2-6}$ alkenyl group or a $C_{2-6}$ alkynyl group, each of which may have a substituent selected from the group consisting of (i) a $C_{6-14}$ aryl group, (ii) hydroxyl group, (iii) halogen, (iv) an optionally halogenated $C_{1-6}$ alkoxy group, (v) a $C_{7-12}$ aralkyloxy group, (vi) a $C_{1-5}$ alkoxy-carbonyl group and (vii) an acylamino group, or a $C_{3-8}$ cycloalkyl group or a $C_{6-14}$ aryl group each of which may have a substituent selected from the group consisting of (i) a $C_{6-14}$ aryl group, (ii) hydroxyl group, (iii) halogen, (iv) an optionally halogenated $C_{1-6}$ alkoxy group, (v) a $C_{7-12}$ aralkyloxy group, (vi) a $C_{1-5}$ alkoxy-carbonyl group and (vii) an optionally halogenated $C_{1-6}$ alkyl group, more preferably (1) a $C_{1-6}$ alkyl group optionally having 1 to 5 substituents selected from the group consisting of (i) a $C_{6-14}$ aryl group (ii) hydroxyl group, (iii) halogen, (iv) a $C_{1-6}$ alkoxy group optionally substituted with 1 to 5 halogens, (v) a $C_{7-12}$ aralkyloxy group and (vi) a $C_{1-6}$ alkxoy-carbonyl group, or (2) a $C_{6-14}$ aryl group optionally having 1 to 5 substituents selected from the group consisting of (i) halogen, (ii) a $C_{1-6}$ alkyl group optionally substituted with 1 to 5 halogens, (iii) a $C_{6-14}$ aryl group, (iv) hydroxyl group, (v) a $C_{1-6}$ alkoxy group optionally substituted with 1 to 5 halogens, (vi) a $C_{7-12}$ aralkyloxy group and (viii) a $C_{1-5}$ alkoxy-carbonyl group, further preferably a $C_{1-6}$ alkyl group optionally having a substituent selected from the group consisting of (i) a $C_{6-14}$ aryl group, (ii) hydroxyl group, (iii) halogen, (iv) an optionally halogenated $C_{1-6}$ alkoxy group, (v) a $C_{7-12}$ aralkyloxy group, (vi) a $C_{1-5}$ alkoxy-carbonyl group and (vii) an acryamino group, or a $C_{3-8}$ cycloalkyl group or a $C_{6-14}$ aryl group each of which may have a substituent selected from the group consisting of (i) a $C_{6-14}$ aryl group, (ii) hydroxyl group, (iii) halogen, (iv) an optionally halogenated $C_{1-6}$ alkoxy group, (v) a $C_{7-12}$ aralkyloxy group, (vi) a $C_{1-5}$ alkoxy-carbonyl group and (vii) an optionally halogenated $C_{1-6}$ alkyl group, inter alia, Q is preferably a $C_{1-6}$ alkyl group optionally substituted with a $C_{6-14}$ aryl group or $C_{6-14}$ aryl group, and Q is particularly preferably phenyl group, or methyl or tert-butyl group.

An acidic group in the molecule of compound (III) can form a pharmaceutically acceptable base salt with an inorganic base or an organic base, in addition a basic group in the molecule and an inorganic acid or an organic acid can form a pharmaceutically acceptable acid addition salt.

Examples of one preferable aspect of compound (III) of the present invention include a compound in which D is a bond, and Q is an optionally substituted alkyl group or an optionally substituted aryl group.

Examples of the inorganic base salt of compound (III) include salts with alkali metals (e.g. sodium, potassium etc.), alkaline earth metals (e.g. calcium etc.), or ammonia, and examples of the organic base salt of compound (III) include salts with dimethylamine, triethylamine, piperazine, pyrrolidine, piperidine, 2-phenylethylamine, benzylamine, ethanolamine, diethanolamine, pyridine, or collidine.

Examples of the acid addition salt of compound (III) include inorganic acid salts (e.g. hydrochloride, sulfate, hydrobromide, phosphate etc.), and organic acid salts (e.g. acetate, trifluoroacetate, sccinate, maleate, fumarate, propionate, citrate, tartarate, lactate, oxalate, methanesulfonate, p-toluenesulfonate etc.).

The compound (III) of the present invention includes a hydrate. Examples of the "hydrate" include a 0.5 hydrate to 5.0 hydrate. Among them, a 0.5 hydrate, 1.0 hydrate, a 1.5 hydrate, and a 2.0 hydrate are preferred.

The compound (III) of the present invention includes a recemic compound and an optically active compound. As an optically active compound, a compound in which one of enantiomers has enantiomer excess (e.e.) of 90% or more is preferred, and a compound in which one of enantiomers has enantiomer excess of 99% or more is more preferred. As an optically active compound, a (R) isomer represented by the general formula:

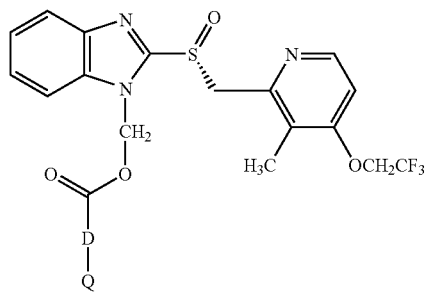

wherein, symbols in the formula are as defined above, is preferred.

The compound (III) can be prepared by a method known per se, and can be prepared by the method described, for example, in JP-A 2002-187890, and WO 02/30920, or a similar method thereto. The optically active compound (III) can be obtained by a method such as an optical resolution method (fractional recrystallization method, chiral column method, diastereomer method, method using microorganism or enzyme), and asymmetric oxidation. As PPI of derivatives of other benzimidazole compound, the compound described in WO 03/27098 can be also applied to the present invention.

Examples of a preferable drug composition of the present invention include a capsule containing the granules, fine particles or tablets of the present invention, and a tablet containing the granules or fine particles of the present invention. Such composition of final form may be a composition containing a combination of two or more kinds of the granules, fine particles or tablets of the present invention having different release properties or conditions. For example, in the case of a capsule containing benzimidazole PPI represented by the formula (I) such as lansoprazole or an optically active compound (R-isomer etc.), or a prodrug-type imidazole PPI represented by the formula (II) or (III), the capsule may be filled with combining two or more kinds of the tablets, granules or fine particles having different release modes (e.g. two kinds of granules of a type of relatively rapidly releasing an active ingredient and a type of slowly releasing an active ingredient) using release-controlling membranes having different release properties or conditions. More specifically, a more preferable aspect includes a capsule containing tablets, granules or fine particles which have been coated with usual enteric film, and tablets, granules or fine particles which have been coated with a release controlling film. Alternatively, two or more layers of these two kinds of release controlling films may be stacked in each granule, fine particle or tablet. By preparing a preparation (preferably capsule) containing granules obtained by forming an intermediate film on a core particle containing the aforementioned active ingredient, if necessary, and merely coating with a conventional enteric film thereon (therefore, among the aforementioned release controlled granules and fine particles of the present invention, a granules which relatively rapidly releases an active ingredient) in addition to tablets, granules or fine particles having a release-controlling film and a digestive tract residing gel forming polymer, or by administering jointly a capsule containing the aforementioned tablets, granules or fine particles having a release controlling film and a digestive tract residing gel forming polymer, and a preparation containing only granules which have been coated with an usual enteric film, it becomes possible that a blood concentration is increased at an early stage to begin exerting drug efficacy, and thereafter, drug efficacy is sustained due to the expression of drug efficacy of the release-controlled granules. In the case of such combinatorial preparation or combinatorial administration, a preparation expressing two peaks such that preferably, a blood concentration is increased at an early stage to initiate exerting drug efficacy and a blood concentration reaches a first maximum blood concentration and, thereafter, a blood concentration reaches a second maximum blood concentration due to release of an active ingredient by a release controlled granules, can be obtained. In addition, a sustained preparation such as the aforementioned sustained capsule and a usual type of capsule, which releases an active ingredient relatively rapidly, may be administered simultaneously or at different times. A high blood concentration of an active ingredient can be maintained over a long period of time by such simultaneous administration.

In addition, as the gel-forming polymer, a polymer which rapidly forms a gel having a high viscosity by contact with water and prolongs residence in a digestive tract is enough. As such the gel forming polymer, a polymer wherein the viscosity of 5% aqueous solution at 25° C. is about 3000 mPa·s or higher is preferred. In addition, usually, as the gel-forming polymer, a polymer having a molecular weight of about 400000 to 10000000 is generally preferred. Such gel-forming polymer, which is powder, granular or fine particulate is suitable from a viewpoint of formulating a preparation. Examples of such gel forming polymer include polyethylene oxide (PEO, for example, Polyox WSR-303 molecular weight 7000000, Polyox WSR Coagulant molecular weight 5000000, Polyox WSR 301 molecular weight 4000000, Polyox WSR N-60K molecular weight 2000000, Polyox WSR 205 molecular weight 600000; manufactured by Dow Chemical), hydroxypropylmethylcellulose (HPMC, Metlose 90SH10000, Metlose 90SH50000, Metlose 90SH30000, manufactured by Shin-Etsu Chemical Co., Ltd.), carboxymethylcellulose (CMC-Na, Sanlose F-1000 mC), hydroxypropylcellulose (HPC, e.g. HPC-H, manufactured by Nippon Soda Co., Ltd.), hydroxyethylcellulose (HEC), carboxyvinylpolymer (Hiviswako(R)103, 104, 105, manufactured by Wako Pure Chemical Industries, Ltd.); Carbopol 943, manufactured by Goodrich), chitosan, sodium alginate, and pectin. These may be used alone, or may be used by mixing at least two or more kinds of powders at an appropriate ratio. Inter alia, PEO, HPMC, HPC, CMC-Na, and carboxyvinylpolymer are preferably used as the gel-forming polymer.

Among the preparations of the present invention, since the preparation containing a benzimidazole PPI compound represented by the general formula (I) such as lansoprazole or an optically active compound thereof, or a prodrug-type PPI of the derivative of imidazole compound (inter alia, a compound represented by the general formula (II) or (III) or an optically active compound thereof) as an active ingredient, has an excellent anti-ulcer activity, gastric acid secretion suppressing activity, mucosal protecting activity and anti-*Helicobacter pylori* activity in vivo, and has low toxicity, it is useful as a medicine. In particular, since the imidazole compound represented by the general formula (II) is stable to an acid, it is not necessary to formulate it into an enteric preparation upon oral administration, and this saves an expense of formulating an enteric preparation, and a preparation becomes small, therefore, a sick person having a weak swallowing force, particularly, elderly or children can easily take it. Moreover, since an active ingredient is absorbed more rapidly than in an enteric preparation, gastric acid secretion suppressing activity appears rapidly, in addition, since the compound is gradually converted into an original compound in a living body, the preparation has long lasting property, and is useful as an anti-ulcer agent. The PPI compound such as compound (I) of the present invention or a salt thereof has low toxicity, and can be safely administered orally or parenterally (e.g. local, rectal, intravenous administration etc.) as it is, or as a drug composition mixed with a pharmaceutically acceptable carrier according to a method known per se, for example, a preparation such as a tablet (including sugar-coated tablet and film coating tablet), a powder, a granule, a capsule (including soft capsule), an oral disintegrating tablet, a solution, an injectable, a suppository, a sustained-release agent and a patch.

The tablet, granule and fine particle of the present invention can be orally administered to a mammal (e.g. human, monkey, sheep, horse, dog, cat, rabbit, rat, mouse, etc.) for the purpose of treating and preventing digestive ulcer (e.g. stomach ulcer, duodenum ulcer, stomal ulcer etc.), Zollinger-Ellison syndrome, gastritis, reflux esophagitis, Symptomatic Gastroeso p Hageal Reflux Disease (Symptomatic GERD), NUD (Non Ulcer Dyspepsia), stomach cancer (including stomach cancer accompanied with promotion of production of interleukin-1β due to interleukin-1 genetic polymorphism), stomach MALT lymphoma or the like, removing Helicobacter pylori, suppressing upper digestive tract bleeding due to digestive ulcer, acute stress ulcer and bleeding gastritis, suppressing upper digestive tract bleeding due to invasive stress (stress caused from big operation requiring intensive control after operation, or cerebrovascular disorder, head trauma, multiple organ failure and diffuse burn requiring intensive care), treating and preventing ulcer derived from non-steroidal anti-inflammatory; treating and preventing gastric hyperacidity and ulcer due to post-operation stress. For removing Helicobacter pylori, the granule or the capsule of the present invention may be used together with other active ingredient (e.g. 1 to 3 kinds of active ingredients).

Examples of the "other active ingredient" include an antibacterial agent such as an anti-Helicobacter pylori active substance, an imidazole compound, and a quinolone compound, and a bismuth salt. Inter alia, a medicine of a combination of the granule or the capsule of the present invention and an antibacterial agent is preferred. Among this, combined use with an antibacterial agent such as an anti-Helicobacter pylori active substance and an imidazole compound is preferred. Examples of the "anti-Helicobacter pylori active substance" include a penicillin antibiotic (e.g. amoxicillin, benzylpenicillin, piperacillin, mecillinam etc.), a cephem antibiotic (e.g. cefixime, cefaclor etc.), a macrolide antibiotic (e.g. erythromycin antibiotic such as erythromycin, clarithromycin etc.), a tetracycline antibiotic (e.g. tetracycline, minocycline, streptomycin etc.), an aminoglycoside antibiotic (e.g. gentamycin, amikacin etc.), and imipenem. Inter alia, a penicillin antibiotic, and a macrolide antibiotic are preferred.

Examples of the "imidazole compound" include metronidazole and miconazole. Examples of the "bismuth salt" include bismuth acetate, and bismuth citrate. An antibacterial agent of the "quinolone compound" is also preferable, and ofloxacin, ciproxacin and the like are exemplified. Inter alia, for removing Helicobacter pylori, it is preferable to use the granule or the capsule of the present invention together with a penicillin antibiotic (e.g. amoxicillin, etc.) and/or an erythromycin antibiotic (e.g. clarithromycin etc.).

In addition, for example, in the case of lansoprazole, previously, a crystalline lansoprazole 15 mg-containing capsule was filled in a No. 3 capsule, and a 30 mg-containing capsule was filed in a No. 1 capsule in many cases, but since the amount of components other than active ingredient can be reduced without destabilizing the active ingredient and the preparation by preparing a granule containing an active ingredient at an unexpectedly high concentration by providing an intermediate coating layer, blending a basic inorganic salt stabilizer, or adjusting a particle size of a granule, a 15 mg-contaning capsule can be dowmsized to a No. 4 to No. 5 capsule, and a 30 mg-contaning capsule can be downsized to a No. 3 to No. 5 capsule, respectively.

Further, also in case of a 60 mg-containing capsule, a No. 1 to No. 3 capsule can be used.

In addition, in the case of optically active compound of lansoprazole, a No. 3 to No. 5 capsule, a No. 2 to No. 4 capsule, and a No. 1 to No. 3 capsule can be used for a capsule containing 30 mg, 40 mg and 60 mg, respectively.

For example, a capsule containing 60 mg of lansoprazole or a lansoprazole R isomer is particularly suitable for treating acid excessive secretion symptom including Zollinger-Ellinson syndrome, since a capsule containing an active ingredient at a high concentration and being downsized is easy to take.

A daily dosage differs depending on the degree of symptom, the age, sex and weight of subject to be administered, the time and interval of administration, and the kind of active ingredient, etc., and is not particularly limited, but for example, when orally administered as an anti-ulcer agent to an adult (60 kg), the dosage is about 0.5 to 1500 mg/day, preferably about 5 to 150 mg/day in terms of an active component. These preparations containing benzimidazole or imidazole compound may be administered once or by dividing into 2 to 3 times daily.

Further, stabilization in a package form may be also provided in order to improve the stability of the solid preparation of the present invention at storage or transportation. For example, the stabilization of the capsule preparation containing the benzimidazole or imidazole compound of the present invention can be improved by using package form such as package suppressing the permeation of moisture or oxygen, package replaced with gas (namely, package replaced with gas other than oxygen), vacuum package and package enclosed with a deoxidizer. Using these package forms, the stabilization is improved by reducing oxygen amount with which the solid preparation is directly brought in contact. When a deoxidizer is enclosed, the pharmaceutical solid preparation is packed with an oxygen permeating material, and then another packing may be carried out together with the package.

EXAMPLES

The present invention is hereinafter illustrated in more detailed by Synthetic Examples, Reference Examples, Examples, and Experiment Examples, but the present invention is not limited to these Examples.

As for corn starch, hydroxypropyl cellulose (HPC-L), (sterilized) talc, hydroxypropyl methylcellulose, polyethylene glycol 6000, and titanium oxide, products that meet the Japanese Pharmacopoeia, Fourteenth Edition were used.

In the Reference Synthetic Examples and Synthetic Examples, room temperature means a temperature of about 15 to 30° C.

$^1$H-NMR was measured using Varian Gemini-200 or Mercury-300, $CDCl_3$, DMSO-$d_6$ and $CD_3OD$ were used as solvent, and chemical shift δ (ppm) from tetramethylsilane of internal standard was shown.

Other symbols in the present specification have the following meanings.

| | |
|---|---|
| s: | singlet |
| d: | doublet |
| t: | triplet |
| q: | quartet |
| m: | multiplet |
| br: | broad |
| bs: | broad singlet |
| bm: | broad multiplet |
| J: | coupling constant |

Reference Synthetic Example 1 tert-Butyl 2-hydroxyethyl(methyl)carbamate

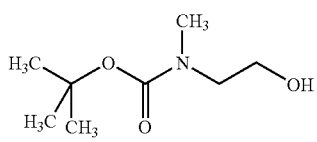

To a mixture of 2-(methylamino)ethanol (30.04 g) and ethyl acetate (90 mL) was added a mixture of di-tert-butyl dicarbonate (87.30 g) and ethyl acetate (10 mL) under ice-cooling. The reaction solution was stirred at room temperature for 2 hrs, and concentrated under reduced pressure. The residue was dissolved in ethyl acetate (150 mL), washed with water (150 mL), and dried over anhydrous magnesium sulfate. The solution was concentrated under reduced pressure to give title compound as colorless oil (66.19 g).

$^1$H-NMR(CDCl3): 1.47(9H,s), 2.92(3H,s), 3.40(2H,t, J=5.1 Hz), 3.72-3.80(2H,m).

Reference Synthetic Example 2

2-(Methylamino)ethyl acetate hydrochloride

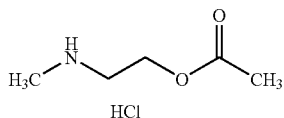

To a mixture of 2-(methylamino)ethanol (1.50 g) and ethyl acetate (20 mL) was added di-tert-butyl dicarbonate (4.37 g) under ice-cooling. The reaction solution was stirred for 1.5 hrs under ice-cooling, and acetic anhydride (2.08 mL), pyridine (1.78 mL) and 4-dimethylaminopyridine (0.12 g) were added thereeto. The reaction solution was stirred at room temperature for 2 hrs, then, ethyl acetate (50 mL) was added thereto, and the mixture was washed sequentially with water (50 mL), 5% aqueous solution of citric acid (50 mL) and saturated saline (50 mL). The solution was dried over anhydrous magnesium sulfate, and concentrated under reduced pressure. To the residue was added 4N hydrogen chloride-ethyl acetate solution (20 mL), and stirred at room temperature for 2 hrs. Diethyl ether (10 mL) was added thereto, and the depositing solid was collected by filtration. The solid was dried under reduced pressure to give title compound as white solid (2.93 g).

$^1$H-NMR(DMSO-d$_6$): 2.07(3H,s), 2.53(3H,s), 3.12-3.17 (2H,m), 4.24-4.30(2H,m), 9.29(2H,br).

Reference Synthetic Example 3

2-(Methylamino)ethyl trimethylacetate hydrochloride

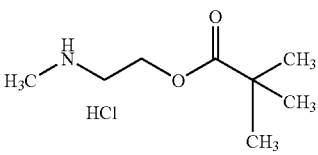

To a mixture of tert-butyl 2-hydroxyethyl(methyl)carbamate (1.75 g) obtained in Reference Synthetic Example 1 and ethyl acetate (15 mL) was added triethylamine (1.67 mL), and a mixture of trimethylacetyl chloride (1.35 mL) and ethyl acetate (5 mL) was added dropwise. The reaction solution was stirred at room temperature for 2 hrs, then, pyridine (1.62 mL) was added thereto, and stirred overnight at room temperature. To the reaction solution was added ethyl acetate (50 mL), and washed sequentially with water (50 mL), 5% aqueous solution of citric acid (50 mL) and saturated saline (50 mL), and dried over anhydrous magnesium sulfate. The solution was concentrated under reduced pressure, and to the residue was added 4N hydrogen chloride-ethyl acetate solution (10 mL). After stirring at room temperature for 2 hrs, diethyl ether (10 mL) was added thereto, and the depositting solid was collected by filtration. The solid was dried under reduced pressure to give title compound as white solid (1.65 g).

$^1$H-NMR(DMSO-d$_6$): 1.18 (9H,s), 2.56 (3H,s), 3.17 (2H, t,J=10.5 Hz), 4.22-4.28 (2H,m), 9.19 (2H,br).

Reference Synthetic Example 4

2-(Methylamino)ethyl cyclohexanecarboxylate hydrochloride

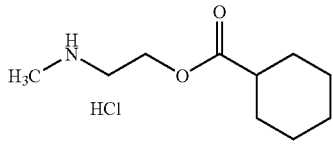

To a mixture of tert-butyl 2-hydroxyethyl(methyl)carbamate (1.75 g) obtained in Reference Synthetic Example 1 and ethyl acetate (20 mL) were added pyridine (0.97 mL) and 4-dimethylaminopyridine (catalytic amount), and cyclohexanecarbonyl chloride (1.60 mL) was added thereto. After stirring at room temperature for 2 hrs, pyridine (0.65 mL) and cyclohexanecarbonyl chloride (0.58 mL) was further added, and stirred overnight at room temperature. To the reaction solution was added ethyl acetate (50 mL), and washed sequentially with water (50 mL), 5% aqueous solution of citric acid (50 mL) and saturated saline (50 mL), and dried over anhydrous magnesium sulfate. The solution was concentrated under reduced pressure, and to the residue was added 4N hydrogen chloride-ethyl acetate solution (10 mL). After stirring at room temperature for 2 hrs, diethyl ether (10 mL)

was added thereto, and the depositing solid was collected by filtration. The solid was dried under reduced pressure to give title compound as white solid (1.88 g).

$^1$H-NMR(DMSO-d$_6$): 1.10-1.45(5H,m), 1.54-1.73(3H,m), 1.83-1.93(2H,m), 2.29-2.42(1H,m), 2.54(3H,s), 3.12-3.18(2H,m), 4.23-4.29(2H,m), 9.23(2H,br).

Reference Synthetic Example 5

2-(Methylamino)ethyl benzoate hydrochloride

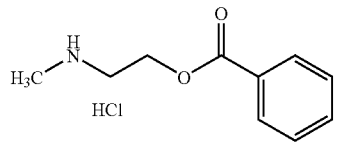

To a mixture of 2-(methylamino)ethanol (30.04 g) and ethyl acetate (90 mL) was added a mixture of di-tert-butyl dicarbonate (87.30 g) and ethyl acetate (10 mL) under ice-cooling. The reaction solution was stirred at room temperature for 1 hr, and benzoyl chloride (61.8 g) and pyridine (38.8 mL) were added thereeto under ice-cooling. The reaction solution was stirred at room temperature for 1 hr, and solid was filtered off. The solid was washed with ethyl acetate (100 mL), and the filtrate and washings were combined and washed with water (100 mL), then saturated saline (100 mL). The solution was dried over anhydrous magnesium sulfate, and concentrated under reduced pressure. The residue was dissolved in ethyl acetate (100 mL), and added 4N hydrogen chloride-ethyl acetate solution (200 mL), followed by stirring at room temperature for 30 minutes. Diethyl ether (100 mL) was added thereto, and solid was collected by filtration. After washing two times with ethyl acetate (100 mL), the solid was dried at 60° C. under reduced pressure to give title compound as white solid (57.4 g).

$^1$H-NMR(DMSO-d$_6$): 2.62(3H,s), 3.32(2H,m), 4.53(2H,t, J=9.9 Hz), 7.51-7.57(2H,m), 7.68(1H,m), 8.11(2H,d,J=7.8 Hz), 9.26(2H,bs).

Reference Synthetic Example 6

2-(Methylamino)ethyl 4-methoxybenzoate hydrochloride

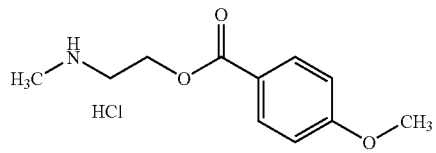

To a mixture of tert-butyl 2-hydroxyethyl(methyl)carbamate (1.75 g) obtained in Reference Synthetic Example 1 and ethyl acetate (10 mL) were added 4-methoxybenzoyl chloride (1.88 g) and pyridine (0.97 mL). After stirring at room temperature for 14 hrs, 4-methoxybenzoyl chloride (0.70 g) and pyridine (0.97 mL) was further added, and stirred at room temperature for 1 hr. To the reaction solution was added ethyl acetate (80 mL), and washed sequentially with water (20 mL), saturated aqueous solution of sodium bicarbonate (20 mL) and water (20 mL), and dried over anhydrous magnesium sulfate. The solution was concentrated under reduced pressure, and the residue was dissolved in ethyl acetate (10 mL), followed by adding 4N hydrogen chloride-ethyl acetate solution (10 mL). After stirring at room temperature for 1 hr, diethyl ether (20 mL) was added, and the depositing solid was collected by filtration. The solid was washed twice with ethyl acetate (15 mL), and dried at 60° C. under reduced pressure to give title compound as white solid (1.99 g).

$^1$H-NMR(DMSO-d$_6$): 2.62(3H,s), 3.32(2H,m), 4.48(2H,t, J=5.0 Hz), 7.07(2H,d,J=8.7 Hz), 8.06(2H,d,J=8.7 Hz), 9.04(2H,bs).

Reference Synthetic Example 7

2-(Methylamino)ethyl 3-chlorobenzoate hydrochloride

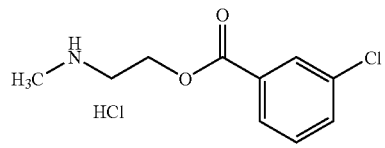

To a mixture of tert-butyl 2-hydroxyethyl(methyl)carbamate (1.75 g) obtained in Reference Synthetic Example 1 and ethyl acetate (10 mL) were added 3-chlorobenzoyl chloride (1.92 g) and pyridine (0.97 mL). After stirring at room temperature for 1 hr, the reaction solution was stirred at 60° C. for 6 hrs. To the reaction solution was added ethyl acetate (80 mL), and washed sequentially with water (20 mL), saturated aqueous solution of sodium bicarbonate (20 mL) and water (20 mL), and dried over anhydrous magnesium sulfate. The solution was concentrated under reduced pressure, and to the residue was added 4N hydrogen chloride-ethyl acetate solution (10 mL). After stirring at room temperature for 22 hrs, diethyl ether (15 mL) was added, and the depositing solid was collected by filtration. The solid was washed twice with ethyl acetate (15 mL), and dried at 60° C. under reduced pressure to give title compound as white solid (2.01 g).

$^1$H-NMR(DMSO-d$_6$): 2.63(3H,s), 3.32(2H,m), 4.53(2H,t, J=4.9 Hz), 7.60(1H,t,J=8.0 Hz), 7.78(1H,d,J=8.0 Hz), 8.05 (1H,d,J=8.0 Hz), 8.15(1H,s), 9.07(2H,bs).

Reference Synthetic Example 8

2-(Methylamino)ethyl 3,4-difluorobenzoate hydrochloride

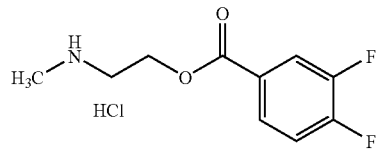

To a mixture of tert-butyl 2-hydroxyethyl(methyl)carbamate (1.75 g) obtained in Reference Synthetic Example 1 and ethyl acetate (10 mL) were added 3,4-difluorobenzoyl chloride (1.77 g) and pyridine (0.97 mL). After stirring at room temperature for 3 days, ethyl acetate (80 mL) was added to the reaction solution, and washed sequentially with water (20 mL), saturated aqueous solution of sodium bicarbonate (20 mL) and water (20 mL), and dried over anhydrous magnesium sulfate. The solution was concentrated under reduced pressure, and to the residue was added 4N hydrogen chloride-ethyl acetate solution (10 mL). After stirring at room temperature for 4 hrs, the solution was concentrated under reduced pressure. The residue was washed with ethyl acetate (15 mL), and dried at 60° C. under reduced pressure to give title compound as white solid (2.05 g).

$^1$H-NMR(DMSO-$d_6$): 2.62(3H,s), 3.32(2H,m), 4.53(2H,t, J=5.0 Hz), 7.64(1H,m), 8.00(1H,m), 8.25(1H,m), 9.25(2H, bs).

Reference Synthetic Example 9

2-(Methylamino)ethyl 4-trifluoromethoxybenzoate hydrochloride

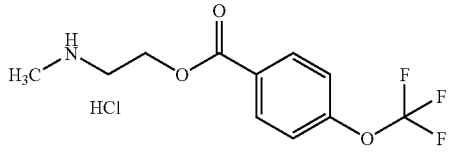 [SMILES: CNCCOC(=O)c1ccc(OC(F)(F)F)cc1 ; Cl]

To a mixture of tert-butyl 2-hydroxyethyl(methyl)carbamate (1.30 g) obtained in Reference Synthetic Example 1 and ethyl acetate (10 mL) were added 4-trifluoromethoxybenzoyl chloride (1.83 g) and pyridine (0.72 mL). The reaction solution was stirred at 60° C. for 25 hrs. Ethyl acetate (60 mL) was added to the reaction solution, and washed sequentially with water (30 mL), saturated aqueous solution of sodium bicarbonate (20 mL) and water (20 mL), followed by drying over anhydrous magnesium sulfate. The solution was concentrated under reduced pressure, and to the residue was added 4N hydrogen chloride-ethyl acetate solution (10 mL). After stirring at room temperature for 14.5 hrs, the solution was concentrated under reduced pressure. The residue was washed twice with ethyl acetate (15 mL), and dried at 60° C. under reduced pressure to give title compound as white solid (1.83 g).

$^1$H-NMR(DMSO-$d_6$): 2.63(3H,s), 3.31(2H,m), 4.54(2H,t, J=4.9 Hz), 7.55(2H,d,J=8.5 Hz), 8.24(2H,d,J=8.5 Hz), 9.02 (2H,bs).

Reference Synthetic Example 10

2-(Methylamino)ethyl 4-fluorobenzoate hydrochloride

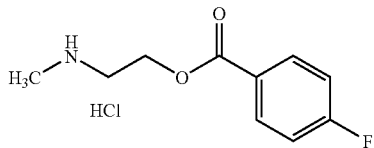

To a mixture of tert-butyl 2-hydroxyethyl(methyl)carbamate (1.75 g) obtained in Reference Synthetic Example 1 and ethyl acetate (10 mL) were added 4-fluorobenzoyl chloride (1.74 g) and pyridine (0.97 mL). The reaction solution was stirred at room temperature for 6.5 hrs. Ethyl acetate (80 mL) was added to the reaction solution, and washed sequentially with water (30 mL), saturated aqueous solution of sodium bicarbonate (30 mL), water (30 mL) and saturated brine (30 mL), followed by drying over anhydrous magnesium sulfate. The solution was concentrated under reduced pressure, and to the residue was added 4N hydrogen chloride-ethyl acetate solution (10 mL). After stirring at room temperature for 1 hr, the depositting solid was collected by filtration. The solid was washed twice with ethyl acetate (15 mL), and dried at 60° C. under reduced pressure to give title compound as white solid (1.89 g).

$^1$H-NMR(DMSO-$d_6$): 2.62(3H,s), 3.32(2H,m), 4.52(2H,t, J=4.9 Hz), 7.34-7.44(2H,m), 8.16-8.24(2H,m), 9.18(2H,bs).

Reference Synthetic Example 11

2-(Methylamino)ethyl 3,4,5-trimehoxybenzoate hydrochloride

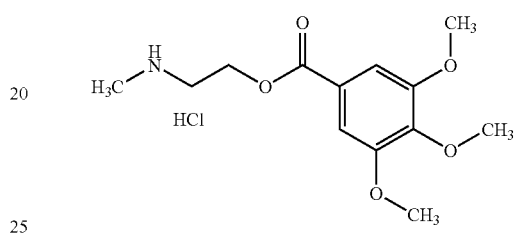

To a mixture of tert-butyl 2-hydroxyethyl(methyl)carbamate (1.75 g) obtained in Reference Synthetic Example 1 and ethyl acetate (10 mL) were added 3,4,5-trimethoxybenzoyl chloride (2.54 g) and pyridine (0.97 mL). After stirring at 60° C. for 14 hrs, to the reaction solution were further added 3,4,5-trimethoxybenzoyl chloride (1.30 g), pyridine (0.97 mL) and ethyl acetate (10 mL), and stirred at 60° C. for 24 hrs. The reaction solution was filtered, and to the filtrate were added ethyl acetate (50 mL) and water (30 mL). After separating the layers, the ethyl acetate layer was washed sequentially with 1 N hydrochloric acid (30 mL), water (30 mL), aqueous solution of copper (II) sulfate (30 mL), water (30 mL) and saturated brine (30 mL), followed by drying over anhydrous magnesium sulfate. The solution was concentrated under reduced pressure, and the residue was purified by silica gel column chromatography (elute with ethyl acetate:hexane=1:1). To the purified materials was added 4N hydrogen chloride-ethyl acetate solution (10 mL). After stirring at room temperature for 4 hrs, the solution was concentrated under reduced pressure. Toluene (10 mL) was added to the residue, and concentrated under reduced pressure. The residue was suspended in ethyl acetate, and the solid was collected by filtration. After washing with ethyl acetate (15 mL), the solid was dried under reduced pressure to give title compound as white solid (1.79 g).

$^1$H-NMR(DMSO-$d_6$): 2.61(3H,s), 3.28-3.35(2H,m), 3.74 (3H,s), 3.87(6H,s), 4.48-4.54(2H,m), 7.40(2H,s), 9.43(2H, br).

Reference Synthetic Example 12

2-(Methylamino)ethyl 2-pyridinecarboxylate dihydrochloride

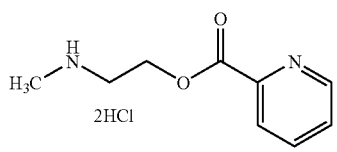

To a tetrahydrofuran solution (100 mL) of tert-butyl 2-hydroxyethyl(methyl)carbamate (1.75 g) obtained in Reference Synthetic Example 1, 2-pyridinecarbonyl chloride hydrochloride (2.67 g), pyridine (1.21 mL) and 4-dimethylaminopyridine (0.122 g) was added dropwise triethylamine (2.09 mL) under ice-cooling, and stirred at room temperature for 6 hrs. To the reaction solution was added water (200 mL), and extracted with ethyl acetate (150 mL). The organic layer was washed sequentially with 5% aqueous solution of copper (II) sulfate (100 mL), water (100 mL) and saturated brine (100 mL), followed by drying over anhydrous magnesium sulfate. The solvent was distiled away under reduced pressure. The residue was dissolved in ethyl acetate (50 mL) and ethanol (100 mL), and added 4N hydrogen chloride-ethyl acetate solution (15 mL) thereto, followed by stirring at room temperature for 1 hr. The depositting solid was collected by filtration, and washed twice with ethyl acetate (100 mL), then, dried at 60° C. under reduced pressure to give title compound as white solid (1.08 g).

$^1$H-NMR(DMSO-$d_6$): 2.62(3H,t,J=5.4 Hz), 3.35(2H,m), 4.63(2H,t,J=5.0 Hz), 5.26(1H,bs), 7.77-7.84(1H,m), 8.14-8.18(1H,m), 8.36-8.40(1H,m), 8.70-8.90(1H,m), 9.48(2H,br).

Reference Synthetic Example 13

2-(Methylamino)ethyl methoxyacetate

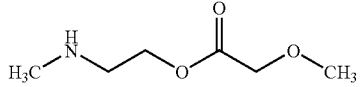

To a mixture of tert-butyl 2-hydroxyethyl(methyl)carbamate (1.75 g) obtained in Reference Synthetic Example 1 and ethyl acetate (10 mL) were added methoxyacetyl chloride (1.20 g) and pyridine (0.97 mL). After stirring at room temperature for 3 hrs, to the reaction solution was added ethyl acetate (70 mL), and washed sequentially with water (20 mL), saturated aqueous solution of sodium bicarbonate (20 mL) and water (20 mL), followed by drying over anhydrous magnesium sulfate. The solution was concentrated under reduced pressure, and the residue was dissolved in ethyl acetate (5 mL), and added 4N hydrogen chloride-ethyl acetate solution (10 mL). After stirring at room temperature for 1 hr, the solution was concentrated under reduced pressure. To the residue was added water (60 mL) and diethyl ether (30 mL), and stirred, then, the aqueous layer was separated. The aqueous layer was made basic with sodium bicarbonate, and extracted twice with ethyl acetate (40 mL). The ethyl acetate layer was dried over anhydrous magnesium sulfate, and concentrated under reduced pressure to give title compound as colorless oil (1.00 g).

$^1$H-NMR(CDCl$_3$): 2.40(1H,bs), 3.06(3H,s), 3.44(3H,s), 3.57(2H,t,J=5.1 Hz), 3.75-3.82(2H,m), 4.13(2H,s).

Reference Synthetic Example 14

Ethyl 2-(methylamino)ethyl carbonate hydrochloride

To a mixture of tert-butyl 2-hydroxyethyl(methyl)carbamate (1.75 g) obtained in Reference Synthetic Example 1 and ethyl acetate (20 mL) were added pyridine (0.97 mL) and 4-dimethylaminopyridine (catalytic amount), and ethyl chlorocarbonate (1.25 mL) was added. After stirring overnight at room temperature, ethyl acetate (50 mL) was added to the reaction solution, and washed sequentially with water (50 mL), 5% aqueous solution of citric acid (50 mL), and saturated saline (50 mL), followed by drying over anhydrous magnesium sulfate. The solution was concentrated under reduced pressure, and to the residue was added 4N hydrogen chloride-ethyl acetate solution (10 mL). After stirring at room temperature for 2 hrs, diethyl ether (10 mL) was added thereto, and the depositting solid was collected by filtration. The solid was dried under reduced pressure to give title compound as white solid (1.66 g).

$^1$H-NMR(DMSO-$d_6$): 1.23(3H,t,J=7.1 Hz), 2.54(3H,s), 3.16-3.22(2H,m), 4.15(2H,q,J=7.1 Hz), 4.32-4.37(2H,m), 9.25(2H,br).

Reference Synthetic Example 15

Isopropyl 2-(methylamino)ethyl carbonate hydrochloride

To a mixture of tert-butyl 2-hydroxyethyl(methyl)carbamate (3.50 g) obtained in Reference Synthetic Example 1 and ethyl acetate (20 mL) were added isopropyl chlorocarbonate (1.23 g) and pyridine (1.94 mL) under ice-cooling. After stirring for 3.5 hrs under ice-cooling, isopropyl chlorocarbonate (1.23 g) was further added, and stirred at room temperature for 2.5 hrs. To the reaction solution was added ethyl acetate (120 mL), and washed with water (50 mL), and saturated saline (50 mL), followed by drying over anhydrous magnesium sulfate. The solution was concentrated under reduced pressure, and to the residue was added 4N hydrogen chloride-ethyl acetate solution (10 mL). After stirring at room temperature for 2 hrs, the depositting solid was collected by filtration. The solid was washed with ethyl acetate (15 mL), and dried at 60° C. under reduced pressure to give title compound as white solid (1.38 g).

$^1$H-NMR(DMSO-$d_6$): 1.25(6H,d,J=6.2 Hz), 2.56(3H,s), 3.20(2H,t,J=5.1 Hz), 4.32(2H,t,J=5.1 Hz), 4.80(1H,m), 8.95 (2H,bs).

Reference Synthetic Example 16

Bebzyl 2-(methylamino)ethyl carbonate hydrochloride

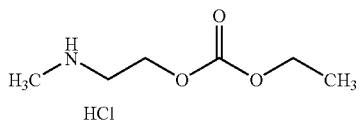

To a mixture of tert-butyl 2-hydroxyethyl(methyl)carbamate (1.75 g) obtained in Reference Synthetic Example 1 and ethyl acetate (20 mL) were added pyridine (0.97 mL) and 4-dimethylaminopyridine (catalytic amount), and benzyl chlorocarbonate (1.57 mL) was added dropwise thereto. After stirring at room temperature for 2 hrs, pyridine (0.65 mL) and benzyl chlorocarbonate (1.28 mL) were further added. After stirring at room temperature for 5 days, pyridine (0.81 mL) was further added under ice-cooling, and a solution of benzyl chlorocarbonate (1.43 mL) in ethyl acetate (5 mL) was slowly added dropwise. The reaction solution was stirred at room temperature for 2 hrs, and added ethyl acetate (50 mL), then, washed with water (50 mL), 5% aqueous solution of citric acid (50 mL), and saturated saline (50 mL), followed by drying over anhydrous magnesium sulfate. The solution was concentrated under reduced pressure, and to the residue was added 4N hydrogen chloride-ethyl acetate solution (10 mL). After stirring at room temperature for 2 hrs, diethyl ether (10 mL) was added, and the depositing solid was collected by filtration. The solid was dried under reduced pressure to give title compound as white solid (1.99 g).

$^1$H-NMR(DMSO-$d_6$): 2.55(3H,s), 3.21(2H,t,J=5.1 Hz), 4.37(2H,t,J=5.1 Hz), 5.18(2H,s), 7.30-7.50(5H,m), 9.07(2H,br).

Reference Synthetic Example 17

2-(Methylamino)ethyl tetrahydropyran-4-yl carbonate hydrochloride

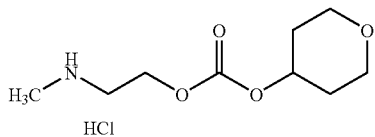

To a solution of bis(trichloromethyl) carbonate (2.97 g) in tetrahydrofuran (40 mL) was added dropwise a solution of pyridine (2.43 mL) in tetrahydrofuran (10 mL) under ice-cooling. The solution was stirred for 10 minutes under ice-cooling, and a solution of tetrahydropyran-4-ol (1.91 g) in tetrahydrofuran (20 mL) was slowly added dropwise. After stirring at room temperature for 2 hrs, the solution was concentrated under reduced pressure, and to the residue were added ethyl acetate (50 mL) and water (50 mL). The ethyl acetate layer was separated, and washed with 0.2 N hydrochloric acid (20 mL), and saturated saline (50 m), followed by drying over anhydrous magnesium sulfate. The solution was concentrated under reduced pressure to give tetrahydropyran-4-yl chlorocarbonate (1.53 g). To a mixture of tert-butyl 2-hydroxyethyl(methyl)carbamate (1.40 g) obtained in Reference Synthetic Example 1 and tetrahydrofuran (20 mL) was added pyridine (0.78 mL), and a solution of tetrahydropyran-4-yl chlorocarbonate (1.53 g) obtained above in tetrahydrofuran (10 mL) was added dropwise thereto, followed by stirring at room temperature overnight. The reaction solution was concentrated under reduced pressure, and to the residue was added water (50 mL), and extracted with ethyl acetate (50 mL). The extract was washed with 5% aqueous solution of citric acid (50 mL), and saturated saline (50 mL), and dried over anhydrous magnesium sulfate. The solution was concentrated under reduced pressure, and the residue was purified by silica gel column chromatography (elute with ethyl acetate hexane=4:1, then 3:2). The obtained colorless oil (2.03 g) was dissolved in diethyl ether (2 mL), and added 4N hydrogen chloride-ethyl acetate solution (5 mL). After stirring at room temperature for 30 minutes, diethyl ether (10 mL) was added, followed by stirring overnight. The depositing solid was collected by filtration, and dried under reduced pressure to give title compound as white solid (1.20 g).

$^1$H-NMR(DMSO-$d_6$): 1.50-1.65(2H,m), 1.87-1.98(2H, m), 2.54(3H,s), 3.20(2H,m), 3.40-3.50(2H,m), 3.74-3.83 (2H,m), 4.36(2H,t,J=5.1 Hz), 4.72-4.83(1H,m), 9.32(2H,br).

Reference Synthetic Example 18

2-Methoxyethyl 2-(methylamino)ethyl carbonate hydrochloride

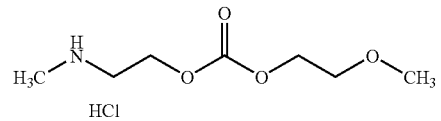

To a mixture of tert-butyl 2-hydroxyethyl(methyl)carbamate (1.75 g) obtained in Reference Synthetic Example 1 and ethyl acetate (20 mL) was added pyridine (1.62 mL), and a solution of 2-methoxyethyl chlorocarbonate (2.77 mL) in ethyl acetate (5 mL) was slowly added dropwise, followed by stirring at room temperature overnight. The reaction solution was concentrated under reduced pressure, and extracted with ethyl acetate (50 mL). The extract was washed with 5% aqueous solution of citric acid (50 mL), and saturated saline (50 mL), and dried over anhydrous magnesium sulfate. The solution was concentrated under reduced pressure, and the residue was dissolved in diethyl ether (2 mL), and added 4N hydrogen chloride-ethyl acetate solution (5 mL). After stirring at room temperature for 30 minutes, diethyl ether (10 mL) was added, and stirred overnight. The depositing solid was collected by filtration, and dried under reduced pressure to give title compound as white solid (1.56 g).

$^1$H-NMR(DMSO-$d_6$): 2.54(3H,s), 3.19(2H,m), 3.26(3H, s), 3.52-3.57(2H,m), 4.20-4.25(2H,m), 4.33-4.39(2H,m), 9.26(2H,br).

Reference Synthetic Example 19 tert-Butyl ethyl(2-hydroxyethyl)carbamate

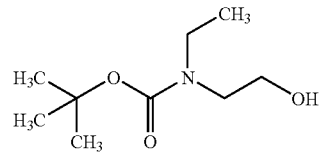

To a mixture of 2-(ethylamino)ethanol (8.91 g) and ethyl acetate (100 mL) was added di-tert-butyl dicarbonate (21.8 g) under ice-cooling. The reaction mixture was stirred at room temperature for 3 days, and washed with saturated brine, then, dried over anhydrous magnesium sulfate. The solution was concentrated under reduced pressure to give title compound as colorless oil (19.0 g).

$^1$H-NMR(CDCl$_3$): 1.11(3H,t,J=7.0 Hz), 1.47(9H,s), 3.27 (2H,q,J=7.0 Hz), 3.37(2H,t,J=5.2 Hz), 3.73(2H,q,J=5.2 Hz).

Reference Synthetic Example 20

2-(Ethylamino)ethyl acetate hydrochloride

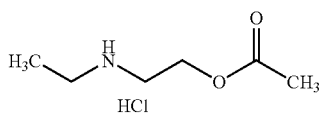

To a mixture of tert-butyl ethyl(2-hydroxyethyl)carbamate (1.89 g) obtained in Reference Synthetic Example 19 and ethyl acetate (20 mL) were added acetic anhydride (1.04 mL), pyridine (0.89 mL) and 4-dimethylaminopyridine (0.061 g). After stirring at room temperature for 3 hrs, ethyl acetate (50 mL) was added to the reaction solution, and washed with water (50 mL), 5% aqueous solution of citric acid (50 mL), and saturated saline (50 mL). The solution was dried over anhydrous magnesium sulfate, and concentrated under reduced pressure. To the residue was added 4N hydrogen chloride-ethyl acetate solution (10 mL), and stirred at room temperature for 1 hr. To the residue were added ethyl acetate (10 mL) and diethyl ether (20 mL), and the depositing solid was collected by filtration. The solid was dried under reduced pressure to give title compound as white solid (1.54 g).

$^1$H-NMR(DMSO-d$_6$): 1.22(3H,t,J=7.3 Hz), 2.07(3H,s), 2.95(2H,q,J=7.3 Hz), 3.15(2H,t,J=5.3 Hz), 4.24-4.30(2H,m), 9.17(2H,br).

Reference Synthetic Example 21 tert-Butyl 2-hydroxyethyl(isopropyl)carbamate

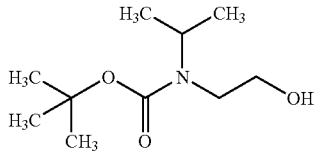

To a solution of 2-(isopropylamino)ethanol (10.0 g) in tetrahydrofuran (30 mL) was added di-tert-butyl dicarbonate (22.2 g), and stirred at room temperature for 1 hr. The reaction solution was concentrated under reduced pressure, and water (100 mL) was added to the residue, followed by extracting with ethyl acetate (200 mL). The ethyl acetate layer was washed with saturated saline (100 mL), dried over anhydrous magnesium sulfate, and concentrated under reduced pressure to give title compound as colorless oil (21.21 g).

$^1$H-NMR(CDCl$_3$): 1.12(6H,d,J=6.6 Hz), 3.30(2H,t,J=5.0 Hz), 3.71(2H,t,J=5.0 Hz), 3.80-4.30(1H,m).

Reference Synthetic Example 22

2-(Isopropylamino)ethyl acetate hydrochloride

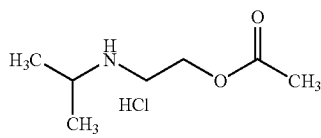

To a solution of tert-butyl 2-hydroxyethyl(isopropyl)carbamate (5.0 g) obtained in Reference Synthetic Example 21 in tetrahydrofuran (15 mL) were added pyridine (6.0 mL) and acetic anhydride (2.79 mL), and stirred at room temperature for 18 hrs. The reaction solution was concentrated under reduced pressure, and to the residue was added water (50 mL), and extracted with ethyl acetate (100 mL). The ethyl acetate layer was washed with 5% aqueous solution of citric acid (50 mL), and saturated saline (50 mL), and dried over anhydrous magnesium sulfate, then concentrated under reduced pressure. The resulting colorless oil was dissolved in 4N hydrogen chloride-ethyl acetate solution (10 mL), and stirred at room temperature for 1 hr. The depositted solid was collected by filtration, and dried under reduced pressure to give title compound as colorless solid (3.14 g).

$^1$H-NMR(DMSO-d$_6$): 1.25(6H,d,J=6.6 Hz), 2.08(3H,s), 3.10-3.40(3H,m), 4.29(2H,t,J=6.0 Hz), 9.11(2H,br).

Reference Synthetic Example 23

Ethyl 2-(isopropylamino)ethyl carbonate hydrochloride

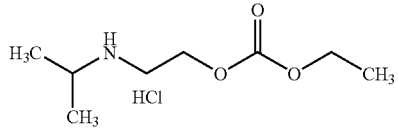

To a solution of tert-butyl 2-hydroxyethyl(isopropyl)carbamate (5.0 g) obtained in Reference Synthetic Example 21 in tetrahydrofuran (15 mL) were added pyridine (6.0 mL) and ethyl chlorocarbonate (2.81 mL), and stirred at room temperature for 18 hrs. The reaction solution was concentrated under reduced pressure, and to the residue was added water (50 mL), and extracted with ethyl acetate (100 mL). The ethyl acetate layer was washed with 5% aqueous solution of citric acid (50 mL), and saturated saline (50 mL), and dried over anhydrous magnesium sulfate, then concentrated under reduced pressure. The resulting colorless oil was dissolved in 4N hydrogen chloride-ethyl acetate solution (10 mL), and stirred at room temperature for 1 hr. The depositted solid was collected by filtration, and dried under reduced pressure to give title compound as colorless solid (3.34 g).

$^1$H-NMR(DMSO-d$_6$): 1.20-1.30(9H,m), 3.10-3.40(3H,m), 4.17(2H,q,J=7.4 Hz), 4.37(2H,t,J=5.6 Hz), 9.13(2H,br).

Reference Synthetic Example 24 tert-Butyl cyclohexyl(2-hydroxyethyl)carbamate

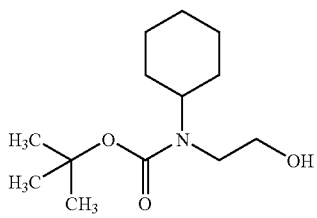 [SMILES: CC(C)(C)OC(=O)N(CCO)C1CCCCC1]

To a solution of 2-(cyclohexylamino)ethanol (14.3 g) in ethanol (200 mL) was added dropwise di-tert-butyl dicarbonate (21.8 g). The reaction solution was stirred at room temperature for 2 days, and concentrated under reduced pressure. The residue was dissolved in ethyl acetate (200 mL), and washed with water (100 mL) and saturated brine (100 mL), then, dried over anhydrous magnesium sulfate. The solution was concentrated under reduced pressure to give title compound as colorless oil (24.2 g).

$^1$H-NMR(CDCl$_3$): 1.26-1.39(4H,m), 1.47(9H,s), 1.61-1.81(6H,m), 3.30-3.40(2H,m), 3.69(2H,t,J=5.4 Hz), 3.66-3.90(2H,br).

Reference Synthetic Example 25

2-(Cyclohexylamino)ethyl acetate hydrochloride

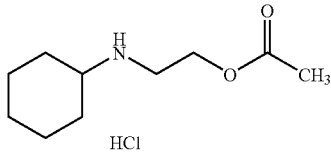

To a solution of tert-butyl cyclohexyl(2-hydroxyethyl)carbamate (2.43 g) obtained in Reference Synthetic Example 24 in tetrahydrofuran (50 mL) were added pyridine (1.05 mL), acetic anhydride (1.23 mL) and 4-dimethylaminopyridine (0.122 g) under ice-cooling, and stirred at room temperature for 12 hrs. To the reaction solution was added ethyl acetate (100 mL), and washed sequentially with saturated aqueous solution of sodium bicarbonate (100 mL), 5% aqueous solution of copper (II) sulfate (100 mL), and saturated brine (100 mL), and dried over anhydrous magnesium sulfate, then concentrated under reduced pressure. The residue was dissolved in ethyl acetate (15 mL), and added 4N hydrogen chloride-ethyl acetate solution (15 mL). After stirring at room temperature for 3 hrs, diisopropyl ether (20 mL) was added to the solution, and the depositing solid was collected by filtration to give title compound as colorless solid (1.78 g).

$^1$H-NMR(DMSO-d$_6$): 1.05-2.03(10H,m), 2.07(3H,s), 2.90-3.10(1H,m), 3.17(2H,t,J=5.2 Hz), 4.29(2H,t,J=5.2 Hz), 9.19(2H,br).

Reference Synthetic Example 26

2-(Cyclohexylamino)ethyl ethyl carbonate hydrochloride

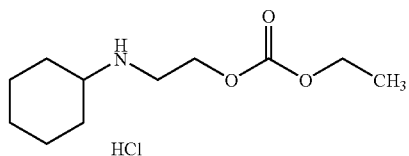

To a solution of tert-butyl cyclohexyl(2-hydroxyethyl)carbamate (2.43 g) obtained in Reference Synthetic Example 24 in tetrahydrofuran (50 mL) were added pyridine (1.45 mL), ethyl chlorocarbonate (1.71 mL) and 4-dimethylaminopyridine (0.122 g) under ice-cooling, and stirred at room temperature for 15 hrs. To the reaction solution was added ethyl acetate (100 mL), and washed sequentially with saturated aqueous solution of sodium bicarbonate (100 mL), 5% aqueous solution of copper (II) sulfate (100 mL), water (100 mL) and saturated brine (100 mL), and dried over anhydrous magnesium sulfate, then concentrated under reduced pressure. The residue was dissolved in ethyl acetate (15 mL), and added 4N hydrogen chloride-ethyl acetate solution (15 mL). After stirring at room temperature for 3 hrs, diisopropyl ether (20 mL) was added to the solution, and the depositing solid was collected by filtration to give title compound as colorless solid (2.12 g).

$^1$H-NMR(DMSO-d$_6$): 1.01-2.08(10H,m), 1.23(3H,t,J=7.0 Hz), 2.90-3.10(1H,m), 3.21(2H,t,J=5.2 Hz), 4.16(2H,q,J=7.0 Hz), 4.39(2H,t,J=5.2 Hz), 9.27(2H,br).

Reference Synthetic Example 27

2-Anilinoethyl acetate hydrochloride

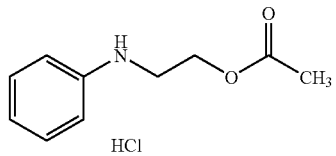

To a solution of 2-anilinoethanol (137 g) in tetrahydrofuran (700 mL) were added pyridine (97.1 mL), acetic anhydride (113.2 mL) and 4-dimethylaminopyridine (12.22 g) under ice-cooling, and stirred at room temperature for 20 hrs. To the reaction solution was added ethyl acetate (1 L), and washed sequentially with water (1 L), saturated aqueous solution of sodium bicarbonate (1 L), 5% aqueous solution of copper (II) sulfate (1 L) and saturated brine (1 L), and dried over anhydrous magnesium sulfate, then concentrated under reduced pressure. To the solution of the resulting residue in ethyl acetate (700 mL) was added 4N hydrogen chloride-ethyl acetate solution (250 mL), and the depositted solid was collected by filtration to give title compound as colorless solid (156 g).

$^1$H-NMR(CD$_3$OD): 2.11(3H,s), 3.71-3.76(2H,m), 4.32-4.37(2H,m), 7.49-7.64 (5H,m).

Reference Synthetic Example 28 tert-Butyl [2-(methylamino)-3-pyridyl]methyl carbonate

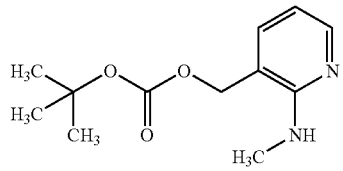 [SMILES: CNc1ncccc1COC(=O)OC(C)(C)C]

To a solution of [2-(methylamino)-3-pyridyl]methanol (2 g: synthesized by a method described in WO 01/32652) in tetrahydrofuran (50 mL) were added di-tert-butyl dicarbonate (3.48 g) and 4-dimethylaminopyridine (0.18 g), and refluxed for 1 hr. To the reaction solution was added water (30 mL), extracted with ethyl acetate (50 mL), and the obtained organic layer was washed with saturated sline (50 mL), followed by drying over anhydrous sodium sulfate. The residue obtained by concentrating the organic layer under reduced pressure was purified with flash silica gel column chromatography (elute with ethyl acetate:hexane=1:5) to give title compound as white solid (1.51 g).

$^1$H-NMR(CDCl$_3$): 1.49(9H,s), 3.02(3H,d,J=4.8 Hz), 4.99 (2H,s), 5.00(1H,bs), 6.55(1H,dd,J=7.0,5.0 Hz), 7.37(1H,dd, J=7.0,1.8 Hz), 8.16(1H,dd,J=5.0,1.8 Hz).

Reference Synthetic Example 29

2-(Methylamino)benzyl acetate

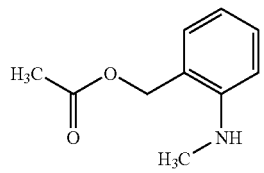

To a solution of 2-(methylamino)phenyl]methanol (1.37 g: synthesized by a method described in WO 01/32652) in tetrahydrofuran (50 mL) were added pyridine (1.05 mL), acetic anhydride (1.23 mL) and 4-dimethylaminopyridine (0.18 g), and stirred at room temperature for 8 hrs. To the reaction solution was added water (100 mL), and extracted with ethyl acetate (50 mL). The organic layer was washed sequentially with 5% aqueous solution of copper (II) sulfate (50 mL), saturated aqueous solution of sodium bicarbonate (50 mL), and saturated brine (50 mL), and dried over anhydrous magnesium sulfate, and then the solvent was distilled away under reduced pressure. The resulting residue was purified with flash silica gel column chromatography (elute with ethyl acetate:hexane=1:5, then 1:3) to give title compound as white solid (0.38 g).

$^1$H-NMR(CDCl$_3$): 2.08(3H,s), 2.87(3H,s), 4.40(1H,br), 5.08(2H,s), 6.64-6.74(2H,m), 7.17-7.32(2H,m).

Reference Synthetic Example 30

2-[(2-Acetyloxyethyl)amino]ethyl acetate hydrochloride

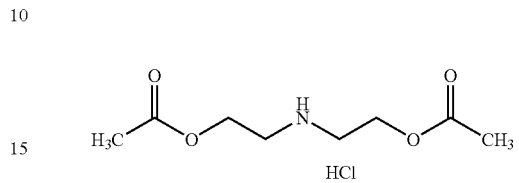

To a mixture of 2,2'-iminodiethanol (2.10 g) and ethyl acetate (20 mL) was added di-tert-butyl dicarbonate (4.37 g). The reaction solution was stirred for 1.5 hrs under ice-cooling, acetic anhydride (2.08 mL), pyridine (1.78 mL) and 4-dimethylaminopyridine (0.12 g) were added thereto. After stirring at room temperature for 2 hrs, to the reaction solution was added ethyl acetate (50 mL), and washed with water (50 mL), 5% aqueous solution of citric acid (50 mL), and saturated saline (50 mL). The obtained solution was dried over anhydrous magnesium sulfate, and concentrated under reduce pressure. To the residue was added 4N hydrogen chloride-ethyl acetate solution (20 mL), and stirred at room temperature for 2 hrs. To the solution were added diethyl ether (10 mL), and the depositting solid was collected by filtration. The solid was dried under reduced pressure to give title compound as white solid (6.18 g)

$^1$H-NMR(DMSO-d$_6$): 2.07(6H,s), 3.23(4H,t,J=5.3 Hz), 4.27-4.33(4H,m), 9.40(2H,br).

Reference Synthetic Example 31

(S)-2-Pyrrolidinylmethyl acetate hydrochloride

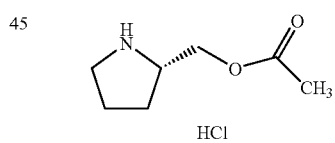

To a mixture of (S)-2-pyrrolidinylmethanol (1.01 g) and ethyl acetate (10 mL) was added di-tert-butyl dicarbonate (2.18 g). The reaction solution was stirred for 1 hr under ice-cooling, acetic anhydride (1.04 mL), pyridine (0.89 mL) and 4-dimethylaminopyridine (0.061 g) were added thereto. After stirring at room temperature for 1 hr, to the reaction solution was added ethyl acetate (50 mL), and washed with water (50 mL), 5% aqueous solution of citric acid (50 mL), and saturated saline (50 mL). The solution was dried over anhydrous magnesium sulfate, and concentrated under reduce pressure. To the residue was added 4N hydrogen chloride-ethyl acetate solution (10 mL), and stirred at room temperature for 1 hr. To the solution were added diethyl ether (10 mL), and the depositting solid was collected by filtration. The solid was dried under reduced pressure to give title compound as pale brown solid (1.68 g)

$^1$H-NMR(DMSO-d$_6$): 1.56-2.10(4H,m), 2.06(3H,s), 3.05-3.24(2H,m), 3.63-3.68(1H,m), 4.15(1H,dd,J=11.8,8.1 Hz), 4.26(1H,dd,J=11.8,4.1 Hz), 9.21(1H,br), 9.87(1H,br).

Reference Synthetic Example 32

3-(Methylamino)propyl benzoate hydrochloride

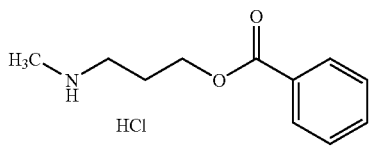

To a mixture of 3-amino-1-propanol (0.75 g) and ethyl acetate (2.25 mL) was added a solution of di-tert-butyl dicarbonate (2.18 g) in ethyl acetate (0.25 mL) under ice-cooling. The reaction solution was stirred at room temperature for 21.5 hrs, and benzoyl chloride (1.30 mL), pyridine (0.98 mL) and 4-dimethylaminopyridine (0.012 g) were added thereto. After stirring at room temperature for 5 hrs, to the reaction solution was added ethyl acetate (32.5 mL), and washed with water (12.5 mL), and saturated saline (12.5 mL). The solution was dried over anhydrous magnesium sulfate, and concentrated under reduce pressure. The residue was dissolved in N,N-dimethylformamide (20 mL), and added methyl iodide (5 mL). To the solution was added 60% sodium hydride (0.4 g) under ice-cooling. After stirring at room temperature for 3 hrs, the reaction solution was poured into ice-cooled aqueous solution of ammonium chloride (60 mL). The solution was extracted with diethyl ether (80 mL), and washed with saturated brine (30 mL). The ether solution was dried over anhydrous magnesium sulfate, and concentrated under reduce pressure. The residue was purified with silica gel column chromatography (ethyl acetate:hexane=2:1, then ethyl acetate, and then acetone:ethyl acetate=1:9) to give 3-[(tert-butoxycarbonyl) (methyl)amino]propyl benzoate as colorless oil (2.52 g). To the oil was added 4N hydrogen chloride-ethyl acetate solution (10 mL), and stirred at room temperature for 1 hr. The solution was concentrated under reduced pressure, and to the residue was added ethyl acetate (10 mL). The depositting solid was collected by filtration. The solid was washed with diethyl ether (10 mL), and dried under reduced pressure to give title compound as colorless solid (1.73 g).

$^1$H-NMR(DMSO-d$_6$): 2.02-2.16(2H,m), 2.56(3H,s), 3.05 (2H,t,J=7.3 Hz), 4.35(2H,t,J=6.1 Hz), 7.51(2H,m), 7.65-7.73 (1H,m), 8.01(2H,d,J=7.2 Hz), 8.95(2H,br).

Reference Synthetic Example 33

2-[(Ethoxycarbonyl)(methyl)amino]ethyl ethyl carbonate

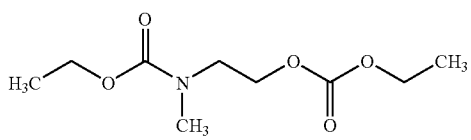

To a solution of 2-(methylamino)ethanol (100 g) in ethyl acetate (1000 mL) was added pyridine (222 mL), and added dropwise ethyl chlorocarbonate (240 mL) over 2 hrs under ice-cooling. After the addition, the reaction solution was stirred at room temperature for 18 hrs. To the solution was added water (300 mL), and the ethyl acetate layer was separated. The ethyl acetate layer was washed with 1 N hydrochloric acid (200 mL) and saturated brine (200 mL), and dried over anhydrous sodium sulfate, followed by concentrating under reduce pressure. The residue was distilled under reduce pressure to give title compound (180 g) as colorless fraction having boiling point of 95-100° C. (pressure: 0.1-0.2 mmHg).

$^1$H-NMR(CDCl$_3$): 1.20-1.40(6H,m), 2.97(3H,s), 3.50-3.60(2H,m), 4.05-4.35(6H,m).

Reference Synthetic Example 34

2-[(Chlorocarbonyl)(methyl)amino]ethyl ethyl carbonate

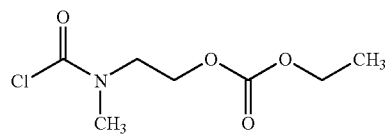

To a solution of 2-[(ethoxycarbonyl) (methyl)amino]ethyl ethyl carbonate (150 g) obtained in Reference Synthetic Example 33 in acetonitrile (1500 mL) was added phosphorus oxychloride (200 mL), and refluxed for 4 days. The reaction solution was concentrated under reduced pressure, and the residue was added little by little with stirring to a mixture of water (500 mL), ice (700 g) and ethyl acetate (300 mL). Stirring 1 minute, saturated brine (500 mL) was added thereto, and and extracted with ethyl acetate (500 mL). The ethyl acetate layer was washed sequentially with saturated brine (300 mL), saturated aqueous solution of sodium bicarbonate (300 mL) and saturated brine (300 mL), and dried over anhydrous sodium sulfate, followed by concentrating under reduce pressure. The residue was distilled under reduce pressure to give title compound (77 g) as colorless fraction having boiling point of 100-105° C. (pressure: 0.1-0.2 mmHg).

$^1$H-NMR(CDCl$_3$): 1.33(3H,t,J=7.2 Hz), 3.12(3H×0.4,s), 3.22(3H×0.6,s), 3.68(2H×0.6,t,J=4.8 Hz), 3.78(2H×0.4,t, J=4.8 Hz), 4.23(2H,q,J=7.2 Hz), 4.30-4.40(2H,m).

Reference Synthetic Example 35 tert-Butyl 4-hydroxybutylcarbamate

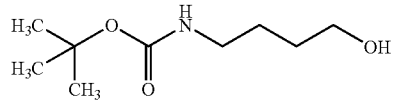

To a mixture of 4-aminobutanol (3.57 g) and ethyl acetate (9 mL) was added dropwise a mixture of di-tert-butyl dicarbonate (8.73 g) and ethyl acetate (1 mL) under ice-cooling. The reaction solution was stirred at room temperature for 24 hrs, and concentrated under reduced pressure. The residue was dissolved in ethyl acetate (200 mL), and washed with water (50 mL), 1 N hydrochloric acid (40 mL), water (30 mL), and saturated brine (30 mL), followed by drying over anhydrous magnesium sulfate. The solution was concentrated under reduced pressure to give title compound as colorless oil (7.54 g).

$^1$H-NMR(CDCl$_3$): 1.44(9H,s), 1.47-1.61(4H,m), 3.07-3.22(2H,m), 3.61-3.76(2H,m), 4.62(1H,bs).

Reference Synthetic Example 36

4-[(tert-Butoxycarbonyl)amino]butyl acetate

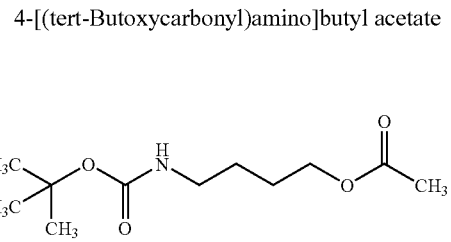

To a mixture of tert-butyl 4-hydroxybutylcarbamate (3.83 g) obtained in Reference Synthetic Example 35 and ethyl acetate (20 mL) were added pyridine (1.80 mL) and acetic anhydride (2.27 g), and stirred at room temperature for 19 hrs. To the reaction solution was added ethyl acetate (100 mL), and washed with water (50 mL), aqueous solution of copper sulfate (30 mL), water (30 mL) and saturated brine (30 mL), followed by drying over anhydrous magnesium sulfate. The solution was concentrated under reduced pressure to give title compound as colorless oil (4.55 g).

$^1$H-NMR(CDCl$_3$): 1.44(9H,s), 1.51-1.69(4H,m), 2.05(3H,s), 3.15(2H,m), 4.07(2H,t,J=6.5 Hz), 4.55(1H,bs).

Reference Synthetic Example 37

4-(Methylamino)butyl acetate hydrochloride

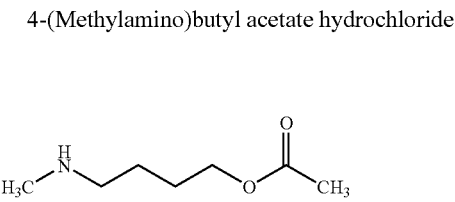

To a solution of 4-[(tert-butoxycarbonyl)amino]butyl acetate (4.50 g) obtained in Reference Synthetic Example 36 and methyl iodide (4.85 mL) in N,N-dimethylformamide (20 mL) was added sodium hydride (60% oil, 0.94 g) under ice-cooling. After stirring at room temperature for 4 hrs, the reaction solution was poured into ice-aqueous solution of ammonium chloride. The solution was extracted with diethyl ether (120 mL), and the diethyl ether layer was washed with saturated brine (30 mL), followed by drying over anhydrous magnesium sulfate. After concentrating under reduced pressure, the residue was purified with silica gel column chromatography (eluted with ethyl acetate:hexane=1:9.) To the purified material was added 4N hydrogen chloride-ethyl acetate solution (20 mL), and stirred at room temperature for 2 hrs. To the solution was added diethyl ether (40 mL), and the depositting solid was collected by filtration. The solid was dried under reduced pressure to give title compound as white solid (2.28 g).

$^1$H-NMR(DMSO-d$_6$): 1.58-1.70(4H,m), 2.01(3H,s), 2.50(3H,s), 2.82-2.90(2H,m), 4.00(2H,t,J=6.0 Hz), 8.90(2H,br).

Reference Synthetic Example 38

4-[(tert-Butoxycarbonyl)amino]butyl ethyl carbonate

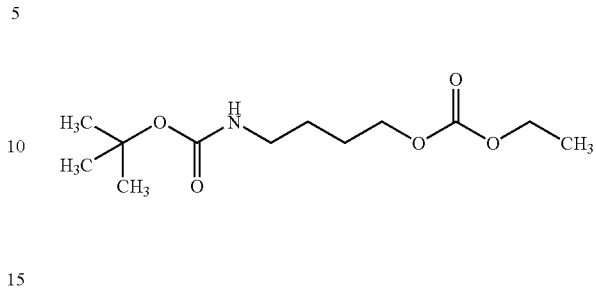

To a mixture of tert-butyl 4-hydroxybutylcarbamate (3.71 g) and ethyl acetate (20 mL) were added pyridine (1.71 g) and ethyl chlorocarbonate (2.25 g) under ice-cooling, and stirred at room temperature for 24 hrs. To the reaction solution was added ethyl acetate (100 mL), and washed with water (50 mL), aqueous solution of copper sulfate (30 mL), water (30 mL) and saturated brine (30 mL), followed by drying over anhydrous magnesium sulfate. The solution was concentrated under reduced pressure to give title compound as colorless oil (4.92 g).

$^1$H-NMR(CDCl$_3$): 1.31(3H,t,J=7.1 Hz), 1.44(9H,s), 1.46-1.80(4H,m), 3.15(2H,m), 4.11-4.25(4H,m), 4.54(1H,bs).

Reference Synthetic Example 39

Ethyl 4-(methylamino)butyl carbonate hydrochloride

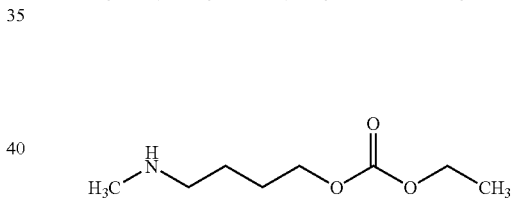

To a solution of 4-[(tert-butoxycarbonyl)amino]butyl ethyl carbonate (4.90 g) obtained in Reference Synthetic Example 38 and methyl iodide (4.67 mL) in N,N-dimethylformamide (20 mL) was added sodium hydride (60% oil, 0.90 g) under ice-cooling. After stirring at room temperature for 6 hrs, the reaction solution was poured into ice-aqueous solution of ammonium chloride, and extracted with diethyl ether (120 mL). The diethyl ether layer was washed with saturated brine (30 mL), and dried over anhydrous magnesium sulfate. After concentrating under reduced pressure, the residue was purified with silica gel column chromatography (eluted with ethyl acetate:hexane=1:9). To the purified material was added 4N hydrogen chloride-ethyl acetate solution (20 mL), and stirred at room temperature for 2 hrs. To the solution was added diethyl ether (40 mL), and the depositting solid was collected by filtration. The solid was dried under reduced pressure to give title compound as white solid (2.86 g).

$^1$H-NMR(DMSO-d$_6$): 1.21(3H,t,J=7.1 Hz), 1.51-1.73(4H,m), 2.50(3H,s), 2.82-2.94(2H,m), 4.05-4.15(4H,m), 8.88(2H,br).

Reference Synthetic Example 40 tert-Butyl 3-hydroxypropylcarbamate

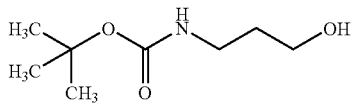

To a mixture of 3-aminopropanol (7.51 g) and ethyl acetate (30 mL) was added dropwise a mixture of di-tert-butyl dicarbonate (21.8 g) and ethyl acetate (3 mL) under ice-cooling. The reaction solution was stirred at room temperature for 22 hrs, and concentrated under reduced pressure. The residue was dissolved in ethyl acetate (200 mL), and washed with water (80 mL), 1 N hydrochloric acid (60 mL), water (50 mL), and saturated brine (50 mL), followed by drying over anhydrous magnesium sulfate. The solution was concentrated under reduced pressure to give title compound as colorless oil (16.01 g).
$^1$H-NMR(CDCl$_3$): 1.45(9H,s), 1.62-1.70(2H,m), 3.24(2H, q,J=6.6 Hz), 3.66(2H,q,J=5.1 Hz), 4.73(1H,bs).

Reference Synthetic Example 41

3-[(tert-Butoxycarbonyl)amino]propyl acetate

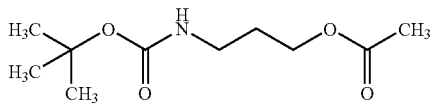

To a mixture of tert-butyl 3-hydroxypropylcarbamate (8.00 g) obtained in Reference Synthetic Example 40 and ethyl acetate (50 mL) were added pyridine (4.06 mL) and acetic anhydride (5.13 g), and stirred at room temperature for 21 hrs. To the reaction solution was added ethyl acetate (200 mL), and washed with water (100 mL), aqueous solution of copper sulfate (40 mL), water (60 mL) and saturated brine (60 mL), followed by drying over anhydrous sodium sulfate. The solution was concentrated under reduced pressure to give title compound as colorless oil (8.34 g).
$^1$H-NMR(CDCl$_3$): 1.44(9H,s), 1.77-1.86(2H,m), 2.06(3H, s), 3.20(2H,q,J=6.3 Hz), 4.12(2H,t,J=6.3 Hz), 4.67(1H,bs).

Reference Synthetic Example 42

3-(methylamino)propyl acetate hydrochloride

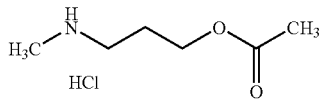

To a solution of 3-[(tert-butoxycarbonyl)amino]propyl acetate (17.28 g) obtained in Reference Synthetic Example 41 and methyl iodide (19.8 mL) in N,N-dimethylformamide (80 mL) was added sodium hydride (60% oil, 3.82 g) under ice-cooling. After stirring at room temperature for 15 hrs, the reaction solution was poured into ice-aqueous solution of ammonium chloride, and extracted with diethyl ether (300 mL). The diethyl ether layer was washed with saturated brine (100 mL), and dried over anhydrous sodium sulfate. After concentrating under reduced pressure, the residue was purified with silica gel column chromatography (eluted with ethyl acetate:hexane=1:8). To the purified material was added 4N hydrogen chloride-ethyl acetate solution (40 mL), and stirred at room temperature for 2 hrs. To the solution was added diethyl ether (100 mL), and the depositting solid was collected by filtration. The solid was dried under reduced pressure to give title compound as white solid (2.93 g).
$^1$H-NMR(DMSO-d$_6$): 1.85-1.97(2H,m), 2.02(3H,s), 2.50 (3H,s), 2.87-2.96(2H,m), 4.06(2H,t,J=6.3 Hz), 8.87(2H,br).

Reference Synthetic Example 43

3-[(tert-Butoxycarbonyl)amino]propyl ethyl carbonate

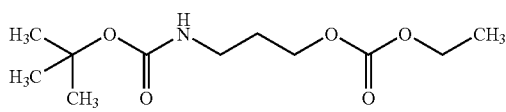 [SMILES: CCOC(=O)OCCCNC(=O)OC(C)(C)C]

To a mixture of tert-butyl 3-hydroxypropylcarbamate (8.00 g) obtained in Reference Synthetic Example 40 and ethyl acetate (50 mL) were added pyridine (4.06 mL) and ethyl chlorocarbonate (5.95 g) under ice-cooling, and stirred at room temperature for 24 hrs. To the reaction solution was added ethyl acetate (100 mL), and washed with water (50 mL), aqueous solution of copper sulfate (30 mL), water (30 mL) and saturated brine (30 mL), followed by drying over anhydrous sodium sulfate. The solution was concentrated under reduced pressure to give title compound as colorless oil (9.31 g).
$^1$H-NMR(CDCl$_3$): 1.31(3H,t,J=7.1 Hz), 1.44(9H,s), 1.82-1.90(2H,m), 3.22(2H,t,J=6.3 Hz), 4.15-4.23(4H,m), 4.68(1H,bs).

Reference Synthetic Example 44

Ethyl 3-(methylamino)propyl carbonate hydrochloride

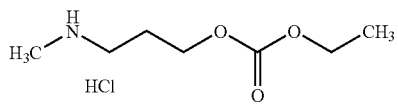

To a solution of 3-[(tert-butoxycarbonyl)amino]propyl ethyl carbonate (9.31 g) obtained in Reference Synthetic Example 43 and methyl iodide (9.00 mL) in N,N-dimethylformamide (40 mL) was added sodium hydride (60% oil, 1.82 g) under ice-cooling. After stirring at room temperature for 12 hrs, the reaction solution was poured into ice-aqueous solution of ammonium chloride, and extracted with diethyl ether (200 mL). The diethyl ether layer was washed with saturated brine (100 mL), and dried over anhydrous sodium sulfate. After concentrating under reduced pressure, the residue was purified with silica gel column chromatography (eluted with ethyl acetate:hexane=1:8). To the purified material was added 4N hydrogen chloride-ethyl acetate solution (40 mL), and stirred at room temperature for 2 hrs. To the solution was added diethyl ether (200 mL), and the depositing solid was collected by filtration. The solid was dried under reduced pressure to give title compound as white solid (4.98 g).

$^1$H-NMR(DMSO-d$_6$): 1.21(3H,t,J=7.1 Hz), 1.91-2.00(2H, m), 2.50(3H,s), 2.88-2.98(2H,m), 4.08-4.16(4H,m), 8.90(2H,br).

Reference Synthetic Example 45 tert-Butyl (2,3-hydroxypropyl)methylcarbamate

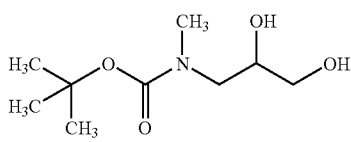

To a mixture of 3-(methylamino)-1,2-propanediol (24.5 g) and ethyl acetate (50 mL) was added dropwise a mixture of di-tert-butyl dicarbonate (51.4 g) and ethyl acetate (10 mL) under ice-cooling. The reaction solution was stirred at room temperature for 15 hrs, and concentrated under reduced pressure. The residue was dissolved in ethyl acetate (150 mL), and washed with water (80 mL), 1 N hydrochloric acid (60 mL), water (50 mL), and saturated brine (50 mL), followed by drying over anhydrous sodium sulfate. The solution was concentrated under reduced pressure to give title compound as colorless oil (26.9 g).

$^1$ H-NMR(CDCl$_3$): 1.47(9H,s), 2.92(3H,s), 3.20-3.36(2H, m), 3.41(2H,bs), 3.50-3.62(2H,m), 3.73-3.88(1H,m).

Reference Synthetic Example 46

3-(Methylamino)propan-1,2-diyl diacetate hydrochloride

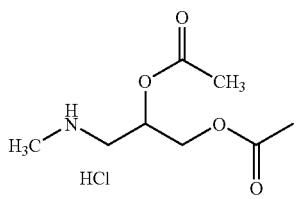

To a mixture of tert-butyl (2,3-hydroxypropyl)methylcarbamate (10.26 g) obtained in Reference Synthetic Example 45 and ethyl acetate (50 mL) were added pyridine (10.11 mL) and acetic anhydride (12.76 g), and stirred at room temperature for 24 hrs. To the reaction solution was added ethyl acetate (300 mL), and washed with water (150 mL), aqueous solution of copper sulfate (100 mL), water (100 mL) and saturated brine (100 mL), followed by drying over anhydrous sodium sulfate. After concentrating under reduced pressure, the residue was purified with silica gel column chromatography (eluted with ethyl acetate:hexane=1:8). To the purified material was added 4N hydrogen chloride-ethyl acetate solution (40 mL), and stirred at room temperature for 3 hrs. To the solution was added diethyl ether (100 mL), and the depositing solid was collected by filtration. The solid was dried under reduced pressure to give title compound as white solid (2.76 g).

$^1$H-NMR(DMSO-d$_6$): 2.03(3H,s), 2.07(3H,s), 2.55(3H,s), 3.18-3.22(2H,m), 4.09-4.28(2H,m), 5.20-5.27(1H,m), 9.01(2H,br).

Reference Synthetic Example 47

Diethyl 3-(methylamino)propan-1,2-diyl biscarbonate hydrochloride

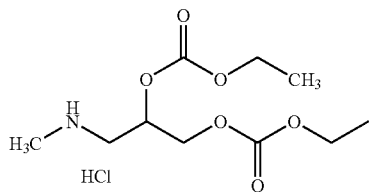 [SMILES: CCOC(=O)OCC(CNC)OC(=O)OCC ; Cl]

To a mixture of tert-butyl (2,3-hydroxypropyl)methylcarbamate (15.53 g) obtained in Reference Synthetic Example 45 and ethyl acetate (100 mL) were added pyridine (18.35 mL) and ethyl chlorocarbonate (24.62 g) under ice-cooling, and stirred at room temperature for 96 hrs. To the reaction solution was added ethyl acetate (300 mL), and washed with water (150 mL), aqueous solution of copper sulfate (100 mL), water (100 mL) and saturated brine (100 mL), followed by drying over anhydrous sodium sulfate. After concentrating under reduced pressure, the residue was purified with silica gel column chromatography (eluted with ethyl acetate:hexane=1:6). To the purified material was added 4N hydrogen chloride-ethyl acetate solution (80 mL), and stirred at room temperature for 3 hrs. To the solution was added diethyl ether (200 mL), and the depositing solid was collected by filtration. The solid was dried under reduced pressure to give title compound as white solid (5.93 g).

$^1$H-NMR(DMSO-d$_6$): 1.20-1.28(6H,m), 2.57(3H,s), 3.12-3.28(2H,m), 4.10-4.43(6H,m), 5.-13-5.22(1H,m), 9.14(2H, br).

Reference Synthetic Example 48

2-Ethoxyethyl 2-(methylamino)ethyl carbonate hydrochloride

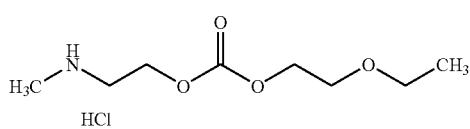

To a solution of bis(trichloromethyl) carbonate (2.97 g) in tetrahydrofuran (20 mL) was added dropwise a solution of 2-ethoxyethanol (1.80 g) in tetrahydrofuran (10 mL) under ice-cooling. Then, a solution of pyridine (2.43 mL) in tetrahydrofuran (10 mL) was added dropwise thereto, and stirred at room temperature for 2 hrs. The reaction solution was concentrated under reduced pressure, and to the residue was added water (50 mL), and extracted with ethyl acetate (50 mL). The ethyl acetate layer was washed with 0.2 N hydrochloric acid (20 mL) and saturated brine (50 mL), and dried over anhydrous magnesium sulfate. The solution was concentrated under reduced pressure to give 2-ethoxyethyl chlorocarbonate (1.29 g). To a solution of tert-butyl 2-hydroxyethyl (methyl)carbamate (1.23 g) obtained in Reference Synthetic Example 1 in tetrahydrofuran (15 mL) was added pyridine (0.68 mL), then a solution of 2-ethoxyethyl chlorocarbonate obtained above in tetrahydrofuran (5 mL) was added dropwise thereto, and stirred at room temperature for 3 days. The reaction solution was concentrated under reduced pressure, and water (50 mL) was added thereto, and then, extracted with ethyl acetate (50 mL). The ethyl acetate layer was washed with 5% aqueous solution of citric acid (50 mL) and saturated saline (50 mL), and dried over anhydrous magnesium sulfate, followed by concentrating under reduced pressure. The residue was purified with silica gel column chromatography (eluted with ethyl acetate:hexane=1:5, then 2:3). The purified material was dissolved in diethyl ether (3 mL), and added 4N hydrogen chloride-ethyl acetate solution (3 mL). After stirring at room temperature overnight, the depositing solid was collected by filtration, and dried under reduced pressure to give title compound as white solid (0.94 g).

$^1$H-NMR(DMSO-$d_6$): 1.10(3H,t,J=7.0 Hz), 2.57(3H,s), 3.18-3.25(2H,m), 3.44(2H,q,J=7.0 Hz), 3.56-3.60(2H,m), 4.19-4.24(2H,m), 4.30-4.37(2H,m), 8.79(2H,br).

Reference Synthetic Example 49

3-Methoxypropyl 2-(methylamino)ethyl carbonate hydrochloride

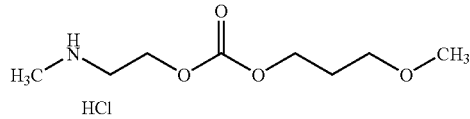

To a mixture of lithium aluminium hydride (2.85 g) and diethyl ether (100 mL) was slowly added dropwise a solution of methyl 3-methoxypropanoate (11.8 g) in tetrahydrofuran (50 mL). After stirring at room temperature for 1 hr, the reaction solution was ice-cooled again, and water (3 mL) and 10% aqueous solution of sodium hydroxide (3 mL) were added dropwise. The reacton solution was warmed to room temperature, and water (9 mL) was added dropwise, followed by stirring for a while. The precipitate was filtered off, and the filtrate was concentrated under reduced pressure to give 3-methoxypropanol as colorless oil (7.64 g).

$^1$H-NMR(CDCl$_3$): 1.83(2H,quintet,J=5.8 Hz), 2.43(1H,t,J=5.3 Hz), 3.36(3H,s), 3.57(2H,t,J=6.0 Hz), 3.77(2H,q,J=5.5 Hz).

To a solution of bis(trichloromethyl) carbonate (4.45 g) in tetrahydrofuran (50 mL) was added dropwise N-ethyldiisopropylamine (5.75 mL) under ice-cooling. After stirring for a while, a solution of 3-methoxypropanol obtained above (2.70 g) in tetrahydrofuran (15 mL) was added dropwise thereto. The reaction solution was stirred under ice-cooling for 30 minutes, and at room temperature for 1 day. The reaction solution was concentrated under reduced pressure, and to the residue was added dilute hydrochloric acid (50 mL), and extracted with ethyl acetate (80 mL). The ethyl acetate layer was washed with 0.2 N hydrochloric acid (30 mL) and saturated brine (30 mL), and dried over anhydrous magnesium sulfate. The solution was concentrated under reduced pressure to give 3-methoxypropyl chlorocarbonate (4.39 g). To a solution of tert-butyl 2-hydroxyethyl(methyl)carbamate (1.75 g) obtained in Reference Synthetic Example 1 in tetrahydrofuran (20 mL) was added pyridine (0.97 mL), then a solution of 3-methoxypropyl chlorocarbonate obtained above (1.83 g) in tetrahydrofuran (5 mL) was added dropwise thereto, and stirred at room temperature for 2 hrs. A solution of pyridine (0.65 mL) and 3-methoxypropyl chlorocarbonate (1.22 g) in tetrahydrofuran (5 mL) was further added, stirred for 1 hr, and the reaction solution was concentrated under reduced pressure. To the residue was added water (50 mL), and extracted with ethyl acetate (80 mL). The ethyl acetate layer was washed with 5% aqueous solution of citric acid (50 mL) and saturated saline (50 mL), and dried over anhydrous magnesium sulfate, followed by concentrating under reduced pressure. The residue was purified with silica gel column chromatography (eluted with ethyl acetate:hexane=1:9, then 3:7). The purified material (3.40 g) was dissolved in diethyl ether (5 mL), and added 4N hydrogen chloride-ethyl acetate solution (5 mL). After stirring at room temperature overnight, the reaction solution was concentrated under reduced pressure. By adding diethyl ether to crystallize, the title compound was obtained as colorless solid (2.06 g).

$^1$H-NMR(DMSO-$d_6$): 1.78-1.90(2H,m), 2.54(3H,s), 3.15-3.25(2H,m), 3.23(3H,s), 3.33-3.42(2H,m), 4.16(2H,t,J=6.0 Hz), 4.36(2H,t,J=6.0 Hz), 9.27(2H,br).

Reference Synthetic Example 50

2-(Methylamino)ethyl N,N-dimethylglycinate dihydrochloride

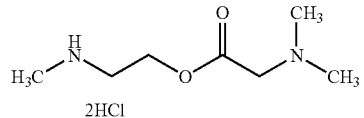

A mixture of tert-butyl 2-hydroxyethyl(methyl)carbamate (3.50 g) obtained in Reference Synthetic Example 1, N,N-dimethylglycine hydrochloride (5.29 g), 1-ethyl-3-[3-(dimethylamino)propyl]carbodiimide hydrochloride (7.67 g), triethylamine (5.58 mL), 4-dimethylaminopyridine (1.22 g) and N,N-dimethylformamide (50 mL) was stirred at room temperature overnight. The reaction solution was concentrated under reduced pressure, and to the residue was added saturated aqueous solution of sodium bicarbonate (50 mL), and extracted with ethyl acetate (100 mL). The ethyl acetate layeer was washed with saturated brine (50 mL), and dried over anhydrous magnesium sulfate, followed by concentrating under reduced pressure. The residue was purified with silica gel column chromatography (eluted with methanol:ethyl acetate=5:95, then 20:80). To the purified material (2.46 g) was added 1 N hydrochloric acid (24 mL), and stirred at room temperature overnight. The reaction solution was concentrated under reduced pressure to give title compound as colorless solid (2.14 g).

$^1$H-NMR(DMSO-$d_6$): 2.52(3H,s), 2.85(6H,s), 3.20(2H,m), 4.30(2H,s), 4.43-4.49(2H,m), 9.60(2H,br), 10.81(1H,br).

Reference Synthetic Example 51

S-[2-(Methylamino)ethyl]thioacetate hydrochloride

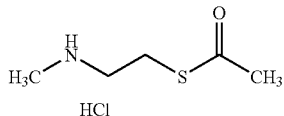

To a solution of tert-butyl 2-hydroxyethyl(methyl)carbamate (3.50 g) obtained in Reference Synthetic Example 1, thioacetic acid (1.72 mL) and triphenylphosphine (7.87 g) in tetrahydrofuran (50 mL) was slowly added dropwise a solution of diisopropyl azodicarboxylate (5.91 mL) in tetrahydrofuran (10 mL) under ice-cooling. The reaction solution was stirred under ice-cooling for 1 hr and at room temperature for 2 hrs. The reaction solution was ice-cooled again, and a solution of triphenylphosphine (7.87 g) and diisopropyl azodicarboxylate (5.91 mL) in tetrahydrofuran (10 mL) was further added thereto under ice-cooling, and stirred under ice-cooling for 30 minutes. Thioacetic acid (1.14 mL) was further added, and stirred under ice-cooling for 30 minutes and further at room temperature overnight. The reaction solution was concentrated under reduced pressure, and to the residue were added hexane and diisopropyl ether. The precipitate was filtered off, and the filtrate was concentrated under reduced pressure. After repeating this operation again, saturated aqueous solution of sodium bicarbonate (50 mL) was added, and extracted with ethyl acetate (100 mL). The ethyl acetate layer was washed with saturated brine (50 mL), and dried over anhydrous magnesium sulfate, followed by concentrating under reduced pressure. The residue was purified with silica gel column chromatography (eluted with ethyl acetate:hexane=5:95, then 15:85). To the purified material (4.47 g) was added 4N hydrogen chloride-ethyl acetate solution (10 mL), and stirred at room temperature overnight. The reaction solution was concentrated under reduced pressure, and to the residue were added ethyl acetate and diethyl ether to crystallize, which gave title compound as pale yellow solid (1.79 g). $^1$H-NMR(DMSO-d$_6$): 2.38(3H,s), 2.52(3H,s), 2.96-3.08(2H,m), 3.12-3.20(2H,m), 9.35(2H,br).

Reference Synthetic Example 52

Ethyl 2-[2-(methylamino)ethoxy]ethyl carbonate hydrochloride

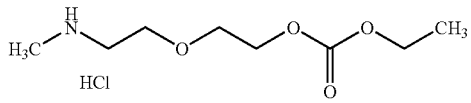

To a mixture of 2-(2-aminoethoxy)ethanol (99.52 g) and ethyl acetate (200 mL) was added dropwise a mixture of di-tert-butyl dicarbonate (208.57 g) and ethyl acetate (50 mL) under ice-cooling. The reaction solution was stirred at room temperature for 60 hrs, and concentrated under reduced pressure. The residue was dissolved in ethyl acetate (500 mL), and washed with water (200 mL), 1 N hydrochloric acid (200 mL), water (300 mL), and saturated brine (300 mL), followed by drying over anhydrous sodium sulfate. The solution was concentrated under reduced pressure to give tert-butyl [2-(2-hydroxyethoxy)ethyl]carbamate as colorless oil (169.2 g).

$^1$H-NMR(cdcl$_3$): 1.45(9H,s), 3.33(2H,q,J=5.1 Hz), 3.54-3.59(4H,m), 3.74(2H,q,J=5.1 Hz), 4.88(2H,bs).

To a mixture of tert-butyl [2-(2-hydroxyethoxy)ethyl]carbamate (53.93 g) obtained above and ethyl acetate (350 mL) were added pyridine (53.78 mL) and ethyl chlorocarbonate (70.57 g) under ice-cooling, and stirred at room temperature for 96 hrs. To the reaction solution was added ethyl acetate (500 mL), and washed with water (500 mL), aqueous solution of copper sulfate (200 mL), water (300 mL) and saturated brine (300 mL), followed by drying over anhydrous sodium sulfate. The solution was concentrated under reduced pressure to give 2-[2-[(tert-butoxycarbonyl)amino]ethoxy]ethyl ethyl carbonate as colorless oil (93.19 g).

$^1$H-NMR(CDCl$_3$): 1.32(3H,t,J=7.2 Hz), 1.44(9H,s), 3.32(2H,t J=5.1 Hz), 3.54(2H,t J=5.1 Hz), 3.67-3.74(2H,m), 4.21(2H,q J=7.2 Hz), 4.26-4.31(2H,m), 4.91(1H,bs).

To a solution of 2-[2-[(tert-butoxycarbonyl)amino]ethoxy]ethyl ethyl carbonate (93.15 g) obtained above and methyl iodide (83.6 mL) in N,N-dimethylformamide (350 mL) was added sodium hydride (60% oil, 16.12 g) under ice-cooling. After stirring at room temperature for 24 hrs, the reaction solution was poured into ice-aqueous solution of ammonium chloride, and extracted with diethyl ether (800 mL). The diethyl ether layer was washed with saturated brine (300 mL), and dried over anhydrous magnesium sulfate. After concentrating under reduced pressure, the residue was purified with silica gel column chromatography (eluted with ethyl acetate:hexane=1:8). To the purified material was added 4N hydrogen chloride-ethyl acetate solution (300 mL), and stirred at room temperature for 2 hrs. To the solution was added diethyl ether (300 mL), and the depositting solid was collected by filtration. The solid was dried under reduced pressure to give title compound as white solid (33.21 g).

$^1$H-NMR(DMSO-d$_6$): 1.21(3H,t,J=7.2 Hz), 2.51(3H,s), 3.02-3.09(2H,m), 3.65-3.72(4H,m), 4.12(2H,q,J=7.2 Hz), 4.22(2H,t,J=4.5 Hz), 9.06(2H,br).

Reference Synthetic Example 53

Ethyl 2-[methyl[[2-(methylamino)ethoxy]carbonyl]amino]ethyl carbonate hydrochloride

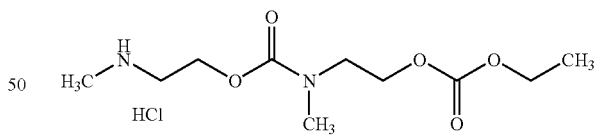

To a solution of bis(trichloromethyl) carbonate (11.87 g) in tetrahydrofuran (100 mL) was added dropwise a solution of pyridine (9.71 mL) in tetrahydrofuran (200 mL) under ice-cooling. After stirring for 30 minutes under ice-cooling, a solution of tert-butyl 2-hydroxyethyl(methyl)carbamate (17.52 g) obtained in Reference Synthetic Example 1 in tetrahydrofuran (20 mL) was added, and stirred at room temperature for 15 hrs. The reaction solution was concentrated under reduced pressure, and to the residue were added water (500 mL) and, anhydrous sodium sulfate. The mixture was filtered, and the filtrate was concentrated under reduced pressure. To the resulting residue were added a solution of 2-(methylamino)ethanol (5.00 g) in ethyl acetate (50 mL), and triethylamine (10.0 mL) under ice-cooling, and stirred at room temperature for 15 hrs. To the reaction solution was added ethyl acetate (300 mL), and washed with water (150 mL) and saturated saline (200 mL), and dried over anhydrous sodium sulfate. After concentrating under reduced pressure, to a mixture of the residue and ethyl acetate (100 mL) were added pyridine (2.91 mL) and ethyl chlorocarbonate (3.44 g), and stirred at room temperature for 48 hrs. To the reaction solution was added ethyl acetate (200 mL), and was washed with water (100 mL), aqueous solution of copper sulfate (50 mL), water (50 mL) and saturated brine (50 mL), followed by drying over anhydrous sodium sulfate. After concentrating under reduced pressure, the residue was purified with silica gel column chromatography (eluted with ethyl acetate:hexane=1:3). To the purified material was added 4N hydrogen chloride-ethyl acetate solution (30 mL), and stirred at room temperature for 3 hrs. Diethyl ether (100 mL) was added, and the depositted solid was collected by filtration. The solid was dried under reduced pressure to give title compound as white solid (2.90 g).

$^1$H-NMR(DMSO-$d_6$): 1.21(3H,t,J=7.2 Hz), 2.57(3H,bs), 2.86(1.5H,s), 2.93(1.5H,s), 3.16(2H,bs), 3.34(1H,bs), 3.48 (1H,t,J=5.1 Hz), 3.58(1H,t,J=5.1 Hz), 4.12(2H,q,J=7.2 Hz), 4.16-4.24(4H,m), 8.94(1H,br).

Reference Synthetic Example 54

2-(Methylamino)ethyl 1-methylpiperidine-4-carboxylate dihydrochloride

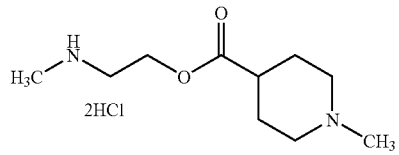

A mixture of ethyl piperidine-4-carboxylate (4.72 g), methyl iodide (2.24 mL), potassium carbonate (8.29 g) and acetonitrile (50 mL) was stirred at room temperature for 2 hrs. The reaction solution was concentrated under reduced pressure, and water (150 mL) was added thereto, followed by extracting with ethyl acetate (150 mL). The ethyl acetate layer was washed with saturated brine (100 mL), and dried over anhydrous magnesium sulfate, then concentrated under reduced pressure. To the residue (2.64 g) was added 1 N aqueous solution of sodium hydroxide (20 mL), and stirred at room temperature overnight. To the reaction solution was added 1 N hydrochloric acid (20 mL) to neutralize, and concentrated under reduced pressure. To the residue was added ethanol, and the precipitate was filtered off, and the filtrate was concentrated under reduced pressure. After repeating this operation again, to the residue were added ethanol and ethyl acetate to crystallize, which gave 1-methylpiperidine-4-carboxylic acid as colorless solid (1.79 g).

$^1$H-NMR(CD$_3$OD) 1.80-1.98(2H,m), 2.00-2.14(2H,m), 2.28-2.42(1H,m), 2.78(3H,s), 2.88-3.04(2H.m), 3.32-3.44 (2H.m).

A mixture of 1-methylpiperidine-4-carboxylic acid (1.72 g) obtained above, tert-butyl 2-hydroxyethyl(methyl)carbamate (1.75 g) obtained in Reference Synthetic Example 1, 1-ethyl-3-[3-(dimethylamino)propyl]carbodiimide (2.30 g), 4-dimethylaminopyridine (0.24 g) and acetonitrile (50 mL) was stirred at room temperature for 16 hrs. The reaction solution was concentrated under reduced pressure, and to the residue was added saturated aqueous solution of sodium bicarbonate (50 mL), and extracted with ethyl acetate (100 mL). The ethyl acetate layer was washed with saturated brine (50 mL), and dried over anhydrous magnesium sulfate, followed by concentrating under reduced pressure. The residue was purified with basic silica gel column chromatography (eluted with methanol:ethyl acetate=50:50, then 80:20). To the purified material (2.73 g) was added 1 N hydrochloric acid (25 mL), and stirred at room temperature overnight. The reaction solution was concentrated under reduced pressure, and isopropanol was added, then, concentrated again under reduced pressure. The precipitated crystals were collected by filtration to give title compound as colorless solid (1.72 g).

$^1$H-NMR(DMSO-$d_6$): 1.70-2.20(4H,m), 2.40-3.50(13H, m), 4.31(2H,m), 9.25(2H,br), 10.77(1H,br).

Reference Synthetic Example 55

2-[[4-(Aminocarbonyl)phenyl]amino]ethyl acetate

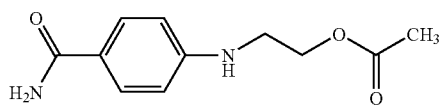 [SMILES: CC(=O)OCCNc1ccc(C(N)=O)cc1]

A mixture of 4-fluorobenzonitrile (6.06 g), 2-aminoethanol (3.71 g), potassium carbonate (8.29 g) and dimethylsulfoxide (50 mL) was stirred at 100° C. overnight. To the reaction solution was added water (200 mL), and extracted with ethyl acetate (200 mL×4). The ethyl acetate layer was washed with saturated brine (100 mL), and dried over anhydrous magnesium sulfate, then concentrated under reduced pressure. The residue was purified with silica gel column chromatography (eluted with ethyl acetate:hexane=30:70, then 50:50, then 80:20, then ethyl acetate) to give 4-[(2-hydroxyethyl)amino]benzonitrile as yellow solid (5.89 g).

$^1$H-NMR(CDCl$_3$): 2.04(1H,t,J=4.8 Hz), 3.33(2H,m), 3.86 (2H,q,J=4.8 Hz), 4.66(1H,br), 6.58(2H,d,J=8.7 Hz), 7.39 (2H,d,J=8.7 Hz).

A mixture of 4-[(2-hydroxyethyl)amino]benzonitrile obtained above (0.81 g), potassium hydroxide (1.12 g) and tert-butanol (20 mL) was stirred at 100° C. for 1 hr. To the reaction solution was added water (100 mL), and extracted with ethyl acetate (100 mL). The ethyl acetate layer was washed with saturated brine (80 mL), and dried over anhydrous magnesium sulfate, then concentrated under reduced pressure. To a solution of the residue (0.83 g), pyridine (0.49 mL) and 4-dimethylaminopyridine (0.061 g) in tetrahydrofuran (10 mL) was added a solution of acetic anhydride (0.57 mL) in tetrahydrofuran (1 mL). After stirring at room temperature for 1 hr, water (80 mL) was added, and extracted with ethyl acetate (100 mL). The ethyl acetate layer was washed with saturated brine (80 mL), and dried over anhydrous magnesium sulfate, then concentrated under reduced pressure. The residue was purified with silica gel column chromatography (eluted with ethyl acetate:hexane=30:70, then 60:40) to give title compound as colorless solid (0.68 g).

¹H-NMR(CDCl₃): 2.08(3H,s), 3.44(2H,q,J=5.6 Hz), 4.29 (2H,t,J=5.4 Hz), 4.48(1H,br), 6.59(2H,d,J=8.9 Hz), 7.43(2H, d,J=8.9 Hz)

Reference Synthetic Example 56

2-(Methylamino)ethyl 1-methyl-4-piperidinyl carbonate dihydrochloride

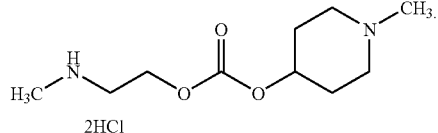

To a solution of N,N'-carbonyldiimidazole (3.36 g) in tetrahydrofuran (40 mL) was slowly added dropwise a solution of tert-butyl 2-hydroxyethyl(methyl)carbamate (3.30 g) obtained in Reference Synthetic Example 1 in tetrahydrofuran (10 mL) under ice-cooling. The reaction solution was stirred for 40 minutes under ice-cooling, and for 2 hrs at room temperature, and N,N'-carbonyldiimidazole (0.31 g) was added, and furtheer stirred for 3 days. The reaction solution was concentrated under reduced pressure, and to the residue was added ethyl acetate (150 mL), and washed with saturated brine (100 mL×2), water (50 mL×3) and saturated brine (50 mL), then dried over anhydrous magnesium sulfate, followed by concentrating under reduced pressure to give 2-[(tert-butoxycarbonyl)(methyl)amino]ethyl 1H-imidazole-1-carboxylate as colorless oil (5.24 g).

¹H-NMR(CDCl₃): 1.39(9H×0.5,s), 1.42(9H×0.5,s), 2.94 (3H,m), 3.63(2H,m), 4.51(2H,t,J=5.3 Hz), 7.06(1H,m), 7.42 (1H,m), 8.13(1H,s).

A mixture of 2-[(tert-butoxycarbonyl)(methyl)amino] ethyl 1H-imidazole-1-carboxylate (1.35 g), 1-methyl-4-piperidinol (1.38 g) and acetonitrile (20 mL) was stirred at room temperature overnight. 1-Methyl-4-piperidinol (0.92 g) was added, and further was stirred overnight. The reaction solution was concentrated under reduced pressure, and to the residue was added saturated aqueous solution of sodium bicarbonate (50 mL), and extracted with ethyl acetate (100 mL). The ethyl acetate was washed with saturated brine (50 mL), and dried over anhydrous magnesium sulfate, followed by concentrating under reduced pressure. To the residue (1.60 g) was added 1 N hydrochloric acid (12 mL), and stirred at room temperature overnight. The reaction solution was concentrated under reduced pressure, and to the residue were added water, isopropanol and ethyl acetate. The precipitated solid was collected by filtration to give title compound as colorless solid (1.09 g).

¹H-NMR(DMSO-d₆): 1.85-2.20(4H,m), 2.55(3H,s), 2.70 (3H×0.5,s), 2.73(3H×0.5,s), 2.90-3.50(6H,m), 4.38(2H,m), 4.65-5.00(1H,m), 9.21(2H,br), 11.10(1H,br).

Synthetic Example 1

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate

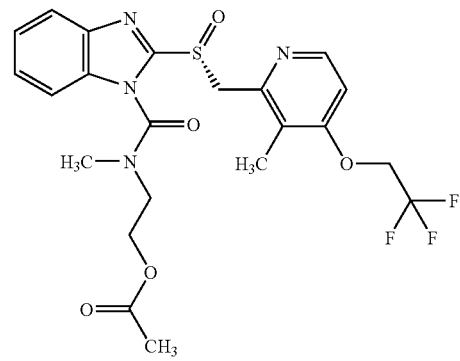 [SMILES: CC(=O)OCCN(C)C(=O)n1c([S@](=O)Cc2nccc(OCC(F)(F)F)c2C)nc2ccccc21]

To a solution of bis(trichloromethyl) carbonate (0.50 g) in tetrahydrofuran (20 mL) was added dropwise a solution of pyridine (0.40 mL) in tetrahydrofuran (1 mL) under ice-cooling. The reaction solution was stirred for 30 minutes under ice-cooling, and 2-(methylamino)ethyl acetate hydrochloride (0.77 g) obtained in Reference Synthetic Example 2 was added. A solution of triethylamine (0.70 mL) in tetrahydrofuran (1 mL) was added dropwise, and stirred at room temperature for 1 hr. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.84 mL) and 4-dimethylaminopyridine (catalytic amount), and stirred at 60° C. overnight. The reaction solution was concentrated under reduced pressure, and to the residue was added water (50 mL), and then, extracted with ethyl acetate (50 mL). The ethyl acetate layer was washed with saturated saline (50 mL), and dried over anhydrous magnesium sulfate. After concentrating under reduced pressure, the residue was purified with basic silica gel column chromatography (eluted with ethyl acetate:hexane=1:1, then ethyl acetate), and further purified with silica gel column chromatography (eluted with ethyl acetate:hexane=2:1, then ethyl acetate, then acetone:ethyl acetate=1:4, then 1:1) to give title compound as yellow amorphous solid (1.13 g).

¹H-NMR(CDCl₃): 2.10(3H,s), 2.24(3H,s), 3.09(3H,bs), 3.60-4.00(2H,br), 4.25-4.50(4H,m), 4.89(1H,d,J=13.3 Hz), 5.05(1H,d,J=13.3 Hz), 6.65(1H,d,J=5.5 Hz), 7.35-7.51(3H, m), 7.80-7.90(1H,m), 8.35(1H,d,J=5.5 Hz).

Synthetic Example 2

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl trimethylacetate

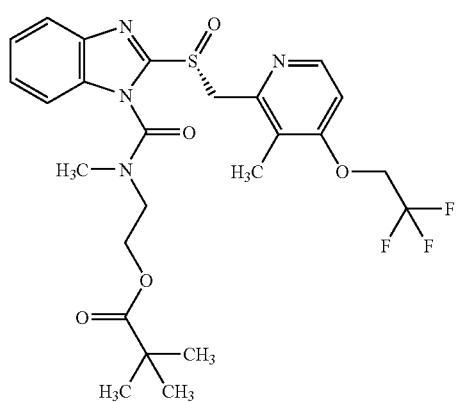 [SMILES: Cc1c(OCC(F)(F)F)ccnc1C[S@@](=O)c1nc2ccccc2n1C(=O)N(C)CCOC(=O)C(C)(C)C]

To a solution of bis(trichloromethyl) carbonate (0.50 g) in tetrahydrofuran (30 mL) was added dropwise a solution of pyridine (0.40 mL) in tetrahydrofuran (1 mL) under ice-cooling. The reaction solution was stirred for 1 hr under ice-cooling, and 2-(methylamino)ethyl trimethylacetate hydrochloride (0.98 g) obtained in Reference Synthetic Example 3 was added. A solution of triethylamine (0.70 mt) in tetrahydrofuran (1 mL) was added dropwise, and stirred at room temperature overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g), and stirred at 60° C. overnight. The reaction solution was concentrated under reduced pressure, and to the residue was added water (50 mL), and then, extracted with ethyl acetate (50 mL). The ethyl acetate layer was washed with saturated saline (50 mL), and dried over anhydrous magnesium sulfate. After concentrating under reduced pressure, the residue was purified with flash silica gel column chromatography (eluted with acetone:hexane=1:3, then 3:2). The purified material was crystallized from acetone-diisopropyl ether, and further recrystallized from acetone-diisopropyl ether to give title compound as colorless solid (1.01 g).

$^1$H-NMR(CDCl$_3$): 1.23(9H,s), 2.23(3H,s), 3.08(3H,bs), 3.40-4.30(2H,br), 4.30-4.50(4H,m), 4.80-5.20(2H,br), 6.64 (1H,d,J=5.7 Hz), 7.35-7.50(3H,m), 7.78-7.88(1H,m), 8.35 (1H,d,J=5.7 Hz).

Synthetic Example 3

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl cyclohexanecarboxylate

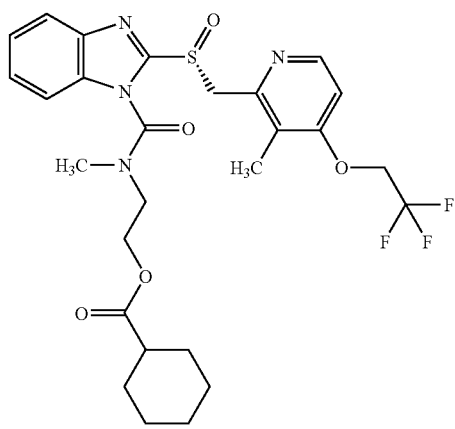 [SMILES: Cc1c(OCC(F)(F)F)ccnc1C[S@@](=O)c1nc2ccccc2n1C(=O)N(C)CCOC(=O)C1CCCCC1]

To a solution of bis(trichloromethyl) carbonate (0.50 g) in tetrahydrofuran (30 mL) was added dropwise a solution of pyridine (0.40 mL) in tetrahydrofuran (1 mL) under ice-cooling. The reaction solution was stirred for 30 minutes under ice-cooling, and 2-(methylamino)ethyl cyclohexanecarboxylate (1.11 g) obtained in Reference Synthetic Example 4 was added. A solution of triethylamine (0.70 mL) in tetrahydrofuran (1 mL) was added dropwise, and stirred at room temperature for 1 hr. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g), and stirred at 60° C. overnight. The reaction solution was concentrated under reduced pressure, and to the residue was added water (50 mL), and then, extracted with ethyl acetate (50 mL). The ethyl acetate layer was washed with saturated saline (50 mL), and dried over anhydrous magnesium sulfate. After concentrating under reduced pressure, the residue was purified with flash silica gel column chromatography (eluted with acetone:hexane=1:3, then 3:2). The purified material was crystallized from acetone-diisopropyl ether, and further recrystallized from acetone-diisopropyl ether to give title compound as colorless solid (1.11 g).

$^1$H-NMR(CDCl$_3$): 1.10-1.55(5H,m), 1.55-1.82(3H,m), 1.84-1.98(2H,m), 2.23(3H,s), 2.27-2.40(1H,m), 3.08(3H,bs), 3.40-4.30(2H,br), 4.30-4.50(4H,m), 4.80-5.15(2H,br), 6.64 (1H,d,J=5.4 Hz), 7.35-7.48(3H,m), 7.84(1H,d,J=6.9 Hz), 8.34(1H,d,J=5.4 Hz).

Synthetic Example 4

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl benzoate

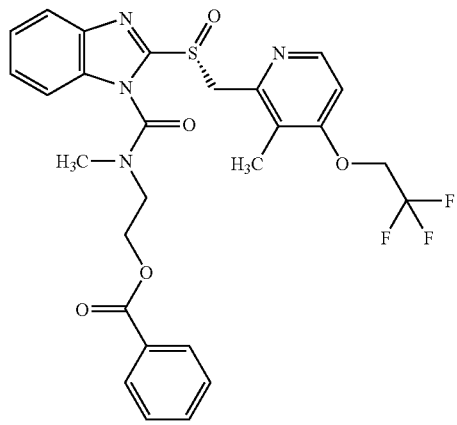 [SMILES: Cc1c(OCC(F)(F)F)ccnc1C[S@@](=O)c1nc2ccccc2n1C(=O)N(C)CCOC(=O)c1ccccc1]

To a solution of bis(trichloromethyl) carbonate (0.50 g) in tetrahydrofuran (30 mL) was added dropwise a solution of pyridine (0.40 mL) in tetrahydrofuran (1 mL) under ice-cooling. The reaction solution was stirred for 1 hr under ice-cooling, and 2-(methylamino)ethyl benzoate hydrochlride (1.08 g) obtained in Reference Synthetic Example 5 was added. A solution of triethylamine (0.70 mL) in tetrahydrofuran (1 mL) was added dropwise, and stirred at room temperature overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g), and stirred at 60° C. overnight. The reaction solution was concentrated under reduced pressure, and to the residue was added water (50 mL), and then, extracted with ethyl acetate (50 mL). The ethyl acetate layer was washed with saturated saline (50 mL), and dried over anhydrous magnesium sulfate. After concentrating under reduced pressure, the residue was purified with flash silica gel column chromatography (eluted with acetone:hexane=1:3, then 3:2). The purified material was crystallized from acetone-diethyl ether, and further recrystallized from acetone-diethyl ether to give title compound as colorless solid (1.09 g).

$^1$H-NMR(CDCl$_3$): 2.22(3H,s), 3.12(3H,bs), 3.50-4.30 (2H,br), 4.37(2H,q,J=7.8 Hz), 4.68(2H,m), 4.80-5.20(2H,br), 6.63(1H,d,J=5.7 Hz), 7.26-7.48(5H,m), 7.53-7.61(1H,m), 7.82(1H,d,J=8.1 Hz), 8.04(2H,d,J=7.2 Hz), 8.33(1H,d,J=5.7 Hz).

Synthetic Example 5

2-[Methyl[[2-[[[3-methyl-4-(2,2,2-trifluoroethoxy)-2-pyridyl]methyl]sulfinyl]-1H-benzimidazol-1-yl]carbonyl]amino]ethyl benzoate

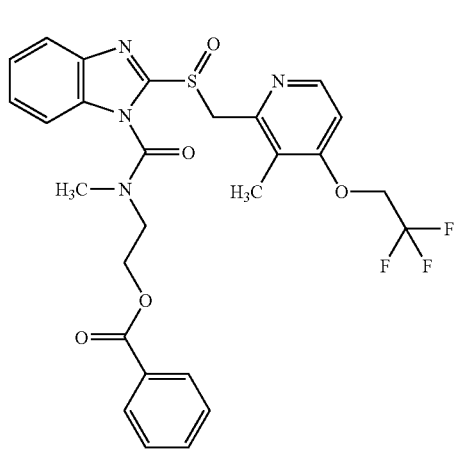 [SMILES: Cc1c(OCC(F)(F)F)ccnc1CS(=O)c1nc2ccccc2n1C(=O)N(C)CCOC(=O)c1ccccc1]

To a solution of bis(trichloromethyl) carbonate (0.99 g) in tetrahydrofuran (30 mL) was added dropwise a solution of pyridine (0.81 mL) in tetrahydrofuran (2 mL) under ice-cooling. The reaction solution was stirred for 30 minutes under ice-cooling, and 2-(methylamino)ethyl benzoate hydrochlride (2.16 g) obtained in Reference Synthetic Example 5 was added. A solution of triethylamine (1.39 mL) in tetrahydrofuran (2 mL) was added dropwise, and stirred at room temperature for 1 hr. The reaction solution was concentrated under reduced pressure, and to the residue were added ethyl acetate (100 mL) and water (100 mL), followed by stirring. The ethyl acetate layer was separated, and washed with saturated brine (50 mL), and dried over anhydrous magnesium sulfate. The solution was concentrated under reduced pressure, and the residue was dissolved in tetrahydrofuran (40 mL). To the solution were added 2-[[[3-methyl-4-(2,2,2-trifluoroethoxy)-2-pyridyl]methyl]sulfinyl]-1H-benzimidazole (2.90 g), triethylamine (2.20 mL) and 4-dimethylaminopyridine (0.096 g), and stirred at 60° C. for 2 hrs. The reaction solution was concentrated under reduced pressure, and to the residue were added ethyl acetate (150 mL) and water (80 mL), followed by stirring. The ethyl acetate layer was separated, and washed with saturated saline (50 mL), and then dried over anhydrous magnesium sulfate. After concentrating under reduced pressure, the residue was purified with silica gel column chromatography (eluted with ethyl acetate:hexane=1:1, then ethyl acetate). The purified material was recrystallized from acetone to give title compound as colorless solid (2.62 g).

$^1$H-NMR(CDCl$_3$): 2.22(3H,s), 3.13(3H,bs), 3.68-3.98 (2H,bm), 4.38(2H,q,J=7.8 Hz), 4.69(2H,m), 4.80-5.10(2H,bm), 6.64(1H,d,J=5.7 Hz), 7.27-7.48(5H,m), 7.59(1H,m), 7.83(1H,m), 8.06(2H,d,J=6.0 Hz), 8.35(1H,d,J=5.7 Hz).

Synthetic Example 6

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-methoxybenzoate

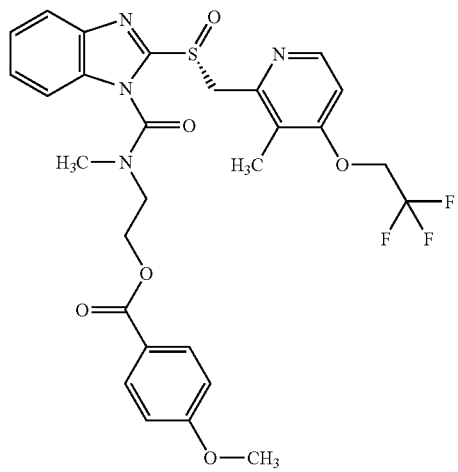 [SMILES: COc1ccc(C(=O)OCCN(C)C(=O)n2c([S@](=O)Cc3nccc(OCC(F)(F)F)c3C)nc3ccccc32)cc1]

To a solution of bis(trichloromethyl) carbonate (0.584 g) in tetrahydrofuran (18 mL) was added dropwise a solution of pyridine (0.49 mL) in tetrahydrofuran (1 mL) under ice-cooling. The reaction solution was stirred for 40 minutes under ice-cooling, and 2-(methylamino)ethyl 4-methoxybenzoate hydrochlride (1.48 g) obtained in Reference Synthetic Example 6 was added. A solution of triethylamine (0.84 mL) in tetrahydrofuran (1 mL) was added, and stirred at room temperature for 80 minutes. The reaction solution was concentrated under reduced pressure, and to the residue were added ethyl acetate (80 mL) and water (50 mL), followed by stirring. The ethyl acetate layer was separated, and washed with saturated brine (30 mL), and dried over anhydrous magnesium sulfate. The solution was concentrated under reduced pressure, and the residue was dissolved in tetrahydrofuran (25 mL). To the solution were added (R)-2-[[[3-methyl-4-(2,2,2-trifluoroethoxy)-2-pyridyl]methyl]sulfinyl]-1H-benzimidazole (1.55 g), triethylamine (1.17 mL) and 4-dimethylaminopyridine (0.051 g), and stirred at 60° C. for 3 hrs. The reaction solution was concentrated under reduced pressure, and to the residue were added ethyl acetate (150 mL) and water (50 mL), followed by stirring. The ethyl acetate layer was separated, and washed with saturated saline (50 mL), and then dried over anhydrous magnesium sulfate. After concentrating under reduced pressure, the residue was purified with silica gel column chromatography (eluted with ethyl acetate:hexane=1:1, then ethyl acetate). The purified material was recrystallized from ethyl acetate-hexane to give title compound as colorless solid (1.08 g).

$^1$H-NMR(CDCl$_3$): 2.22(3H,s), 3.11(3H,bs), 3.68-3.90 (2H,bm), 3.85(3H,s), 4.37(2H,q,J=7.9 Hz), 4.58-4.72(2H, m), 4.82-5.14(2H,bm), 6.63(1H,d,J=5.7 Hz), 6.91(2H,d, J=9.0 Hz), 7.27-7.40(3H,m), 7.82(1H,m), 7.99(2H,d,J=9.0 Hz), 8.33(1H,d,J=5.7 Hz).

Synthetic Example 7

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3-chlorobenzoate

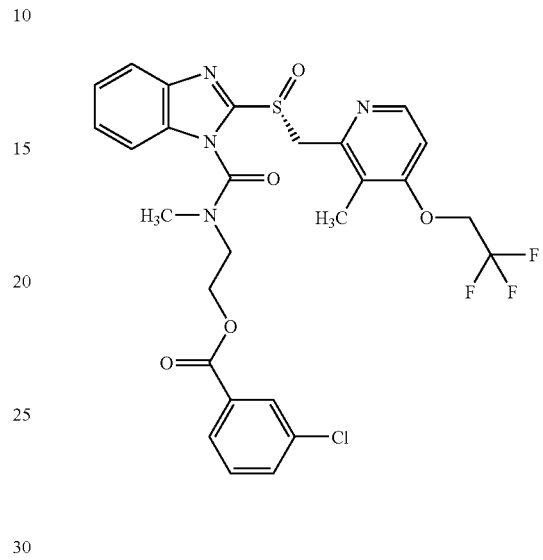

To a solution of bis(trichloromethyl) carbonate (0.582 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and 2-(methylamino)ethyl 3-chlorobenzoate hydrochlride (1.50 g) obtained in Reference Synthetic Example 7 was added. A solution of triethylamine (0.84 mL) in tetrahydrofuran (1 mL) was added, and stirred at room temperature for 2 hrs. The reaction solution was concentrated under reduced pressure, and to the residue were added ethyl acetate (80 mL) and water (40 mL), followed by stirring. The ethyl acetate layer was separated, and washed with saturated brine (25 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.44 g), triethylamine (1.09 mL) and 4-dimethylaminopyridine (0.048 g), and stirred at 60° C. for 3 hrs. The reaction solution was concentrated under reduced pressure, and to the residue were added ethyl acetate (80 mL) and water (40 mL), followed by stirring. The ethyl acetate layer was separated, and washed with saturated saline (30 mL), and then dried over anhydrous magnesium sulfate. After concentrating under reduced pressure, the residue was purified with basic silica gel column chromatography (eluted with ethyl acetate:hexane=1:2, then 1:1) to give title compound as colorless sirup (0.84 g).

$^1$H-NMR(CDCl$_3$): 2.21(3H,s), 3.12(3H,bs), 3.78-4.08 (2H,bm), 4.38(2H,q,J=7.8 Hz), 4.64-5.08(4H,bm), 6.64(1H, d,J=5.2 Hz), 7.34-7.42(4H,m), 7.56(1H,m), 7.82(1H,m), 7.94(1H,d,J=7.6 Hz), 8.02(1H,s), 8.34(1H,d,J=5.2 Hz).

Synthetic Example 8

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4-difluorobenzoate

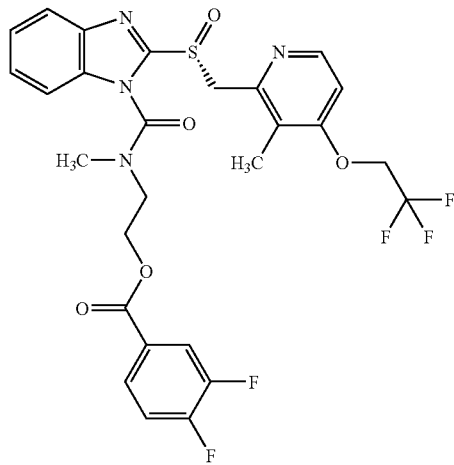 [SMILES: Cc1c(OCC(F)(F)F)ccnc1C[S@@](=O)c1nc2ccccc2n1C(=O)N(C)CCOC(=O)c1ccc(F)c(F)c1]

To a solution of bis(trichloromethyl) carbonate (0.582 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and 2-(methylamino)ethyl 3,4-difluorobenzoate hydrochlride (1.51 g) obtained in Reference Synthetic Example 8 was added. A solution of triethylamine (0.84 mL) in tetrahydrofuran (1 mL) was added, and stirred at room temperature for 3 hrs. The reaction solution was concentrated under reduced pressure, and to the residue were added ethyl acetate (80 mL) and water (50 mL), followed by stirring. The ethyl acetate layer was separated, and washed with saturated brine (30 mL), and dried over anhydrous magnesium sulfate. The solution was concentrated under reduced pressure, and the residue was dissolved in tetrahydrofuran (25 mL). To the solution were added (R)-2-[[[3-methyl-4-(2,2,2-trifluoroethoxy)-2-pyridyl]methyl]sulfinyl]-1H-benzimidazole (1.71 g), triethylamine (1.29 mL) and 4-dimethylaminopyridine (0.056 g), and stirred at 60° C. for 17 hrs. The reaction solution was concentrated under reduced pressure, and to the residue were added ethyl acetate (100 mL) and water (50 mL), followed by stirring. The ethyl acetate layer was separated, and the aqueous layer was extracted with ethyl acetate (20 mL). The ethyl acetate layers were combined, and washed with saturated saline (30 mL), and then dried over anhydrous magnesium sulfate. After concentrating under reduced pressure, the residue was purified with silica gel column chromatography (eluted with ethyl acetate:hexane=1:1, then 2:1), and further purified with basic silica gel column chromatography (eluted with ethyl acetate:hexane=1:1). The purified material was crystallized from acetone-diisopropyl ether, and further recrystallized from ethyl acetate-hexane to give title compound as colorless solid (1.37 g).

[1] H-NMR(CDCl$_3$): 2.21(3H,s), 3.11(3H,bs), 3.82-4.08 (2H,bm), 4.38(2H,q,J=7.8 Hz), 4.60-5.14(4H,bm), 6.63(1H, d,J=5.7 Hz), 7.20(1H,m), 7.33-7.41(3H,m), 7.78-7.92(3H, m), 8.33(1H,d,J=5.7 Hz).

Synthetic Example 9

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-trifluoromethoxybenzoate

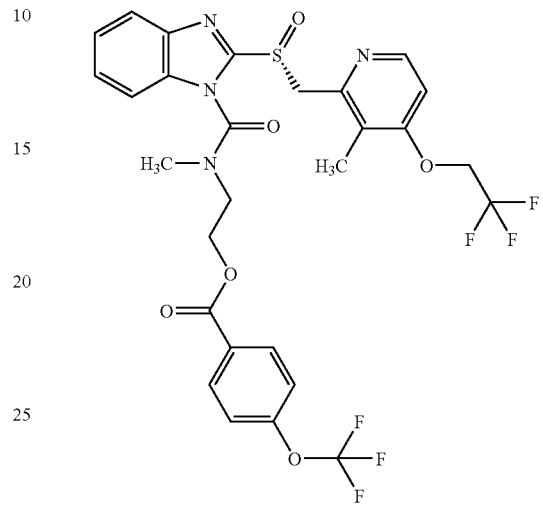

To a solution of bis(trichloromethyl) carbonate (0.582 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and 2-(methylamino)ethyl 4-trifluoromethoxybenzoate hydrochlride (1.79 g) obtained in Reference Synthetic Example 9 was added. A solution of triethylamine (0.84 mL) in tetrahydrofuran (1 mL) was added, and stirred at room temperature for 1.5 hrs. The reaction solution was concentrated under reduced pressure, and to the residue were added ethyl acetate (80 mL) and water (50 mL), followed by stirring. The ethyl acetate layer was separated, and washed with saturated brine (30 mL), and dried over anhydrous magnesium sulfate. The solution was concentrated under reduced pressure, and the residue was dissolved in tetrahydrofuran (25 mL). To the solution were added (R)-2-[[[3-methyl-4-(2,2,2-trifluoroethoxy)-2-pyridyl]methyl] sulfinyl]-1H-benzimidazole (1.57 g), triethylamine (1.18 mL) and 4-dimethylaminopyridine (0.052 g), and stirred at 60° C. for 4.5 hrs. The reaction solution was concentrated under reduced pressure, and to the residue were added ethyl acetate (100 mL) and water (50 mL), followed by stirring. The ethyl acetate layer was separated, and the aqueous layer was extracted with ethyl acetate (20 mL). The ethyl acetate layers were combined, and washed with saturated saline (30 mL), and then dried over anhydrous magnesium sulfate. After concentrating under reduced pressure, the residue was purified with basic silica gel column chromatography (eluted with ethyl acetate:hexane=1:1), and further purified with basic silica gel column chromatography (eluted with ethyl acetate: hexane=1:1) to give title compound as colorless sirup (1.44 g).

$^1$H-NMR(CDCl$_3$): 2.22(3H,s), 3.11(3H,bs), 3.85-4.05 (2H,bm), 4.38(2H,q,J=7.8 Hz), 4.60-5.12(4H,bm), 6.64(1H, d,J=5.7 Hz), 7.24(2H,d,J=8.7 Hz), 7.25-7.40(3H,m), 7.82 (1H,d,J=7.2 Hz), 8.09(2H,d,J=8.7 Hz), 8.33(1H,d,J=5.7 Hz).

Synthetic Example 10

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 4-fluorobenzoate

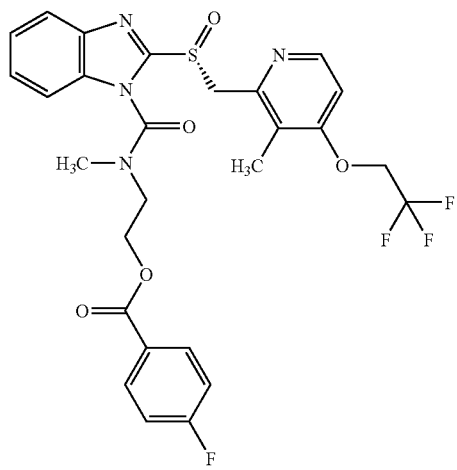 [SMILES: Cc1c(OCC(F)(F)F)ccnc1C[S@@](=O)c1nc2ccccc2n1C(=O)N(C)CCOC(=O)c1ccc(F)cc1]

To a solution of bis(trichloromethyl) carbonate (0.582 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and 2-(methylamino)ethyl 4-fluorobenzoate hydrochlride (1.40 g) obtained in Reference Synthetic Example 10 was added. A solution of triethylamine (0.84 mL) in tetrahydrofuran (1 mL) was added, and stirred at room temperature for 2 hrs. The reaction solution was concentrated under reduced pressure, and to the residue were added ethyl acetate (80 mL) and water (40 mL), followed by stirring. The ethyl acetate layer was separated, and washed with saturated brine (30 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.32 g), triethylamine (1.00 mL) and 4-dimethylaminopyridine (0.049 g), and stirred at 60° C. for 14.5 hrs. The reaction solution was concentrated under reduced pressure, and to the residue were added ethyl acetate (150 mL) and water (50 mL), followed by stirring. The ethyl acetate layer was separated, and washed with saturated saline (30 mL), and then dried over anhydrous magnesium sulfate. After concentrating under reduced pressure, the residue was crystallized from ethyl acetate-hexane, and collected by filtration. The resulting crystals were further recrystallized from acetone to give title compound as colorless solid (1.39 g).

$^1$H-NMR(CDCl$_3$): 2.22(3H,s), 3.12(3H,bs), 3.78-4.20 (2H,bm), 4.38(2H,q,J=7.8 Hz), 4.58-5.08(4H,bm), 6.65(1H, d,J=5.6 Hz), 7.11(2H,t,J=8.4 Hz), 7.28-7.44(3H,m), 7.81-7.86(1H,m), 8.03-8.11(2H,m), 8.35(1H,d,J=5.6 Hz).

Synthetic Example 11

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 3,4,5-trimethoxybenzoate

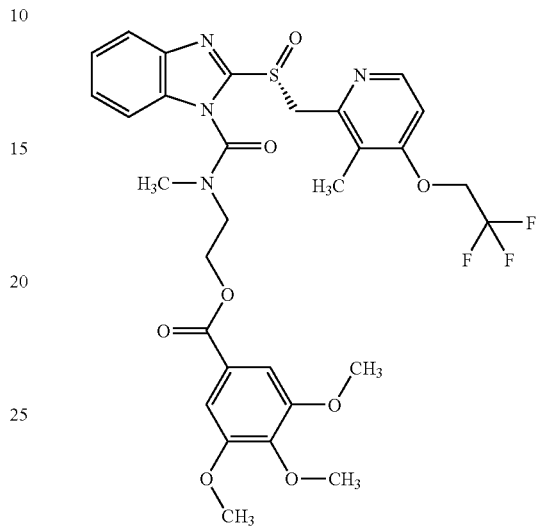

To a solution of bis(trichloromethyl) carbonate (0.60 g) in tetrahydrofuran (30 mL) was added dropwise a solution of pyridine (0.49 mL) in tetrahydrofuran (1 mL) under ice-cooling. The reaction solution was stirred for 10 minutes under ice-cooling, and 2-(methylamino)ethyl 3,4,5-trimethoxybenzoate hydrochlride (1.22 g) obtained in Reference Synthetic Example 11 was added. A solution of triethylamine (0.84 mL) in tetrahydrofuran (1 mL) was added, and stirred at room temperature for 1 hr. The reaction solution was concentrated under reduced pressure, and to the residue was added water (50 mL), and then extracted with ethyl acetate (50 mL). The ethyl acetate layer was washed with dilute hydrochloric acid (20 mL), and saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g), and stirred at 60° C. for 3 hrs, and at room temperature for 2 days. The reaction solution was concentrated under reduced pressure, and to the residue was added water (50 mL), and extracted with ethyl acetate (50 mL). The ethyl acetate layer was washed with saturated saline (50 mL), and dried over anhydrous magnesium sulfate. After concentrating under reduced pressure, the residue was purified with flash silica gel column chromatography (eluted with acetone:hexane=1:3, then 3:2) to give title compound as yellow amorphous solid (1.56 g).

$^1$H-NMR(CDCl$_3$): 2.21(3H,s), 3.12(3H,bs), 3.50-4.30 (2H,br), 3.83(6H,s), 3.90(3H,s), 4.38(2H,q,J=7.8 Hz), 4.67 (2H,m), 4.80-5.15(2H,br), 6.64(1H,d,J=5.7 Hz), 7.25-7.40 (5H,m), 7.78-7.86(1H,m), 8.33(1H,d,J=5.7 Hz).

Synthetic Example 12

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 2-pyridinecarboxylate

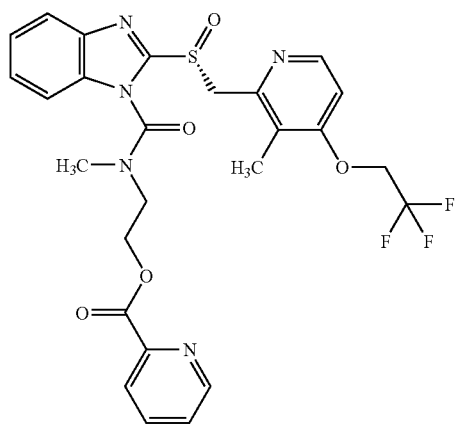 [SMILES: Cc1c(OCC(F)(F)F)ccnc1C[S@@](=O)c1nc2ccccc2n1C(=O)N(C)CCOC(=O)c1ccccn1]

To a solution of bis(trichloromethyl) carbonate (0.422 g) in tetrahydrofuran (30 mL) was added dropwise pyridine (0.345 mL) under ice-cooling. The reaction solution was stirred for 30 minutes under ice-cooling, and 2-(methylamino)ethyl 2-pyridinecarboxylate dihydrochlride (1.08 g) obtained in Reference Synthetic Example 12 was added, and then, triethylamine (1.19 mL) was added dropwise, followed by stirring at room temperature for 2 hrs. The precipitated crystals were collected by filtration, and the filtrate was concentrated under reduced pressure. The residue was dissolved in tetrahydrofuran (10 mL), and added (R)-2-[[[3-methyl-4-(2,2,2-trifluoroethoxy)-2-pyridyl]methyl]sulfinyl]-1H-benzimidazole (1.31 g), triethylamine (0.99 mL) and 4-dimethylaminopyridine (0.043 g), followed by stirring at 60° C. for 24 hrs. To the reaction solution was added ethyl acetate (100 mL), and washed with water (100 mL), and saturated saline (100 mL), and then, dried over anhydrous magnesium sulfate, followed by concentrating under reduced pressure. The residue was purified with basic silica gel column chromatography (eluted with ethyl acetate:hexane=4:1). The purified material was crystallized from acetone-diethyl ether to give title compound as white solid (0.9 g).

$^1$H-NMR(CDCl$_3$): 2.22(3H,s), 3.16(3H,s), 3.80-4.20(2H, m), 4.38(2H,q,J=7.8 Hz), 4.60-5.10(4H,m), 6.64(1H,d,J=5.8 Hz), 7.29-7.40(2H,m), 7.47-7.52(2H,m), 7.81-7.89(2H,m), 8.14(1H,d,J=7.8 Hz), 8.34(1H,d,J=5.8 Hz), 8.75-8.79(1H, m).

Synthetic Example 13

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl methoxyacetate

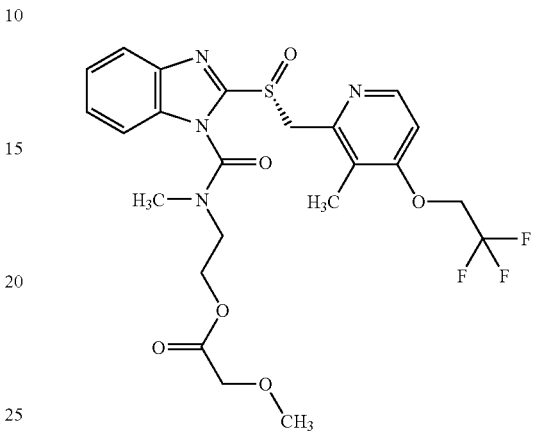

To a solution of bis(trichloromethyl) carbonate (0.652 g) in tetrahydrofuran (15 mL) was added dropwise a solution of pyridine (0.55 mL) in tetrahydrofuran (1 mL) under ice-cooling. The reaction solution was stirred for 30 minutes under ice-cooling, and 2-(methylamino)ethyl methoxyacetate (0.99 g) obtained in Reference Synthetic Example 13 was added. The reaction solution was stirred at room temperature for 3 hrs. The reaction solution was concentrated under reduced pressure, and to the residue were added ethyl acetate (80 mL) and water (50 mL), followed by stirring. The ethyl acetate layer was separated, and washed with saturated brine (30 mL), and dried over anhydrous magnesium sulfate. The solution was concentrated under reduced pressure, and the residue was dissolved in tetrahydrofuran (15 mL). To the solution were added (R)-2-[[[3-methyl-4-(2,2,2-trifluoroethoxy)-2-pyridyl]methyl]sulfinyl]-1H-benzimidazole (1.13 g), triethylamine (0.86 mL) and 4-dimethylaminopyridine (0.037 g), and stirred at 60° C. for 4 days. The reaction solution was concentrated under reduced pressure, and to the residue was added ethyl acetate (80 mL) and water (30 mL), followed by stirring. The ethyl acetate layer was separated, and washed with saturated aqueous solution of sodium bicarbonate (30 mL) and water (30 mL), and then, dried over anhydrous magnesium sulfate. After concentrating under reduced pressure, the residue was purified with silica gel column chromatography (eluted with ethyl acetate, then acetone:ethyl acetate=1:3), and further basic silica gel column chromatography (eluted with ethyl acetate:hexane=1:1, then 3:1) to give title compound as colorless sirup (0.588 g).

$^1$H-NMR(CDCl$_3$): 2.32(3H,s), 2.68(3H,s), 3.48(3H,s), 3.69-4.02(4H,m), 4.38(2H,q,J=7.8 Hz), 4.67(2H,t,J=6.6 Hz), 4.99(1H,d,J=13.9 Hz), 5.12(1H,d,J=13.9 Hz), 6.63(1H,d, J=5.7 Hz), 7.29-7.46(2H,m), 7.62(1H,m), 7.81(1H,m), 8.25 (1H,d,J=5.7 Hz).

Synthetic Example 14

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

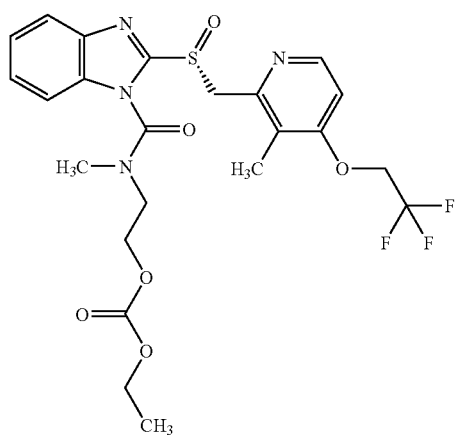 [SMILES: CCOC(=O)OCCN(C)C(=O)n1c([S@](=O)Cc2nccc(OCC(F)(F)F)c2C)nc2ccccc21]

To a solution of bis(trichloromethyl) carbonate (1.31 g) in tetrahydrofuran (40 mL) was added dropwise a solution of pyridine (1.07 mL) in tetrahydrofuran (2 mL) under ice-cooling. The reaction solution was stirred for 10 minutes under ice-cooling, and 2-(methylamino)ethyl carbonate hydrochlride (2.02 g) obtained in Reference Synthetic Example 14 was added. A solution of triethylamine (1.84 mL) in tetrahydrofuran (2 mL) was added dropwise, and stirred at room temperature for 1 hr. The reaction solution was concentrated under reduced pressure, and to the residue was added water (100 mL), and extracted with ethyl acetate (100 mL). The ethyl acetate layer was washed with 0.2 N hydrochloric acid (50 mL), and saturated brine (100 mL), followed by drying over anhydrous magnesium sulfate. The solution was concentrated under reduced pressure, and the residue was dissolved in tetrahydrofuran (50 mL). To the solution were added (R)-2-[[[3-methyl-4-(2,2,2-trifluoroethoxy)-2-pyridyl]methyl]sulfinyl]-1H-benzimidazole (3.69 g), triethylamine (2.09 mL) and 4-dimethylaminopyridine (0.12 g), and stirred at 60° C. for 6 hrs, and at room temperature for 8 hrs. The reaction solution was concentrated under reduced pressure, and to the residue was added water (100 mL), and extracted with ethyl acetate (100 mL). The ethyl acetate layer was washed with saturated saline (100 mL), and dried over anhydrous magnesium sulfate. After concentrating under reduced pressure, the residue was purified with basic silica gel column chromatography (eluted with ethyl acetate:hexane=3:7, then ethyl acetate). The purified material was crystallized from diethyl ether, and further recrystallized from diethyl ether to give title compound as colorless solid (3.84 g).

$^1$H-NMR(CDCl$_3$): 1.32(3H,t,J=7.2 Hz), 2.23(3H,s), 3.10 (3H,bs), 3.50-4.20(2H,br), 4.22(2H,q,J=7.2 Hz), 4.39(2H,q, J=7.9 Hz), 4.45(2H,m), 4.80-5.15(2H,br), 6.65(1H,d,J=5.6 Hz), 7.36-7.50(3H,m), 7.84(1H,d,J=7.8 Hz), 8.35(1H,d, J=5.6 Hz).

Synthetic Example 15

Isopropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

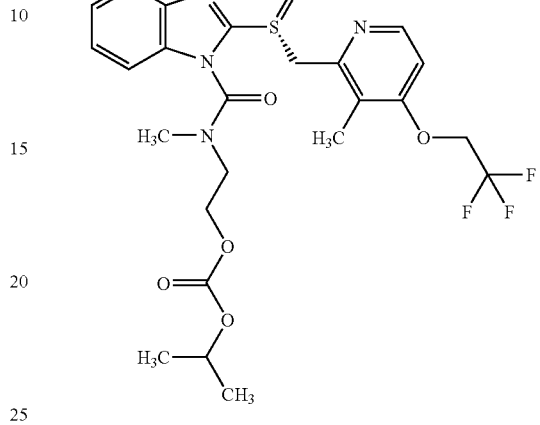

To a solution of bis(trichloromethyl) carbonate (0.50 g) in tetrahydrofuran (30 mL) was added dropwise a solution of pyridine (0.40 mL) in tetrahydrofuran (1 mL) under ice-cooling. The reaction solution was stirred for 1 hr under ice-cooling, and isopropyl 2-(methylamino)ethyl carbonate hydrochlride (0.99 g) obtained in Reference Synthetic Example 15 was added. A solution of triethylamine (0.84 mL) in tetrahydrofuran (1 mL) was added dropwise, and stirred at room temperature for 1 hr. To the reaction solution was added sequentially bis(trichloromethyl) carbonate (0.50 g), a solution of pyridine (0.40 mL) in tetrahydrofuran (1 mL), and a solution of triethylamine (0.70 mL) in tetrahydrofuran (1 mL), and stirred at room temperature for 1 hr. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g), and stirred at 60° C. for 12 hrs, then at room temperature for 3 days. The reaction solution was concentrated under reduced pressure, and to the residue was added water (50 mL), and extracted with ethyl acetate (50 mL). The ethyl acetate layer was washed with saturated saline (50 mL), and dried over anhydrous magnesium sulfate. After concentrating under reduced pressure, the residue was purified with flash silica gel column chromatography (eluted with acetone:hexane=1:3, then 3:2), and further purified with basic silica gel column chromatography (eluted with ethyl acetate: hexane=3:1, then ethyl acetate). The purified material was crystallized from diethyl ether, and further recrystallized from acetone-diisopropyl ether to give title compound as colorless solid (0.58 g).

$^1$H-NMR(CDCl$_3$): 1.31(6H,d,J=6.3 Hz), 2.23(3H,s), 3.08 (3H,bs), 3.40-4.30(2H,br), 4.37(2H,q,J=7.9 Hz), 4.32-4.53 (2H,m), 4.80-5.20(3H,m), 6.63(1H,d,J=5.7 Hz), 7.35-7.50 (3H,m), 7.83(1H,d,J=7.2 Hz), 8.34(1H,d,J=5.7 Hz).

Synthetic Example 16

Isopropyl 2-[methyl[[2-[[[3-methyl-4-(2,2,2-trifluoroethoxy)-2-pyridyl]methyl]sulfinyl]-1H-benzimidazol-1-yl]carbonyl]amino]ethyl carbonate

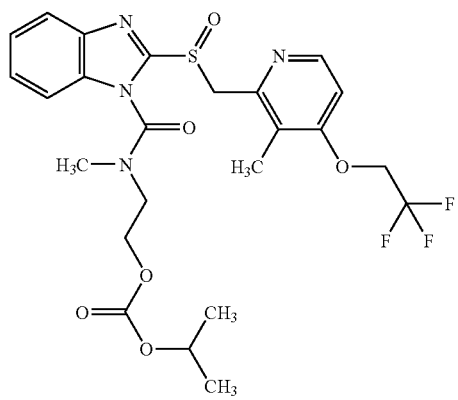 [SMILES: Cc1c(OCC(F)(F)F)ccnc1CS(=O)c1nc2ccccc2n1C(=O)N(C)CCOC(=O)OC(C)C]

To a solution of bis(trichloromethyl) carbonate (0.582 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and isopropyl 2-(methylamino)ethyl carbonate hydrochlride (1.18 g) obtained in Reference Synthetic Example 15 was added. A solution of triethylamine (0.84 mL) in tetrahydrofuran (1 mL) was added, and stirred at room temperature for 2 hrs. The reaction solution was concentrated under reduced pressure, and to the residue were added ethyl acetate (80 mL) and water (30 mL), followed by stirring. The ethyl acetate layer was separated, and washed with saturated brine (30 mL), and dried over anhydrous magnesium sulfate. The solution was concentrated under reduced pressure, and the residue was dissolved in tetrahydrofuran (25 mL). To the solution were added 2-[[[3-methyl-4-(2,2,2-trifluoroethoxy)-2-pyridyl]methyl]sulfinyl]-1H-benzimidazole (1.73 g), triethylamine (1.31 mL) and 4-dimethylaminopyridine (0.057 g), and stirred at 60° C. for 5 hrs. The reaction solution was concentrated under reduced pressure, and to the residue were added ethyl acetate (100 mL) and water (50 mL), followed by stirring. The ethyl acetate layer was separated, and washed with saturated saline (50 mL), and dried over anhydrous magnesium sulfate. After concentrating under reduced pressure, the residue was purified with basic silica gel column chromatography (eluted with ethyl acetate:hexane=1:1), and further purified with silica gel column chromatography (eluted with ethyl acetate:hexane=1:1, then 2:1). The purified material was crystallized from diisopropyl ether-hexane, and further recrystallized from diisopropyl ether to give title compound as colorless solid (1.20 g).

$^1$H-NMR(CDCl$_3$): 1.31(6H,d,J=6.6 Hz), 2.23(3H,s), 3.08(3H,bs), 3.50-3.90(2H,bm), 4.38(2H,q,J=7.8 Hz), 4.36-4.58(2H,bm), 4.79-5.15(3H,m), 6.64(1H,d,J=5.7 Hz), 7.35-7.48(3H,m), 7.83(1H,d,J=7.5 Hz), 8.34(1H,d,J=5.7 Hz).

Synthetic Example 17

Benzyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

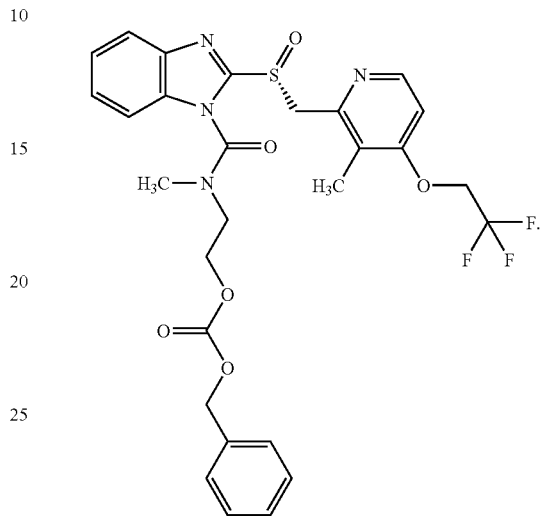

To a solution of bis(trichloromethyl) carbonate (0.50 g) in tetrahydrofuran (30 mL) was added dropwise a solution of pyridine (0.40 mL) in tetrahydrofuran (1 mL) under ice-cooling. The reaction solution was stirred for 1 hr under ice-cooling, and benzyl 2-(methylamino)ethyl carbonate hydrochlride (1.08 g) obtained in Reference Synthetic Example 16 was added. A solution of triethylamine (0.70 mL) in tetrahydrofuran (1 mL) was added dropwise, and stirred at room temperature overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g), and stirred at 60° C. overnight. The reaction solution was concentrated under reduced pressure, and to the residue was added water (50 mL), and extracted with ethyl acetate (50 mL). The ethyl acetate layer was washed with saturated saline (50 mL), and dried over anhydrous magnesium sulfate. After concentrating under reduced pressure, the residue was purified with flash silica gel column chromatography (eluted with acetone:hexane=1:3, then 3:2). The purified material was crystallized from acetone-diethyl ether, and further recrystallized from acetone-diethyl ether to give title compound as colorless solid (1.17 g).

$^1$H-NMR(CDCl$_3$): 2.22(3H,s), 3.05(3H,bs), 3.50-4.20(2H,br), 4.37(2H,q,J=7.8 Hz), 4.46(2H,m), 4.80-5.10(2H,br), 5.17(2H,s), 6.62(1H,d,J=5.6 Hz), 7.26-7.48(8H,m), 7.77-7.88(1H,m), 8.33(1H,d,J=5.6 Hz).

Synthetic Example 18

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate

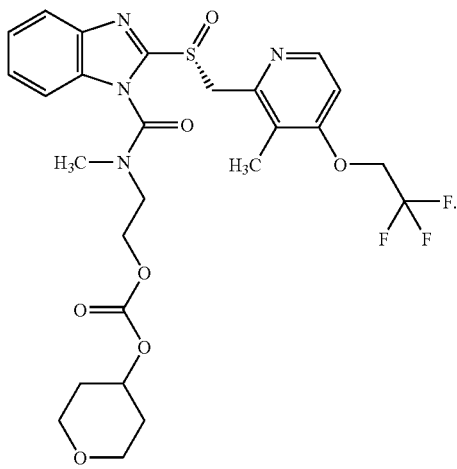 [SMILES: Cc1c(OCC(F)(F)F)ccnc1C[S@@](=O)c1nc2ccccc2n1C(=O)N(C)CCOC(=O)OC1CCOCC1]

To a solution of bis(trichloromethyl)carbonate (0.48 g) in tetrahydrofuran (20 mL) was added dropwise a solution of pyridine (0.39 mL) in tetrahydrofuran (1 mL) under ice-cooling. The reaction solution was stirred for 20 minutes under ice-cooling, and 2-(methylamino)ethyl tetrahydropyran-4-yl carbonate hydrochlride (0.96 g) obtained in Reference Synthetic Example 17 was added. A solution of triethylamine (0.67 mL) in tetrahydrofuran (1 mL) was added dropwise, and stirred at room temperature for 2 hrs. The reaction solution was concentrated under reduced pressure, and to the residue was added water (50 mL), and extracted with ethyl acetate (50 mL). The ethyl acetate layer was washed with 0.2 N hydrocloric acid (20 mL), and saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.26 g), triethylamine (0.71 mL) and 4-dimethylaminopyridine (0.042 g), and stirred at 60° C. for 6 hrs, and then at room temperature for 8 hrs. The reaction solution was concentrated under reduced pressure, and to the residue was added water (50 mL), and extracted with ethyl acetate (50 mL). The ethyl acetate layer was washed with saturated saline (50 mL), and dried over anhydrous magnesium sulfate. After concentrating under reduced pressure, the residue was purified with basic silica gel column chromatography (eluted with ethyl acetate:hexane=3:7, then ethyl acetate). The purified material was crystallized from diethyl ether, and further recrystallized from acetone-diisopropyl ether to give title compound as colorless solid (1.45 g).

$^1$H-NMR(CDCl$_3$): 1.64-1.81(2H,m), 1.92-2.03(2H,m), 2.23(3H,s), 3.09(3H,bs), 3.40-4.30(2H,br), 3.45-3.57(2H,m), 3.87-3.97(2H,m), 4.38(2H,q,J=7.8 Hz), 4.45(2H,m), 4.77-5.15(3H,m), 6.64(1H,d,J=5.7 Hz), 7.35-7.50(3H,m), 7.83(1H,d,J=6.9 Hz), 8.35(1H,d,J=5.7 Hz).

Synthetic Example 19

2-Methoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

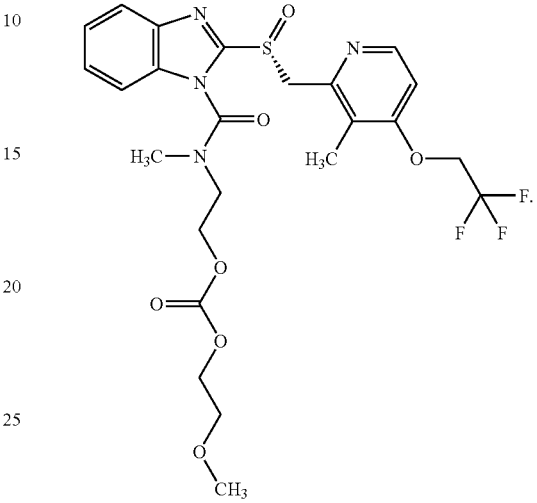

To a solution of bis(trichloromethyl)carbonate (0.59 g) in tetrahydrofuran (20 mL) was added dropwise a solution of pyridine (0.49 mL) in tetrahydrofuran (1 mL) under ice-cooling. The reaction solution was stirred for 10 minutes under ice-cooling, and 2-methoxyethyl 2-(methylamino) ethyl carbonate hydrochlride (1.07 g) obtained in Reference Synthetic Example 18 was added. A solution of triethylamine (0.84 mL) in tetrahydrofuran (1 mL) was added dropwise, and stirred at room temperature for 1 hr. The reaction solution was concentrated under reduced pressure, and to the residue was added water (50 mL), and extracted with ethyl acetate (50 mL). The ethyl acetate layer was washed with 0.2 N hydrocloric acid (20 mL), and saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.85 g), triethylamine (1.05 mL) and 4-dimethylaminopyridine (0.061 g), and stirred at 60° C. for 6 hrs, and then at room temperature for 8 hrs. The reaction solution was concentrated under reduced pressure, and to the residue was added water (50 mL), and extracted with ethyl acetate (50 mL). The ethyl acetate layer was washed with saturated saline (50 mL), and dried over anhydrous magnesium sulfate. After concentrating under reduced pressure, the residue was purified with basic silica gel column chromatography (eluted with ethyl acetate:hexane=3:7, then ethyl acetate). The purified material was crystallized from ethyl acetate-diethyl ether, and further recrystallized from ethyl acetate-diisopropyl ether to give title compound as colorless solid (1.39 g).

$^1$H-NMR(CDCl$_3$): 2.23(3H,s), 3.09(3H,bs), 3.37(3H,s), 3.50-4.20(2H,br), 3.59-3.65(2H,m), 4.28-4.33(2H,m), 4.38 (2H,q,J=7.8 Hz), 4.46(2H,m), 4.80-5.15(2H,br), 6.64(1H,d, J=5.7 Hz), 7.35-7.47(3H,m), 7.83(1H,d,J=7.8 Hz), 8.34 (1H, d,J=5.7 Hz).

Synthetic Example 20

2-[Ethyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate

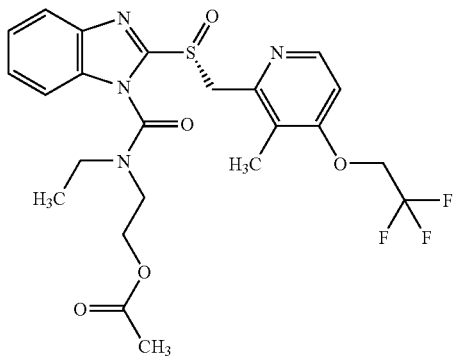 [SMILES: CCN(CCOC(C)=O)C(=O)n1c([S@](=O)Cc2nccc(OCC(F)(F)F)c2C)nc2ccccc21]

To a solution of bis(trichloromethyl)carbonate (0.59 g) in tetrahydrofuran (30 mL) was added dropwise a solution of pyridine (0.49 mL) in tetrahydrofuran (1 mL) under ice-cooling. The reaction solution was stirred for 10 minutes under ice-cooling, and 2-(ethylamino)ethyl acetate hydrochloride (0.67 g) obtained in Reference Synthetic Example 20 was added. A solution of triethylamine (0.84 mL) in tetrahydrofuran (1 mL) was added dropwise, and stirred at room temperature for 1 hr. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.84 mL) and 4-dimethylaminopyridine (0.037 g), and stirred at 60° C. overnight. The reaction solution was concentrated under reduced pressure, and to the residue was added water (50 mL), and extracted with ethyl acetate (50 mL). The ethyl acetate layer was washed with saturated saline (50 mL), and dried over anhydrous magnesium sulfate. After concentrating under reduced pressure, the residue was purified with basic silica gel column chromatography (eluted with ethyl acetate:hexane=3:7, then ethyl acetate) to give title compound as yellow amorphous solid(1.58 g).

$^1$H-NMR(CDCl$_3$): 1.25(3H,m), 2.08(3H,s), 2.23(3H,s), 3.30-4.10(4H,br), 4.23-4.45(2H,m), 4.38(2H,q,J=7.8 Hz), 4.75-5.20(2H,br), 6.64(1H,d,J=5.7 Hz), 7.35-7.46(3H,m), 7.84(1H,d,J=6.9 Hz), 8.36(1H,d,J=5.7 Hz).

Synthetic Example 21

2-[Isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate

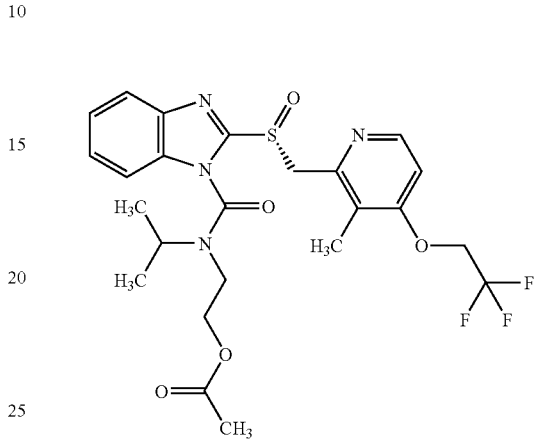

To a solution of bis(trichloromethyl)carbonate (0.543 g) in tetrahydrofuran (10 mL) was added dropwise a solution of pyridine (0.445 mL) in tetrahydrofuran (5 mL) under ice-cooling, and stirred for 30 minutes at 0° C. To the reaction solution was added 2-(isopropylamino)ethyl acetate hydrochlride (1.0 g) obtained in Reference Synthetic Example 22. A solution of triethylamine (0.805 mL) in tetrahydrofuran (5 mL) was added, and stirred at room temperature for 30 minutes. The reaction solution was concentrated under reduced pressure, and to the residue was added water (30 mL), and extracted with ethyl acetate (50 mL). The ethyl acetate layer was washed with saturated brine (30 mL), and dried over anhydrous magnesium sulfate, followed by concentrating under reduced pressure. The resulting oil was dissolved in tetrahydrofuran (5 mL), and added to a solution of (R)-2-[[[3-methyl-4-(2,2,2-trifluoroethoxy)-2-pyridyl]methyl]sulfinyl]-1H-benzimidazole (1.73 g), triethylamine (1.53 mL) and 4-dimethylaminopyridine (0.134 g) in tetrahydrofuran (20 mL), and stirred at 40° C. for 12 hrs. The reaction solution was concentrated under reduced pressure, and to the residue was added water (30 mL), and extracted with ethyl acetate (50 mL). The ethyl acetate layer was washed with saturated saline (30 mL), dried over anhydrous sodium sulfate, and concentrated under reduced pressure. The residue was purified with silica gel column chromatography (eluted with ethyl acetate:hexane=2:1, then ethyl acetate) to give title compound as pale yellow amorphous solid(1.50 g).

$^1$H-NMR(CDCl$_3$): 1.20-1.40(6H,m), 2.05(3H×0.4,s), 2.11 (3H×0.6,s), 2.18(3H×0.6,s), 2.27(3H×0.4,s), 3.40-3.60(1H, m), 3.70-4.60(6H,m), 4.70-5.25(2H,m), 6.65(1H,d,J=5.8 Hz), 7.30-7.50(3H,m), 7.75-7.90(1H,m), 8.37(1H,d,J=5.8 Hz).

Synthetic Example 22

Ethyl 2-[isopropyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

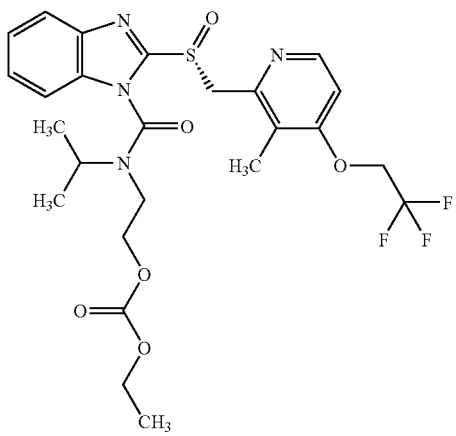 [SMILES: CCOC(=O)OCCN(C(=O)n1c([S@](=O)Cc2nccc(OCC(F)(F)F)c2C)nc2ccccc21)C(C)C]

To a solution of bis(trichloromethyl)carbonate (0.467 g) in tetrahydrofuran (10 mL) was added dropwise a solution of pyridine (0.381 mL) in tetrahydrofuran (5 mL) under ice-cooling, and stirred for 30 minutes at 0° C. To the reaction solution was added ethyl 2-(isopropylamino)ethyl carbonate hydrochlride (1.0 g) obtained in Reference Synthetic Example 23. A solution of triethylamine (0.69 mL) in tetrahydrofuran (5 mL) was added, and stirred at 0° C. for 15 minutes, and then at room temperature for 30 minutes. The reaction solution was concentrated under reduced pressure, and to the residue was added water (30 mL), and extracted with ethyl acetate (50 mL). The ethyl acetate layer was washed with saturated brine (30 mL), and dried over anhydrous sodium sulfate, followed by concentrating under reduced pressure. The resulting oil was dissolved in tetrahydrofuran (5 mL), and added to a solution of (R)-2-[[[3-methyl-4-(2,2,2-trifluoroethoxy)-2-pyridyl]methyl]sulfinyl]-1H-benzimidazole (1.48 g), triethylamine (1.32 mL) and 4-dimethylaminopyridine (0.115 g) in tetrahydrofuran (20 mL), and stirred at 40° C. for 12 hrs. The reaction solution was concentrated under reduced pressure, and to the residue was added water (30 mL), and extracted with ethyl acetate (50 mL). The ethyl acetate layer was washed with saturated saline (30 mL), dried over anhydrous sodium sulfate, and concentrated under reduced pressure. The residue was purified with silica gel column chromatography (eluted with ethyl acetate:hexane=2:1, then ethyl acetate) to give title compound as pale yellow amorphous solid(1.20 g).

$^1$H-NMR(CDCl$_3$): 1.20-1.40(9H,m), 2.17(3H×0.6,s), 2.27 (3H×0.4,s), 3.40-3.70(1H,m), 3.75-4.65(8H,m), 4.70-5.30 (2H,m), 6.64(1H,d,J=5.8 Hz), 7.35-7.55(3H,m), 7.75-7.90 (1H,m), 8.38(1H,d,J=5.8 Hz).

Synthetic Example 23

2-[Cyclohexyl[[(R)-2-[[[3-methyl-4-(2,2,2-trifluoroethoxy)-2-pyridyl]methyl]sulfinyl]-1H-benzimidazol-1-yl]carbonyl]amino]ethyl acetate

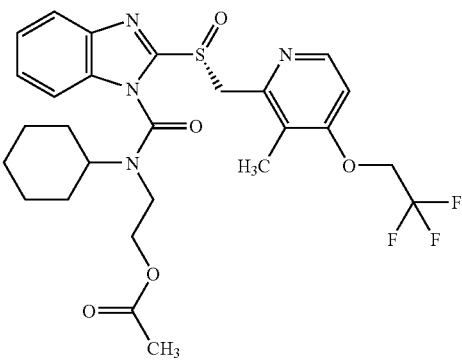 [SMILES: CC(=O)OCCN(C(=O)n1c([S@](=O)Cc2nccc(OCC(F)(F)F)c2C)nc2ccccc21)C1CCCCC1]

To a solution of bis(trichloromethyl)carbonate (0.593 g) in tetrahydrofuran (10 mL) was added dropwise pyridine (0.485 mL) under ice-cooling. The reaction solution was stirred for 30 minutes under ice-cooling, and 2-(cyclohexylamino)ethyl acetate hydrochlride (1.33 g) obtained in Reference Synthetic Example 25 was added thereto. Triethylamine (0.84 mL) was added dropwise, and stirred at room temperature for 2 hrs. To the reaction solution was added ethyl acetate (50 mL), and washed with water (50 mL) and saturated brine (50 mL), and then, dried over anhydrous magnesium sulfate, followed by concentrating under reduced pressure. The residue was dissolved in tetrahydrofuran (20 mL), and (R)-2-[[[3-methyl-4-(2,2,2-trifluoroethoxy)-2-pyridyl]methyl]sulfinyl]-1H-benzimidazole (1.61 g), triethylamine (1.21 mL) and 4-dimethylaminopyridine (0.053 g) were added thereto, and stirred at 60° C. for 24 hrs. To the reaction solution was added ethyl acetate (50 mL), and washed with water (20 mL) and saturated brine (50 mL), and then, dried over anhydrous sodium sulfate, followed by concentrating under reduced pressure. The residue was purified with flash silica gel column chromatography (eluted with ethyl acetate:hexane=1:4, then ethyl acetate) to give title compound as pale yellow amorphous solid (2.12 g).

$^1$H-NMR(CDCl$_3$): 1.00-2.42(16H,m), 3.30-3.70(2H,m), 3.80-4.00(1H,m), 4.27-4.42(2H,m), 4.40(2H,q,J=8.2 Hz), 4.78(1H×0.5,d,J=13.2 Hz), 4.97(2H×0.5,s), 5.20(1H×0.5,d, J=13.2 Hz), 6.67(1H,d,J=5.8 Hz), 7.36-7.46(3H,m), 7.81-7.91(1H,m), 8.39(1H,d,J=5.8 Hz).

Synthetic Example 24

2-[Cyclohexyl[[(R)-2-[[[3-methyl-4-(2,2,2-trifluoro-ethoxy)-2-pyridyl]methyl]sulfinyl]-1H-benzimidazol-1-yl]carbonyl]amino]ethyl ethyl carbonate

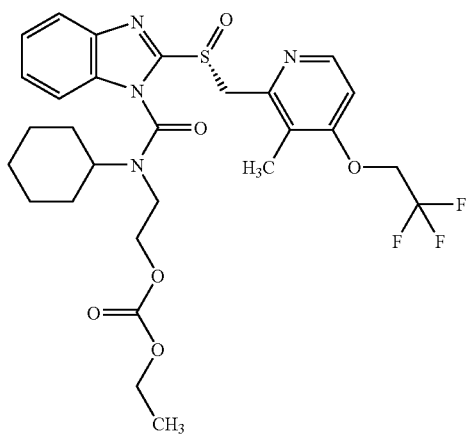 [SMILES: CCOC(=O)OCCN(C(=O)n1c([S@](=O)Cc2nccc(OCC(F)(F)F)c2C)nc2ccccc21)C1CCCCC1]

To a solution of bis(trichloromethyl)carbonate (0.238 g) in tetrahydrofuran (10 mL) was added dropwise pyridine (0.20 mL) under ice-cooling. The reaction solution was stirred for 30 minutes under ice-cooling, and 2-(cyclohexylamino)ethyl ethyl carbonate hydrochlride (0.605 g) obtained in Reference Synthetic Example 26 was added thereto. Triethylamine (0.335 mL) was added dropwise, and stirred at room temperature for 2 hrs. To the reaction solution was added ethyl acetate (50 mL), and washed with water (50 mL) and saturated brine (50 mL), and then, dried over anhydrous magnesium sulfate, followed by concentrating under reduced pressure. The residue was dissolved in tetrahydrofuran (10 mL), and (R)-2-[[[3-methyl-4-(2,2,2-trifluoroethoxy)-2-pyridyl]methyl]sulfinyl]-1H-benzimidazole (0.60 g), triethylamine (0.45 mL) and 4-dimethylaminopyridine (0.02 g) were added thereto, and stirred at 60° C. for 24 hrs. To the reaction solution was added ethyl acetate (50 mL), and washed with water (20 mL) and saturated brine (50 mL), and then, dried over anhydrous sodium sulfate, followed by concentrating under reduced pressure. The residue was purified with flash silica gel column chromatography (eluted with ethyl acetate: hexane=1:4, then ethyl acetate) to give title compound as pale yellow amorphous solid (0.92 g).

$^1$H-NMR(CDCl$_3$): 1.02-2.27(16H,m), 3.40-4.60(9H,m), 4.78(1H×0.5,d,J=13.2 Hz), 4.97(2H×0.5,s), 5.44(1H×0.5,d, J=13.2 Hz), 6.69(1H,d,J=5.6 Hz), 7.32-7.54(3H,m), 7.80-7.91(1H,m), 8.38(1H,d,J=5.6 Hz).

Synthetic Example 25

2-[[[(R)-2-[[[3-methyl-4-(2,2,2-trifluoroethoxy)-2-pyridyl]methyl]sulfinyl]-1H-benzimidazol-1-yl]carbonyl](phenyl)amino]ethyl acetate

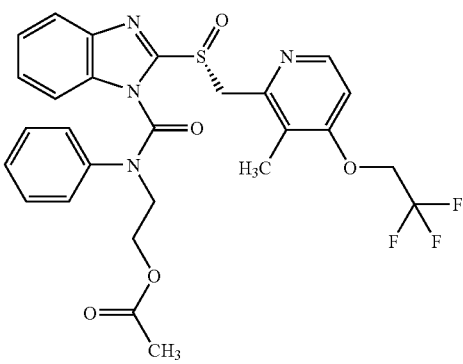 [SMILES: CC(=O)OCCN(C(=O)n1c([S@](=O)Cc2nccc(OCC(F)(F)F)c2C)nc2ccccc21)c1ccccc1]

To a solution of bis(trichloromethyl)carbonate (13.4 g) in tetrahydrofuran (350 mL) was added dropwise pyridine (10.38 mL) under ice-cooling. The reaction solution was stirred for 30 minutes under ice-cooling, and 2-anilinoethyl acetate hydrochlride (25.9 g) obtained in Reference Synthetic Example 27 was added thereto. Triethylamine (18.4 mL) was added dropwise, and stirred at room temperature for 2 hrs. The reaction solution was concentrated under reduced pressure, and to the residue were added ethyl acetate (500 mL) and water (500 mL), followed by stirring. The ethyl acetate layer was separated, and washed with saturated brine (500 mL), and then, dried over anhydrous magnesium sulfate, followed by concentrating under reduced pressure to give 2-[(chlorocarbonyl)(phenyl)amino]ethyl acetate. This was dissolved in tetrahydrofuran (300 mL), and (R)-2-[[[3-methyl-4-(2,2,2-trifluoroethoxy)-2-pyridyl]methyl]sulfinyl]-1H-benzimidazole (41.2 g), triethylamine (15.6 mL) and 4-dimethylaminopyridine (1.363 g) were added thereto, and stirred at 60° C. for 3 hrs. To the reaction solution was added ethyl acetate (800 mL), and washed twice with water (800 mL), and further with saturated brine (800 mL), and then, dried over anhydrous sodium sulfate, followed by concentrating under reduced pressure. The residue was purified with basic silica gel column chromatography (eluted with ethyl acetate:hexane=3:7, then 1:1). The purified material was crystallized from diethyl ether to give title compound as white solid (54.1 g).

$^1$H-NMR(CDCl$_3$): 2.00(3H,s), 2.25(3H,s), 4.15-4.48(6H, m), 4.83(1H,d,J=13.6 Hz), 5.05(1H,d,J=13.6 Hz), 6.67(1H, d,J=5.4 Hz), 7.03-7.45(8H,m), 7.64-7.69(1H,m), 8.40(1H,d, J=5.4 Hz).

Synthetic Example 26

2-[[[2-[[[3-methyl-4-(2,2,2-trifluoroethoxy)-2-pyridyl]methyl]sulfinyl]-1H-benzimidazol-1-yl]carbonyl](phenyl)amino]ethyl acetate

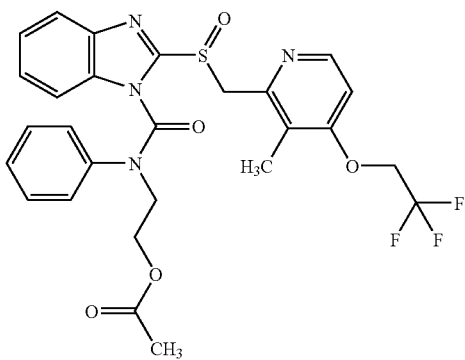 [SMILES: CC(=O)OCCN(C(=O)n1c(S(=O)Cc2nccc(OCC(F)(F)F)c2C)nc2ccccc21)c1ccccc1]

To a solution of 2-[(chlorocarbonyl)(phenyl)amino]ethyl acetate (0.58 g) prepared in the same way as in Synthetic Example 25 in tetrahydrofuran (10 mL) were added 2-[[[3-methyl-4-(2,2,2-trifluoroethoxy)-2-pyridyl]methyl]sulfinyl]-1H-benzimidazole (0.73 g), triethylamine (0.558 mL) and 4-dimethylaminopyridine (0.024 g), and stirred at 60° C. for 15 hrs. To the reaction solution was added ethyl acetate (30 mL), and washed with water (50 mL) and saturated brine (50 mL), and then, dried over anhydrous sodium sulfate, followed by concentrating under reduced pressure. The residue was purified with flash silica gel column chromatography (eluted with acetone:hexane=1:4, then 3:2). The purified material was crystallized from diethyl ether to give title compound as white solid (0.779 g).

$^1$H-NMR(CDCl$_3$): 1.99(3H,s), 2.25(3H,s), 4.20-4.48(6H, m), 4.83(1H,d,J=13.6 Hz), 5.05(1H,d,J=13.6 Hz), 6.67(1H, d,J=5.8 Hz), 7.03-7.45(8H,m), 7.64-7.69(1H,m), 8.40(1H,d, J=5.8 Hz).

Synthetic Example 27 tert-Butyl [2-[methyl[[(R)-2-[[[3-methyl-4-(2,2,2-trifluoroethoxy)-2-pyridyl]methyl]sulfinyl]-1H-benzimidazol-1-yl]carbonyl]amino]-3-pyridyl]methyl carbonate

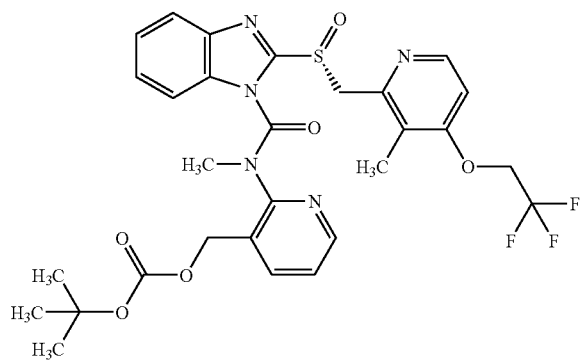 [SMILES: Cc1c(OCC(F)(F)F)ccnc1C[S@@](=O)c1nc2ccccc2n1C(=O)N(C)c1ncccc1COC(=O)OC(C)(C)C]

To a solution of bis(trichloromethyl)carbonate (0.30 g) in tetrahydrofuran (20 mL) was added dropwise pyridine (0.24 mL) under ice-cooling. The reaction solution was stirred for 30 minutes under ice-cooling, and tert-butyl [2-(methylamino)-3-pyridyl]methyl carbonate (0.71 g) obtained in Reference Synthetic Example 28 was added thereto, and further stirred at room temperature for 2 hrs. The precipitated solid was filtered off, and the filtrate was concentrated under reduced pressure. The residue was dissolved in tetrahydrofuran (20 mL), and (R)-2-[[[3-methyl-4-(2,2,2-trifluoroethoxy)-2-pyridyl]methyl]sulfinyl]-1H-benzimidazole (0.92 g), triethylamine (0.70 mL) and 4-dimethylaminopyridine (0.031 g) were added thereto, and stirred at 60° C. for 1 hr. To the reaction solution was added water (50 mL), and extracted twice with ethyl acetate (50 mL). The ethyl acetate layer was washed with saturated brine (50 mL), and dried over anhydrous sodium sulfate, followed by concentrating under reduced pressure. The residue was purified with flash silica gel column chromatography (eluted with acetone hexane=1:2), and further with basic silica gel column chromatography (eluted with ethyl acetate) to give title compound as pale yellow amorphous solid (0.38 g).

$^1$H-NMR(CDCl$_3$): 1.46(9H,s), 2.25(3H,s), 3.54(3H,s), 4.37(2H,q,J=8.0 Hz), 4.95(2H,s), 5.15(1H,d,J=14.0 Hz), 5.27(1H,d,J=14.0 Hz), 6.63(1H,d,J=5.4 Hz), 7.26-7.45(3H, m), 7.69-7.87(3H,m), 8.33(1H,d,J=5.4 Hz), 8.44-8.46(1H, m).

Synthetic Example 28

2-[Methyl[[(R)-2-[[[3-methyl-4-(2,2,2-trifluoroethoxy)-2-pyridyl]methyl]sulfinyl]-1H-benzimidazol-1-yl]carbonyl]amino]benzyl acetate

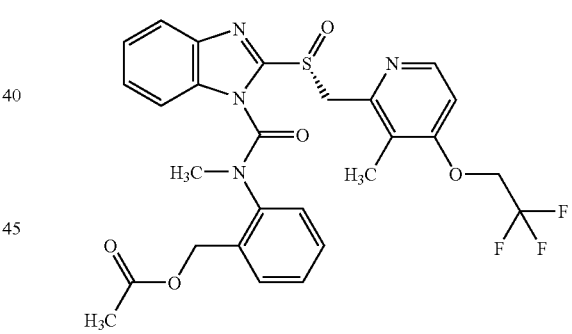

To a solution of bis(trichloromethyl)carbonate (1.46 g) in tetrahydrofuran (30 mL) was added dropwise pyridine (1.16 mL) under ice-cooling. The reaction solution was stirred for 30 minutes under ice-cooling, and 2-(methylamino)benzyl acetate (2.57 g) obtained in Reference Synthetic Example 29 was added thereto, and further stirred at room temperature for 3 hrs. The precipitated solid was filtered off, and the filtrate was concentrated under reduced pressure. The residue was dissolved in tetrahydrofuran (40 mL), and (R)-2-[[[3-methyl-4-(2,2,2-trifluoroethoxy)-2-pyridyl]methyl]sulfinyl]-1H-benzimidazole (4.41 g), triethylamine (3.33 mL) and 4-dimethylaminopyridine (0.15 g) were added thereto, and stirred at 60° C. for 18 hrs. To the reaction solution was added water (100 mL), and extracted with ethyl acetate (100 mL). The ethyl acetate layer was washed with saturated brine (100 mL), and dried over anhydrous sodium sulfate, followed by concentrating under reduced pressure. The residue was purified with flash silica gel column chromatography (eluted with acetone:hexane=1:4, then 1:2). The purified material was crystallized from ethyl acetate-diethyl ether-hexane to give title compound as white solid (2.76 g).

¹H-NMR(CDCl₃): 2.10(3H,s), 2.00-2.30(3H,br), 3.20-3.50(3H,br), 4.38(2H,q,J=7.6 Hz), 4.70-5.20(2H,m), 5.20-5.50(2H,m), 6.65(1H,d,J=5.4 Hz), 7.10-7.82(8H,m), 8.38(1H,d,J=5.4 Hz).

Synthetic Example 29

2-[[2-(Acetyloxy)ethyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate

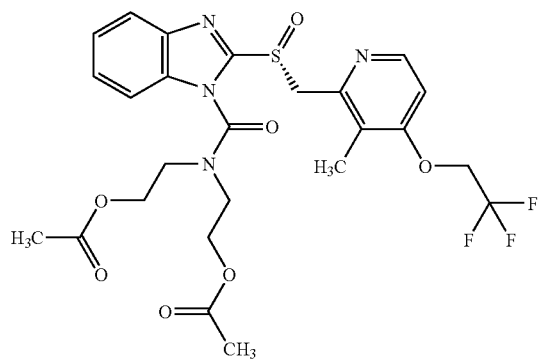 [SMILES: CC(=O)OCCN(CCOC(C)=O)C(=O)n1c([S@](=O)Cc2nccc(OCC(F)(F)F)c2C)nc2ccccc21]

To a solution of bis(trichloromethyl)carbonate (0.50 g) in tetrahydrofuran (30 mL) was added dropwise a solution of pyridine (0.40 mL) in tetrahydrofuran (1 mL) under ice-cooling. The reaction solution was stirred for 10 minutes under ice-cooling, and 2-[(2-acetyloxyethyl)amino]ethyl acetate hydrochloride (1.13 g) obtained in Reference Synthetic Example 30 was added thereto. A solution of triethylamine (0.70 mL) in tetrahydrofuran (1 mL) was added, and stirred at room temperature for 2 hrs. The precipitated solid was filtered off, and the filtrate was concentrated under reduced pressure. To the residue was added ethyl acetate (20 mL), and the precipitated solid was filtered off, and then, the filtrate was concentrated under reduced pressure. The residue was dissolved in tetrahydrofuran (30 mL). To the solution were added (R)-2-[[[3-methyl-4-(2,2,2-trifluoroethoxy)-2-pyridyl]methyl]sulfinyl]-1H-benzimidazole (1.48 g), triethylamine (1.12 mL) and 4-dimethylaminopyridine (catalytic amount), and stirred at 60° C. overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with silica gel column chromatography (eluted with ethyl acetate:hexane=1:1, then ethyl acetate), and further with basic silica gel column chromatography (eluted with ethyl acetate:hexane=1:1, then ethyl acetate). The purified material was dissolved in ethyl acetate (20 mL), and activated charcoal was added thereto, followed by stirring overnight. The activated charcoal was filtered off, and the filtrate was concentrated under reduced pressure to give title compound as yellow amorphous solid (1.60 g).

¹H-NMR(CDCl₃): 2.06(3H,s), 2.08(3H,s), 2.24(3H,s), 3.40-4.45(8H,m), 4.39(2H,q,J=7.9 Hz), 4.88(1H,d,J=13.2 Hz), 5.05(1H,d,J=13.2 Hz), 6.66(1H,d,J=5.6 Hz), 7.38-7.50 (3H,m), 7.87(1H,d,J=6.9 Hz), 8.36(1H,d,J=5.6 Hz).

Synthetic Example 30

[(2S)-1-[[(R)-2-[[[3-methyl-4-(2,2,2-trifluoroethoxy)-2-pyridyl]methyl]sulfinyl]-1H-benzimidazol-1-yl]carbonyl]-2-pyrrolidinyl]methyl acetate

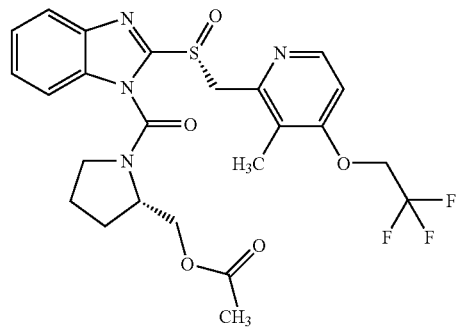 [SMILES: CC(=O)OC[C@@H]1CCCN1C(=O)n1c([S@](=O)Cc2nccc(OCC(F)(F)F)c2C)nc2ccccc21]

To a solution of bis(trichloromethyl)carbonate (0.50 g) in tetrahydrofuran (30 mL) was added dropwise a solution of pyridine (0.40 mL) in tetrahydrofuran (1 mL) under ice-cooling. The reaction solution was stirred for 1 hr under ice-cooling, and (S)-2-pyrrolidinylmethyl acetate hydrochloride (0.90 g) obtained in Reference Synthetic Example 31 was added thereto. A solution of triethylamine (0.70 mL) in tetrahydrofuran (1 mL) was added dropwise, and stirred at room temperature for 2 hrs. The reaction solution was concentrated under reduced pressure. To the residue was added water (50 mL), and extracted with ethyl acetate (50 mL), and then, dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl] sulfinyl]-1H-benzimidazole (1.11 g), triethylamine (0.84 mL) and 4-dimethylaminopyridine (0.037 g), and stirred at 60° C. for 1 day, and then at room temperature for 2 days. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:1, then ethyl acetate), and further with silica gel column chromatography (eluted with ethyl acetate:hexane=3:1, then ethyl acetate, then acetone:ethyl acetate=1:4, then 2:3) to give title compound as pale yellow amorphous solid (0.80 g).

¹H-NMR(CDCl₃): 1.80-2.30(4H,m), 2.09(3H,s), 2.30(3H, s), 3.39(1H,m), 3.50-3.62(1H,m), 4.20-4.45(4H,m), 4.58(1H,m), 4.89(1H,d,J=13.5 Hz), 4.96(1H,d,J=13.5 Hz), 6.65(1H,d,J=5.9 Hz), 7.36-7.48(3H,m), 7.89(1H,d,J=8.7 Hz), 8.38 (1H,d,J=5.9 Hz).

Synthetic Example 31

Ethyl [methyl-[[(R)-2-[[[3-methyl-4-(2,2,2-trifluoro-ethoxy)-2-pyridyl]methyl]sulfinyl]-1H-benzimidazol-1-yl]carbonyl]amino]actate

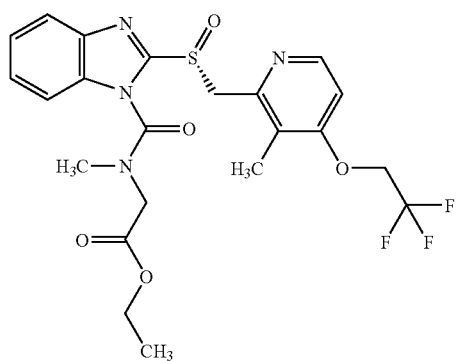 [SMILES: CCOC(=O)CN(C)C(=O)n1c([S@](=O)Cc2nccc(OCC(F)(F)F)c2C)nc2ccccc21]

To a solution of bis(trichloromethyl)carbonate (0.50 g) in tetrahydrofuran (30 mL) was added dropwise a solution of pyridine (0.40 mL) in tetrahydrofuran (1 mL) under ice-cooling. The reaction solution was stirred for 30 minutes under ice-cooling, and sarcosine ethyl ester hydrochloride (0.77 g) was added thereto. A solution of triethylamine (0.70 mL) in tetrahydrofuran (1 mL) was added dropwise, and stirred at room temperature for 1 hr. The precipitated solid was filtered off, and the filtrate was concentrated under reduced pressure. To the residue was added water (50 mL), and extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (33 mL). To the solution were added (R)-2-[[[3-methyl-4-(2,2,2-trifluoroethoxy)-2-pyridyl]methyl]sulfinyl]-1H-benzimidazole sodium salt (1.37 g) and 4-dimethylaminopyridine (catalytic amount), and stirred at 60° C. overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:1, then ethyl acetate) to give title compound as yellow amorphous solid (0.40 g).

$^1$H-NMR(CDCl$_3$): 1.33(3H,t,J=7.1 Hz), 2.24(3H,s), 3.10 (3H,bs), 3.70-4.30(2H,br), 4.28(2H,q,J=7.1 Hz), 4.38(2H,q, J=7.8 Hz), 4.82-5.10(2H,br), 6.63(1H,d,J=5.5 Hz), 7.34-7.52 (2H,m), 7.70-7.90(2H,m), 8.32(1H,d,J=5.5 Hz).

Synthetic Example 32

2-[[[5-Methoxy-2-[[(4-methoxy-3,5-dimethyl-2-pyridyl]methyl]sulfinyl]-1H-benzimidazol-1-yl]carbonyl](methyl)amino]ethyl benzoate

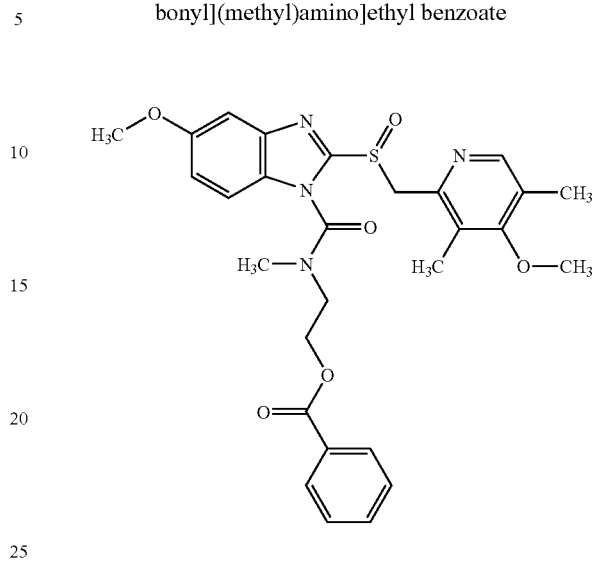

To a solution of bis(trichloromethyl)carbonate (0.344 g) in tetrahydrofuran (10 mL) was added dropwise a solution of pyridine (0.281 mL) in tetrahydrofuran (5 mL) under ice-cooling, and stirred for 30 minutes at 0° C. To the reaction solution was added 2-(methylamino)ethyl benzoate hydrochloride (0.750 g) obtained in Reference Synthetic Example 5. A solution of triethylamine (0.485 mL) in tetrahydrofuran (5 mL) was added, and stirred at 0° C. for 1 hr, and further at room temperature for 30 minutes. The reaction solution was concentrated under reduced pressure, and to the residue was added water (30 mL), and then extracted with ethyl acetate (50 mL). The ethyl acetate layer was washed with saturated brine (30 mL), and dried over anhydrous sodium sulfate, followed by concentrating under reduced pressure. The resulting oil was dissolved in tetrahydrofuran (5 mL), and the solution was added to a solution of 5-methoxy-2-[[(4-methoxy-3,5-dimethyl-2-pyridyl)methyl]sulfinyl]-1H-benzimidazole (1.0 g), triethylamine (0.808 mL) and 4-dimethylaminopyridine (0.071 g) in tetrahydrofuran (10 mL), and stirred at 40° C. for 18 hrs. The reaction solution was concentrated under reduced pressure, and to the residue was added water (30 mL), and extracted with ethyl acetate (50 mL). The ethyl acetate layer was washed with saturated brine (30 mL), and dried over anhydrous sodium sulfate, followed by concentrating under reduced pressure. The residue was purified with silica gel column chromatography (eluted with ethyl acetate:hexane=1:1, then ethyl acetate) to give a mixture of 1:1 of title compound and 2-[[[6-methoxy-2-[[(4-methoxy-3,5-dimethyl-2-pyridyl]methyl]sulfinyl]-1H-benzimidazol-1-yl]carbonyl](methyl)amino]ethyl benzoate as pale yellow amorphous solid (1.50 g).

¹H-NMR(CDCl₃): 2.05-2.35(6H,m), 3.00-3.30(3H,br), 3.60-4.40(8H,m), 4.60-5.10(4H,m), 6.80-7.00(2H,m), 7.20-7.70(4H,m), 7.95-8.25(3H,m).

Synthetic Example 33

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propyl benzoate

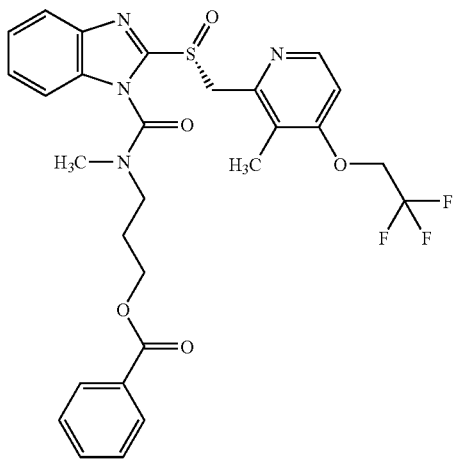 [SMILES: Cc1c(OCC(F)(F)F)ccnc1C[S@@](=O)c1nc2ccccc2n1C(=O)N(C)CCCOC(=O)c1ccccc1]

To a solution of bis(trichloromethyl)carbonate (0.582 g) in tetrahydrofuran (20 mL) was added dropwise a solution of pyridine (0.485 mL) in tetrahydrofuran (1 mL) under ice-cooling. The reaction solution was stirred for 1 hr under ice-cooling, and 3-(methylamino)propyl benzoate hydrochloride (1.38 g) obtained in Reference Synthetic Example 32 was added thereto. A solution of triethylamine (0.84 mL) in tetrahydrofuran (1 mL) was added dropwise, and stirred at room temperature for 2 hrs. The reaction solution was concentrated under reduced pressure, and to the residue was added water (40 mL), and then extracted with ethyl acetate (80 mL). The ethyl acetate layer was washed with saturated brine (25 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.054 g), and stirred at 60° C. for 4 hrs. The reaction solution was concentrated under reduced pressure, and to the residue was added water (40 mL), and extracted with ethyl acetate (80 mL). The ethyl acetate layer was washed with saturated brine (30 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (1.26 g).

¹H-NMR(CDCl₃): 2.21(3H,s), 2.20-2.30(2H,bm), 3.06(3H,bs), 3.60-3.75(2H,bm), 4.36(2H,q,J=7.8 Hz), 4.30-4.50(2H,bm), 4.80-5.15(2H,bm), 6.62(1H,d,J=5.7 Hz), 7.26-7.44(5H,m), 7.54(1H,m), 7.81(1H,m), 7.93-8.03(2H,bm), 8.35(1H,d,J=5.7 Hz).

Synthetic Example 34

2-[Methyl[[2-[[[3-methyl-4-(2,2,2-trifluoroethoxy)-2-pyridyl]methyl]sulfinyl]-1H-benzimidazol-1-yl]carbonyl]amino]ethyl tetrahydropyran-4-yl carbonate

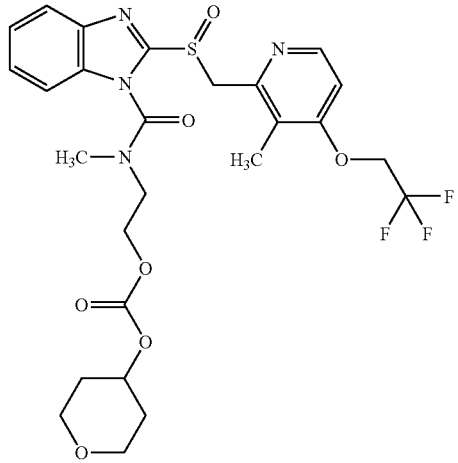 [SMILES: Cc1c(OCC(F)(F)F)ccnc1CS(=O)c1nc2ccccc2n1C(=O)N(C)CCOC(=O)OC1CCOCC1]

To a solution of bis(trichloromethyl)carbonate (0.582 g) in tetrahydrofuran (20 mL) was added dropwise a solution of pyridine (0.485 mL) in tetrahydrofuran (1 mL) under ice-cooling. The reaction solution was stirred for 20 minutes under ice-cooling, and 2-(methylamino)ethyl tetrahydropyran-4-yl carbonate hydrochloride (1.43 g) obtained in Reference Synthetic Example 17 was added thereto. A solution of triethylamine (0.84 mL) in tetrahydrofuran (1 mL) was added dropwise, and stirred at room temperature for 3 hrs. The reaction solution was concentrated under reduced pressure, and to the residue was added water (30 mL), and then extracted with ethyl acetate (80 mL). The ethyl acetate layer was washed with saturated brine (20 mL), and dried over anhydrous magnesium sulfate. The solution was concentrated under reduced pressure, and the residue was dissolved in tetrahydrofuran (20 mL). To the solution were added 2-[[[3-methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.027 g), and stirred at 60° C. for 17.5 hrs. The reaction solution was concentrated under reduced pressure, and to the residue was added water (50 mL), and extracted with ethyl acetate (120 mL). The ethyl acetate layer was washed with saturated brine (30 mL), and dried over anhydrous magnesium sulfate. After concentrating under reduced pressure, the residue was purified with basic silica gel column chromatography (eluted with ethyl acetate:hexane=1:2, then 1:1), and further purified with silica gel column chromatography (eluted with ethyl acetate:hexane=1:1, then 2:1). The purified material was crystallized from diethyl ether to give title compound as colorless solid (1.23 g).

¹H-NMR(CDCl₃): 1.64-1.81(2H,m), 1.92-2.03(2H,m), 2.23(3H,s), 3.10(3H,bs), 3.40-4.30(2H,br), 3.46-3.59(2H,m), 3.87-3.99(2H,m), 4.39(2H,q,J=7.9 Hz), 4.45(2H,m), 4.77-5.15(3H,m), 6.65(1H,d,J=5.4 Hz), 7.35-7.50(3H,m), 7.85(1H,m), 8.36(1H,d,J=5.4 Hz).

Synthetic Example 35

Ethyl 2-[methyl[[2-([[3-methyl-4-(2,2,2-trifluoroethoxy)-2-pyridyl]methyl]sulfinyl]-1H-benzimidazol-1-yl]carbonyl]amino]ethyl carbonate

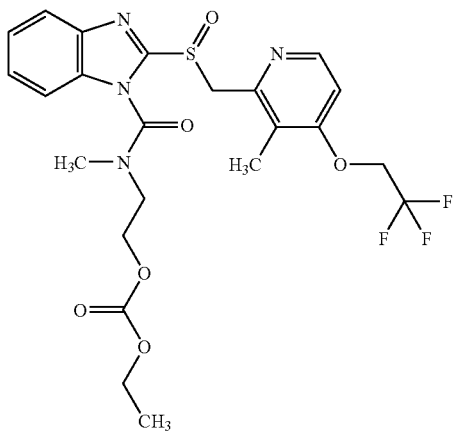

To a solution of bis(trichloromethyl)carbonate (0.582 g) in tetrahydrofuran (20 mL) was added dropwise a solution of pyridine (0.485 mL) in tetrahydrofuran (1 mL) under ice-cooling. The reaction solution was stirred for 30 minutes under ice-cooling, and ethyl 2-(methylamino)ethyl carbonate hydrochloride (1.10 g) obtained in Reference Synthetic Example 14 was added thereto. A solution of triethylamine (0.84 mL) in tetrahydrofuran (1 mL) was added dropwise, and stirred at room temperature for 3 hrs. The reaction solution was concentrated under reduced pressure, and to the residue was added water (30 mL), and then extracted with ethyl acetate (80 mL). The ethyl acetate layer was washed with saturated brine (30 mL), and dried over anhydrous magnesium sulfate. The solution was concentrated under reduced pressure, and the residue was dissolved in tetrahydrofuran (20 mL). To the solution were added 2-[[[3-methyl-4-(2,2,2-trifluoroethoxy)-2-pyridyl]methyl]sulfinyl]-1H-benzimidazole (1.63 g), triethylamine (1.23 mL) and 4-dimethylaminopyridine (0.054 g), and stirred at 60° C. for 14 hrs. The reaction solution was concentrated under reduced pressure, and to the residue was added water (40 mL), and extracted with ethyl acetate (100 mL). The ethyl acetate layer was washed with saturated brine (30 mL), and dried over anhydrous magnesium sulfate. After concentrating under reduced pressure, the residue was purified with basic silica gel column chromatography (eluted with ethyl acetate:hexane=1:2, then 1:1), and further purified with silica gel column chromatography (eluted with ethyl acetate:hexane=1:1, then 2:1) to give title compound as yellow amorphous solid (1.27 g).

$^1$H-NMR(CDCl$_3$): 1.32(3H,t,J=7.1 Hz), 2.23(3H,s), 3.09 (3H,bs), 3.50-4.76(4H,br), 4.21(2H,q,J=7.1 Hz), 4.38(2H,q, J=7.9 Hz), 4.84-5.14(2H,m), 6.64(1H,d,J=5.6 Hz), 7.36-7.46 (3H,m), 7.83(1H,d,J=7.2 Hz), 8.34(1H,d,J=5.6 Hz).

Synthetic Example 36

Ethyl 2-[methyl[[(S)-2-[[[3-methyl-4-(2,2,2-trifluoroethoxy)-2-pyridyl]methyl]sulfinyl]-1H-benzimidazol-1-yl]carbonyl]amino]ethyl carbonate

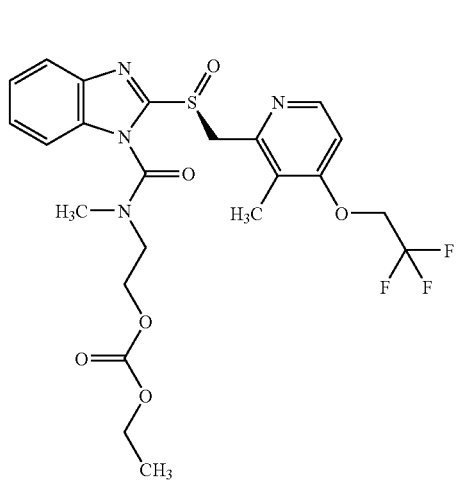 [SMILES: CCOC(=O)OCCN(C)C(=O)n1c([S@@](=O)Cc2nccc(OCC(F)(F)F)c2C)nc2ccccc21]

To a solution of bis(trichloromethyl)carbonate (0.582 g) in tetrahydrofuran (20 mL) was added dropwise a solution of pyridine (0.485 mL) in tetrahydrofuran (1 mL) under ice-cooling. The reaction solution was stirred for 1 hr under ice-cooling, and ethyl 2-(methylamino)ethyl carbonate hydrochloride (1.10 g) obtained in Reference Synthetic Example 14 was added thereto. A solution of triethylamine (0.84 mL) in tetrahydrofuran (1 mL) was added dropwise, and stirred at room temperature for 2 hrs. The reaction solution was concentrated under reduced pressure, and to the residue was added water (30 mL), and then extracted with ethyl acetate (80 mL). The ethyl acetate layer was washed with saturated brine (30 mL), and dried over anhydrous magnesium sulfate. The solution was concentrated under reduced pressure, and the residue was dissolved in tetrahydrofuran (20 mL). To the solution were added (S)-2-[[[3-methyl-4-(2,2,2-trifluoroethoxy)-2-pyridyl]methyl]sulfinyl]-1H-benzimidazole (1.15 g), triethylamine (0.87 mL) and 4-dimethylaminopyridine (0.035 g), and stirred at 60° C. for 12 hrs. The reaction solution was concentrated under reduced pressure, and to the residue was added water (30 mL), and extracted with ethyl acetate (100 mL). The ethyl acetate layer was washed with saturated brine (30 mL), and dried over anhydrous magnesium sulfate. After concentrating under reduced pressure, the residue was purified with basic silica gel column chromatography (eluted with ethyl acetate:hexane=1:2, then 1:1). The purified material was crystallized from diethyl ether to give title compound as colorless solid (0.40 g).

$^1$H-NMR(CDCl$_3$): 1.32(3H,t,J=7.2 Hz), 2.23(3H,s), 3.10 (3H,bs), 3.50-4.56(4H,br), 4.22(2H,q,J=7.2 Hz), 4.38(2H,q, J=7.9 Hz), 4.84-5.14(2H,m), 6.65(1H,d,J=5.6 Hz), 7.34-7.50 (3H,m), 7.85(1H,m), 8.36(1H,d,J=5.6 Hz).

Synthetic Example 37

Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate

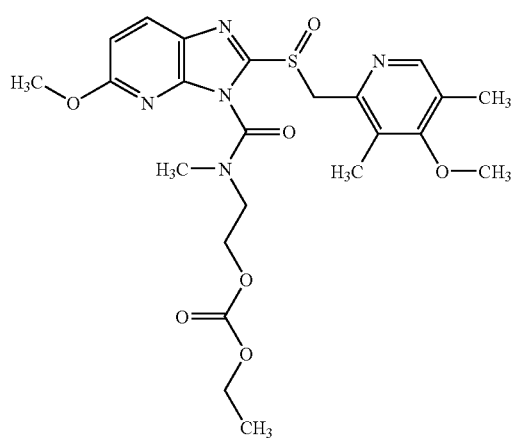

To a solution of bis(trichloromethyl)carbonate (0.582 g) in tetrahydrofuran (20 mL) was added dropwise a solution of pyridine (0.485 mL) in tetrahydrofuran (1 mL) under ice-cooling. The reaction solution was stirred for 30 minutes under ice-cooling, and ethyl 2-(methylamino)ethyl carbonate hydrochloride (1.10 g) obtained in Reference Synthetic Example 14 was added thereto. A solution of triethylamine (0.84 mL) in tetrahydrofuran (1 mL) was added dropwise, and stirred at room temperature for 2.5 hrs. The reaction solution was concentrated under reduced pressure, and to the residue was added water (30 mL), and then extracted with ethyl acetate (80 mL). The ethyl acetate layer was washed with saturated brine (30 mL), and dried over anhydrous magnesium sulfate. The solution was concentrated under reduced pressure, and the residue was dissolved in tetrahydrofuran (20 mL). To the solution were added 5-methoxy-2-[[(4-methoxy-3,5-dimethyl-2-pyridyl)methyl]sulfinyl]-1H-imidazo[4,5-b]pyridine (1.44 g) synthesized by a method described in JP-A 63-146882, triethylamine (1.16 mL) and 4-dimethylaminopyridine (0.049 g), and stirred at 60° C. for 6 hrs. The reaction solution was concentrated under reduced pressure, and to the residue was added water (30 mL), and extracted with ethyl acetate (100 mL). The ethyl acetate layer was washed with saturated brine (30 mL), and dried over anhydrous magnesium sulfate. After concentrating under reduced pressure, the residue was purified with basic silica gel column chromatography (eluted with ethyl acetate:hexane=1:2, then 1:1). The purified material was crystallized from diethyl ether to give title compound as colorless solid (0.721 g).

$^1$H-NMR(CDCl$_3$): 1.25-1.34(3H,m), 2.23(6H,s), 3.15, 3.32(total 3H,s), 3.72(3H,s), 3.90-4.53(9H,m), 4.86(1H,d, J=13.4 Hz), 4.95(1H,d,J=13.4 Hz), 6.79(1H,d,J=8.7 Hz), 7.95(1H,d,J=8.7 Hz), 8.22(1H,s).

Synthetic Example 38

2-[[[5-Methoxy-2-[[(4-methoxy-3,5-dimethyl-2-pyridyl)methyl]sulfinyl]-3H-imidazo[4,5-b]pyridin-3-yl]carbonyl](methyl)amino]ethyl acetate

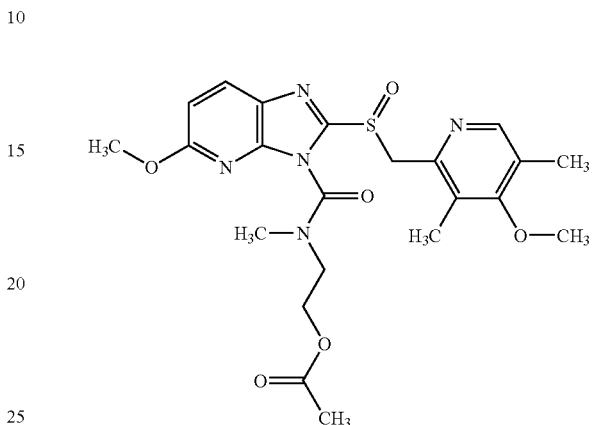

To a solution of bis(trichloromethyl)carbonate (0.582 g) in tetrahydrofuran (20 mL) was added dropwise a solution of pyridine (0.485 mL) in tetrahydrofuran (1 mL) under ice-cooling. The reaction solution was stirred for 30 minutes under ice-cooling, and 2-(methylamino)ethyl acetate hydrochloride (0.922 g) obtained in Reference Synthetic Example 2 was added thereto. A solution of triethylamine (0.84 mL) in tetrahydrofuran (1 mL) was added dropwise, and stirred at room temperature for 2 hrs. The reaction solution was concentrated under reduced pressure, and to the residue was added water (30 mL), and then extracted with ethyl acetate (80 mL). The ethyl acetate layer was washed with saturated brine (30 mL), and dried over anhydrous magnesium sulfate. The solution was concentrated under reduced pressure, and the residue was dissolved in tetrahydrofuran (20 mL). To the solution were added 5-methoxy-2-[[(4-methoxy-3,5-dimethyl-2-pyridyl)methyl]sulfinyl]-1H-imidazo[4,5-b]pyridine (0.85 g) synthesized by a method described in JP-A 63-146882, triethylamine (0.70 mL) and 4-dimethylaminopyridine (0.025 g), and stirred at 60° C. for 5 hrs. The reaction solution was concentrated under reduced pressure, and to the residue was added water (30 mL), and extracted with ethyl acetate (90 mL). The ethyl acetate layer was washed with saturated brine (30 mL), and dried over anhydrous magnesium sulfate. After concentrating under reduced pressure, the residue was purified with basic silica gel column chromatography (eluted with ethyl acetate:hexane=1:2, then 1:1). The purified material was crystallized from diethyl ether to give title compound as colorless solid (0.173 g).

$^1$H-NMR(CDCl$_3$): 2.04,2.09(total 3H,s), 2.24(6H,s), 3.13, 3.30(total 3H,s), 3.45-3.97(2H,m), 3.72(3H,s), 3.97(3H,s), 4.15-4.50(2H,m), 4.85(1H,d,J=13.1 Hz), 4.96(1H,d,J=13.1 Hz), 6.80(1H,d,J=8.9 Hz), 7.96(1H,d,J=8.9 Hz), 8.22(1H,s).

Synthetic Example 39

2-[[[5-Methoxy-2-[[(4-methoxy-3,5-dimethyl-2-pyridyl)methyl]sulfinyl]-3H-imidazo[4,5-b]pyridin-3-yl]carbonyl](phenyl)amino]ethyl acetate

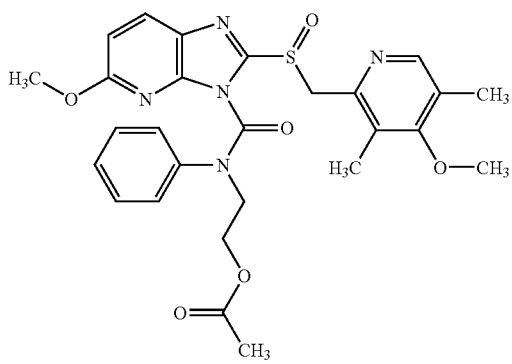

To a solution of bis(trichloromethyl)carbonate (0.291 g) in tetrahydrofuran (10 mL) was added dropwise a solution of pyridine (0.243 mL) in tetrahydrofuran (1 mL) under ice-cooling. The reaction solution was stirred for 30 minutes under ice-cooling, and 2-anilinoethyl acetate hydrochloride (0.647 g) obtained in Reference Synthetic Example 27 was added thereto. A solution of triethylamine (0.419 mL) in tetrahydrofuran (1 mL) was added dropwise, and stirred at room temperature for 3 hrs. The reaction solution was concentrated under reduced pressure, and to the residue was added water (20 mL), and then extracted with ethyl acetate (50 mL). The ethyl acetate layer was washed with saturated brine (15 mL), and dried over anhydrous magnesium sulfate. The solution was concentrated under reduced pressure, and the residue was dissolved in tetrahydrofuran (10 mL). To the solution were added 5-methoxy-2-[[(4-methoxy-3,5-dimethyl-2-pyridyl)methyl]sulfinyl]-1H-imidazo[4,5-b]pyridine (0.867 g) synthesized by a method described in JP-A 63-146882, triethylamine (0.697 mL) and 4-dimethylaminopyridine (0.020 g), and stirred at 60° C. for 10 hrs. The reaction solution was concentrated under reduced pressure, and to the residue was added water (20 mL), and extracted with ethyl acetate (50 mL). The ethyl acetate layer was washed with saturated brine (15 mL), and dried over anhydrous magnesium sulfate. After concentrating under reduced pressure, the residue was purified with basic silica gel column chromatography (eluted with ethyl acetate:hexane=1:1). The purified material was crystallized from diethyl ether to give title compound as colorless solid (0.311 g).

$^1$H-NMR(CDCl$_3$): 1.96(3H,s), 2.23(3H,s), 2.25(3H,s), 3.72(3H,s), 4.01(3H,s), 4.12-4.52(4H,m), 4.78-5.22(2H,m), 6.62(1H,d,J=8.7 Hz), 7.02-7.18(3H,m), 7.32-7.48(2H,m), 7.73(1H,d,J=8.7 Hz), 8.26(1H,s).

Synthetic Example 40

4-[Methyl[[(R)-2-[[[3-methyl-4-(2,2,2-trifluoroethoxy)-2-pyridyl]methyl]sulfinyl]-1H-benzimidazol-1-yl]carbonyl]amino]butyl acetate

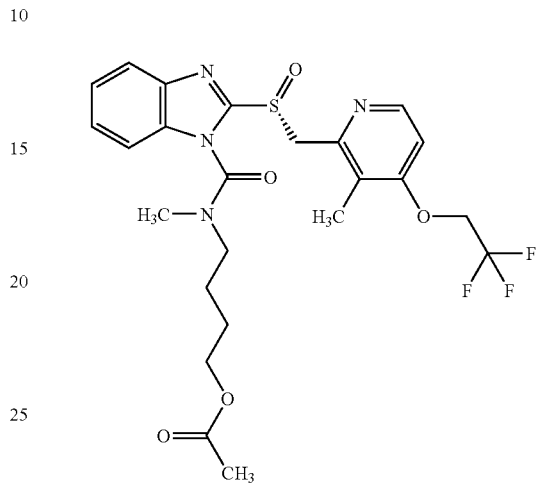

To a solution of bis(trichloromethyl)carbonate (0.59 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and 4-(methylamino)butyl acetate hydrochloride (1.08 g) obtained in Reference Synthetic Example 37 was added thereto. A solution of triethylamine (0.84 mL) in tetrahydrofuran (1 mL) was added dropwise, and stirred at room temperature for 3 hrs. The reaction solution was concentrated under reduced pressure, and to the residue was added water (50 mL), and then extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.02 g), triethylamine (0.77 mL) and 4-dimethylaminopyridine (catalytic amount), and stirred at 60° C. overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (0.93 g).

$^1$H-NMR(CDCl$_3$): 1.65-1.85(4H,m), 2.03(3H,s), 2.23(3H,s), 3.02(3H,bs), 3.45-3.63(2H,m), 4.03-4.13(2H,m), 4.37 (2H,q,J=7.8 Hz), 4.85-5.13(2H,m), 6.64(1H,d,J=5.6 Hz), 7.36-7.46(3H,m), 7.84(1H,d,J=8.4 Hz), 8.35(1H,d,J=5.6 Hz).

Synthetic Example 41

Ethyl 4-[methyl[[(R)-2-[[[3-methyl-4-(2,2,2-trifluoroethoxy)-2-pyridyl]methyl]sulfinyl]-1H-benzimidazol-1-yl]carbonyl]amino]butyl carbonate

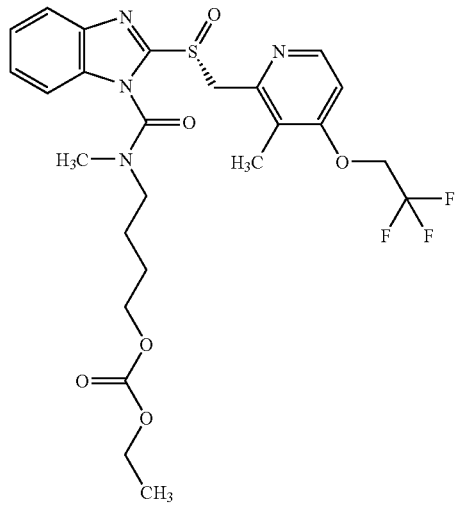 [SMILES: CCOC(=O)OCCCCN(C)C(=O)n1c([S@](=O)Cc2nccc(OCC(F)(F)F)c2C)nc2ccccc21]

To a solution of bis(trichloromethyl)carbonate (0.59 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and ethyl 4-(methylamino)butyl carbonate hydrochloride (1.27 g) obtained in Reference Synthetic Example 39 was added thereto. A solution of triethylamine (0.84 mL) in tetrahydrofuran (1 mL) was added dropwise, and stirred at room temperature for 3 hrs. The reaction solution was concentrated under reduced pressure, and to the residue was added water (50 mL), and then extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.26 g), triethylamine (0.95 mL) and 4-dimethylaminopyridine (catalytic amount), and stirred at 60° C. overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (1.08 g).

$^1$H-NMR(CDCl$_3$): 1.31(3H,t,J=7.2 Hz), 1.73-1.91(4H,m), 2.23(3H,s), 3.01(3H,bs), 3.50-3.62(2H,m), 4.15-4.22(4H,m), 4.38(2H,q,J=7.8 Hz), 4.87-5.13(2H,m), 6.64(1H,d,J=5.4 Hz), 7.35-7.46(3H,m), 7.83(1H,d,J=7.8 Hz), 8.35(1H,d, J=5.4 Hz).

Synthetic Example 42

Ethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propyl carbonate

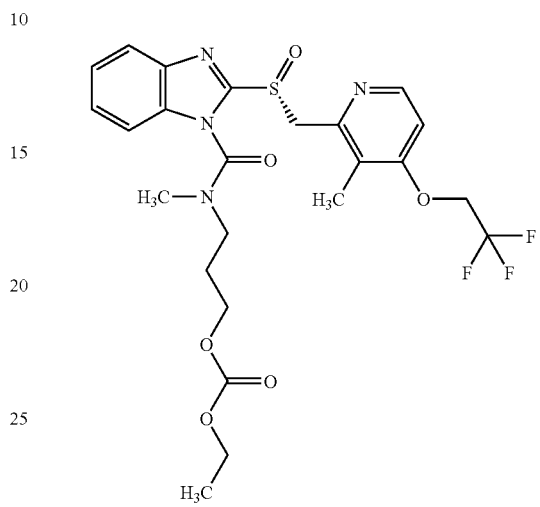

To a solution of bis(trichloromethyl)carbonate (0.59 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and ethyl 4-(methylamino)propyl carbonate hydrochloride (1.18 g) obtained in Reference Synthetic Example 44 was added thereto. A solution of triethylamine (0.84 mL) in tetrahydrofuran (1 mL) was added dropwise, and stirred at room temperature for 3 hrs. The reaction solution was concentrated under reduced pressure, and to the residue was added water (50 mL), and then extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.10 g), triethylamine (0.83 mL) and 4-dimethylaminopyridine (catalytic amount), and stirred at 60° C. overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (0.88 g).

$^1$H-NMR(CDCl$_3$): 1.29(3H,t,J=7.2 Hz), 2.10-2.20(2H,m), 2.22(3H,s), 3.02(3H,bs), 3.55-3.77(2H,m), 4.14-4.30(4H,m), 4.37(2H,q,J=7.8 Hz), 4.83-5.13(2H,m), 6.64(1H,d,J=5.6 Hz), 7.35-7.46(3H,m), 7.82(1H,d,J=8.1 Hz), 8.35(1H,d, J=5.6 Hz).

Synthetic Example 43

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propyl acetate

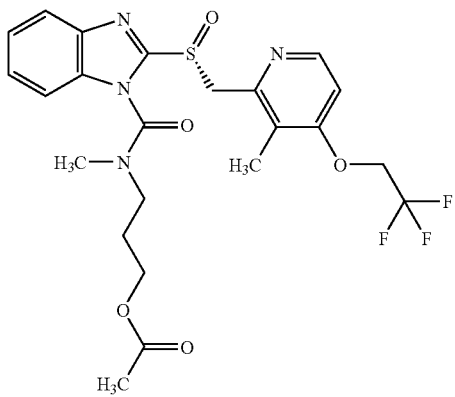 [SMILES: CC(=O)OCCCN(C)C(=O)n1c([S@](=O)Cc2nccc(OCC(F)(F)F)c2C)nc2ccccc21]

To a solution of bis(trichloromethyl)carbonate (1.19 g) in tetrahydrofuran (40 mL) was added dropwise a solution of pyridine (0.95 mL) in tetrahydrofuran (2 mL) under ice-cooling. The reaction solution was stirred for 30 minutes under ice-cooling, and 3-(methylamino)propyl acetate hydrochloride (1.90 g) obtained in Reference Synthetic Example 42 was added thereto. A solution of triethylamine (1.68 mL) in tetrahydrofuran (2 mL) was added dropwise, and stirred at room temperature for 3 hrs. The reaction solution was concentrated under reduced pressure, and to the residue was added water (100 mL), and then extracted with ethyl acetate (100 mL). The ethyl acetate layer was washed with saturated brine (100 mL), and dried over anhydrous magnesium sulfate. The solution was concentrated under reduced pressure, and the residue was dissolved in tetrahydrofuran (40 mL). To the solution were added (R)-2-[[[3-methyl-4-(2,2,2-trifluoroethoxy)-2-pyridyl]methyl]sulfinyl]-1H-benzimidazole (1.99 g), triethylamine (1.50 mL) and 4-dimethylaminopyridine (catalytic amount), and stirred at 60° C. overnight. The reaction solution was concentrated under reduced pressure, and to the residue was added water (100 mL), and extracted with ethyl acetate (100 mL). The ethyl acetate layer was washed with saturated brine (100 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (1.22 g).

$^1$H-NMR(CDCl$_3$): 1.97(3H,s), 2.05-2.15(2H,m), 2.22(3H, s), 3.03(3H,bs), 3.42-3.72(2H,m), 4.10-4.22(2H,m), 4.37 (2H,q,J=7.8 Hz), 4.85-5.13(2H,m), 6.64(1H,d,J=5.6 Hz), 7.24-7.44(3H,m), 7.83(1H,d,J=7.5 Hz), 8.35(1H,d,J=5.6 Hz).

Synthetic Example 44

3-[Methyl[[(R)-2-[[[3-methyl-4-(2,2,2-trifluoroethoxy)-2-pyridyl]methyl]sulfinyl]-1H-benzimidazol-1-yl]carbonyl]amino]propan-1,2-diyl diacetate

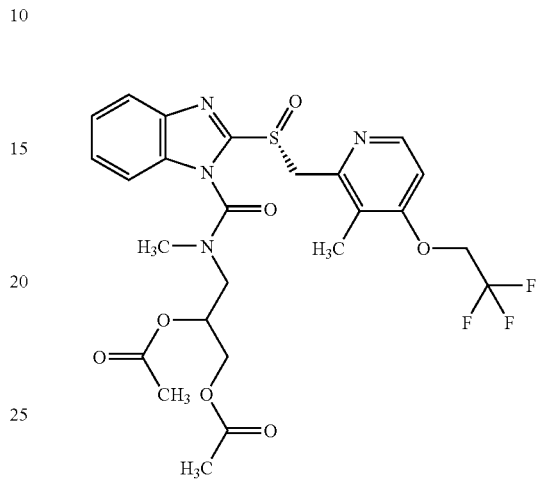

To a solution of bis(trichloromethyl)carbonate (0.59 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and 3-(methylamino)propan-1,2-diyl diacetate hydrochloride (1.35 g) obtained in Reference Synthetic Example 46 was added thereto. A solution of triethylamine (0.84 mL) in tetrahydrofuran (1 mL) was added dropwise, and stirred at room temperature for 3 hrs. The reaction solution was concentrated under reduced pressure, and to the residue was added water (50 mL), and then extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.27 g), triethylamine (0.96 mL) and 4-dimethylaminopyridine (catalytic amount), and stirred at 60° C. overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (0.64 g).

$^1$H-NMR(CDCl$_3$): 2.05(3H,s), 2.13(3H,s), 2.23(3H,s), 3.07(3H,bs), 3.42-3.95(2H,m), 4.06-4.43(2H,m), 4.38(2H,q, J=7.8 Hz), 4.85-5.05(2H,m), 5.42-5.50(1H,m), 6.63-6.66 (1H,m), 7.38-7.51(3H,m), 7.78-7.85(1H,m), 8.33-8.36(1H, m).

Synthetic Example 45

Diethyl 3-[methyl[[(R)-2-[[[3-methyl-4-(2,2,2-trifluoroethoxy)-2-pyridyl]methyl]sulfinyl]-1H-benzimidazol-1-yl]carbonyl]amino]propan-1,2-diyl bis-carbonate

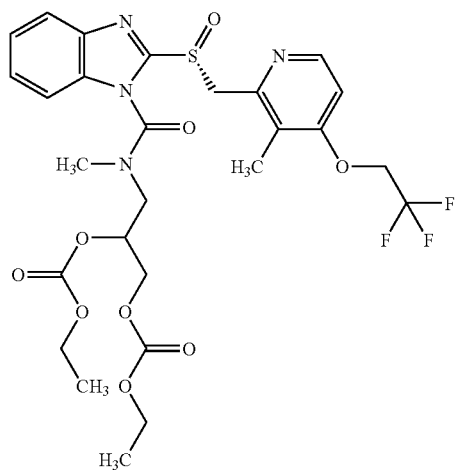 [SMILES: CCOC(=O)OCC(CN(C)C(=O)n1c([S@](=O)Cc2nccc(OCC(F)(F)F)c2C)nc2ccccc21)OC(=O)OCC]

To a solution of bis(trichloromethyl)carbonate (0.59 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and diethyl 3-(methylamino)propan-1,2-diyl biscarbonate hydrochloride (1.71 g) obtained in Reference Synthetic Example 47 was added thereto. A solution of triethylamine (0.84 mL) in tetrahydrofuran (1 mL) was added dropwise, and stirred at room temperature for 3 hrs. The reaction solution was concentrated under reduced pressure, and to the residue was added water (50 mL), and then extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.53 g), triethylamine (1.16 mL) and 4-dimethylaminopyridine (catalytic amount), and stirred at 60° C. overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (1.42 g).

$^1$H-NMR(CDCl$_3$): 1.28-1.34(6H,m), 2.22(3H,s), 3.07(3H,bs), 3.42-4.60(10H,m), 4.85-5.08(2H,m), 5.30-5.42(1H,m), 6.62-6.64(1H,m), 7.37-7.42(3H,m), 7.80-7.83(1H,m), 8.32-8.35(1H,m).

Synthetic Example 46

2-[[[5-Methoxy-2-[[(4-methoxy-3,5-dimethyl-2-pyridyl)methyl]sulfinyl]-3H-imidazo[4,5-b]pyridin-3-yl]carbonyl](methyl)amino]ethyl 3-chlorobenzoate

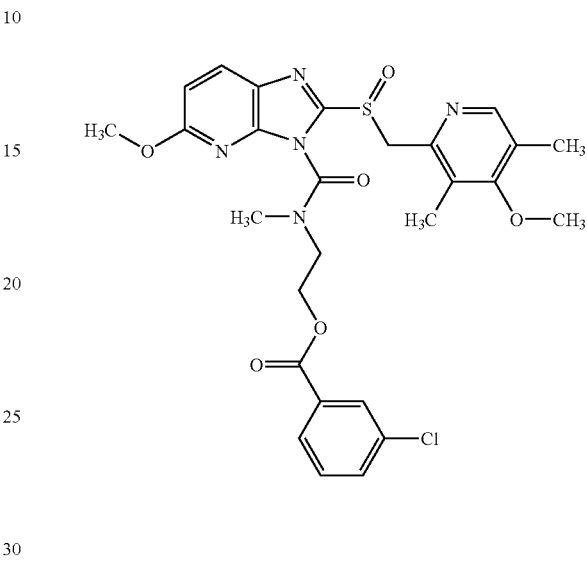

To a solution of bis(trichloromethyl)carbonate (0.194 g) in tetrahydrofuran (7 mL) was added dropwise a solution of pyridine (0.162 mL) in tetrahydrofuran (1 mL) under ice-cooling. The reaction solution was stirred for 30 minutes under ice-cooling, and 2-(methylamino)ethyl 3-chlorobenzoate hydrochloride (0.50 g) obtained in Reference Synthetic Example 7 was added thereto. A solution of triethylamine (0.279 mL) in tetrahydrofuran (1 mL) was added dropwise, and stirred at room temperature for 2.5 hrs. The reaction solution was concentrated under reduced pressure, and to the residue was added water (15 mL), and then extracted with ethyl acetate (50 mL). The ethyl acetate layer was washed with saturated brine (15 mL), and dried over anhydrous magnesium sulfate. The solution was concentrated under reduced pressure, and the residue was dissolved in tetrahydrofuran (10 mL). To the solution were added 5-methoxy-2-[[(4-methoxy-3,5-dimethyl-2-pyridyl)methyl]sulfinyl]-1H-imidazo[4,5-b]pyridine (0.445 g) synthesized by a method described in JP-A 63-146882, triethylamine (0.357 mL) and 4-dimethylaminopyridine (0.012 g), and stirred at 60° C. for 14 hrs. The reaction solution was concentrated under reduced pressure, and to the residue was added water (30 mL), and extracted with ethyl acetate (70 mL). The ethyl acetate layer was washed with saturated brine (20 mL), and dried over anhydrous magnesium sulfate. After concentrating under reduced pressure, the residue was purified with basic silica gel column chromatography (eluted with ethyl acetate:hexane=1:2, then 1:1) to give title compound as colorless amorphous solid (0.360 g).

$^1$H-NMR(CDCl$_3$): 2.21(3H,s), 2.23(3H,s), 3.32,3.38(total 3H,s), 3.72(3H,s), 3.81(3H,s), 3.92-4.09(2H,m), 4.50-4.73 (2H,m), 4.87(1H,d,J=13.4 Hz), 4.94(1H,d,J=13.4 Hz), 6.77 (1H,d,J=8.8 Hz), 7.36(1H,m), 7.52(1H,m), 7.80-8.03(3H,m), 8.20(1H,s).

Synthetic Example 47

2-[Methyl[[2-[[[3-methyl-4-(2,2,2-trifluoroethoxy)-2-pyridyl]methyl]sulfinyl]-1H-benzimidazol-1-yl]carbonyl]amino]ethyl acetate

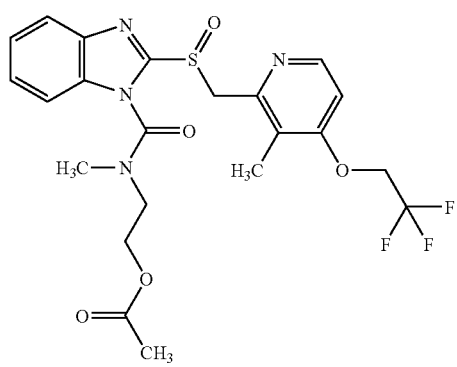

To a solution of bis(trichloromethyl)carbonate (0.582 g) in tetrahydrofuran (20 mL) was added dropwise a solution of pyridine (0.485 mL) in tetrahydrofuran (1 mL) under ice-cooling. The reaction solution was stirred for 1 hr under ice-cooling, and 2-(methylamino)ethyl acetate hydrochloride (0.922 g) obtained in Reference Synthetic Example 2 was added thereto. A solution of triethylamine (0.84 mL) in tetrahydrofuran (1 mL) was added dropwise, and stirred at room temperature for 2.5 hrs. The reaction solution was concentrated under reduced pressure, and to the residue was added water (40 mL), and then extracted with ethyl acetate (80 mL). The ethyl acetate layer was washed with saturated brine (25 mL), and dried over anhydrous magnesium sulfate. The solution was concentrated under reduced pressure, and the residue was dissolved in tetrahydrofuran (15 mL). To the solution were added 2-[[[3-methyl-4-(2,2,2-trifluoroethoxy)-2-pyridyl]methyl]sulfinyl]-1H-benzimidazole (1.10 g), triethylamine (0.84 mL) and 4-dimethylaminopyridine (0.036 g), and stirred at 60° C. for 4.5 hrs. The reaction solution was concentrated under reduced pressure, and to the residue was added water (40 mL), and extracted with ethyl acetate (80 mL). The ethyl acetate layer was washed with saturated brine (30 mL), and dried over anhydrous magnesium sulfate. After concentrating under reduced pressure, the residue was purified with silica gel column chromatography (eluted with ethyl acetate:hexane=1:1, then 2:1) to give title compound as colorless solid (1.18 g).

$^1$H-NMR(CDCl$_3$): 2.10(3H,s), 2.24(3H,s), 3.09(3H,bs), 3.60-4.00(2H,br), 4.25-4.50(2H,m), 4.38(2H,q,J=7.8 Hz), 4.84-5.18(2H,m), 6.64(1H,d,J=5.6 Hz), 7.36-7.48(3H,m), 7.85(1H,d,J=7.8 Hz), 8.35(1H,d,J=5.6 Hz).

Synthetic Example 48

Ethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate A solution of (R)-2-[[[3-methyl-4-(2,2,2-trifluoroethoxy)-2-pyridyl]methyl]sulfinyl]-1H-benzimidazole (130 g), triethylamine (63.8 mL) and 4-dimethylaminopyridine (0.86 g) and 2-[(chlorocarbonyl)(methyl)amino]ethyl ethyl carbonate (84.8 g) obtained in Reference Synthetic Example 34 in tetrahydrofuran (813 mL) was stirred at 45-60° C. for 18 hrs. The reaction solution was concentrated under reduced pressure, and to the residue was added water (300 mL), and then extracted with ethyl acetate (700 mL). The ethyl acetate layer was washed three times with saturated brine (300 mL), and added anhydrous magnesium sulfate (130 g) and activated charcoal (13 g) thereto. The mixture was stirred at room temperature for 30 minutes, and filtered. The filtrate was concentrated under reduced pressure, and the residue was dissolved in diethyl ether (600 mL) containing triethylamine (0.49 mL), and then, concentrated under reduced pressure. This operation was further repeated two times. The resulting oil was dissolved in ethanol (200 mL) containing triethylamine (2.45 mL), and water (120 mL) was added dropwise thereto under ice-cooling. The precipitated crystals were collected by filtration, and washed three times with ice-cooled ethanol-water (volume ratio 1:1, 150 mL), followed by drying to give title compound as colorless solid (172.2 g). $^1$H-NMR (CDCL$_3$) showed the same chart as that of the compound obtained in Synthetic Example 14.

125

Synthetic Example 49

2-Ethoxyethyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

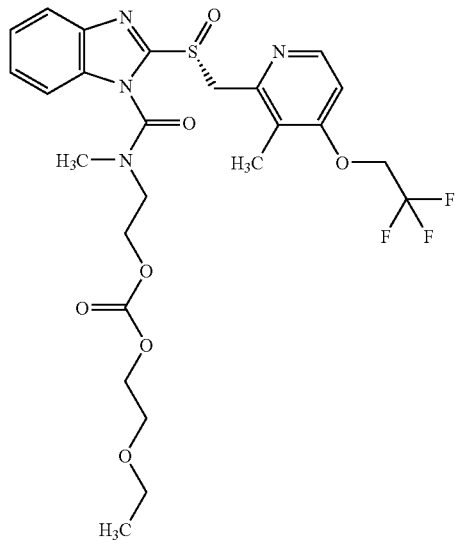 [SMILES: CCOCCOC(=O)OCCN(C)C(=O)n1c([S@](=O)Cc2nccc(OCC(F)(F)F)c2C)nc2ccccc21]

To a solution of bis(trichloromethyl)carbonate (0.43 g) in tetrahydrofuran (20 mL) was added dropwise a solution of pyridine (0.35 mL) in tetrahydrofuran (1 mL) under ice-cooling. The reaction solution was stirred for 10 minutes under ice-cooling, and 2-ethoxyethyl 2-(methylamino)ethyl carbonate hydrochloride (0.82 g) obtained in Reference Synthetic Example 48 was added thereto. A solution of triethylamine (0.60 mL) in tetrahydrofuran (1 mL) was added dropwise, and stirred at room temperature for 3 days. The reaction solution was concentrated under reduced pressure, and to the residue was added water (50 mL), and then extracted with ethyl acetate (50 mL). The ethyl acetate layer was washed with 0.2 N hydrochloric acid (20 mL) and saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g), and stirred at 60° C. for 6 hrs, and further at room temperature for 11 hrs. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=3:7, then ethyl acetate:hexane=7:3) to give title compound as yellow amorphous solid (1.39 g).

$^1$H-NMR(CDCl$_3$): 1.19(3H,t,J=6.9 Hz), 2.23(3H,s), 3.09(3H,bs), 3.40-4.20(2H,br), 3.53(2H,q,J=6.9 Hz), 3.63-3.69(2H,m), 4.27-4.34(2H,m), 4.39(2H,q,J=7.8 Hz), 4.47(2H,m), 4.80-5.20(2H,m), 6.65(1H,d,J=5.6 Hz), 7.30-7.52(3H,m), 7.84(1H,d,J=7.5 Hz), 8.35(1H,d,J=5.6 Hz).

126

Synthetic Example 50

3-Methoxypropyl 2-[methyl[[(R)-2-[[[3-methyl-4-(2,2,2-trifluoroethoxy)-2-pyridyl]methyl]sulfinyl]-1H-benzimidazol-1-yl]carbonyl]amino]ethyl carbonate

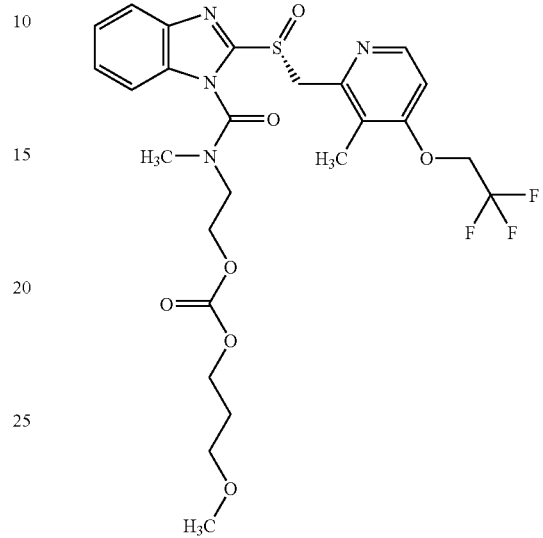

To a solution of bis(trichloromethyl)carbonate (0.53 g) in tetrahydrofuran (20 mL) was added dropwise a solution of pyridine (0.44 mL) in tetrahydrofuran (1 mL) under ice-cooling. The reaction solution was stirred for 5 minutes under ice-cooling, and 3-methoxypropyl 2-(methylamino)ethyl carbonate hydrochloride (0.82 g) obtained in Reference Synthetic Example 49 was added thereto. A solution of triethylamine (0.75 mL) in tetrahydrofuran (1 mL) was added dropwise, and stirred at room temperature for 1 hr. The reaction solution was concentrated under reduced pressure, and to the residue was added water (50 mL), and then extracted with ethyl acetate (50 mL). The ethyl acetate layer was washed with 0.2 N hydrochloric acid (20 mL) and saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g), and stirred at 60° C. for 6 hrs, and further at room temperature for 6 hrs. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=3:7, then ethyl acetate:hexane=7:3). The purified material was crystallized from diethyl ether to give title compound as colorless solid (0.70 g).

$^1$H-NMR(CDCl$_3$): 1.94(2H,quintet,J=6.2 Hz), 2.23(3H,s), 3.09(3H,bs), 3.31(3H,s), 3.40-4.20(2H,br), 3.44(2H,t,J=6.2 Hz), 4.25(2H,t,J=6.5 Hz), 4.38(2H,q,J=7.8 Hz), 4.44(2H,m), 4.80-5.20(2H,m), 6.64(1H,d,J=5.6 Hz), 7.35-7.48(3H,m), 7.83(1H,d,J=7.8 Hz), 8.34(1H,d,J=5.6 Hz).

Synthetic Example 51

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl N,N-dimethylglycinate

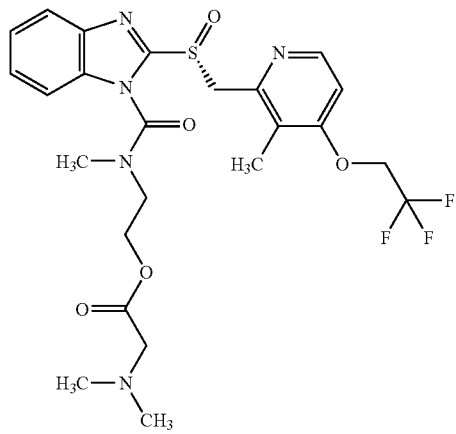

2-(Methylamino)ethyl N,N-dimethylglycinate dihydrochloride (1.06 g) obtained in Reference Synthetic Example 50 was added to tetrahydrofuran (40 mL), and stirred for a while, then bis(trichloromethyl)carbonate (0.77 g) was added thereto. After ice-cooling, a solution of triethylamine (2.17 mL) in tetrahydrofuran (5 mL) was added dropwise, and stirred at room temperature for 3 hrs. The precipitated solid was filtered off, and ethyl acetate (80 mL) was added, then washed with ice-cooled aqueous solution of sodium bicarbonate (50 mL) and saturated brine (50 mL×2), followed by drying over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g), and stirred at 60° C. for 6 hrs, and further at room temperature for 3 days. 4-Dimethylaminopyridine (0.037 g) was added, and further stirred at 60° C. for 6 hrs. The reaction solution was concentrated under reduced pressure, and to the residue was added aqueous solution of sodium bicarbonate (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:1, then ethyl acetate, then methanol:ethyl acetate=1:19). The purified material was crystallized from diethyl ether to give title compound as colorless solid (0.41 g).

$^1$H-NMR(CDCl$_3$): 2.23(3H,s), 2.35(6H,s),3.08(3H,bs), 3.21(2H,s), 3.50-4.20(2H,br), 4.38(2H,q,J=7.8 Hz), 4.44(2H, m), 4.80-5.18(2H,m), 6.64(1H,d,J=5.6 Hz), 7.36-7.48(3H, m), 7.84(1H,d,J=6.9 Hz), 8.35(1H,d,J=5.6 Hz).

Synthetic Example 52

S-[2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl]thioacetate

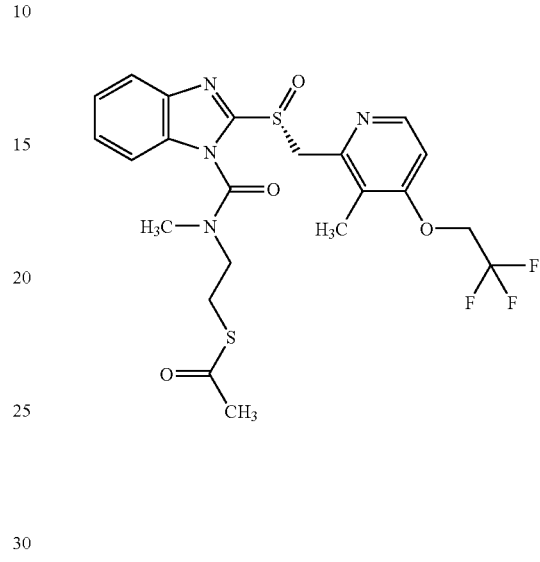

S-[2-(Methylamino)ethyl]thioacetate hydrochloride (0.75 g) obtained in Reference Synthetic Example 51 was added to tetrahydrofuran (30 mL), and stirred for a while, then bis(trichloromethyl)carbonate (0.66 g) was added thereto. After ice-cooling, a solution of triethylamine (1.85 mL) in tetrahydrofuran (10 mL) was added dropwise, and stirred under ice-cooling for 30 minutes, and further at room temperature for 30 minutes. The precipitated solid was filtered off, and to the filtrate was added ethyl acetate (50 mL), then washed with ice-cooled 0.2 N hydrochloric acid (20 mL) and saturated brine (50 mL), followed by drying over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (0.96 g), triethylamine (0.54 mL) and 4-dimethylaminopyridine (0.032 g), and stirred at 60° C. for 6 hrs, and further at room temperature for 8 hrs. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with silica gel column chromatography (eluted with acetone:hexane=3:7, then acetone:hexane=7:3) to give title compound as yellow amorphous solid (1.19 g).

$^1$H-NMR(CDCl$_3$): 2.23(3H,s), 2.34(3H,s), 3.10(3H,bs), 3.22(2H,t,J=6.6 Hz), 3.67(2H,m), 4.38(2H,q,J=7.8 Hz), 4.80-5.20(2H,m), 6.64(1H,d,J=5.7 Hz), 7.35-7.50(3H,m), 7.83(1H,d,J=6.9 Hz), 8.35(1H,d,J=5.7 Hz).

Synthetic Example 53

Ethyl 2-[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]ethyl carbonate

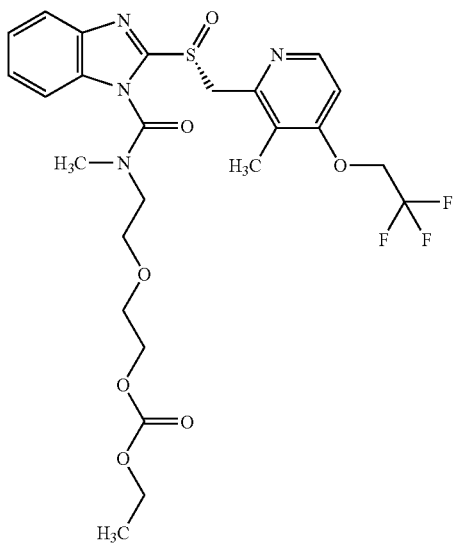 [SMILES: CCOC(=O)OCCOCCN(C)C(=O)n1c([S@](=O)Cc2nccc(OCC(F)(F)F)c2C)nc2ccccc21]

To a solution of bis(trichloromethyl)carbonate (1.19 g) in tetrahydrofuran (40 mL) was added dropwise a solution of pyridine (0.95 mL) in tetrahydrofuran (2 mL) under ice-cooling. The reaction solution was stirred for 30 minutes under ice-cooling, and ethyl 2-[2-(methylamino)ethoxy]ethyl carbonate hydrochloride (2.73 g) obtained in Reference Synthetic Example 52 was added thereto. A solution of triethylamine (1.68 mL) in tetrahydrofuran (2 mL) was added dropwise, and stirred at room temperature for 3 hrs. The reaction solution was concentrated under reduced pressure, and to the residue was added water (100 mL), and then extracted with ethyl acetate (100 mL). The ethyl acetate layer was washed with saturated brine (100 mL), and dried over anhydrous magnesium sulfate. The solution was concentrated under reduced pressure, and the residue was dissolved in tetrahydrofuran (40 mL). To the solution were added (R)-2-[[[3-methyl-4-(2,2,2-trifluoroethoxy)-2-pyridyl]methyl]sulfinyl]-1H-benzimidazole (2.80 g), triethylamine (2.11 mL) and 4-dimethylaminopyridine (catalytic amount), and stirred at 60° C. overnight. The reaction solution was concentrated under reduced pressure, and to the residue was added water (100 mL), and extracted with ethyl acetate (100 mL). The ethyl acetate layer was washed with saturated brine (100 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (2.19 g).

$^1$H-NMR(CDCl$_3$): 1.28(3H,t,J=7.2 Hz), 2.24(3H,s), 3.10(3H,bs), 3.38-3.80(6H,m), 4.18(2H,q,J=7.2 Hz), 4.27-4.34(2H,m), 4.38(2H,q,J=8.4 Hz), 4.83-5.30(2H,m), 6.65(1H,d,J=5.7 Hz), 7.35-7.50(3H,m), 7.84(1H,d,J=7.8 Hz), 8.36(1H,d,J=5.7 Hz).

Synthetic Example 54

Ethyl 2-[methyl[[2-[methyl[[(R)-2-[[[3-methyl-4-(2,2,2-trifluoroethoxy)-2-pyridyl]methyl]sulfinyl]-1H-benzimidazol-1-yl]carbonyl]amino]ethoxy]carbonyl]amino]ethyl carbonate

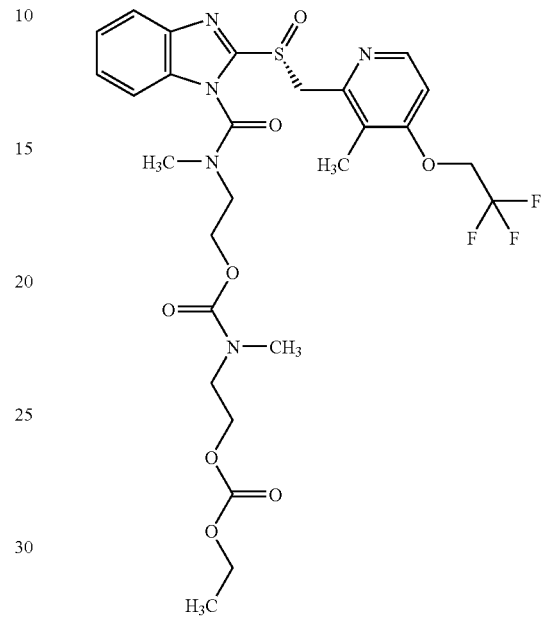

To a solution of bis(trichloromethyl)carbonate (0.59 g) in tetrahydrofuran (20 mL) was added dropwise a solution of pyridine (0.49 mL) in tetrahydrofuran (1 mL) under ice-cooling. The reaction solution was stirred for 30 minutes under ice-cooling, and ethyl 2-[methyl[[2-(methylamino)ethoxy]carbonyl]amino]ethyl carbonate hydrochloride (1.71 g) obtained in Reference Synthetic Example 53 was added thereto. A solution of triethylamine (0.84 mL) in tetrahydrofuran (1 mL) was added dropwise, and stirred at room temperature for 3 hrs. The reaction solution was concentrated under reduced pressure, and to the residue was added water (50 mL), and then extracted with ethyl acetate (50 mL). The ethyl acetate layer was washed with saturated brine (50 mL), and dried over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.59 g), triethylamine (1.20 mL) and 4-dimethylaminopyridine (catalytic amount), and stirred at 60° C. overnight. The reaction solution was concentrated under reduced pressure, and to the residue was added water (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:2, then 1:1) to give title compound as yellow amorphous solid (1.62 g).

$^1$H-NMR(CDCl$_3$): 1.24-1.31(3H,m), 2.24(3H,bs), 2.97-2.99(3H,m), 3.10(3H,bs), 3.55-3.58(2H,m), 4.09-4.50(10H,m), 4.88-5.08(2H,m), 6.65(1H,t,J=5.7 Hz), 7.36-7.48(3H,m), 7.85(1H,d,J=6.9 Hz), 8.36(1H,d,J=5.7 Hz).

Synthetic Example 55

Ethyl 2-[[[5-methoxy-2-[[(4-methoxy-3,5-dimethyl-2-pyridyl)methyl]sulfinyl]-1H-benzimidazol-1-yl]carbonyl](methyl)amino]ethyl carbonate

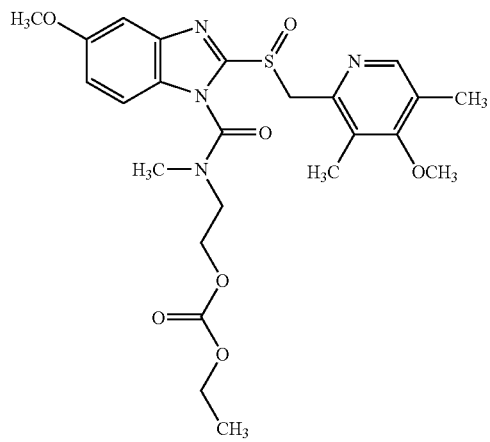 [SMILES: CCOC(=O)OCCN(C)C(=O)n1c(S(=O)Cc2ncc(C)c(OC)c2C)nc2cc(OC)ccc21]

To a solution of bis(trichloromethyl)carbonate (0.291 g) in tetrahydrofuran (10 mL) was added dropwise a solution of pyridine (0.243 mL) in tetrahydrofuran (1 mL) under ice-cooling. The reaction solution was stirred for 1 hr under ice-cooling, and ethyl 2-(methylamino)ethyl carbonate hydrochloride (0.551 g) obtained in Reference Synthetic Example 14 was added thereto. A solution of triethylamine (0.418 mL) in tetrahydrofuran (1 mL) was added dropwise, and stirred at room temperature for 2 hrs. The reaction solution was concentrated under reduced pressure, and to the residue was added water (15 mL), and then extracted with ethyl acetate (50 mL). The ethyl acetate layer was washed with saturated brine (15 mL), and dried over anhydrous magnesium sulfate. The solution was concentrated under reduced pressure, and the residue was dissolved in tetrahydrofuran (10 mL). To the solution were added 5-methoxy-2-[[(4-methoxy-3,5-dimethyl-2-pyridyl)methyl]sulfinyl]-1H-benzimidazole (0.817 g), triethylamine (0.661 mL) and 4-dimethylaminopyridine (0.012 g), and stirred at 60° C. for 12 hrs. The reaction solution was concentrated under reduced pressure, and to the residue was added water (20 mL), and extracted with ethyl acetate (50 mL). The ethyl acetate layer was washed with saturated brine (15 mL), and dried over anhydrous magnesium sulfate. After concentrating under reduced pressure, the residue was purified with basic silica gel column chromatography (eluted with ethyl acetate:hexane=1:2, then 1:1) to give a mixture of 3:2 of title compound and ethyl 2-[[[6-methoxy-2-[[(4-methoxy-3,5-dimethyl-2-pyridyl)methyl]sulfinyl]-1H-benzimidazol-1-yl]carbonyl](methyl)amino]ethyl carbonate as pale yellow amorphous solid (0.92 g).

$^1$H-NMR(CDCl$_3$): 1.27-1.34(3H,m), 2.10-2.30(3H,m), 2.23(3H,s), 2.99-3.23(3H,m), 3.40-3.85(2H,m), 3.69(6/5H,s), 3.71(9/5H,s), 3.86(6/5H,s), 3.88(9/5H,s), 4.14-4.25(2H,m), 4.38-4.60(2H,m), 4.82-5.06(2H,m), 6.92-7.08(7/5H,m), 7.33(3/5H,d,J=9.0 Hz), 7.66(1H,m), 8.21(1H,s).

Synthetic Example 56

2-[[[5-Methoxy-2-[[(4-methoxy-3,5-dimethyl-2-pyridyl)methyl]sulfinyl]-1H-benzimidazol-1-yl]carbonyl](phenyl)amino]ethyl acetate

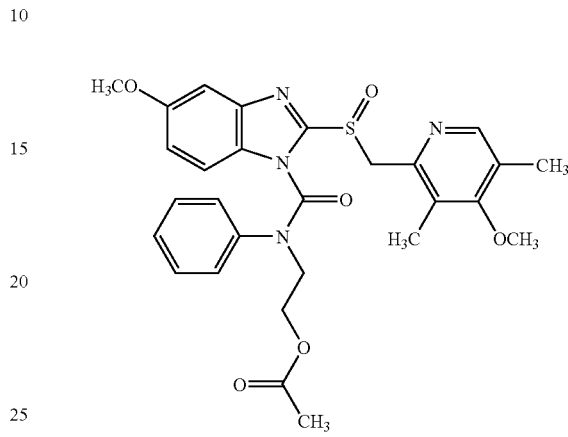

To a solution of bis(trichloromethyl)carbonate (0.291 g) in tetrahydrofuran (10 mL) was added dropwise a solution of pyridine (0.243 mL) in tetrahydrofuran (1 mL) under ice-cooling. The reaction solution was stirred for 30 minutes under ice-cooling, and 2-anilinoethyl acetate hydrochloride (0.647 g) obtained in Reference Synthetic Example 27 was added thereto. A solution of triethylamine (0.419 mL) in tetrahydrofuran (1 mL) was added dropwise, and stirred at room temperature for 3 hrs. The reaction solution was concentrated under reduced pressure, and to the residue was added water (20 mL), and then extracted with ethyl acetate (50 mL). The ethyl acetate layer was washed with saturated brine (15 mL), and dried over anhydrous magnesium sulfate. The solution was concentrated under reduced pressure, and the residue was dissolved in tetrahydrofuran (10 mL). To the solution were added 5-methoxy-2-[[(4-methoxy-3,5-dimethyl-2-pyridyl)methyl]sulfinyl]-1H-benzimidazole (0.829 g), triethylamine (0.669 mL) and 4-dimethylaminopyridine (0.012 g), and stirred at 60° C. for 14 hrs. The reaction solution was concentrated under reduced pressure, and to the residue was added water (40 mL), and extracted with ethyl acetate (80 mL). The ethyl acetate layer was washed with saturated brine (15 mL), and dried over anhydrous magnesium sulfate. After concentrating under reduced pressure, the residue was purified with basic silica gel column chromatography (eluted with ethyl acetate:hexane=1:2) to give a mixture of 1:1 of title compound and 2-[[[6-methoxy-2-[[(4-methoxy-3,5-dimethyl-2-pyridyl)methyl]sulfinyl]-1H-benzimidazol-1-yl]carbonyl](phenyl)amino]ethyl acetate as colorless amorphous solid (1.10 g).

$^1$H-NMR(CDCl$_3$): 1.99(3H,s), 2.19(1.5H.s), 2.21(1.5H,s), 2.25(3H,s), 3.70(1.5H,s), 3.71(3H,s), 3.78(1.5H,s), 3.84(1.5H,s), 4.15-4.56(4H,m), 4.74-4.80(1H,m), 4.91-4.98(1H,m), 6.83-6.91(1.5H,m), 7.04-7.19(3.5H,m), 7.25-7.53(2.5H,m), 7.51(0.5H,d,J=8.7 Hz), 8.25(1H,s).

Synthetic Example 57

Ethyl 2-[[[(S)-5-methoxy-2-[[(4-methoxy-3,5-dimethyl-2-pyridyl)methyl]sulfinyl]-1H-benzimidazol-1-yl]carbonyl](methyl)amino]ethyl carbonate

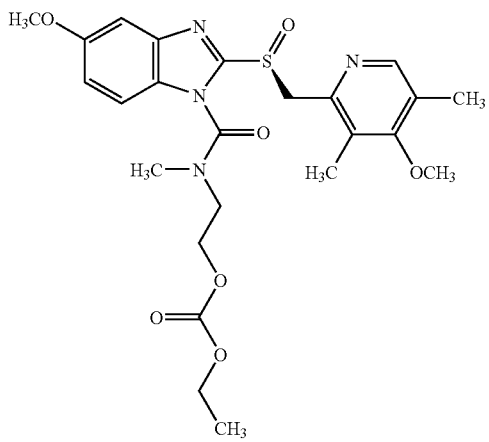 [SMILES: CCOC(=O)OCCN(C)C(=O)n1c([S@@](=O)Cc2ncc(C)c(OC)c2C)nc2cc(OC)ccc21]

To a solution of (S)-5-methoxy-2-[[(4-methoxy-3,5-dimethyl-2-pyridyl)methyl]sulfinyl]-1H-benzimidazole (1.34 g) synthesized by a method described in Synthetic Example 1 of JP-A 10-504290 in tetrahydrofuran (10 mL) were added 2-[(chlorocarbonyl)(methyl)amino]ethyl ethyl carbonate (0.9 mL) obtained in Reference Synthetic Example 34, triethylamine (1.08 mL) and 4-dimethylaminopyridine (0.010 g), and stirred at 60° C. for 6 hrs. The reaction solution was concentrated under reduced pressure, and to the residue was added water (30 mL), and extracted with ethyl acetate (50 mL). The ethyl acetate layer was washed with saturated brine (15 mL), and dried over anhydrous magnesium sulfate. After concentrating under reduced pressure, the residue was purified with basic silica gel column chromatography (eluted with ethyl acetate:hexane=1:2, then 1:1) to give a mixture of 3:2 of title compound and ethyl 2-[[[(S)-6-methoxy-2-[[(4-methoxy-3,5-dimethyl-2-pyridyl)methyl]sulfinyl]-1H-benzimidazol-1-yl]carbonyl](methyl)amino]ethyl carbonate as pale yellow amorphous solid (0.92 g).

$^1$H-NMR(CDCl$_3$): 1.25-1.34(3H,m), 2.10-2.30(3H,m), 2.23(3H,s), 2.99-3.23(3H,m), 3.40-3.85(2H,m), 3.69(6/5H,s), 3.71(9/5H,s), 3.86(6/5H,s), 3.88(9/5H,s), 4.14-4.25(2H,m), 4.38-4.60(2H,m), 4.79-5.05(2H,m), 6.92-7.08(7/5H,m), 7.33(3/5H,d,J=9.3 Hz), 7.65(1H,m), 8.21(1H,s).

Synthetic Example 58

Ethyl 2-[[[2-[[[4-(3-methoxypropoxy)-3-methyl-2-pyridyl)methyl]sulfinyl]-1H-benzimidazol-1-yl]carbonyl](methyl)amino]ethyl carbonate

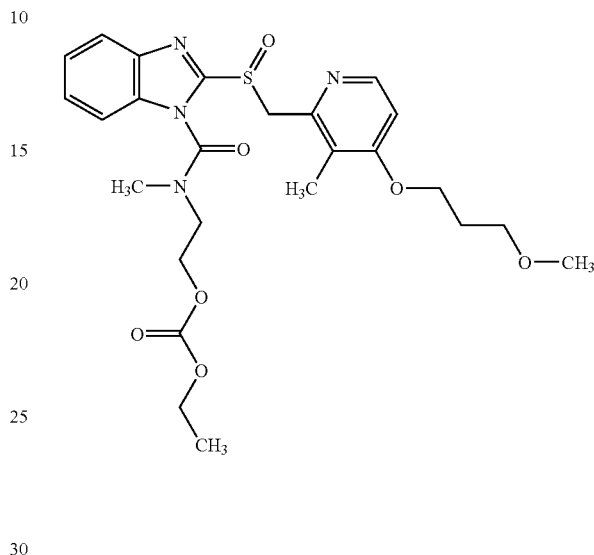

To a solution of bis(trichloromethyl)carbonate (0.291 g) in tetrahydrofuran (10 mL) was added dropwise a solution of pyridine (0.243 mL) in tetrahydrofuran (1 mL) under ice-cooling. The reaction solution was stirred for 30 minutes under ice-cooling, and ethyl 2-(methylamino)ethyl carbonate hydrochloride (0.551 g) obtained in Reference Synthetic Example 14 was added thereto. A solution of triethylamine (0.418 mL) in tetrahydrofuran (1 mL) was added dropwise, and stirred at room temperature for 2.5 hrs. The reaction solution was concentrated under reduced pressure, and to the residue was added water (15 mL), and then extracted with ethyl acetate (50 mL). The ethyl acetate layer was washed with saturated brine (15 mL), and dried over anhydrous magnesium sulfate. The solution was concentrated under reduced pressure, and the residue was dissolved in tetrahydrofuran (10 mL). To the solution were added 2-[[[4-(3-methoxypropoxy)-3-methyl-2-pyridyl)methyl]sulfinyl]-1H-benzimidazole (0.723 g), triethylamine (0.528 mL) and 4-dimethylaminopyridine (0.012 g), and stirred at 60° C. for 17 hrs. The reaction solution was concentrated under reduced pressure, and to the residue was added water (40 mL), and extracted with ethyl acetate (80 mL). The ethyl acetate layer was washed with saturated brine (15 mL), and dried over anhydrous magnesium sulfate. After concentrating under reduced pressure, the residue was purified with basic silica gel column chromatography (eluted with ethyl acetate:hexane=1:2), and further with silica gel column chromatography (eluted with ethyl acetate:hexane=1:1, then ethyl acetate) to give title compound as colorless amorphous solid (0.44 g).

$^1$H-NMR(CDCl$_3$): 1.31(3H,t,J=7.1 Hz), 2.05(2H,m), 2.18(3H,s), 3.08(3H,bs), 3.34(3H,s), 3.54(2H,t,J=6.1 Hz), 3.61-4.01(2H,m), 4.08(2H,t,J=6.3 Hz), 4.21(2H,t,J=7.1 Hz), 4.38-4.54(2H,m), 4.81-5.12(2H,m), 6.68(1H,d,J=5.6 Hz), 7.34-7.48(3H,m), 7.83(1H,d,J=7.8 Hz), 8.27(1H,d,J=5.6 Hz).

Synthetic Example 59

2-[[[2-[[[4-(3-Methoxypropoxy)-3-methyl-2-pyridyl)methyl]sulfinyl]-1H-benzimidazol-1-yl]carbonyl](phenyl)amino]ethyl acetate

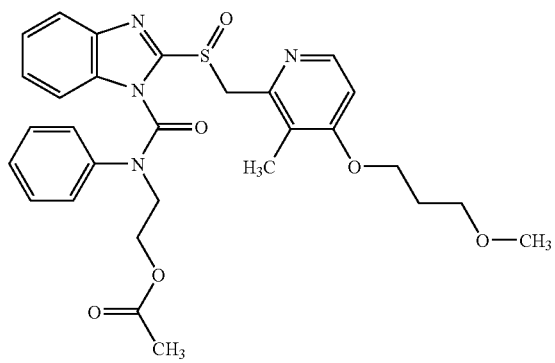 [SMILES: COCCCOc1ccnc(CS(=O)c2nc3ccccc3n2C(=O)N(CCOC(C)=O)c2ccccc2)c1C]

To a solution of bis(trichloromethyl)carbonate (0.291 g) in tetrahydrofuran (10 mL) was added dropwise a solution of pyridine (0.243 mL) in tetrahydrofuran (1 mL) under ice-cooling. The reaction solution was stirred for 30 minutes under ice-cooling, and 2-anilinoethyl acetate hydrochloride (0.647 g) obtained in Reference Synthetic Example 27 was added thereto. A solution of triethylamine (0.419 mL) in tetrahydrofuran (1 mL) was added dropwise, and stirred at room temperature for 3 hrs. The reaction solution was concentrated under reduced pressure, and to the residue was added water (20 mL), and then extracted with ethyl acetate (50 mL). The ethyl acetate layer was washed with saturated brine (15 mL), and dried over anhydrous magnesium sulfate. The solution was concentrated under reduced pressure, and the residue was dissolved in tetrahydrofuran (10 mL). To the solution were added 2-[[[4-(3-methoxypropoxy)-3-methyl-2-pyridyl)methyl]sulfinyl]-1H-benzimidazole (0.877 g), triethylamine (0.641 mL) and 4-dimethylaminopyridine (0.012 g), and stirred at 60° C. for 16 hrs. The reaction solution was concentrated under reduced pressure, and to the residue was added water (40 mL), and extracted with ethyl acetate (80 mL). The ethyl acetate layer was washed with saturated brine (15 mL), and dried over anhydrous magnesium sulfate. After concentrating under reduced pressure, the residue was purified with basic silica gel column chromatography (eluted with ethyl acetate:hexane=1:2), and further with silica gel column chromatography (eluted with ethyl acetate) to give title compound as colorless amorphous solid (0.93 g).

$^1$H-NMR(CDCl$_3$): 1.99(3H,s), 2.07(3H,s), 2.19(3H,s), 3.35(3H,s), 3.54(2H,t,J=6.2 Hz), 4.09(2H,t,J=6.2 Hz), 4.14-4.40(4H,m), 4.80(1H,d,J=13.7 Hz), 5.00(1H,d,J=13.7 Hz), 6.71(1H,d,J=5.7 Hz), 7.03-7.34(7H,m), 7.38(1H,m), 7.65(1H,m), 8.32(1H,d,J=5.7 Hz).

Synthetic Example 60

2-[[[5-(Difluoromethoxy)-2-[[(3,4-dimethoxy-2-pyridyl)methyl]sulfinyl]-1H-benzimidazol-1-yl]carbonyl](methyl)amino]ethyl ethyl carbonate

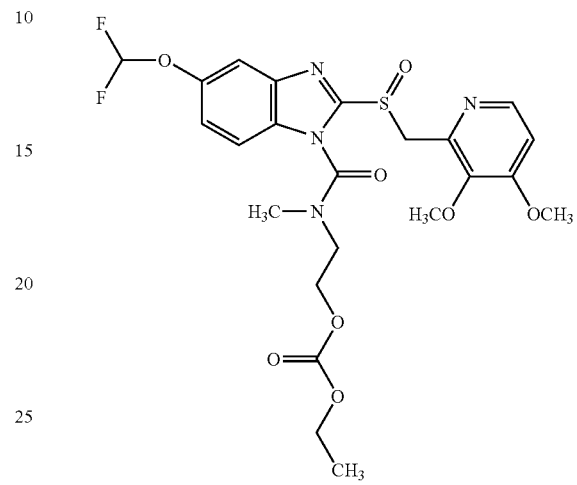

To a solution of bis(trichloromethyl)carbonate (0.174 g) in tetrahydrofuran (8 mL) was added dropwise a solution of pyridine (0.146 mL) in tetrahydrofuran (1 mL) under ice-cooling. The reaction solution was stirred for 1 hr under ice-cooling, and ethyl 2-(methylamino)ethyl carbonate hydrochloride (0.330 g) obtained in Reference Synthetic Example 14 was added thereto. A solution of triethylamine (0.250 mL) in tetrahydrofuran (1 mL) was added dropwise, and stirred at room temperature for 3 hrs. The reaction solution was concentrated under reduced pressure, and to the residue was added water (10 mL), and then extracted with ethyl acetate (30 mL). The ethyl acetate layer was washed with saturated brine (10 mL), and dried over anhydrous magnesium sulfate. The solution was concentrated under reduced pressure, and the residue was dissolved in tetrahydrofuran (8 mL). To the solution were added 5-(difluoromethoxy)-2-[[(3,4-dimethoxy-2-pyridyl)methyl]sulfinyl]-1H-benzimidazole (0.432 g), triethylamine (0.279 mL) and 4-dimethylaminopyridine (0.008 g), and stirred at 60° C. for 17.5 hrs. The reaction solution was concentrated under reduced pressure, and to the residue was added water (20 mL), and extracted with ethyl acetate (50 mL). The ethyl acetate layer was washed with saturated brine (10 mL), and dried over anhydrous magnesium sulfate. After concentrating under reduced pressure, the residue was purified with basic silica gel column chromatography (eluted with ethyl acetate:hexane=1:2, then 1:1), and further with silica gel column chromatography (eluted with ethyl acetate:hexane=2:1, then ethyl acetate) to give a mixture of 1:1 of title compound and 2-[[[6-(difluoromethoxy)-2-[[(3,4-dimethoxy-2-pyridyl)methyl]sulfinyl]-1H-benzimidazol-1-yl]carbonyl]methylamino]ethyl ethyl carbonate as pale yellow amorphous solid (0.09 g).

$^1$H-NMR(CDCl$_3$): 1.31(3H,t,J=7.2 Hz), 3.06(3H,s), 3.42-3.98(2H,m), 3.87(3H,s), 3.90(3H,s), 4.21(2H,q,J=7.2 Hz), 4.36-4.54(2H,m), 4.90(1H,d,J=13.2 Hz), 4.98(1H,d,J=13.2 Hz), 6.54(0.5H,t,J=73.5 Hz), 6.61(0.5H,t,J=73.5 Hz), 6.78

(1H,d,J=5.3 Hz), 7.15-7.25(1.5H,m), 7.44(0.5H,d,J=9.0 Hz), 7.59(0.5H,s), 7.80(0.5H,d,J=9.0 Hz), 8.17(1H,d,J=5.3 Hz).

Synthetic Example 61

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methylpiperidine-4-carboxylate

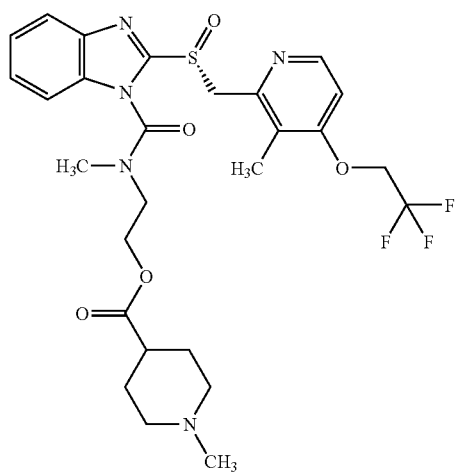 [SMILES: Cc1c(OCC(F)(F)F)ccnc1C[S@@](=O)c1nc2ccccc2n1C(=O)N(C)CCOC(=O)C1CCN(C)CC1]

2-(Methylamino)ethyl 1-methylpiperidine-4-carboxylate dihydrochloride (0.98 g) obtained in Reference Synthetic Example 54 was added to tetrahydrofuran (50 mL), and stirred for a while, then bis(trichloromethyl)carbonate (0.53 g) was added thereto. After ice-cooling, a solution of triethylamine (2.01 mL) in tetrahydrofuran (50 mL) was added dropwise, and stirred at room temperature for 3 hrs. Ethyl acetate (100 mL) was added, and washed with aqueous solution of sodium bicarbonate (100 mL) and saturated brine (80 mL), followed by drying over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (0.74 g), triethylamine (0.56 mL) and 4-dimethylaminopyridine (0.049 g), and stirred at 60° C. overnight. The reaction solution was concentrated under reduced pressure, and to the residue was added aqueous solution of sodium bicarbonate (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=7:3, then ethyl acetate, then methanol:ethyl acetate=1:19) to give title compound as yellow-green amorphous solid (0.78 g).

$^1$H-NMR(CDCl$_3$): 1.65-2.05(6H,m), 2.23(3H,s), 2.25(3H,s), 2.24-2.38(1H,m), 2.75-2.85(2H,m), 3.07(3H,bs), 3.40-4.10(2H,br), 4.38(2H,q,J=7.8 Hz), 4.40(2H,m), 4.80-5.10(2H,br), 6.64(1H,d,J=5.6 Hz), 7.36-7.47(3H,m), 7.84(1H,d,J=7.8 Hz), 8.35(1H,d,J=5.6 Hz).

Synthetic Example 62

2-[[4-(Aminocarbonyl)phenyl][[(R)-2-[[[3-methyl-4-(2,2,2-trifluoroethoxy)-2-pyridyl]methyl]sulfinyl]-1H-benzimidazol-1-yl]carbonyl]amino]ethyl acetate

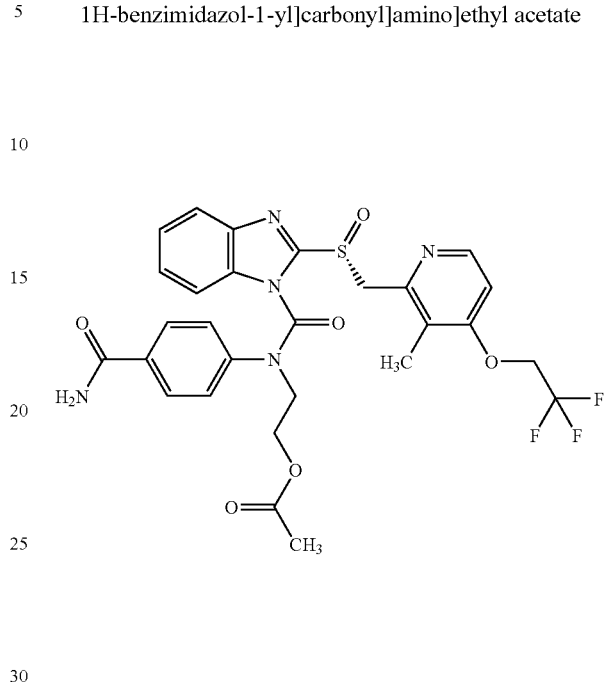

To a solution of bis(trichloromethyl)carbonate (0.45 g) in tetrahydrofuran (20 mL) was added dropwise a solution of 2-[[4-(Aminocarbonyl)phenyl]amino]ethyl acetate (0.67 g) obtained in Reference Synthetic Example 55 and triethylamine (0.63 mL) in tetrahydrofuran (10 mL) under ice-cooling, and stirred at room temperature for 1 hr. The reaction solution was concentrated under reduced pressure, and to the residue was added water (50 mL), and then extracted with ethyl acetate (50 mL). The ethyl acetate layer was washed with 0.2 N hydrochloric acid (20 mL) and saturated brine (50 mL), and dried over anhydrous magnesium sulfate. The solution was concentrated under reduced pressure, and the residue was dissolved in tetrahydrofuran (30 mL). To the solution were added (R)-2-[[[3-methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g), and stirred at 60° C. for 30 minutes, and further at room temperature overnight. The reaction solution was concentrated under reduced pressure, and to the residue was added aqueous solution of sodium bicarbonate (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=4:6, then 6:4, then 8:2) to give title compound as yellow amorphous solid (1.26 g).

$^1$H-NMR(CDCl$_3$): 1.99(3H,s), 2.26(3H,s), 4.15-4.55(4H,m), 4.41(2H,q,J=7.9 Hz), 4.80-5.20(2H,br), 6.69(1H,d,J=5.7 Hz), 7.26-7.38(3H,m), 7.48(2H,d,J=8.9 Hz), 7.54(2H,d,J=8.9 Hz), 7.66-7.73(1H,m), 8.39(1H,d,J=5.7 Hz).

Synthetic Example 63

2-[Methyl[[(R)-2-[[[3-methyl-4-(2,2,2-trifluoroethoxy)-2-pyridyl]methyl]sulfinyl]-1H-benzimidazol-1-yl]carbonyl]amino]ethyl 1-methyl-4-piperidinyl carbonate

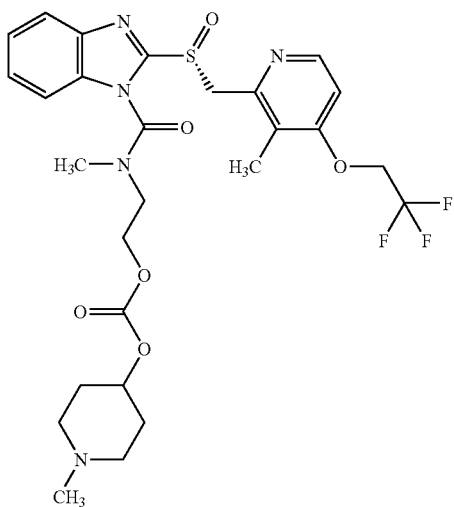 [SMILES: Cc1c(OCC(F)(F)F)ccnc1C[S@@](=O)c1nc2ccccc2n1C(=O)N(C)CCOC(=O)OC1CCN(C)CC1]

2-(Methylamino)ethyl 1-methyl-4-piperidinyl carbonate dihydrochloride (1.01 g) obtained in Reference Synthetic Example 56 was added to tetrahydrofuran (30 mL), and stirred for a while, then ice-cooled. To the solution was added bis(trichloromethyl)carbonate (0.69 g), and a solution of triethylamine (1.95 mL) in tetrahydrofuran (10 mL) was added dropwise thereto. The reaction solution was stirred under ice-cooling for 1 hr, and further at room temperature for 1 hr, and the precipitated solid was filtered off. The filtrate was concentrated under reduced pressure, and ethyl acetate (50 mL) was added thereto, then washed with ice-cooled aqueous solution of sodium bicarbonate (50 mL) and saturated brine (50 mL), followed by drying over anhydrous magnesium sulfate. The solution was concentrated under reduced pressure, and the residue was dissolved in tetrahydrofuran (20 mL). To the solution were added (R)-2-[[[3-methyl-4-(2,2,2-trifluoroethoxy)-2-pyridyl]methyl]sulfinyl]-1H-benzimidazole (1.11 g), triethylamine (0.63 mL) and 4-dimethylaminopyridine (0.037 g), and stirred at 60° C. overnight. The reaction solution was concentrated under reduced pressure, and to the residue was added aqueous solution of sodium bicarbonate (50 mL), and extracted with ethyl acetate (50 mL). The ethyl acetate layer was washed with saturated brine (50 mL), and dried over anhydrous magnesium sulfate. After concentrating under reduced pressure, the residue was purified with basic silica gel column chromatography (eluted with ethyl acetate:hexane=1:1, then ethyl acetate, then methanol:ethyl acetate=1:19) to give title compound as yellow amorphous solid (0.70 g).

$^1$H-NMR(CDCl$_3$): 1.70-1.86(2H,m), 1.90-2.04(2H,m), 2.23(3H,s), 2.28(3H,s), 2.10-2.35(2H,m), 2.60-2.72(2H,m), 3.08(3H,bs), 3.40-4.20(2H,br), 4.39(2H,q,J=7.9 Hz), 4.44(2H,m), 4.60-4.74(1H,m), 4.80-5.15(2H,br), 6.65(1H,d,J=5.9 Hz), 7.35-7.52(3H,m), 7.84(1H,d,J=7.5 Hz), 8.35(1H,d,J=5.9 Hz).

Synthetic Example 64

2-[[4-(Aminocarbonyl)phenyl][[2-[[[3-methyl-4-(2,2,2-trifluoroethoxy)-2-pyridyl]methyl]sulfinyl]-1H-benzimidazol-1-yl]carbonyl]amino]ethyl acetate

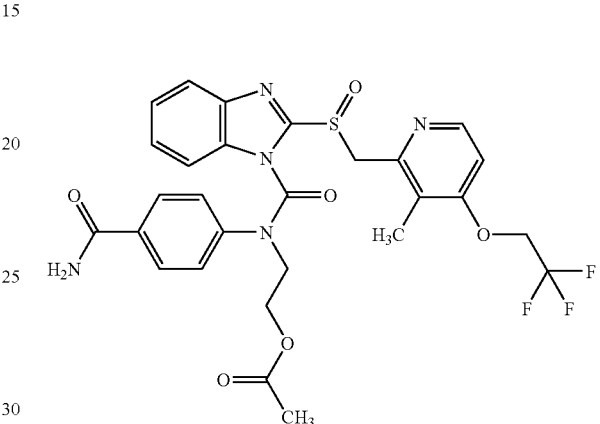

To a solution of bis(trichloromethyl)carbonate (0.12 g) in tetrahydrofuran (5 mL) was added dropwise a solution of 2-[[4-(aminocarbonyl)phenyl]amino]ethyl acetate (0.22 g) obtained in Reference Synthetic Example 55 and triethylamine (0.17 mL) in tetrahydrofuran (5 mL) under ice-cooling, and stirred at room temperature for 30 minutes. To the reaction solution was added water (20 mL), and extracted with ethyl acetate (30 mL). The ethyl acetate layer was washed with saturated brine (20 mL), and dried over anhydrous magnesium sulfate. The solution was concentrated under reduced pressure, and the residue was dissolved in tetrahydrofuran (10 mL). To the solution were added 2-[[[3-methyl-4-(2,2,2-trifluoroethoxy)-2-pyridyl]methyl]sulfinyl]-1H-benzimidazole (0.37 g), triethylamine (0.28 mL) and 4-dimethylaminopyridine (0.012 g), and stirred at 60° C. for 1 hr. The reaction solution was concentrated under reduced pressure, and to the residue was added aqueous solution of sodium bicarbonate (20 mL), and extracted with ethyl acetate (30 mL). The ethyl acetate layer was washed with saturated brine (20 mL), and dried over anhydrous magnesium sulfate. After concentrating under reduced pressure, the residue was purified with basic silica gel column chromatography (eluted with ethyl acetate:hexane=3:7, then 5:5, then 8:2) to give title compound as pale yellow amorphous solid (0.34 g).

$^1$H-NMR(CDCl$_3$): 1.99(3H,s), 2.26(3H,s), 4.15-4.55(4H,m), 4.41(2H,q,J=7.9 Hz), 4.80-5.20(2H,br), 6.69(1H,d,J=5.9 Hz), 7.26-7.40(3H,m), 7.47(2H,d,J=8.8 Hz), 7.54(2H,d,J=8.8 Hz), 7.65-7.74(1H,m), 8.38(1H,d,J=5.9 Hz).

Synthetic Example 65

(−)-Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate

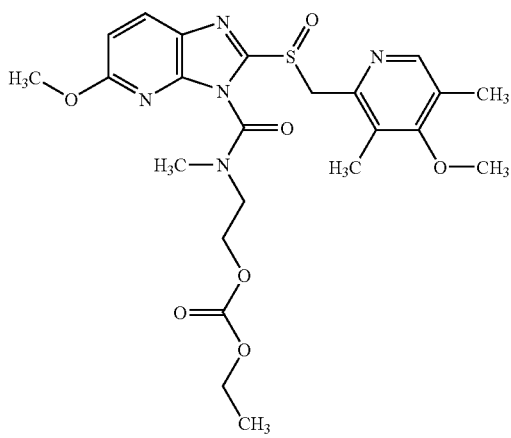

To a solution of (−)-enantiomer (0.10 g) in tetrahydrofuran (5 mL), which was obtained by optically resolving 5-methoxy-2-[[(4-methoxy-3,5-dimethyl-2-pyridyl)methyl]sulfinyl]-1H-imidazo[4,5-b]pyridine synthesized by a method described in JP-A 63-146882 with preparative HPLC, were added 2-[(chlorocarbonyl)(methyl)amino]ethyl ethyl carbonate (0.081 g) obtained in Reference Synthetic Example 34, triethylamine (0.080 mL) and 4-dimethylaminopyridine (0.007 g), and stirred at 50° C. for 18 hrs. The reaction solution was concentrated under reduced pressure, and to the residue was added water (30 mL), and extracted with ethyl acetate (50 mL). The ethyl acetate layer was washed with saturated brine (30 mL), and dried over anhydrous sodium sulfate. After concentrating under reduced pressure, the residue was purified with basic silica gel column chromatography (eluted with ethyl acetate:hexane=2:1) to give title compound as colorless oil (0.053 g).

$^1$H-NMR(CDCl$_3$): 1.30(3H,t,J=7.1 Hz), 2.24(6H,s), 3.15, 3.32(total 3H,s), 3.73(3H,s), 3.90-4.55(9H,m), 4.85(1H,d, J=13.2 Hz), 4.97(1H,d,J=13.2 Hz), 6.80(1H,d,J=8.8 Hz), 7.96(1H,d,J=8.8 Hz), 8.23(1H,s).

Synthetic Example 66

(+)-Ethyl 2-[[[5-methoxy-2-[[(4-methoxy-3,5-dimethyl-2-pyridyl)methyl]sulfinyl]-3H-imidazo[4,5-b]pyridin-3-yl]carbonyl](methyl)amino]ethyl carbonate

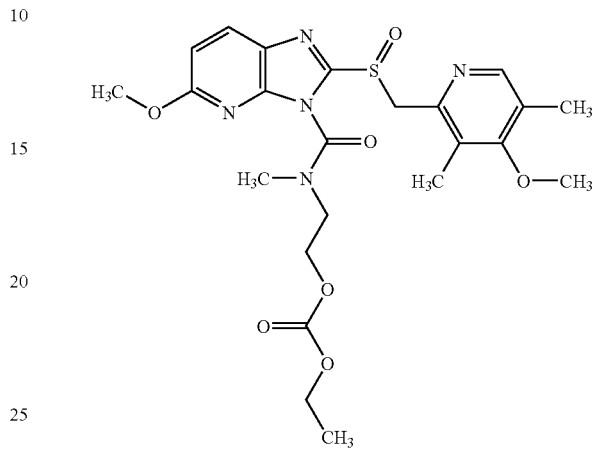

To a solution of (+)-enantiomer (0.10 g) in tetrahydrofuran (5 mL), which was obtained by optically resolving 5-methoxy-2-[[(4-methoxy-3,5-dimethyl-2-pyridyl)methyl]sulfinyl]-1H-imidazo[4,5-b]pyridine synthesized by a method described in JP-A 63-146882 with preparative HPLC, were added 2-[(chlorocarbonyl)(methyl)amino]ethyl ethyl carbonate (0.081 g) obtained in Reference Synthetic Example 34, triethylamine (0.080 mL) and 4-dimethylaminopyridine (0.007 g), and stirred at 50° C. for 18 hrs. The reaction solution was concentrated under reduced pressure, and to the residue was added water (30 mL), and extracted with ethyl acetate (50 mL). The ethyl acetate layer was washed with saturated brine (30 mL), and dried over anhydrous sodium sulfate. After concentrating under reduced pressure, the residue was purified with basic silica gel column chromatography (eluted with ethyl acetate:hexane=2:1) to give a mixture of 2:1 of title compound and (+)-ethyl 2-[[[5-methoxy-2-[[(4-methoxy-3,5-dimethyl-2-pyridyl)methyl]sulfinyl]-1H-imidazo[4,5-b]pyridin-1-yl]carbonyl](methyl)amino]ethyl carbonate as colorless oil (0.115 g).

$^1$H-NMR(CDCl$_3$): 1.20-1.38(3H,m), 2.24(6H,s), 3.08, 3.15,3.33(total 3H,s), 3.73(3H,s), 3.88-4.55(9H,m), 4.78-5.05(2H,m), 6.80,6.86(1H,d,J=8.8 Hz), 7.76,7.96(1H,d, J=8.8 Hz), 8.21,8.22(total 1H,s).

Reference Example 1

Lansoprazole R-isomer (hereinafter, referred to as "compound A"; 300 g), magnesium carbonate (105 g), purified sucrose (195 g) and low-substituted hydroxypropyl cellulose (75 g) were thoroughly mixed to obtain a dusting powder for active ingredient layer. Purified sucrose (75 g), titanium oxide (48.8 g) and low-substituted hydroxypropyl cellulose (18.8 g) were thoroughly mixed to obtain a dusting powder for intermediate layer. Sucrose/starch spherical granules (375 g) were placed in a centrifugal tumbling granulator (CF-360, manufactured by Freund Industrial Co., Ltd.) and the above dusting powder for active ingredient layer was coated on the sucrose/starch spherical granules while spraying a hydroxypropyl cellulose solution (2 w/w%) to obtain spherical granules. Then, the above dusting powder for intermediate layer was coated on the obtained spherical granules while spraying a hydroxypropyl cellulose solution (2 w/w %) to obtain spherical granules. The obtained spherical granules were dried at 40° C. for 16 hrs under vacuum and passed through a round sieve to give granules of 710 µm-1400 µm.

| Composition in Granules 120.0 mg | |
|---|---|
| sucrose/starch spherical granules | 37.5 mg |
| hydroxypropyl cellulose | 0.75 mg |
| Dusting Powder for Active Ingredient | |
| Compound A | 30.0 mg |
| magnesium carbonate | 10.5 mg |
| purified sucrose | 19.5 mg |
| low-substituted hydroxypropyl cellulose | 7.5 mg |
| Dusting Powder for Intermediate Layer | |
| purified sucrose | 7.5 mg |
| low-substituted hydroxypropyl cellulose | 1.875 mg |
| titanium oxide | 4.875 mg |
| Total | 120 mg |

Reference Example 2

Talc (78 g), titanium oxide (25 g) and methacrylic acid copolymer LD (866.7 g; 260 g as solid) were dispersed in a solution obtained by dissolving macrogol 6000 (25 g) and polysorbate 80 (10 g) in purified water (1206 g) to prepare enteric coating suspension. The enteric coating suspension was coated on the granules obtained in Reference Example 1 in a tumbling fluidized bed granulator (SPIR-A-FLOW, manufactured by Freund Industrial Co., Ltd.) under a condition of inlet air temperature: 45° C., rotor rotating rate: 200 rpm, coating suspension spray rate: 3.8 g/min., and spray air pressure: 1.0 kg/cm², which was dried as such, and passed through a round sieve to obtain enteric granules I of 710 µm to 1400 µm having following composition. The resultant spherical granules were dried under vacuum at 40° C. for 16 hrs.

| Composition in Enteric Granules I 149.86 mg | |
|---|---|
| granules of Reference Example 1 | 120.00 mg |
| methacrylic acid copolymer LD | 65 mg (19.5 mg as solid) |
| talc | 5.85 mg |
| macrogol 6000 | 1.88 mg |
| titanium oxide | 1.88 mg |
| polysorbate 80 | 0.75 mg |
| Total | 149.86 mg |

Reference Example 3

Talc (24 g) was dispersed in a solution obtained by dissolving methacrylic acid copolymer S (36 g), methacrylic acid copolymer L (12 g) and triethyl citrate (4.8 g) in a mixture of purified water (69.12 g) and absolute ethanol (622.08 g) to prepare coating suspension. The coating suspension was coated on the enteric granules I (100 g) obtained in Reference Example 2 in a tumbling fluidized bed granulator (SPIR-A-FLOW, manufactured by Freund Industrial Co., Ltd.) under a condition of inlet air temperature: 30° C., rotor rotating rate: 150 rpm, coating suspension spray rate: 3.3 g/min., and spray air pressure: 1.0 kg/cm². The obtained spherical granules were passed through a round sieve to obtain enteric granules II of 710 µm to 1400 µm. The resultant spherical granules were dried under vacuum at 40° C. for 16 hrs.

| Composition in Enteric Granules II 221.86 mg | |
|---|---|
| enteric granules I | 149.86 mg |
| methacrylic acid copolymer S | 33.75 mg |
| methacrylic acid copolymer L | 11.25 mg |
| talc | 22.5 mg |
| triethyl citrate | 4.5 mg |
| Total | 221.86 mg |

Reference Example 4

Talc (24 g) was dispersed in a solution obtained by dissolving methacrylic acid copolymer S (24 g), methacrylic acid copolymer L (24 g) and triethyl citrate (4.8 g) in a mixture of purified water (69.12 g) and absolute ethanol (622.08 g) to prepare coating suspension. The coating suspension was coated on the enteric granules I (100 g) obtained in Reference Example 2 in a tumbling fluidized bed granulator (SPIR-A-FLOW, manufactured by Freund Industrial Co., Ltd.) under a condition of inlet air temperature: 30° C., rotor rotating rate: 150 rpm, coating suspension spray rate: 3.3 g/min., and spray air pressure: 1.0 kg/cm². The obtained spherical granules were passed through a round sieve to obtain enteric granules III of 710 µm to 1400 µm. The resultant spherical granules were dried under vacuum at 40° C. for 16 hrs.

| Composition in Enteric Granules III 221.86 mg | |
|---|---|
| enteric granules I | 149.86 mg |
| methacrylic acid copolymer S | 22.5 mg |
| methacrylic acid copolymer L | 22.5 mg |
| talc | 22.5 mg |
| triethyl citrate | 4.5 mg |
| Total | 221.86 mg |

Reference Example 5

The enteric granules I (37.5 mg) obtained in Reference Example 2 and the enteric granules II (167 mg) obtained in Reference Example 3 were mixed, and further polyethylene oxide (68.2 mg) was added thereto. The mixture was filled in one size No. 1 capsule (corresponds to compound A: 30 mg) to give capsule I.

Reference Example 6

The enteric granules I (37.5 mg) obtained in Reference Example 2 and the enteric granules III (167 mg) obtained in Reference Example 4 were mixed, and further polyethylene oxide (68.2 mg) was added thereto. The mixture was filled in one size No. 1 capsule (corresponds to compound A: 30 mg) to give capsule II.

Reference Example 7

Compound A (225 g), magnesium carbonate (75 g), low-substituted hydroxypropyl cellulose (37.5 g) and hydroxypropyl cellulose (37.5 g) were suspended in purified water (2122.5 g) to obtain spray suspension. Microcrystalline cellulose (particles, 100 g) was placed in a tumbling fluidized bed granulator (SPIR-A-FLOW, manufactured by Freund Industrial Co., Ltd.), and was coated with the spray suspension by spraying under a condition of inlet air temperature: 62° C., rotor rotating rate: 300 rpm, coating suspension spray rate: 10 g/min. and spray air pressure: 1.0 kg/cm² to obtain spherical granules. The obtained spherical granules were dried under vacuum at 40° C. for 16 hrs, and passed through a round sieve to give granules of 500 μm to 1400 μm.

The above granules were coated with coating suspension for intermediate layer using a tumbling fluidized bed granulator (SPIR-A-FLOW, manufactured by Freund Industrial Co., Ltd.), which were dried as such to give granules having the following composition. The coating suspension for intermediate layer was prepared by dissolving hydroxypropylmethylcellulose 2910 (20.09 g) in purified water (361.55 g) and then by dispersing titanium oxide (8.03 g) and talc (12.05 g) in the obtained solution. Coating operation is carried out under the condition of inlet air temperature: 62° C., rotor rotating rate: 200 rpm, coating suspension spray rate: 3.0 g/min. and spray air pressure: 1.0 kg/cm². The obtained spherical granules were dried at 40° C. for 16 hrs under vacuum, and passed through a round sieve to give granules of 710 μm-1400 μm.

| Composition in Granules 80 mg | |
| --- | --- |
| microcrystalline cellulose (particles) | 20.0 mg |
| compound A | 30.0 mg |
| magnesium carbonate | 10.0 mg |
| low-substituted hydroxypropyl cellulose | 5.0 mg |
| hydroxypropyl cellulose | 5.0 mg |
| hydroxypropylmethylcellulose 2910 | 5.0 mg |
| talc | 3.0 mg |
| titanium oxide | 2.0 mg |
| Total | 80.0 mg |

Reference Example 8

Talc (78 g), titanium oxide (25 g) and methacrylic acid copolymer LD (866.7 g; 260 g as solid) were dispersed in a solution obtained by dissolving macrogol 6000 (25 g) and polysorbate 80 (10 g) in purified water (1206 g) to prepare enteric coating suspension. The enteric coating suspension was coated on the granules obtained in Reference Example 7 in a tumbling fluidized bed granulator (SPIR-A-FLOW, manufactured by Freund Industrial Co., Ltd.) under a condition of inlet air temperature: 45° C., rotor rotating rate: 200 rpm, coating suspension spray rate: 3.8 g/min., and spray air pressure: 1.0 kg/cm², which was dried as such, and passed through a round sieve to obtain enteric granules IV of 710 μm to 1400 μm having the following composition. The resultant spherical granules were dried under vacuum at 40° C. for 16 hrs.

| Composition in Enteric Granules IV 99.9 mg | |
| --- | --- |
| granules of Reference Example 7 | 80.00 mg |
| methacrylic acid copolymer LD | 43.3 mg (13.0 mg as solid) |
| talc | 4.0 mg |
| macrogol 6000 | 1.2 mg |

| Composition in Enteric Granules IV 99.9 mg (continued) | |
| --- | --- |
| titanium oxide | 1.2 mg |
| polysorbate 80 | 0.5 mg |
| Total | 99.9 mg |

Reference Example 9

Talc (24 g) was dispersed in a solution obtained by dissolving methacrylic acid copolymer S (36 g), methacrylic acid copolymer L (12 g) and triethyl citrate (4.8 g) in a mixture of purified water (69.12 g) and absolute ethanol (622.08 g) to prepare coating suspension. The coating suspension was coated on the granules (100 g) obtained in Reference Example 7 in a tumbling fluidized bed granulator (SPIR-A-FLOW, manufactured by Freund Industrial Co., Ltd.) under a condition of inlet air temperature: 30° C., rotor rotating rate: 100 rpm, coating suspension spray rate: 3.0 g/min., and spray air pressure: 1.0 kg/cm². The obtained spherical granules were passed through a round sieve to obtain enteric granules V of 1180 μm to 1700 μm. The resultant spherical granules were dried under vacuum at 40° C. for 16 hrs.

| Composition in Enteric Granules V 118.4 mg | |
| --- | --- |
| granules of Reference Example 7 | 80.0 mg |
| methacrylic acid copolymer S | 18.0 mg |
| methacrylic acid copolymer L | 6.0 mg |
| talc | 12.0 mg |
| triethyl citrate | 2.4 mg |
| Total | 118.4 mg |

Reference Example 10

Talc (24 g) was dispersed in a solution obtained by dissolving methacrylic acid copolymer S (24 g), methacrylic acid copolymer L (24 g) and triethyl citrate (4.8 g) in a mixture of purified water (69.12 g) and absolute ethanol (622.08 g) to prepare coating suspension. The coating suspension was coated on the granules (100 g) obtained in Reference Example 7 in a tumbling fluidized bed granulator (SPIR-A-FLOW, manufactured by Freund Industrial Co., Ltd.) under a condition of inlet air temperature: 30° C., rotor rotating rate: 100 rpm, coating suspension spray rate: 3.0 g/min., and spray air pressure: 1.0 kg/cm². The obtained spherical granules were passed through a round sieve to obtain enteric granules VI of 1180 μm to 1700 μm. The resultant spherical granules were dried under vacuum at 40° C. for 16 hrs.

| Composition in Enteric Granules VI 118.4 mg | |
| --- | --- |
| granules of Reference Example 7 | 80.0 mg |
| methacrylic acid copolymer S | 12.0 mg |
| methacrylic acid copolymer L | 12.0 mg |
| talc | 12.0 mg |
| triethyl citrate | 2.4 mg |
| Total | 118.4 mg |

Reference Example 11

The enteric granules IV (25 mg) obtained in Reference Example 8 and the enteric granules V (88.8 mg) obtained in Reference Example 9 were mixed, and further polyethylene oxide (37.9 mg) was added thereto. The mixture was filled in one size No. 3 capsule (corresponds to compound A: 30 mg) to give capsule III.

Reference Example 12

The enteric granules IV (25 mg) obtained in Reference Example 8 and the enteric granules VI (88.8 mg) obtained in Reference Example 10 were mixed, and further polyethylene oxide (37.9 mg) was added thereto. The mixture was filled in one size No. 3 capsule (corresponds to compound A: 30 mg) to give capsule IV.

Reference Example 13

Compound A (150 g), magnesium carbonate (50 g), low-substituted hydroxypropyl cellulose (25 g) and hydroxypropyl cellulose (25 g) were suspended in purified water (1420 g) to obtain spray suspension. Microcrystalline cellulose (particles, 200 g) was placed in a tumbling fluidized bed granulator (SPIR-A-FLOW, manufactured by Freund Industrial Co., Ltd.), and was coated with the spray suspension by spraying under a condition of inlet air temperature: 62° C., rotor rotating rate: 300 rpm, coating suspension spray rate: 10 g/min. and spray air pressure: 1.0 kg/cm² to obtain spherical granules having the following composition. The resultant spherical granules were dried under vacuum at 40° C. for 16 hrs, and passed through a round sieve to give granules of 500 μm to 1400 μm.

| Composition in Granules 41.25 mg | |
|---|---|
| microcrystalline cellulose (particles) | 22.5 mg |
| compound A | 11.25 mg |
| magnesium carbonate | 3.75 mg |
| low-substituted hydroxypropyl cellulose | 1.87 mg |
| hydroxypropyl cellulose | 1.87 mg |
| Total | 41.24 mg |

Example 1

Compound A (90 g), magnesium carbonate (31.5 g), purified sucrose (58.5 g) and low-substituted hydroxypropyl cellulose (22.5 g) were thoroughly mixed to obtain a dusting powder for active ingredient layer. The granules (100 g) obtained in Reference Example 13 were placed in a centrifugal tumbling granulator (CF-mini, manufactured by Freund Industrial Co., Ltd.) and the above dusting powder for active ingredient layer was coated on the granules while spraying a hydroxypropyl cellulose solution (2 w/w %) to obtain spherical granules having the following composition. The resulting spherical granules were dried at 40° C. for 16 hrs under vacuum, and passed through a round sieve to give granules of 710 μm-1400 μm.

| Composition in Granules 118 mg | |
|---|---|
| granules of Reference Example 13 | 41.25 mg |
| Compound A | 33.75 mg |
| magnesium carbonate | 11.81 mg |
| purified sucrose | 21.94 mg |
| low-substituted hydroxypropyl cellulose | 8.44 mg |
| hydroxypropyl cellulose | 0.84 mg |
| Total | 118.03 mg |

Example 2

The granules obtained in Example 1 were coated with coating suspension for intermediate layer using a tumbling fluidized bed granulator (SPIR-A-FLOW, manufactured by Freund Industrial Co., Ltd.), which were dried as such to give granules having the following composition. The coating suspension for intermediate layer was prepared by dissolving hydroxypropylmethylcellulose 2910 (20.09 g) in purified water (361.55 g) and then by dispersing titanium oxide (8.03 g) and talc (12.05 g) in the obtained suspension. Coating operation is carried out under the condition of inlet air temperature: 62° C., rotor rotating rate: 200 rpm, coating suspension spray rate: 3.0 g/min. and spray air pressure: 1.0 kg/cm². The resulting spherical granules were dried at 40° C. for 16 hrs under vacuum, and passed through a round sieve to give granules of 710 μm-1400 μm.

| Composition in Granules 133.0 mg | |
|---|---|
| granules of Example 1 | 118.03 mg |
| hydroxypropylmethylcellulose 2910 | 7.5 mg |
| talc | 4.5 mg |
| titanium oxide | 3.0 mg |
| Total | 133.03 mg |

Example 3

Talc (78 g), titanium oxide (25 g) and methacrylic acid copolymer LD (866.7 g; 260 g as solid) were dispersed in a solution obtained by dissolving macrogol 6000 (25 g) and polysorbate 80 (10 g) in purified water (1206 g) to prepare enteric coating suspension. The enteric coating suspension was coated on the granules obtained in Example 2 in a tumbling fluidized bed granulator (SPIR-A-FLOW, manufactured by Freund Industrial Co., Ltd.) under a condition of inlet air temperature: 45° C., rotor rotating rate: 200 rpm, coating suspension spray rate: 3.8 g/min., and spray air pressure: 1.0 kg/cm², which was dried as such, and passed through a round sieve to obtain enteric granules VII of 710 μm to 1400 μm having the following composition. The resultant spherical granules were dried under vacuum at 40° C. for 16 hrs.

| Composition in Enteric Granules VII 165.18 mg | |
|---|---|
| granules of Example 2 | 133.03 mg |
| methacrylic acid copolymer LD | 70 mg (21.00 mg as solid) |
| Talc | 6.30 mg |
| macrogol 6000 | 2.02 mg |

| Composition in Enteric Granules VII 165.18 mg | |
|---|---|
| titanium oxide | 2.02 mg |
| polysorbate 80 | 0.81 mg |
| Total | 165.18 mg |

| Composition in Enteric Granules IX 196.88 mg | |
|---|---|
| granules of Example 2 | 133.03 mg |
| methacrylic acid copolymer S | 19.95 mg |
| methacrylic acid copolymer L | 19.95 mg |
| Talc | 19.95 mg |
| triethyl citrate | 3.99 mg |
| Total | 196.88 mg |

Example 4

Talc (24 g) was dispersed in a solution obtained by dissolving methacrylic acid copolymer S (36 g), methacrylic acid copolymer L (12 g) and triethyl citrate (4.8 g) in a mixture of purified water (69.12 g) and absolute ethanol (622.08 g) to prepare coating suspension. The coating suspension was coated on the granules (100 g) obtained in Example 2 in a tumbling fluidized bed granulator (SPIR-A-FLOW, manufactured by Freund Industrial Co., Ltd.) under a condition of inlet air temperature: 30° C., rotor rotating rate: 100 rpm, coating suspension spray rate: 3.0 g/min., and spray air pressure: 1.0 kg/cm². The obtained spherical granules were passed through a round sieve to obtain enteric granules VIII of 1180 μm to 1700 μm. The resultant spherical granules were dried under vacuum at 40° C. for 16 hrs.

| Composition in Enteric Granules VIII 196.88 mg | |
|---|---|
| granules of Example 2 | 133.03 mg |
| methacrylic acid copolymer S | 29.93 mg |
| methacrylic acid copolymer L | 9.98 mg |
| Talc | 19.95 mg |
| triethyl citrate | 3.99 mg |
| Total | 196.88 mg |

Example 5

Talc (24 g) was dispersed in a solution obtained by dissolving methacrylic acid copolymer S (24 g), methacrylic acid copolymer L (24 g) and triethyl citrate (4.8 g) in a mixture of purified water (69.12 g) and absolute ethanol (622.08 g) to prepare coating suspension. The coating suspension was coated on the granules (100 g) obtained in Example 2 in a tumbling fluidized bed granulator (SPIR-A-FLOW, manufactured by Freund Industrial Co., Ltd.) under a condition of inlet air temperature: 30° C., rotor rotating speed: 100 rpm, coating suspension spray rate: 3.0 g/min., and spray air pressure: 1.0 kg/cm². The obtained spherical granules were passed through a round sieve to obtain enteric granules IX of 1180 μm to 1700 μm. The resultant spherical granules were dried under vacuum at 40° C. for 16 hrs.

Example 6

The enteric granules VII (28 mg) obtained in Example 3 and the enteric granules VIII (98.7 mg) obtained in Example 4 were mixed, and further polyethylene oxide (42.3 mg) was added thereto. The mixture was filled in one size No. 1 capsule (corresponds to compound A: 30 mg) to give capsule V.

Example 7

The enteric granules VII (28 mg) obtained in Example 3 and the enteric granules IX (98.7 mg) obtained in Example 5 were mixed, and further polyethylene oxide (42.3 mg) was added thereto. The mixture was filled in one size No. 1 capsule (corresponds to compound A: 30 mg) to give capsule VI.

Example 8

The enteric granules VII (56 mg) obtained in Example 3 and the enteric granules IX (97.4 mg) obtained in Example 5 were mixed, and filled in one size No. 2 capsule (corresponds to compound A: 60 mg) to give capsule VII.

Example 9

The enteric granules VII (84 mg) obtained in Example 3 and the enteric granules IX (296.1 mg) obtained in Example 5 were mixed, and filled in one size No. 1 capsule (corresponds to compound A: 90 mg) to give capsule VIII.

Example 10

The enteric granules VII (42 mg) obtained in Example 3 and the enteric granules IX (148.05 mg) obtained in Example 5 were mixed, and filled in one size No. 3 capsule (corresponds to compound A: 45 mg) to give capsule IX.

Experiment 1

Comparison of active ingredient content rate with form
(1) Test Sample
(A) Enteric granules II of Reference Example 3
(B) Enteric granules III of Reference Example 4
(C) Enteric granules V of Reference Example 9
(D) Enteric granules VI of Reference Example 10
(E) Enteric granules VIII of Example 4
(F) Enteric granules IX of Example 5
(2) Result
Summary table for the active ingredient content rate and form is shown in Table 1 below.

TABLE 1

|  | normal granule | | high content granule | | | |
|---|---|---|---|---|---|---|
|  | dusting method | | solution adding method | | dusting + solution adding method | |
|  | Reference Example 3 | Reference Example 4 | Reference Example 9 | Reference Example 10 | Example 4 | Example 5 |
| compound A (mg) | 5 | 45 | 45 | 45 | 45 | 45 |
| granule amount (mg) | 333 | 333 | 177.6 | 177.6 | 197.4 | 197.4 |
| content of active ingredient (%) | 13.51 | 13.51 | 25.34 | 25.34 | 22.80 | 22.80 |
| form | ○ | ○ | ○ | ○ | ○ | ○ |

Experiment 2

Dissolution test (pH 6.8)
(1) Test Sample
(A) Enteric granules III of Reference Example 4
(B) Enteric granules VI of Reference Example 10
(C) Enteric granules IX of Example 5
(2) Test Method
Test was carried out for 50 mg in terms of compound A using phosphate buffer of pH 6.8 (900 mL) as test solution according to the dissolution test second method (paddle method) of the Japanese Pharmacopoeia, Fourteenth Edition, and the dissolved solution after a given time from the start of each dissolution test under 75 rpm was assayed.
(3) Result
The dissolution profile of compound A is shown in FIG. 1. From FIG. 1, in the enteric granules VI of Reference Example 10 prepared by solution addition method, the dissolution was delayed compared to those by other methods. However, the enteric granules IX of Example 5 of the present invention showed a good dissolution feature.

Experiment 3

Figure 2:
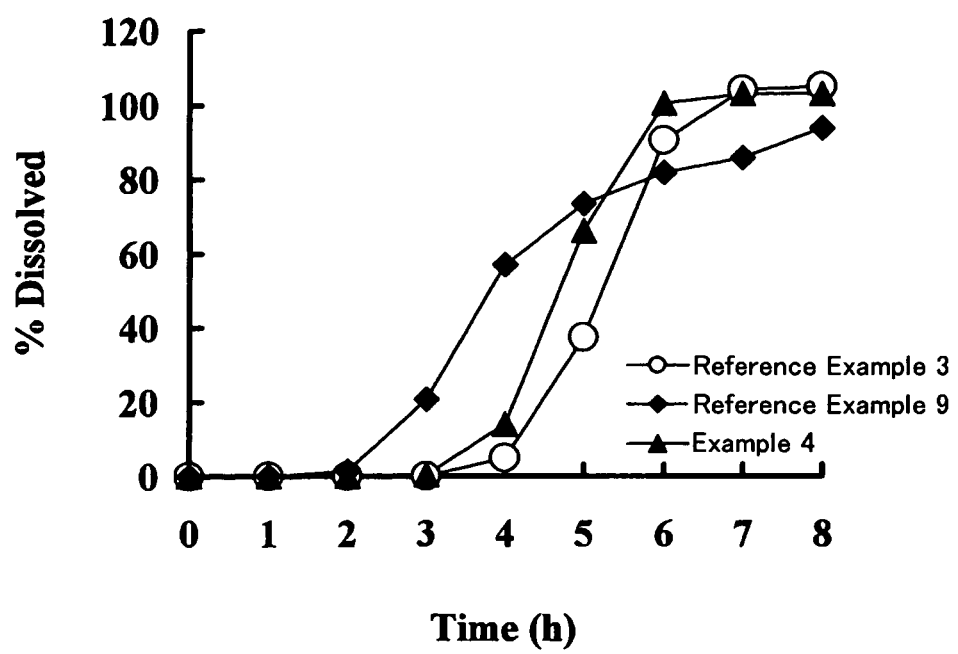
FIG. 2 shows dissolution profiles of compound A of enteric granules obtained in Reference Examples 3 and 9, and Example 4.

Dissolution test (pH 6.8)
(1) Test Sample
(A) Enteric granules II of Reference Example 3
(B) Enteric granules V of Reference Example 9
(C) Enteric granules VIII of Example 4
(2) Test Method
Test was carried out for 50 mg in terms of compound A using phosphate buffer of pH 6.8 (900 mL) as test solution according to the dissolution test second method (paddle method) of the Japanese Pharmacopoeia, Fourteenth Edition, and the dissolved solution after a given time from the start of each dissolution test under 75 rpm was assayed.
(3) Result
The dissolution profile of compound A is shown in FIG. 2. From FIG. 2, in the enteric granules V of Reference Example 9 prepared by solution addition method, the dissolution was delayed compared to those by other methods. However, the enteric granules VIII of Example 4 of the present invention showed a good dissolution feature.

Experiment 4

Figure 3:
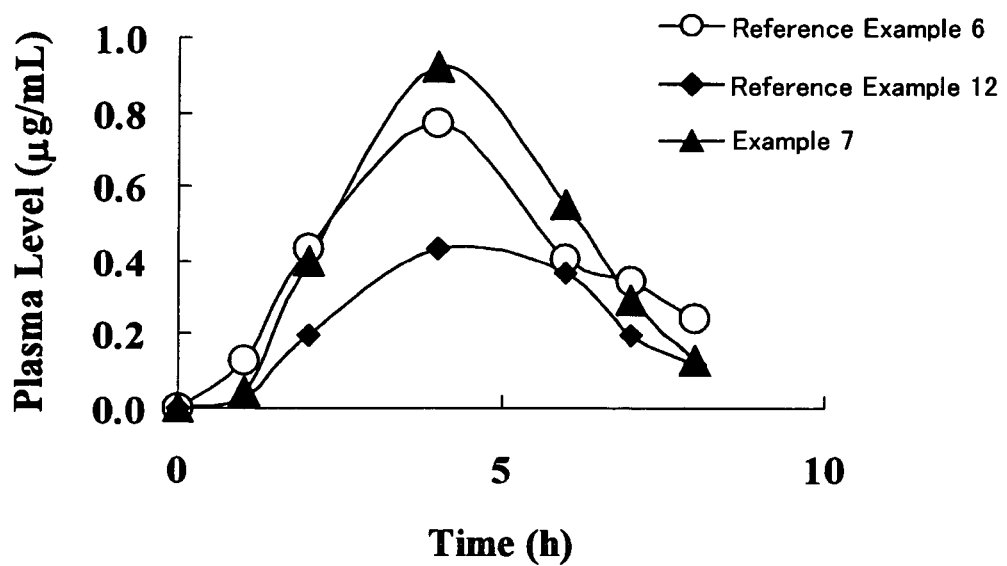
FIG. 3 shows plasma level profiles of compound A when each of capsules obtained in Reference Examples 6 and 12 and Example 7 is administered to beagle dogs under fasted condition.

Absorbability in beagle
(1) Test Sample
(A) Capsule II of Reference Example 6
(B) Capsule IV of Reference Example 12
(C) Capsule VI of Example 7
(2) Test Method
The capsule was orally administered with a dose of 30 mg/dog together with 30 mL of water to fasted beagle dogs. The plasma levels of compound A at 1 hr, 2 hrs, 4 hrs, 6 hrs, 7 hrs and 8 hrs after the administration were measured.
(3) Result
The plasma level profile of compound A is shown in FIG. 3. From FIG. 3, in the capsule IV of Reference Example 12 wherein the granules were prepared by solution adding method, the absorption was less compared to those by other methods. However, the capsule VI of Example 7 of the present invention showed a good absorbability.

Industrial Applicability

In the granule, fine particle or tablet of the present invention, an active ingredient is blended with high content, and exerts an effect of quickly dissolving. In addition, final preparations such as a capsule containing these granule, fine particle or tablet can be designed to an easy-to-dose size, therefore compliance with dosing can be improved, and further the cost of production can also be lowered.

Furthermore, by preparing a controlled release preparation using the granule and the like of the present invention, the persistence of effective level for treatment is made possible since the release of active ingredient is controlled over a long period of time, therefore a preparation wherein not only administration time is decreased but also treatment with low dose is effective and side effects due to initial rising of blood level are alleviated, can be provided.

The invention claimed is:
1. A granule or tablet having an inert core particle, and on said core particle, an active ingredient-containing A layer formed by spraying a solution or suspension containing an active ingredient and a binder, and an active ingredient-containing B layer formed by dispersing a dusting powder containing an active ingredient while spraying a solution containing a binder, wherein the total content of the active ingredient in the A and B layers relative to the whole granule or tablet is 10 to 40 w/w %, and wherein the A layer is formed on the inner side, and the B layer is formed on the outer side, whereby there is no intermediate layer between the A layer and the B layer, wherein the granule or tablet is coated with a release-controlling film.
2. The granule or tablet according to claim 1, wherein the release-controlling film contains a pH dependently dissolved polymer.
3. The granule or tablet according to claim 1, wherein the active ingredient is a proton pump inhibitor (PPI).
4. The granule or tablet according to claim 3, wherein the PPI is a benzimidazole compound represented by the formula (I):

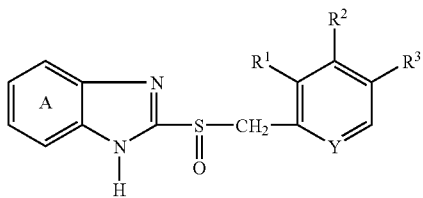

(I)

wherein ring A represents an optionally substituted benzene ring, $R^1$, $R^2$ and $R^3$ are the same or different and represent a hydrogen atom, an optionally substituted alkyl group, an optionally substituted alkoxy group or an optionally substituted amino group, and Y represents a nitrogen atom or CH, or an optically active compound thereof or a salt thereof.

5. The granule or tablet according to claim 3, wherein the PPI is lansoprazole, omeprazole, rabeprazole, pantoprazole, leminoprazole, tenatoprazole (TU-199), or an optically active compound thereof or a salt thereof.

6. The granule or tablet according to claim 3, wherein the PPI is lansoprazole, or an optically active compound thereof or a pharmaceutically acceptable salt thereof.

7. The granule or tablet according to claim 3, wherein a basic inorganic salt is contained in the A layer and the B layer.

8. The granule or tablet according to claim 7, wherein the basic inorganic salt is a salt of magnesium or a salt of calcium.

9. The granule or tablet according to claim 3, which is further coated with an enteric film.

10. The granule or tablet according to claim 3, which is further coated with an intermediate layer under the release-controlling film.

11. The granule or tablet according to claim 1, wherein an intermediate layer is provided for preventing direct contact between the core particle and the A layer.

12. The granule or tablet according to claim 1, wherein an intermediate layer is provided for preventing direct contact between the core particle, the A layer, and the release-controlling film.

13. A solid dosage form comprising the granule or tablet according to claim 9.

14. A manufacturing process for a granule or tablet, comprising a combination of:
   a step of spraying a solution or suspension containing an active ingredient and a binder on an inert core particle to form an active ingredient-containing A layer,
   a step of dispersing a dusting powder containing an active ingredient while spraying a solution containing a binder, to form an active ingredient-containing B layer, and
   a step of coating the granule or tablet with a release-controlling film,
   wherein the total content of the active ingredient in the A and B layers relative to the whole granule or tablet is 10 to 40 w/w %, the A layer is formed on the inner side, and the B layer is formed on the outer side, and there is no intermediate layer between the A layer and the B layer.

15. The manufacturing process for a granule or tablet according to claim 14, wherein the A layer is first formed on the inert core particle, and the B layer is formed on the A layer.

16. A solid dosage form comprising the granule or tablet according to claim 1.

17. The solid dosage form according to claim 16, which is a capsule.

18. A method for controlling dissolution of an active ingredient and a size of a solid dosage form containing a granule or a tablet, comprising a combination of, on an inert core particle, a method of spraying a solution or suspension containing an active ingredient and a binder to form an active ingredient-containing A layer, a method of dispersing a dusting powder containing an active ingredient while spraying a solution containing a binder to form an active ingredient-containing B layer to obtain the granule or tablet, and a method of coating the granule or tablet with a release-controlling film, wherein the total content of the active ingredient in the A and B layers relative to the whole granule or tablet is 10 to 40 w/w %, the A layer is formed on the inner side, and the B layer is formed on the outer side, and there is no intermediate layer between the A layer and the B layer.

* * * * *